US012685767B2

(12) United States Patent
Coffin

(10) Patent No.: US 12,685,767 B2
(45) **Date of Patent: \*Jul. 21, 2026**

(54) TREATMENT USING ONCOLYTIC VIRUS

(71) Applicant: REPLIMUNE LIMITED, Oxfordshire (GB)

(72) Inventor: Robert Stuart Coffin, Oxfordshire (GB)

(73) Assignee: Replimune Limited, Oxfordshire (GB)

( \* ) Notice: Subject to any disclaimer, the term of this patent is extended or adjusted under 35 U.S.C. 154(b) by 1095 days.

This patent is subject to a terminal disclaimer.

(21) Appl. No.: 17/250,205

(22) PCT Filed: Jun. 21, 2019

(86) PCT No.: PCT/GB2019/051769

§ 371 (c)(1),
(2) Date: Dec. 14, 2020

(87) PCT Pub. No.: WO2019/243847

PCT Pub. Date: Dec. 26, 2019

(65) Prior Publication Data

US 2021/0252135 A1 Aug. 19, 2021

Related U.S. Application Data

(60) Provisional application No. 62/687,931, filed on Jun. 21, 2018, provisional application No. 62/687,920, (Continued)

(51) Int. Cl.
| | |
|---|---|
| *A61K 39/245* | (2006.01) |
| *A61K 38/17* | (2006.01) |
| *A61K 38/19* | (2006.01) |
| *A61K 39/395* | (2006.01) |
| *A61K 47/50* | (2017.01) |
(Continued)

(52) U.S. Cl.
CPC .......... *A61K 39/245* (2013.01); *A61K 38/177* (2013.01); *A61K 38/193* (2013.01); *A61K 39/3955* (2013.01); *A61K 47/50* (2017.08); *A61P 35/00* (2018.01); *C12N 7/00* (2013.01); *A61K 2039/5254* (2013.01); *A61K 2039/5256* (2013.01); *A61K 2039/545* (2013.01); *A61K 2039/585* (2013.01); *C12N 2710/16634* (2013.01); *C12N 2710/16643* (2013.01); *C12N 2710/16671* (2013.01)

(58) Field of Classification Search
None
See application file for complete search history.

(56) References Cited

U.S. PATENT DOCUMENTS 5,122,458 A 6/1992 Post et al.
5,168,062 A 12/1992 Stinski
(Continued)

FOREIGN PATENT DOCUMENTS

EP 1235853 B1 7/2009
JP 2013511549 A 4/2013
(Continued)

OTHER PUBLICATIONS

Stedman's Medical dictionary, 2000, lines 1-3 (Year: 2000).\*
Diefenbach et al., "Oncolytic virotherapy using herpes simplex virus: how far have we come?" Oncolytic Virotherapy, Nov. 1, 2015 (Nov. 1, 2015), p. 207.
Inouye et al., "Codon optimization of genes for efficient protein expression in mammalian cells by selection of only preferred human codons", Protein Expression and Purification, 2015, 109:47-54.
Schirrmann et al., "Transient Production of scFv-Fc Fusion Proteins in Mammalian Cells", Antibody Engineering, 2010, vol. 2; Chapter 30, p. 387-398, © Springer-Verlag Berlin Heidelberg.
Shan et al., "Characterization of scFv-Ig Constructs Generated from the Anti-CD20 mAb 1F5 Using Linker Peptides of Varying Lengths". Journal of Immunology, 1999, 162:6589-6595.
(Continued)

*Primary Examiner* — Meera Natarajan
(74) *Attorney, Agent, or Firm* — Norton Rose Fulbright US LLP

(57) ABSTRACT

An oncolytic virus for use in a method of treating or preventing cutaneous squamous cell carcinoma (CSCC), renal cell carcinoma (RCC), non-small cell lung cancer (NSCLC), triple negative breast cancer (TNBC), small cell lung cancer (SCLC), advanced recurrent head and neck cancer, squamous cell carcinoma of the head and neck (SCCHN), nasopharyngeal carcinoma (NPC), hepatocellular carcinoma (HCC), anal cancer, colorectal cancer (CRC), basal cell carcinoma (BCC), Merkel cell carcinoma, appendiceal carcinoma, sarcoma of the skin, recurrent melanoma after surgery, advanced or metastatic urothelial carcinoma, liver metastases, microsatellite instability high cancer (MSI-H), mixed advanced solid tumors, virally caused cancer, locoregionally advanced cancer, pediatric cancer, cancer in patients with no or minimal pre-existing anti-cancer immunity, cancer as first line therapy, cancer in previously treated patients, cancer in patients who have not received checkpoint blockade therapy, and/or cancer in patients who have received checkpoint blockade therapy, wherein the oncolytic virus: is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel; comprises (i) a fusogenic protein-encoding gene; and (ii) an immune stimulatory molecule or an immune stimulatory molecule-encoding gene; comprises (i) a GM-CSF-encoding gene; and (ii) an immune co-stimulatory pathway activating molecule or an immune co-stimulatory pathway activating molecule-encoding gene; and/or comprises a gene encoding a CTLA-4 inhibitor.

29 Claims, 47 Drawing Sheets

Specification includes a Sequence Listing.

Related U.S. Application Data filed on Jun. 21, 2018, provisional application No. 62/687,881, filed on Jun. 21, 2018, provisional application No. 62/687,910, filed on Jun. 21, 2018.

(51) Int. Cl.
| | |
|---|---|
| *A61P 35/00* | (2006.01) |
| *C12N 7/00* | (2006.01) |
| *A61K 39/00* | (2006.01) |

(56) References Cited

U.S. PATENT DOCUMENTS

| | | | |
|---|---|---|---|
| 5,288,641 | A | 2/1994 | Roizman |
| 5,328,688 | A | 7/1994 | Roizman |
| 5,385,839 | A | 1/1995 | Stinski |
| 5,599,691 | A | 2/1997 | Roizman |
| 5,602,007 | A | 2/1997 | Dunn et al. |
| 5,698,531 | A | 12/1997 | Nabel et al. |
| 5,824,318 | A | 10/1998 | Mohr et al. |
| 5,846,707 | A | 12/1998 | Roizman |
| 6,040,169 | A | 3/2000 | Brown et al. |
| 6,071,692 | A | 6/2000 | Roizman |
| 6,120,773 | A | 9/2000 | Roizman |
| 6,172,047 | B1 | 1/2001 | Roizman et al. |
| 6,297,219 | B1 | 10/2001 | Nabel et al. |
| 6,340,673 | B1 | 1/2002 | Roizman et al. |
| 6,423,528 | B1 | 7/2002 | Brown et al. |
| 6,428,968 | B1 | 8/2002 | Molnar-Kimber et al. |
| 6,649,157 | B2 | 11/2003 | Coffey et al. |
| 6,770,274 | B1 | 8/2004 | Martuza et al. |
| 7,063,835 | B2 | 6/2006 | Coffin |
| 7,223,593 | B2 | 5/2007 | Coffin |
| 7,537,924 | B2 | 5/2009 | Coffin |
| 7,749,745 | B2 | 7/2010 | Johnson et al. |
| 7,981,669 | B2 | 7/2011 | Coffin et al. |
| 8,273,568 | B2 | 9/2012 | Martuza et al. |
| 8,277,818 | B2 | 10/2012 | Coffin |
| 8,361,978 | B2 | 1/2013 | Rabkin et al. |
| 8,470,577 | B2 | 6/2013 | Johnson et al. |
| 8,679,830 | B2 | 3/2014 | Coffin et al. |
| 8,680,068 | B2 | 3/2014 | Coffin |
| 8,703,120 | B2 | 4/2014 | Martuza et al. |
| 8,871,193 | B2 | 10/2014 | Johnson et al. |
| 8,986,672 | B2 | 3/2015 | Zhang et al. |
| 9,487,581 | B2 | 11/2016 | Abate et al. |
| 9,492,482 | B2 | 11/2016 | Beech et al. |
| 9,623,059 | B2 * | 4/2017 | Mohr ...................... A61P 35/00 |
| 9,789,182 | B2 | 10/2017 | Graziano et al. |
| 9,827,307 | B2 | 11/2017 | Rabkin et al. |
| 9,868,961 | B2 | 1/2018 | Allison et al. |
| 10,039,796 | B2 | 8/2018 | Zhang et al. |
| 10,287,252 | B2 | 5/2019 | Cowley et al. |
| 10,301,600 | B2 | 5/2019 | Coffin |
| 10,555,981 | B2 | 2/2020 | Silvestre et al. |
| 10,570,377 | B2 | 2/2020 | Coffin |
| 10,612,005 | B2 | 4/2020 | Coffin |
| 10,626,377 | B2 | 4/2020 | Coffin |
| 10,765,710 | B2 | 9/2020 | Zitvogel et al. |
| 10,947,513 | B2 | 3/2021 | Coffin |
| 11,427,810 | B2 | 8/2022 | Coffin |
| 11,473,063 | B2 | 10/2022 | Coffin |
| 2003/0091537 | A1 | 5/2003 | Coffin |
| 2008/0014175 | A1 | 1/2008 | Hallahan et al. |
| 2010/0297072 | A1 | 11/2010 | DePinho |
| 2011/0044953 | A1 | 2/2011 | Allison et al. |
| 2013/0202639 | A1 | 8/2013 | Kousoulas et al. |
| 2014/0154216 | A1 | 6/2014 | Coffin |
| 2014/0271677 | A1 | 9/2014 | Palese et al. |
| 2015/0232812 | A1 | 8/2015 | Coffin |
| 2015/0283234 | A1 | 10/2015 | Graziano et al. |
| 2016/0040186 | A1 | 2/2016 | Liu |
| 2021/0252135 | A1 | 8/2021 | Coffin |
| 2021/0254019 | A1 | 8/2021 | Coffin |
| 2022/0056480 | A1 | 2/2022 | Bell et al. |

FOREIGN PATENT DOCUMENTS

| | | |
|---|---|---|
| JP | 2015/508156 A | 3/2015 |
| JP | 2016509045 A | 3/2016 |
| WO | 97/12623 A1 | 4/1997 |
| WO | 9830707 A2 | 7/1998 |
| WO | 01/53505 | 7/2001 |
| WO | 2001/53506 A2 | 7/2001 |
| WO | 2005/011715 A1 | 2/2005 |
| WO | 2006/002394 A2 | 1/2006 |
| WO | 2006/048749 A1 | 5/2006 |
| WO | 2007/052029 A1 | 5/2007 |
| WO | 2007/123737 A2 | 11/2007 |
| WO | 2010042189 A2 | 4/2010 |
| WO | 2011063309 A1 | 5/2011 |
| WO | 2011/118866 A1 | 9/2011 |
| WO | 2012/038606 A1 | 3/2012 |
| WO | 2013/038066 A1 | 3/2013 |
| WO | 2013112942 A1 | 8/2013 |
| WO | 2014/022138 A2 | 2/2014 |
| WO | 2014/036412 A2 | 3/2014 |
| WO | 2014/066532 A1 | 5/2014 |
| WO | 2014128235 A1 | 8/2014 |
| WO | 2015032755 A1 | 3/2015 |
| WO | 2015/059303 A1 | 4/2015 |
| WO | 2015/077624 A1 | 5/2015 |
| WO | 2015066042 A1 | 5/2015 |
| WO | 2015/128313 A1 | 9/2015 |
| WO | 2015/153417 A1 | 10/2015 |
| WO | 2016/008976 A1 | 1/2016 |
| WO | 2016/118865 A1 | 7/2016 |
| WO | 2017/118864 A1 | 7/2017 |
| WO | 2017/118866 A1 | 7/2017 |
| WO | 2017118867 A1 | 7/2017 |
| WO | 2017/181420 A1 | 10/2017 |
| WO | 2018127713 A1 | 7/2018 |

OTHER PUBLICATIONS

Kelly and Russell, History of Oncolytic Viruses: Genesis to Genetic Engineering, 15(4) Molecular Therapy 651-659 (Apr. 2007).

Choi et al. Polymeric oncolytic adenovirus for cancer gene therapy, 219 Journal of Controlled Release 181-191 (2015).

Ahmed et al, Intratumoral expression of a fusogenic membrane glycoprotein enhances the efficacy of replicating adenovirus therapy, 10 Gene Therapy 1663-71 (2003).

Tesfay et al. PEGylation of Vesicular Stomatitis Virus Extends Virus Persistence in Blood Circulation of Passively Immunized Mice, 87(7) Journal of Virology 3752-59 (Apr. 2013).

Lipson and Drake, Ipilimumab: An Anti-CTLA-4 Antibody for Metastatic Melanoma, 17(22) Clin. Cancer Res. 6958-62 (Nov. 2011).

Ribas, Clinical Development of the Anti-CTLA-4 Antibody Tremelimumab, 37(5) Seminars in Oncology 450-454 (Oct. 2010).

Output from Biocompare search for CTLA-4 Antibodies (performed Nov. 24, 2021), available at https://www.biocompare.com/Search-Antibodies/?search=CTLA-4&said=0.

Smith et al. Studies on the Use of Viruses in the Treatment of Carcinoma of the Cervix, 9(6) Cancer 1211-18 (Nov.-Dec. 1956).

Asada, Treatment of Human Cancer with Mumps Virus, 34(6) Cancer 1907-28 (Dec. 1974).

International Search Report for International Patent Application No. PCT/FI2009/051025, mailed from European Patent Office Mar. 24, 2010.

International Search Report for International Patent Application No. PCT/EP2015/066263, mailed from European Patent Office Oct. 7, 2015.

Documents filed on Jul. 9, 2018 in U.S. Appl. No. 16/068,830, including original application, preliminary amendment, application data sheet, search report, and transmittal form.

Ishikawa et al. Sting regulates intracellular DNA-mediated, type I interferon-dependent innate immunity, 461 Nature 788-792 (Oct. 8, 2009).

Petition for Post-Grant Review of U.S. Pat. No. 10,947,513, filed Dec. 15, 2021 with the TTAB, Petitioner—Transgene and Bioinvent International AB.

(56)          References Cited

OTHER PUBLICATIONS

Croyle et al. PEGylation of a Vesicular Stomatitis Virus G Pseudotyped Lentivirus Vector Prevents Inactivation in Serum, 78(2) Journal of Virology 912-921 (Jan. 2004).

Declaration of John C. Bell, Ph.D. dated Dec. 14, 2021 and Curriculum vitae.

Donovan-Banfield et al. Deep splicing plasticity of the human adenovirus type 5 transcriptome drives virus evolution, 3 Communications Biology (2020) 124.

Lee et al. Enhanced Antitumor Effect of Oncolytic Adenovirus Expressing Interleukin-12 and B7-1in an Immunocompetent Murine Model, 12(19) Clin. Cancer Res. 5859-68 (Oct. 2006).

McDonald et al. A measles virus vaccine strain derivative as a novel oncolytic agent against breast cancer, 99 Breast Cancer Research and Treatment 177-184 (2006).

Msaouel et al. Attenuated oncolytic Measles Virus strains as cancer therapeutics, 13(9) Curr. Pharm. Biotechnol. 1732-41 (Jul. 1, 2012).

Output from antibodies-online.com search for CTLA-4 Antibodies (performed Nov. 24, 2021), available at https://www.antibodies-online.eom/search.php#5qk9.

Output from Antibodypedia search for CTLA-4 Antibodies (performed Nov. 24, 2021), available at https://www.antibodYPedia.eom/gene/1 9961/CTLA4.

Pentcheva-Hoang et al. B7-1 and B7-2 Selectively Recruit CTLA-4 and CD28 to the Immunological Synapse, 21 Immunity 401-413 (Sep. 2004).

Study Details for Clinical Trial NCT02272855 "A Study of Combination Treatment With HF10 and Ipilimumab in Patients With Unresectable or Metastatic Melanoma", last updated Sep. 26, 2018, available at: https://clinicaltrials.gov/ct2/show/NCT02272855.

Study Details for Clinical Trial NCT02620423 "Study of Pembrolizumab with Reolysin® and Chemotherapy in Patients With Advanced Pancreatic Adenocarcinoma", last updated Sep. 13, 2018, available at: https://clinicaltrials.gov/ct2/show/NCT02620423.

Wennier et al. Bugs and Drugs: Oncolytic Virotherapy in Combination with Chemotherapy, 13(9) Curr. Pharm. Biotechnol. 1817-33 (Jul. 2012).

Yang et al. Cascade regulation of vaccinia virus gene expression is modulated by multistage promoters, 447(1-2) Virology 213-220 (Dec. 2013).

Declaration of Dr. Sylvia D. Hall-Ellis dated Nov. 29, 2021 and Curriculum vitae.

Kleinpeter et al. Vectorization in an oncolytic vaccinia virus of an antibody, a Fab and a scFv against programmed cell death-1 (PD-1) allows their intratumoral delivery and an improved tumor-growth inhibition, 5(10) Oncoimmunology e1220467 (2016).

Grandi, et al., Cancer Gene Therapy (2010) 17, 655-663 (Year: 2010).

Excerpts from S. Baron (Ed.), Medical Microbiology, 4th. Ed. University of Texas Medical Branch at Galveston (1996).

Species list extracted from International Committee on Taxonomy of Viruses (ICTY) Master Species List (Jul. 20, 2021), available at: https://talk.ictvonline.org/taxonomy/vmr/.

Output from the National Institutes of Health (NIH) National Center for Biotechnology Information (NCBI) Taxonomy Browser searches for "herpesviridae", "poxviridae", "adenovirdae", "retroviridae", "rhabdoviridae", "paramyxoviridae", and "reoviridae" (performed Nov. 3, 2021), available at: https://www.ncbi.nlm.nih.gov/Taxonomy/Browser/wwwtax.cgi7mode =Root.

List of known isolates within each virus family extracted from NCBI Taxonomy Browser Output of Ex. 1023.

Herpesviridae Information from Virus Pathogen Resource (ViPR) retrieved on Nov. 4, 2021, available at: https://www.viprbrc.org/brc/aboutPathogen.spg7decoratoiHierpes.

Oliveira et al. Poxvirus Host Range Genes and Virus-Host Spectrum: A Critical Review, 9(11) Viruses 2017 331 (Nov. 7, 2017).

Saha et al. The Adenovirus Genome Contributes to the Structural Stability of the Virion, 6(9) Viruses 2014 3563-3583 (Sep. 24, 2014).

Balvay et al. Translational control of retroviruses, 5 Nature Reviews Microbiology 128-140 (Feb. 2007).

Compilation of Virus Information from Swiss Institute of Bioinformatics retrieved on Nov. 3, 2021, available at https://viralzone.expasy.org/.

Reoviridae Information from Virus Pathogen Resource (ViPR) retrieved on Nov. 4, 2021, available at https://www.viprbrc.org/brc/aboutPathogen.spg?decorator=reo.

Summary of Characteristics of Commercial Viral Vectors from ThermoFisher Scientific, retrieved Nov. 4, 2021, available at https ://www.thermofisher. com/us/en/home/references/gibco-cell-culture-basics/transfection-basics/gene-delivery-technologies/viral-delivery/viral-vectors.html.

van den Wollenberg et al. Replicating reoviruses with a transgene replacing the codons for the head domain of the viral spike, 22 Gene Therapy 267-279 (2015).

Majid et al. Recombinant Vesicular Stomatitis Virus (VSV) and Other Strategies in HCV Vaccine Designs and Immunotherapy. Tan SL, (Ed.) Hepatitis C Viruses: Genomes and Molecular Biology, Ch. 15. Norfolk (UK): Horizon Bioscience (2006).

Jacobs et al. HSV-1 based vectors for gene therapy of neurological diseases and brain tumors Part II Vector Systems and Applications, 1(5) Neoplasia 402-416 (Nov. 1999).

Ho et al. Unconventional viral gene expression mechanisms as therapeutic targets, 593 Nature 362-371 (May 2021).

Salzberg, Open questions: How many genes do we have? 16 BMC Biology 94 (Aug. 20, 2018).

Hillier et al. Genomics in C. elegans: so many genes, such a little worm, 15 Genome Research 1651-60 (2005).

Lundstrom, New frontiers in oncolytic viruses: optimizing and selecting for virus strains with improved efficacy, 12 Biologics: Targets and Therapy 43-60 (2018).

Ma et al. Oncolytic herpes simplex virus and immunotherapy, 19 BMC Immunology 40 (2018).

Singh et al. Oncolytic viruses & their specific targeting to tumour cells, 136 Indian J. Med. Res. 571-584 (Oct. 2012).

Riedel et al. Components and Architecture of the Rhabdovirus Ribonucleoprotein Complex, 12(9) Viruses 2020 959 (Aug. 2020).

Dikstein, The unexpected traits associated with core promoter elements, 2(5) Transcription 201-206 (Sep. 2011).

Willemsen and Zwart, On the stability of sequences inserted into viral genomes, 5(2) Virus Evolution vez045 (Jul. 2019).

Brochu-Lafontaine and Lemay, Addition of exogenous polypeptides on the mammalian reovirus outer capsid using reverse genetics, 179 J. Virol. Methods 342-350 (2012).

Belsham and Sonenberg, RNA-protein interactions in regulation of picomavirus RNA translation, 60(3) Microbiological Reviews 499-511 (Sep. 1996).

Yen et al. Vaccinia virus infection & temporal analysis of virus gene expression: Part 2, 2009(26) J. Vis. Exp. 1169 (Apr. 2009).

Wertz et al. Adding genes to the RNA genome of vesicular stomatitis virus: positional effects on stability of expression, 76(15) J. Virol. 7642-50 (Aug. 2002).

Bett et al. Packaging capacity and stability of human adenovirus type 5 vectors, 67(10) J. Virol. 5911-21 (Oct. 1993).

Malhotra et al. Use of an Oncolytic Virus Secreting GM-CSF as Combined Oncolytic and Immunotherapy for Treatment of Colorectal and Hepatic Adenocarcinomas, 141(4) Surgery 520-529 (Apr. 2007).

Engeland et al. CTLA-4 and PD-L1 Checkpoint Blockade Enhances Oncolytic Measles Virus Therapy, 22(11) Molecular Therapy 1949-59 (Nov. 2014).

Guedan et al. GALVexpression enhances the therapeutic efficacy of an oncolytic adenovirus by inducing cell fusion and enhancing virus distribution, 19 Gene Therapy 1048-57 (2012).

Fu et al. Expression of a Fusogenic Membrane Glycoprotein by an Oncolytic Herpes Simplex Virus Potentiates the Viral Antitumor Effect, 7(6) Molecular Therapy 748-754 (Jun. 2003).

Nakamori et al. Potent Antitumor Activity After Systemic Delivery of a Doubly Fusogenic Oncolytic Herpes Simplex Virus Against Metastatic Prostate Cancer, 60 The Prostate 53-60 (2004).

Ebert et al. Syncytia Induction Enhances the Oncolytic Potential of Vesicular Stomatitis Virus in Virotherapy for Cancer, 64 Cancer Research 3265-3270 (May 2004).

(56) References Cited

OTHER PUBLICATIONS

Gömez-Trevino et al. Effects of adenovirus-mediated SV5 fusogenic glycoprotein expression on tumor cells, 5 J. Gene Med. (2003) 483-492.

Sharp and Li, The codon adaptation index—a measure of directional synonymous codon usage bias, and its potential applications, 15(3) Nucleic Acids Research 1281-95 (1987).

Le Boeuf et al. Synergistic Interaction Between Oncolytic Viruses Augments Tumor Killing, 18(5) Molecular Therapy 888-895 (May 2010).

Rojas et al. Defining Effective Combinations of Immune Checkpoint Blockade and Oncolytic Virotherapy, 21(24) Clin. Cancer Res. 5543-51 (Dec. 2015).

Ishihara et al. Systemic CD8+ T Cell-Mediated Tumoricidal Effects by Intratumoral Treatment of Oncolytic Herpes Simplex Virus with the Agonistic Monoclonal Antibody for Murine Glucocorticoid-Induced Tumor Necrosis Factor Receptor, 9(8) PLoS One e104669 (Aug. 2014).

John et al. Oncolytic Virus and Anti-4-IBB Combination Therapy Elicits Strong Antitumor Immunity against Established Cancer, 72(7) Cancer Research 1651-60 (Apr. 2012).

Deguchi et al. Combination of the Tumor Angiogenesis Inhibitor Bevacizumab and Intratumoral Oncolytic Herpes Virus Injections as a Treatment Strategy for Human Gastric Cancers, 59(118) Hepatogastroenterology 1844-50 (Sep. 2012).

Tan et al. Combination therapy of oncolytic herpes simplex virus HF10 and bevacizumab against experimental model of human breast carcinoma xenograft, 136 Int. J. Cancer 1718-30 (2015).

Fukuhara et al. Triple Gene-Deleted Oncolytic Herpes Simplex Virus Vector Double-Armed with Interleukin 18 and Soluble B7-1 Constructed by Bacterial Artificial Chromosome-Mediated System, 65(23) Cancer Res. 10663-68 (Dec. 2005).

Carter et al. Identification of an overprinting gene in Merkel cell polyomavirus provides evolutionary insight into the birth of viral genes, 110(31) Proceedings of the National Academy of Sciences 12744-49 (Jul. 2013).

Danthinne and Imperiale, Production of first generation adenovirus vectors: a review, 7 Gene Therapy 1707-14 (2000).

Blechacz et al. Engineered Measles Virus as a Novel Oncolytic Viral Therapy System for Hepatocellular Carcinoma, 44(6) Hepatology 1465-77 (Dec. 2006).

Kaufmann et al. Chemovirotherapy of Malignant Melanoma with a Targeted and Armed Oncolytic Measles Virus, 133 Journal of Investigative Dermatology 1034-42 (2013).

Jacobs et al. Vaccinia Virus Vaccines: Past, Present and Future, 84(1) Antiviral Res. 1-13 (Oct. 2009).

Sinkovics and Horvath, Natural and genetically engineered viral agents for oncolysis and gene therapy of human cancers, 56 Arch. Immunol. Ther. Exp. 3-59 (2008).

Bateman et al. Cancer Res. Mar. 15, 2000;60(6):1492-7.

Bateman et al. Cancer Res. Nov. 15, 2002;62(22):6566-78.

Haswell et al Eur J Immunol 2001 31 3094-3100.

Hetrologous Expression. In Binder, Hirokawa and Windorst (eds.)—Encyclopedia of Neuroscience. (2009) Springer, Berlin, Heidleberg Https://Doi.org/10.1007/978-3-540-29678-2_2190.

Hoffmann et al. World J Gastroenterol. Mar. 28, 2008 14(12):1842-1850.

Huang et al., Mol Ther, Feb. 2010, vol. 18, No. 2, pp. 264-274.

IGI Global "What is Heterologous Expression" retrieved from https://www.igiglobal.com/dictionary/heterologousexpression/49470.

Kanagavelu et al PlosOne 2014, 9, 2, e90100.

Kanagavelu et al Vaccine 2012 30 691-701.

Kasuya et al., Journal of Japan Surgical Society, 2006, 107, Extra Issue (2), p. 369, No. PS-005-8.

Kim et al Cancer Res 2009, 69, 21, 8516-8525.

Li et al. Int. J. Cancer 2008, 123: 493-499.

Nakano et al., Journal of Japan Surgical Society, 2001,102, Extra Issue, p. 82, No. SF4e-4.

Patentee's response to EPO communication dtd Sep. 25, 2009, EP No. 17701910.6.

Yi et al Cancer Res 2007, 67 20 10027-10037.

Annex A—WO 2017/118864—Figures 3 and 4 published Jul. 13, 2017.

Carson et al., "Oncolytic Herpe Simplex Virus 1 (HSV-1) Vectors: Increasing Treatment Efficacy and Range Throught Strategic Virus Design", Drugs Future. 2010,35(3): 183-195.

Fransen et al., "Controlled Local Delivery of CTLA-4 Blocking Antibody Induces CD8+ T-Cell-Dependent Tumor Eradication and Decreaes Risk of Toxic Side Effects" Clin Cancer Res. 2013, 19(19):5381-9.

Hooren et al., "Abstract B103: Intralesional administration of CTLA-4 blocking monoclonal antibodies as a means to optimize bladder cancer therapy", Cancer Immunol Res. 2016,4 (11_ Supplement): B103.

Hooren et al., "Local checkpoint inhibition of CTLA-4 as a monotherapy or in combination with anti-PD1 prevents the growth of murine bladder cancer" Eur J Immunol. 2017,47(2):385-393.

Marabelle et al., "Intratumoral Anti-CTLA-4 Therapy: Enhancing Efficacy While Avoiding Toxicity", Clin Cancer Res. 2013, 19(19):5261-3.

EPO Opposition "Opponent's Response in opposition proceedings against Replimune's European Patent EP 3400291", provided by the European Patent Office on May 4, 2023.

Fonteneau et al., "Oncolytic immunotherapy: The new clinical outbreak", OncoImmunology, 2016, 5:1,e1066961.

Japanese Notice of Rejection mailed Feb. 28, 2023 during examination of related JP Patent Appl. No. 2019-537074.

Marcos et al., "Mapping of the RNA promoter of Newcastle disease virus", Virology, vol. 331, Issue 2, 2005, pp. 396-406.

Noton and Fearns, "Initiation and regulation of paramyxovirus transcription and replication", Virology, 2015, 479-480, 545-554.

Fielding et al. "A hyperfusogenic gibbon apeleukemia envelope glycoprotein: targeting of a cytotoxic gene by ligand display", Hum Gene Ther. Apr. 10, 2000;11(6):817-26.

Alekseenko et al: "Therapeutic properties of a vector carrying the HSV thymidine kinase and GM-CSF genes and delivered as a complex with a cationic copolymer", Journal of Translational Medicine (2015) 13:78.

Allison et al., "For Their Discovery of Cancer Therapy by Inhibition of Negative Immune in Physiology of Medicine Regulation"; The Nobel Assembly at Karolinska Institutet; 2018 Nobel Prize.

Altschul, S, F et al., I (1990) J Mol Biol 215:403-10.

Altschul, S.F. (1993) J Mol Evol 36:290-300.

Todo, "Special Focus: Glioma Therapy 'Armed' oncolytic herpes simplex vimses for C4 brain tumor therapy," Cell Adhesion & Migration, 2008, 2(3):208-213.

Yan et al., "Developing Novel Oncolytic Adenoviruses through Bioselection," Journal of Virology, 2003, 77(4):2640-2650.

Cell Signaling Technology; Immune Checkpoint Signaling in the Tumor Microenvironment1; Mar. 2018.

Chen et al., Dual silencing of Bcl-2 and Survivin by HSV-1 vector shows better antitumor efficacy in higher PKR phosphorylation tumor cells in vitro and in vivo:, Cancer Gene Ther 22, 380-386; 2015.

Chou et al. (1990) Science 250: 1262-1266.

Devereux et al (1984) Nucleic Acids Research 12, p. 387-395.

Du et al. "Tumor-specific oncolytic adenoviruses expressing granulocyte macrophage colony-stimulating factor or anti-CTLA4 antibody for the treatment of cancers", Cancer Gene Therapy, vol. 21, No. 8, Jul. 18, 2014 (Jul. 18, 2014), pp. 340-348.

Gangi et al., "The safety of talimogene laherparepvec for the treatment of advanced melanoma", Expert Opinion on Drug Safety, Dec. 28, 2016 (Dec. 28, 2016), pp. 1-5.

Gibney et al., "Preliminary results from a phase 'A study of INCB024360 combined with ipilimumab (ipi) in patients (pts) with melanoma." 2014 ASCO Annual Meeting, No. 3010.

Henikoff and Henikoff (1992) Proc. Natl. Acad. Sci. USA 89:10915-10919.

Hoffmann et al., World J Gastroenterol. Jun. 14, 2007;13(22):3063-70.

(56) References Cited

OTHER PUBLICATIONS

Karlin and Altschul (1993) Proc. Natl. Acad. Sci. USA 90:5873-5787.

Liu et al. (2003) Gene Therapy 10:292-303.

Loskog, Angelica, "Immunostimulatory Gene Therapy Using Oncolytic Viruses as Vehicles," Viruses, 2015, 7:5780-5791.

Maclean et al. (1991) J. Gen. Virol. 72:631-639.

Piasecki et al., "Talilmogene laherparepvec increases the anti-tumor efficacy of the anti-PD-1 Abstract, Apr. 19, 2015 Immune checkpoint blockade," AACR Annual Meeting Presentation.

Reese et al., "Abstract IA24: New frontiers in oncolytic virus therapy", Cancer Immunology Research, vol. 4, No. 11 Supplement, Nov. 1, 2016 (Nov. 1, 2016).

Robbins et al; "Viral Vectors for Gene Therapy"; Pharmacol, Ther.; vol. 80, No. 1; pp. 35-47; 1998.

Robinson et al., "Novel Immunocompetent Murine Tumor Model for Evaluation of Conditionally Replication-Competent (Oncolytic) Murine Adenoviral Vectors," Journal of Virology, 2009, 83(8):3450-3462.

Senzer et al., "Phase II Clinical Trial of a Granulocyte-Macrophage Colony-Stimulating Factor-Encoding, Second-Generation Oncolytic herpesvims in Patients with Unresectable Metastatic Melanoma" Journal of Clinical Oncology, 2009, 27(34):5763-5771.

Simpson et al., "Combination of a Fusogenic Glycoprotein, Prodrug Activation, and Oncolytic Herpes Simplex Virus for Enhanced Local Tumor Control", Cancer Research, vol. 66, No. 9, May 1, 2006 (May 1, 2006), pp. 4835-4842.

Sokolowski et al., "Oncolytic virotherapy using herpes simplex vims: how far have we come?" Oncolytic Virotherapy, 2015, 4:207-219.

Terada K. et al., "Development of a rapid method to generate multiple oncolytic HSV vectors Gene Therapy, vol. 13, No. 8, (Apr. 1, 2006), pp. 705-714 and their in vivo evaluation using syngeneic mouse tumor models".

Third Party Submission submitted in Related U.S. Appl. No. 16/068,823, dated Jul. 18, 2019.

Third Party Submission submitted in Related U.S. Appl. No. 16/068,826, dated Aug. 7, 2019.

Third Party Submission submitted in Related U.S. Appl. No. 16/068,830, dated Jul. 18, 2019.

Third Party Submission submitted in Related U.S. Appl. No. 16/068,816, dated Jul. 18, 2019.

Ahlers et al: "A push-pull approach to maximize vaccine efficacy: abrogating suppression with an IL-13 inhibitor while augmenting help with granulocyte/macrophage colony-stimulating factor and CD40L", Proc Natl Acad Sci USA, Oct. 1, 2002;99(20):13020-5.

Allison, et al; "Discovery of Cancer Therapy by Inhibition of Negative Immune Regulation"; The Nobel Assembly at Karolinska Institutet; 2018 Nobel Prize in Physiology of Medicine.

Assal et al: "Emerging targets in cancer immunotherapy: beyond CTLA-4 and PD-1", Immunotherapy. 2015;7(11):1169-86.

Bauzon and Hermiston, 2014. Front. Immunol., 5(74): 1-10.

Capece et al: "Targeting costimulatory molecules to improve anti-tumor immunity", J Biomed Biotechnol, 2012; 2012:926321.

Chen et al. (Cancer Gene Therapy 2015, vol. 22, pp. 380-386).

Choi et al., "Concurrent delivery of GM-CSF and B7-1 using an oncolytic adenovirus elicits potent antitumor effect", Gene Therapy (2006) 13, 1010-1020 & 2006 Nature Publishing Group.

Choi et al., "Strengthening of antitumor immune memory and prevention of thymic atrophy mediated by adenovirus expressing IL-12 and GM-CSF", Gene Therapy (2012) 19, 711-723 & 2012 Macmillan Publishers.

Chou et al., "Mapping of Herpes Simplex Virus-1 Neurovirulence to ?134.5, a Gene Nonessential for Growth in Culture," Science, 1990, 250(4985):1262-1266.

Dias et al., 2012. Gene Ther., 19: 988-998.

Hu et al. "A simplified system for generating oncolytic adenovirus vector carrying one or two transgenes", Cancer Gene Therapy (2008) 15, 173-182 r 2008 Nature Publishing Group.

Gao et al: "Recombinant vesicularm stomatitis virus targeted to Her2/neu combined with anti-CTLA4 antibody eliminates implanted mammary tumors", Cancer Gene Ther. Jan. 2009; 16(1):44-52.

Gri et al: "X40 ligand-transduced tumor cell vaccine synergizes with GM-CSF and requires CD40-Apc signaling to boost the host T cell antitumor response", J Immunol. Jan. 1, 2003;170(1):99-106.

Hoggmann et al. W.J. G 2007, Jun. 14, 2013 (22), pp. 3063-30700.

Hurwitz et al: "CTLA-4 blockade synergizes with tumor-derived granulocyte-macrophage colony-stimulating factor for treatment of an experimental mammary carcinoma", Proc Natl Acad Sci USA, Aug. 18, 1998;95(17):10067-71.

Yo, Y-T et al: "Coexpression of Flt3 ligand and GM-CSF genes modulates immune responses induced by HER2/neu DNA vaccine", Cancer Gene Ther. Nov. 2007; 14(11):904-17.

Todo, Tomoki, Armed oncolytic herpes simplex viruses for brain tumor therapy, 208-213, Cell Adhesion* Migration 2:3, Jul./Aug./Sep. 2008.

Third Party Submission submitted in Related U.S. Appl. No. 16/068,816, dated Jul. 16, 2019.

Kaufman et al: "Oncolytic viruses: a new class of immunotherapy drugs", Nat Rev Drug Discov, vol. 14, 642-662 (Sep. 2015).

Lee et al: "Oncolytic potential of E1B 55 kDa-deleted YKL-1 recombinant adenovirus: correlation with p53 functional status" Int J Cancer (2000) 88: 454-463.

Li, B et al: "Established B16 tumors are rejected following treatment with GM-CSF-secreting tumor cell immunotherapy in combination with anti-4-1 BB mAb", Clin Immunol. Oct. 2007;125(1):76-87.

Li, B. et al: "Anti-programmed death-1 synergizes with granulocyte macrophage colony-stimulating factor-secreting tumor cell immunotherapy providing therapeutic benefit to mice with established tumors", Clin Cancer Res. Mar. 1, 2009;15(5):1623-34.

Liu et al., "ICP34.5 deleted herpes simplex cirus with enhanced oncolytic, immune stimulating, and anti-tumour properties," Gene Therapy, 2003, 10(4):292-303.

Maclean et al., "Herpes simplex cirus type 1 deletion variants 1714 and 1716 pinpoint neurovirulence-related sequences in Glasgow strain 17 + between immediate early gene 1 and the 'a' sequence," Journal of General Virology, 1991, 72:631-639.

Murata et al: "X40 costimulation synergizes with GM-CSF whole-cell vaccination to overcome established CD8+ T cell tolerance to an endogenous tumor antigen", J Immunol. Jan. 15, 2006;176(2):974-83.

Office Action issued in European Patent Application No. 1770385, dated May 21, 2019.

Reese, "Abstract IA24: New frontiers in oncolytic virus therapy," Cancer Immunology Research, 2016, 4 (11):1A24-1A24.

Statement of Grounds of Opposition from the Opponent, Margaret Dixon Limited, dated Jun. 7, 2021, EP3400293 (EP Appl. No. 17701910.6).

Sumimoto et al: "GM-CSF and B7-1 (CD80) co-stimulatory signals co-operate in the induction of effective anti-tumor Immunity in syngeneic mice", Int J Cancer. Nov. 14, 1997;73(4):556-61.

Amendment and Reply to Accompany Request for Continued Examination dated Sep. 26, 2018, U.S. Appl. No. 15/325,576, filed Jan. 11, 2017, 65 pages.

Amendment and Reply to Pursuant to 37 CFR §1.112 dated Aug. 26, 2019, U.S. Appl. No. 15/325,576, filed Jan. 11, 2017, 34 pages.

Applicant-Initiated Interview Summary dated Jan. 29, 2021 for U.S. Appl. No. 16/068,830, filed Jul. 9, 2018, 2 pages.

Bell, John C., Transcript of John C. Bell, Sep. 23, 2022, 87 pages.

Chiocca, E.A., Curriculum Vitae of E. Antonio Chiocca, M.D., Ph.D., Oct. 8, 2019, 92 pages.

Chiocca, E.A., Declaration of E. Antonio Chiocca, M.D., Ph.D., Faans, Sep. 28, 2022, 35 pages.

Chiocca, E.A., Transcript of E. Antonio Chiocca, M.D., Ph.D., Nov. 30, 2022, 237 pages.

Correction of Notice of Allowability dated Feb. 1, 2021 for U.S. Appl. No. 16/068,830, filed Jul. 9, 2018, 2 pages.

Decision Granting Institution of Past-Grant Review dated Jun. 16, 2022, Paper 16, AIA Review No. PGR2022-00014, U.S. Pat. No. 10,947,513 issued Mar. 16, 2021, 27 pages.

(56)  References Cited

OTHER PUBLICATIONS

Demonstrative Exhibits of Petitioners, AIA Review No. PGR2022-00014, U.S. Pat. No. 10,947,513 issued Mar. 16, 2021, Exhibit 1107, for Oral Argument Date Mar. 17, 2023, 56 pages.
Disclaimer in Patent Under 37 CFR 1.321(a) filed Mar. 15, 2022 for U.S. Pat. No. 10,947,513 issued Mar. 16, 2021, 6 pages.
Final Written Decision dated May 25, 2023, Paper 38, AIA Review No. PGR2022-00014, U.S. Pat. No. 10,947,513 issued Mar. 16, 2021, 61 pages.
Guo, Z.S et al., "Rapid Generation of Multiple Loci-Engineered Marker-free Poxvirus and Characterization of a Clinical-Grade Oncolytic Vaccinia Virus", Molecular Therapy: Methods & Clinical Development, vol. 7, Dec. 2017, Pittsburgh, PA, USA, pp. 112-122.
Guse, K. et al., "Antiangiogenic Arming of an Oncolytic Vaccinia Virus Enhances Antitumor Efficacy in Renal Cell Cancer Models", Journal of Virology, 84(2), Jan. 2010, pp. 856-866.
Patent Owner Response dated Sep. 28, 2022, AIA Review No. PGR2022-00014, U.S. Pat. No. 10,947,513 issued Mar. 16, 2021, 58 pages.
Patent Owner Sur Reply dated Feb. 1, 2023, AIA Review No. PGR2022-00014, U.S. Pat. No. 10,947,513 issued Mar. 16, 2021, 36 pages.
Patent Owner's Demonstrative Exhibits, AIA Review No. PGR2022-00014, U.S. Pat. No. 10,947,513 issued Mar. 16, 2021, Exhibit 2024, Replimune Limited, 75 pages.
Patent Owner's Objections to Petitioners Evidence dated Jul. 1, 2022, AIA Review No. PGR2022-00014, U.S. Pat. No. 10,947,513 issued Mar. 16, 2021, 33 pages.
Patent Owner's Preliminary Response dated Mar. 22, 2022, AIA Review No. PGR2022-00014, U.S. Pat. No. 10,947,513 issued Mar. 16, 2021, 41 pages.
Patent Owner's Supplemental Brief Regarding Xerox and Intel dated Mar. 31, 2023, AIA Review No. PGR2022-00014, U.S. Pat. No. 10,947,513 issued Mar. 16, 2021, 8 pages.
Petitioners Additional Briefing Regarding Xerox and Intel dated Mar. 31, 2023, AIA Review No. PGR2022-00014, U.S. Pat. No. 10,947,513 issued Mar. 16, 2021, 8 pages.
Petitioners' Reply to Owner's Response dated Dec. 20, 2022, AIA Review No. PGR2022-00014, U.S. Pat. No. 10,947,513 issued Mar. 16, 2021, 42 pages.
Petitioners' Reply to Patent Owner's Preliminary Response dated Apr. 14, 2022, AIA Review No. PGR2022-00014, U.S. Pat. No. 10,947,513 issued Mar. 16, 2021, 8 pages.
Record of Oral Hearing Held Mar. 17, 2023 dated May 22, 2023, Paper 37, AIA Review No. PGR2022-00014, U.S. Pat. No. 10,947,513 issued Mar. 16, 2021, 95 pages.
Reply under 37 CFR 1.111 dated Apr. 30, 2020, U.S. Appl. No. 16/068,830, filed Jan. 9, 2017, 11 pages.
Response to Rule 312 Communication and Applicant-Initiated Interview Summary dated Jan. 13, 2021 for U.S. Appl. No. 16/068,830, filed Jul. 9, 2018, 4 pages.
Third Party Submissions Under 37 CFR §1.290 dated Jul. 30, 2019 for U.S. Appl. No. 16/068,830, filed Jul. 9, 2018, 2 pages.
Dhar et al., "Syrian Hamster Tumor Model to Study Oncolytic ADS-Based Vectors," In: Oncolytic Viruses: Methods and Protocols, edited by David H. Kirn et al., Humana Press, vol. 797, Chapter 4, pp. 53-63, 2012.
Doronin et al., "Construction of Targeted and Armed Oncolytic Adenoviruses," In: Oncolytic Viruses: Methods and Protocols, edited by David H. Kirn et al., Humana Press, vol. 797, Chapter 3, pp. 35-52, 2012.

Fournier et al., "Analysis of Three Properties of Newcastle Disease Virus for Fighting Cancer: Tumor-Selective Replication, Antitumor Cytotoxicity, and Immunostimulation," In: Oncolytic Viruses: Methods and Protocols, edited by David H. Kirn et al., Humana Press, vol. 797, Chapter 13, pp. 177-204, 2012.
Gimenez-Alejandre et al., "Construction of Capsid-Modified Adenoviruses by Recombination in Yeast and Purification of Iodixanol-Gradient," In: Oncolytic Viruses: Methods and Protocols, edited by David H. Kirn et al., Humana Press, vol. 797, Chapter 2, pp. 21-34, 2012.
Goldufsky et al., "Oncolytic virus therapy for cancer," Oncolytic Virotherapy, 2:31-46, 2013.
Jeon et al. Journal of Virological Methods, 2022, vol. 299, pp. 1-7.
Lun, X.Q. et al., "Efficacy of Systemically Administered Oncolytic Vaccinia Virotherapy for Malignant Gliomas is Enhanced by Combination Therapy with Rapamycin or Cyclophosphamide", Clinical Cancer Research 15(8), 2009, pp. 2777-2788.
Rajiani et al. Molecular Therapy, published on May 2015, vol. 23, Supplement 1, S30.
Rintoul, J.L., et al. "A Selectable and Excisable Marker System for the Rapid Creation of Recombinant Poxviruses", PloS one, 6(9), 2011, e24643, pp. 1-12.
Robinson, et al., Gene Therapy 2003 10:292-303 (Year: 2003).
Semmrich, M. et al., "Vectorized Treg-depleting ?CTLA-4 elicits antigen cross-presentation and CD8+ T cell immunity to reject 'cold' tumors", Journal for ImmunoTheraphy of Cancer, 10(1), 2022, 36 pages.
Semmrich, M. et al., "Vectorized Treg-depleting ?CTLA-4 elicits antigen cross-presentation and CD8+ T cell immunity to reject „cold tumors", BioInvent International AB, Lund, Sweden, Transgene S.A., Illkirch-Graffenstaden, France, Abstract #746, 1 page.
Shmulevitz et al., "Exploring Host Factors that Impact Reovirus Replication, Dissemination, and Reovirus-Induced Cell Death in Cancer Versus Normal Cells in Culture," In: Oncolytic Viruses: Methods and Protocols, edited by David H. Kirn et al., Humana Press, vol. 797, Chapter 12, pp. 163-176, 2012.
Takara Bio, 2000 URL: https://www.takarabio.com/documentsNector%20Documents/PT3155-5.pdf; Accessed Apr. 20, 2022 (Year: 2000).
Thomas, S. et al., "Development of a new fusion-enhanced oncolytic immunotherapy platform based on herpes simplex virus type 1", . Journal for ImmunoTherapy of Cancer, 7:214, 2019, 17 pages.
Thorne, "Next-Generation Oncolytic Vaccinia Vectors," In: Oncolytic Viruses: Methods and Protocols, edited by David H. Kirn et al., Humana Press, vol. 797, Chapter 14, pp. 205-215, 2012.
Yamamoto, S., et al., "Imaging immediate-early and strict-late promoter activity during oncolytic herpes simplex virus type 1 infection and replication in tumors", Gene Therapy, 13, 2006, pp. 1731-1736.
Yang, S. et al., "Development of optimal bicistronic lentiviral vectors facilitates high-level TCR gene expression and robust tumor cell recognition", Gene Therapy, 15(21), Nov. 2008, 20 pages.
Woller et al. "Viral infection of tumors overcomes resistance to PD-1-immunotherapy by broadening neoantigenome-directed T-cell responses", Molecular Therapy, vol. 23, No. 10, 2015.
Watanabe, D. and Goshima, F., "Oncolytic Virotherapy by HSV", Human Herpesviruses, Advances in Experimental Medicine and Biology, Jun. 13, 2018, vol. 1045, pp. 63-84, DOI: 10.1007/978-981-10-7230-7_4.
Japanese Notice of Rejection dated Apr. 23, 2026, issued during examination of JP Appl. No. 2020-570967.

* cited by examiner

Figure 5F:
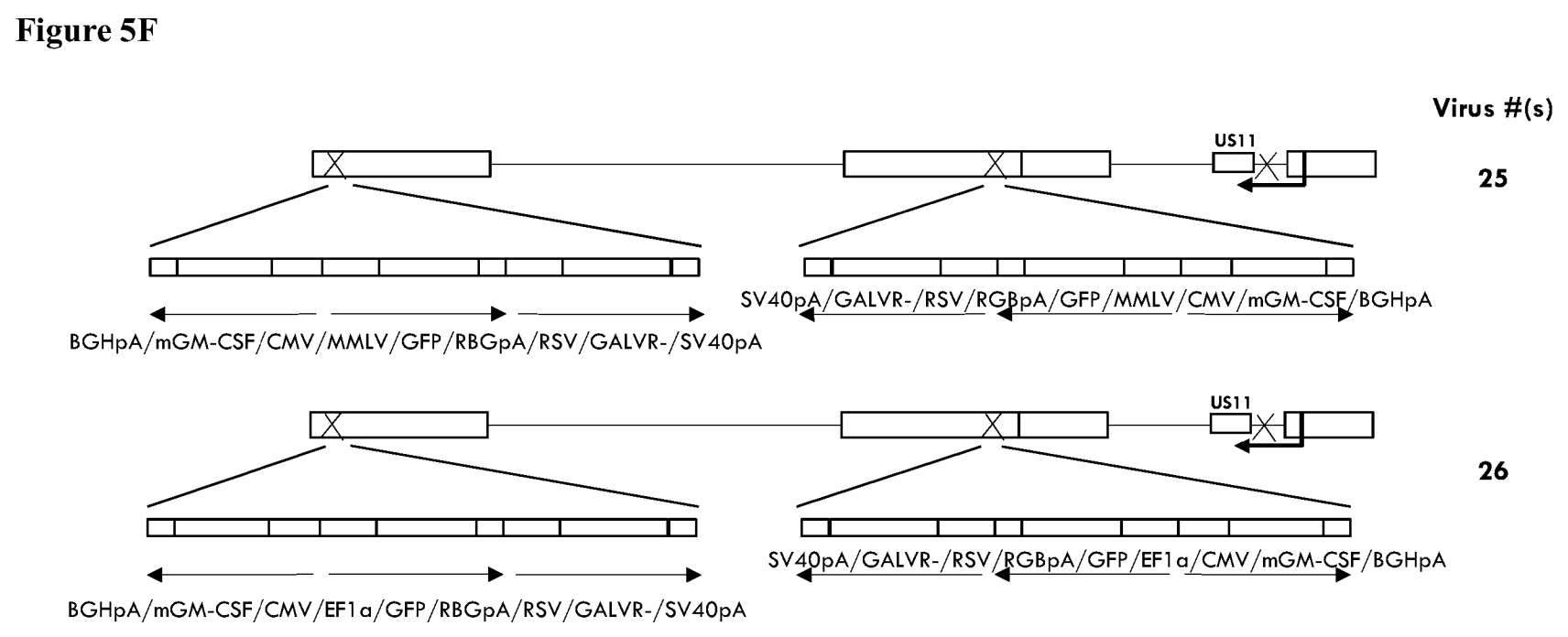

Figure 5G:
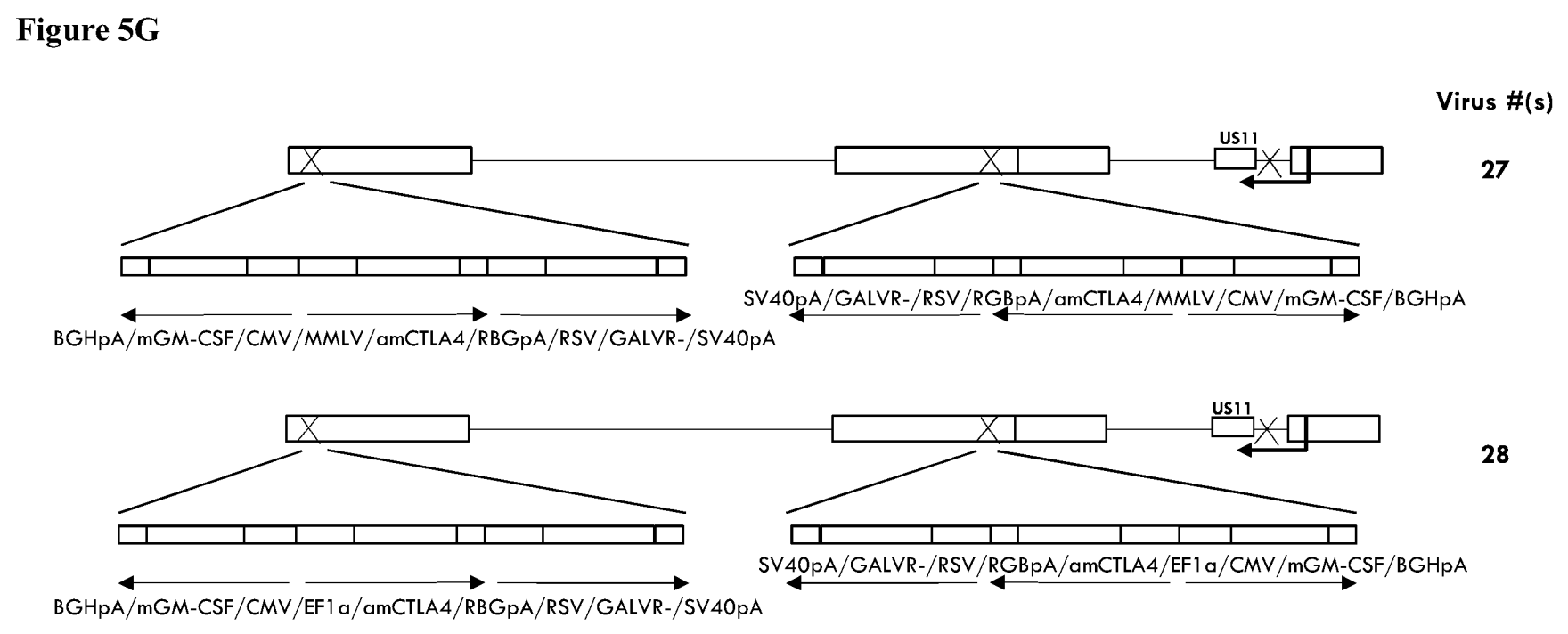

Figure 5H:
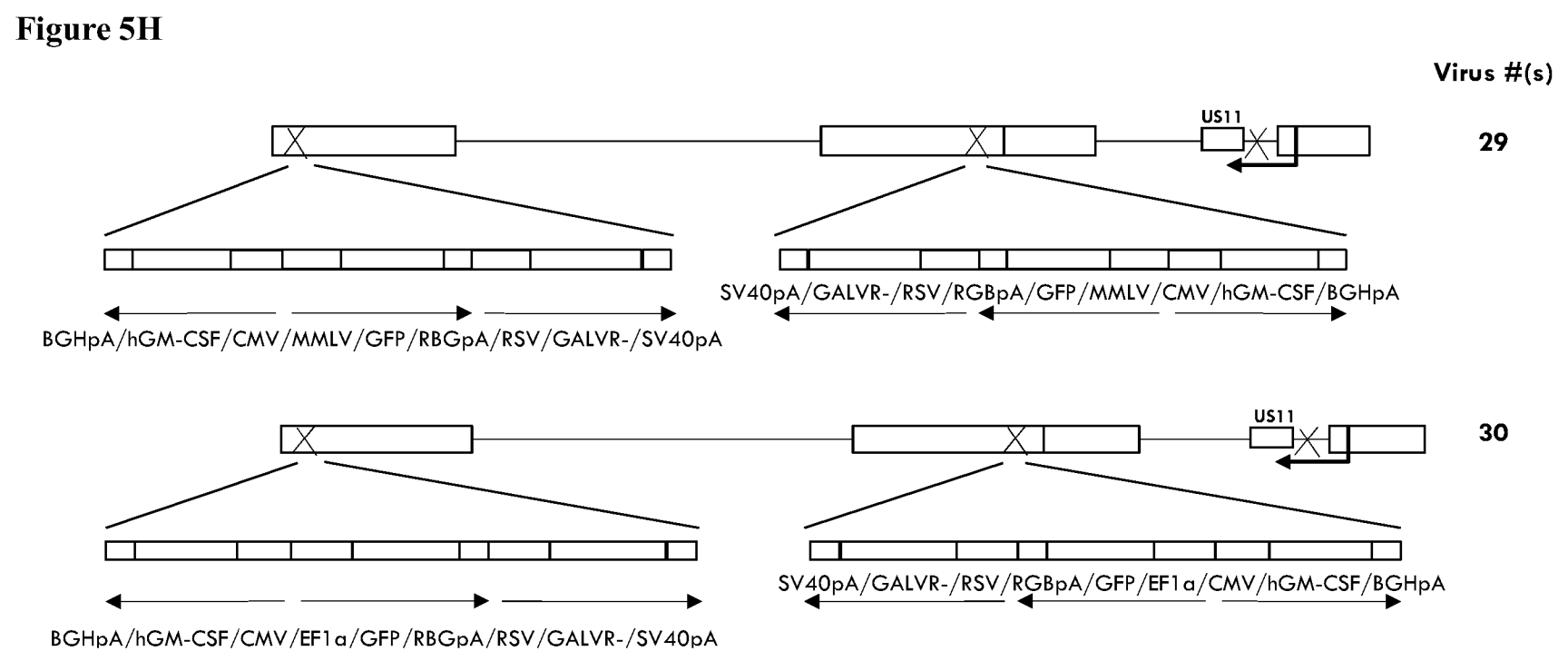

Figure 5J:
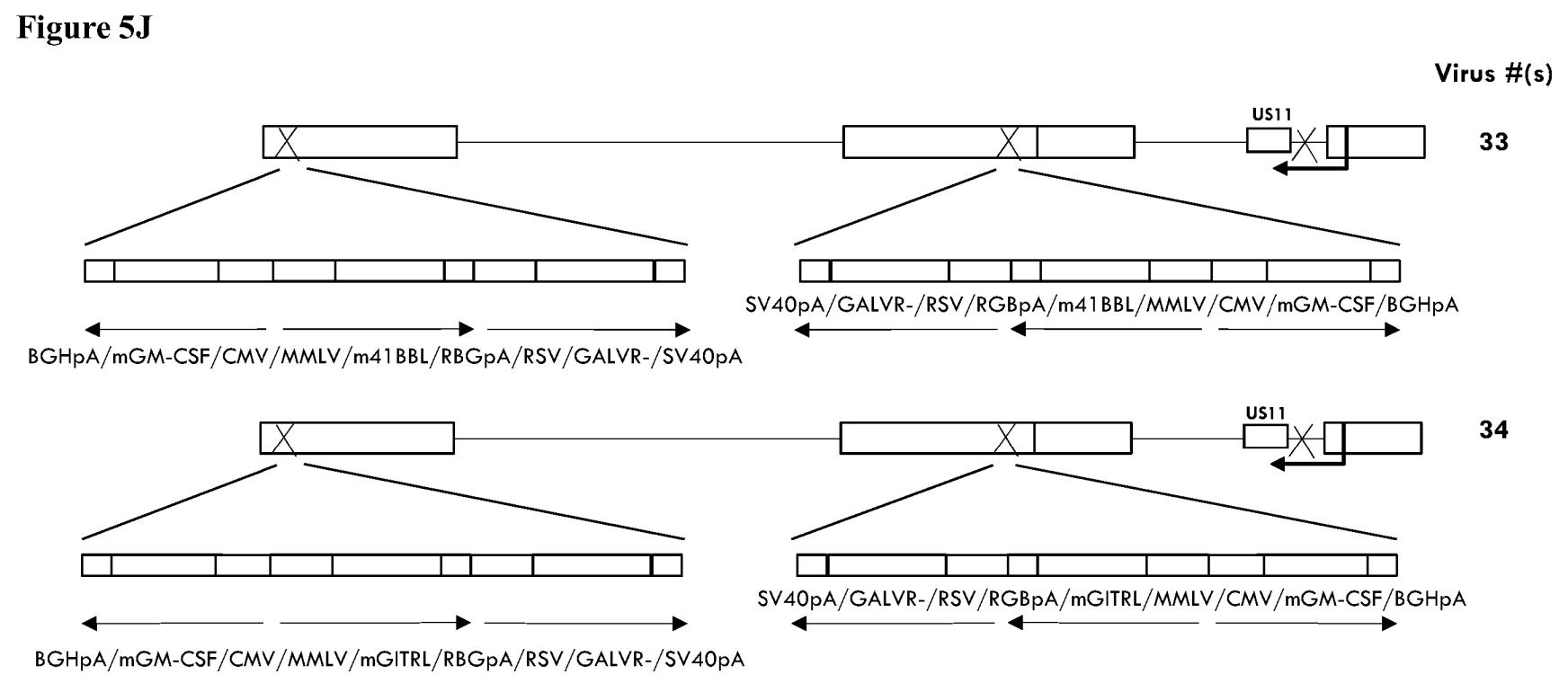

Virus 12
(Strain 18/
ICP34.5-/GFP)

Virus 10
(Strain 18/
ICP34.5-/GALV/
GFP)

MDA-MD-231 MOI 0.01 48hr          MIA-Pa-Ca-2 MOI 0.01 48hr          SK-mel-28  MOI 0.001 24hrs Cell death assessed by crystal violet staining; low magnification

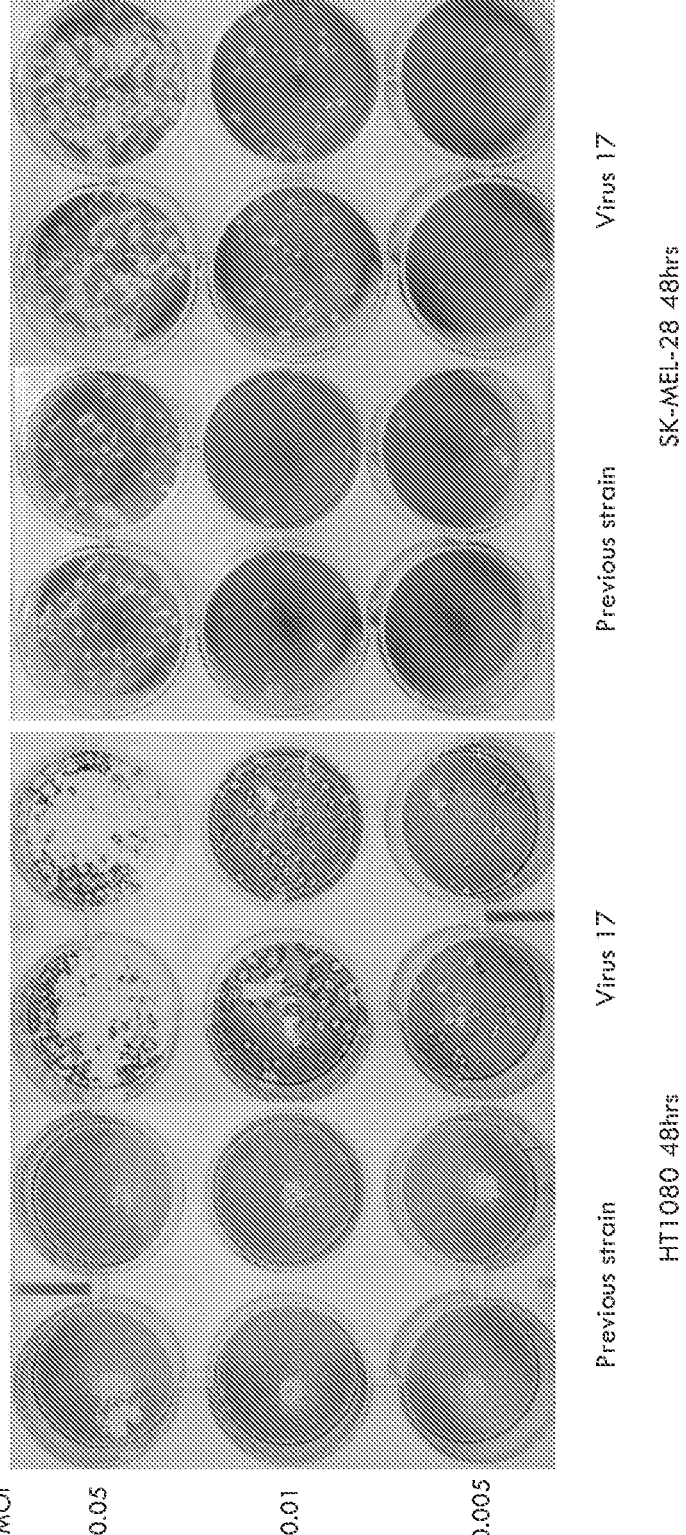

Virus: 5 injections of 5x10⁶ pfu into the right flank tumor only
Anti-CTLA-4: 3mg/kg i.p. Q3Dx9 (clone 9D9; BioXCell)

Human A549 lung cancer tumors in nude mice (no immune effect)

3 injections of Virus 16 or Virus 19 over 1 wk of vehicle or the indicated dose of virus (N=10/group)

Figure 17A

Plasmid 77: pGALVR-/mGM-CSF/MMLV-GFP =
Plasmid 18 cut with PacI and AflII into which is
inserted the PacI/AflII fragment from Plasmid 76

Plasmid 119: pGALVR-/mGM-CSF/MMLV-amCTLA-4 =
Plasmid 77 cut with AflII and AscI into which is
inserted the synthesized anti-mCTLA-4 sequence
flanked by AflII/AscI sites

SEQUENCE LISTING

```
<160> NUMBER OF SEQ ID NOS: 62

<210> SEQ ID NO 1
<211> LENGTH: 426
<212> TYPE: DNA
<213> ORGANISM: Mus musculus

<400> SEQUENCE: 1
atgtggctgc agaatttact tttcctgggc attgtggtct acagcctctc agcacccacc        60
cgctcaccca tcactgtcac ccggccttgg aagcatgtag aggccatcaa agaagccctg       120
aacctcctgg atgacatgcc tgtcacattg aatgaagagg tagaagtcgt ctctaacgag       180
ttctccttca agaagctaac atgtgtgcag acccgcctga agatattcga gcagggtcta       240
cggggcaatt tcaccaaact caagggcgcc ttgaacatga cagccagcta ctaccagaca       300
tactgccccc caactccgga aacggactgt gaaacacaag ttaccaccta tgcggatttc       360
atagacagcc ttaaaacctt tctgactgat atcccctttg aatgcaaaaa accagtccaa       420
aaatga                                                                  426

<210> SEQ ID NO 2
<211> LENGTH: 426
<212> TYPE: DNA
<213> ORGANISM: Mus musculus

<400> SEQUENCE: 2
atgtggctcc agaacctcct cttcctcggt atcgtcgtgt attcactctc cgcacctact        60
```

```
cgctcaccta tcactgtcac cagaccctgg aagcacgtgg aggccatcaa ggaggctctg      120
aacctgctgg acgatatgcc agtgaccctg aacgaggagg tggaggtggt gagcaacgag      180
ttctccttta agaagctgac ctgcgtgcag acaaggctga agatcttcga gcagggcctg      240
agaggaaact ttaccaagct gaagggcgcc ctgaacatga ccgcttctta ctaccagaca      300 tactgcccc ctaccccga gacagactgt gagacacagg tgaccacata cgccgacttc      360
attgatagcc tgaaaacatt cctgaccgac attccatttg agtgtaagaa gcccgtccag      420
aagtaa                                                                 426
```

<210> SEQ ID NO 3
<211> LENGTH: 435
<212> TYPE: DNA
<213> ORGANISM: Homo sapiens

<400> SEQUENCE: 3

```
atgtggctgc agagcctgct gctcttgggc actgtggcct gcagcatctc tgcacccgcc       60
cgctcgccca gccccagcac gcagccctgg gagcatgtga atgccatcca ggaggcccgg      120
cgtctcctga acctgagtag agacactgct gctgagatga atgaaacagt agaagtcatc      180
tcagaaatgt ttgacctcca ggagccgacc tgcctacaga cccgcctgga gctgtacaag      240
cagggcctgc ggggcagcct caccaagctc aagggcccct tgaccatgat ggccagccac      300
tacaagcagc actgccctcc aaccccggaa acttcctgtg caacccagat tatcacctttt      360 gaaagtttca agagaacct gaaggacttt ctgcttgtca tccccttttga ctgctgggag      420 ccagtccagg agtga                                                       435
```

<210> SEQ ID NO 4
<211> LENGTH: 435
<212> TYPE: DNA
<213> ORGANISM: Homo sapiens

<400> SEQUENCE: 4

```
atgtggctgc agtccctgct gctgctgggc accgtcgcct gttctatttc cgcacccgca       60
aggtcaccaa gtccatctac tcagccttgg gagcacgtga acgcaatcca ggaggcacgg      120
cggctgctga acctgagccg ggacaccgcc gccgagatga acgagacagt ggaagtgatc      180
agcgagatgt tcgatctgca ggagcccacc tgcctgcaga caaggctgga gctgtacaag      240
cagggcctgc gcggctctct gaccaagctg aagggcccac tgacaatgat ggccagccac      300
tataagcagc actgccccc taccccgag acaagctgtg ccacccagat catcacattc      360 gagtcctttta aggagaacct gaaggattttt ctgctggtca ttccatttga ttgttgggag      420
cccgtccagg agtaa                                                       435
```

<210> SEQ ID NO 5
<211> LENGTH: 141
<212> TYPE: PRT
<213> ORGANISM: Mus musculus

<400> SEQUENCE: 5

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45
```

-continued

```
Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
                100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140

<210> SEQ ID NO 6
<211> LENGTH: 144
<212> TYPE: PRT
<213> ORGANISM: Homo sapiens

<400> SEQUENCE: 6

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 7
<211> LENGTH: 2010
<212> TYPE: DNA
<213> ORGANISM: Gibbon leukemia virus

<400> SEQUENCE: 7
atggtattgc tgcctgggtc catgcttctc acctcaaacc tgcaccacct tcggcaccag      60
atgagtcctg ggagctggaa aagactgatc atcctcttaa gctgcgtatt cggcggcggc     120
gggacgagtc tgcaaaataa gaaccccac cagcccatga ccctcacttg gcaggtactg      180
tcccaaactg agacgttgt ctgggataca aaggcagtcc agccccttg gacttggtgg       240 cccacactta aacctgatgt atgtgccttg gcggctagtc ttgagtcctg ggatatcccg     300
ggaaccgatg tctcgtcctc taaacgagtc agacctccgg actcagacta tactgccgct     360
tataagcaaa tcacctgggg agccataggg tgcagctacc ctcgggctag gactagaatg     420
gcaagtctta ccttctacgt atgtccccgg gatggccgga cccttttcaga agctagaagg     480 tgcgggggc tagaatccct atactgtaaa gaatgggatt gtgagaccac ggggaccggt     540
```

-continued

```
tattggctat ctaaatcctc aaaagacctc ataactgtaa aatgggacca aaatagcgaa          600
tggactcaaa aatttcaaca gtgtcaccag accggctggt gtaaccccct taaaatagat          660
ttcacagaca aaggaaaatt atccaaggac tggataacgg gaaaaacctg gggattaaga          720
ttctatgtgt ctggacatcc aggcgtacag ttcaccattc gcttaaaaat caccaacatg          780
ccagctgtgg cagtaggtcc tgacctcgtc cttgtggaac aaggacctcc tagaacgtcc          840
ctcgctctcc cacctcctct tcccccaagg gaagcgccac cgccatctct ccccgactct          900
aactccacag ccctggcgac tagtgcacaa actcccacgg tgagaaaaac aattgttacc          960
ctaaacactc cgcctcccac cacaggcgac agacttttg atcttgtgca ggggggccttc        1020 ctaaccttaa atgctaccaa cccagggggcc actgagtctt gctggctttg tttggccatg        1080
ggcccccctt attatgaagc aatagcctca tcaggagagg tcgcctactc caccgacctt        1140
gaccggtgcc gctgggggac ccaaggaaag ctcaccctca ctgaggtctc aggacacggg        1200
ttgtgcatag aaaaggtgcc ctttacccat cagcatctct gcaatcagac cctatccatc        1260
aattcctccg gagaccatca gtatctgctc ccctccaacc atagctggtg ggcttgcagc        1320
actggcctca cccccttgcct ctccacctca gttttttaatc agactagaga tttctgtatc      1380
caggtccagc tgattcctcg catctattac tatcctgaag aagtttttgtt acaggcctat       1440 gacaattctc accccaggac taaaagagag gctgtctcac ttaccctagc tgtttttactg       1500 gggttgggaa tcacggcggg aataggtact ggttcaactg ccttaattaa aggacctata        1560
gacctccagc aaggcctgac aagcctccag atcgccatag atgctgacct ccgggccctc        1620
caagactcag tcagcaagtt agaggactca ctgacttccc tgtccgaggt agtgctccaa        1680
aataggagag gccttgactt gctgtttcta aaagaaggtg gcctctgtgc ggccctaaag        1740
gaagagtgct gtttttacat agaccactca ggtgcagtac gggactccat gaaaaaaactc       1800 aaagaaaaac tggataaaag acagttagag cgccagaaaa gccaaaactg gtatgaagga        1860
tggttcaata actcccccttg gttcactacc ctgctatcaa ccatcgctgg gccctatta       1920 ctcctccttc tgttgctcat cctcgggcca tgcatcatca ataagttagt tcaattcatc       1980
aatgatagga taagtgcagt taaaattttaa                                        2010
```

```
<210> SEQ ID NO 8
<211> LENGTH: 2013
<212> TYPE: DNA
<213> ORGANISM: Gibbon leukemia virus

<400> SEQUENCE: 8
accatggtcc tgctgcctgg gtctatgctg ctgacttcta acctgcacca cctgcgacac           60
cagatgtctc ccggctcatg gaaacggctg atcatcctgc tgagctgcgt gttcggagga          120
ggaggcacct ccctgcagaa caagaatcct caccagccaa tgaccctgac atggcaggtg          180
ctgtcccaga caggcgacgt ggtgtgggat accaaggcag tgcagccacc ttggacatgg          240
tggcccaccc tgaagcctga cgtgtgcgcc ctggccgcct ccctggagtc ttgggacatc          300
cccggcacag acgtgagcag cagcaagagg gtgagaccac ccgactctga ttatacagcc          360
gcctacaagc agatcacctg gggcgccatc ggctgtagct atcctcgggc cgcacaagg           420 atggccagct ccacctttta cgtgtgccca cgcgacggaa ggaccctgtc tgaggcaagg          480
agatgtggcg gcctggagag cctgtattgc aaggagtggg attgtgagac cacaggcaca          540
ggctactggc tgtctaagtc tagcaaggac ctgatcaccg tgaagtggga tcagaacagc          600
gagtggacac agaagttcca gcagtgccac cagaccggct ggtgtaatcc cctgaagatc          660
```

-continued

```
gactttacag ataagggcaa gctgtccaag gactggatca ccggcaagac atggggcctg    720
agattctacg tgtctggcca ccctggcgtg cagtttacaa tccggctgaa gatcaccaac    780
atgccagcag tggcagtggg accagacctg gtgctggtgg agcagggacc tccacgcacc    840
tccctggccc tgcccctcc actgccccct agggaggccc caccccctag cctgcccgat    900
tctaacagca cagccctggc cacctccgcc cagacccta cagtgcgcaa gaccatcgtg    960
acactgaata ccccaccccc taccacaggc gacaggctgt cgatctggt gcagggcgcc    1020 tttctgacac tgaacgccac caatcctggc gcaaccgaga gctgctggct gtgcctggct    1080
atgggcccac cctactatga ggcaatcgcc tcctctggag aggtggcata ttccacagac    1140
ctggatagat gcagatgggg cacccagggc aagctgaccc tgacagaggt gtctggccac    1200
ggcctgtgca tcggcaaggt gccattcaca caccagcacc tgtgcaacca gaccctgagc    1260
atcaatagct ccggcgacca ccagtacctg ctgccaagca accactcctg gtgggcatgc    1320
tccacaggac tgaccccatg tctgagcacc agcgtgttca accagaccag agactttgt    1380 atccaggtgc agctgatccc tcggatctac tattacccag aggaggtgct gctgcaggcc    1440
tatgataatt cccacccaag aacaaagagg gaggccgtgt ctctgaccct ggccgtgctg    1500
ctgggactgg gaatcacagc aggaatcggc acaggcagca ccgccctgat caagggacca    1560
atcgacctgc agcagggact gacctccctg cagatcgcca tcgacgccga tctgagagcc    1620
ctgcaggaca gcgtgtccaa gctggaggat tctctgacct ctctgagcga ggtggtgctg    1680
cagaacagga ggggcctgga cctgctgttc ctgaaggagg gaggactgtg cgccgccctg    1740
aaggaggagt gctgttttta tatcgaccac tctggcgccg tgcgggatag catgaagaag    1800
ctgaaggaga agctggataa gcgccagctg gagaggcaga agagccagaa ttggtacgag    1860
ggctggttca caattcccc ctggtttacc acactgctgt ctaccatcgc aggacctctg    1920
ttattactgc tgctgctgct gatcctgggc ccatgtatca tcaacaagct ggtgcagttt    1980
atcaacgacc gaatctccgc agtgaaaatc taa    2013
```

```
<210> SEQ ID NO 9
<211> LENGTH: 669
<212> TYPE: PRT
<213> ORGANISM: Gibbon leukemia virus

<400> SEQUENCE: 9

Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Trp Thr Trp Trp
65                  70                  75                  80

Pro Thr Leu Lys Pro Asp Val Cys Ala Leu Ala Ala Ser Leu Glu Ser
            85                  90                  95

Trp Asp Ile Pro Gly Thr Asp Val Ser Ser Ser Lys Arg Val Arg Pro
            100                 105                 110

Pro Asp Ser Asp Tyr Thr Ala Ala Tyr Lys Gln Ile Thr Trp Gly Ala
        115                 120                 125
```

-continued

```
Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
                180                 185                 190

Val Lys Trp Asp Gln Asn Ser Glu Trp Thr Gln Lys Phe Gln Gln Cys
            195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
                260                 265                 270

Glu Gln Gly Pro Pro Arg Thr Ser Leu Ala Leu Pro Pro Pro Leu Pro
            275                 280                 285

Pro Arg Glu Ala Pro Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320

Leu Asn Thr Pro Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
                340                 345                 350

Ser Cys Trp Leu Cys Leu Ala Met Gly Pro Pro Tyr Tyr Glu Ala Ile
            355                 360                 365

Ala Ser Ser Gly Glu Val Ala Tyr Ser Thr Asp Leu Asp Arg Cys Arg
    370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln
                405                 410                 415

Thr Leu Ser Ile Asn Ser Ser Gly Asp His Gln Tyr Leu Leu Pro Ser
                420                 425                 430

Asn His Ser Trp Trp Ala Cys Ser Thr Gly Leu Thr Pro Cys Leu Ser
            435                 440                 445

Thr Ser Val Phe Asn Gln Thr Arg Asp Phe Cys Ile Gln Val Gln Leu
    450                 455                 460

Ile Pro Arg Ile Tyr Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
                500                 505                 510

Thr Ala Leu Ile Lys Gly Pro Ile Asp Leu Gln Gln Gly Leu Thr Ser
            515                 520                 525

Leu Gln Ile Ala Ile Asp Ala Asp Leu Arg Ala Leu Gln Asp Ser Val
    530                 535                 540

Ser Lys Leu Glu Asp Ser Leu Thr Ser Leu Ser Glu Val Val Leu Gln
```

-continued

```
545                 550                 555                 560
Asn Arg Arg Gly Leu Asp Leu Leu Phe Leu Lys Glu Gly Gly Leu Cys
                565                 570                 575
Ala Ala Leu Lys Glu Glu Cys Cys Phe Tyr Ile Asp His Ser Gly Ala
            580                 585                 590
Val Arg Asp Ser Met Lys Lys Leu Lys Glu Lys Leu Asp Lys Arg Gln
        595                 600                 605
Leu Glu Arg Gln Lys Ser Gln Asn Trp Tyr Glu Gly Trp Phe Asn Asn
    610                 615                 620
Ser Pro Trp Phe Thr Thr Leu Leu Ser Thr Ile Ala Gly Pro Leu Leu
625                 630                 635                 640
Leu Leu Leu Leu Leu Leu Ile Leu Gly Pro Cys Ile Ile Asn Lys Leu
                645                 650                 655
Val Gln Phe Ile Asn Asp Arg Ile Ser Ala Val Lys Ile
            660                 665
```

<210> SEQ ID NO 10
<211> LENGTH: 759
<212> TYPE: DNA
<213> ORGANISM: Artificial Sequence
<220> FEATURE:
<223> OTHER INFORMATION: Homo sapiens

<400> SEQUENCE: 10

```
atgatcgaga cctacaatca gacaagccca cggtccgccg caaccggact gcctatcagc      60
atgaagatct tcatgtacct gctgaccgtg tttctgatca cacagatgat cggctccgcc     120
ctgttcgccg tgtatctgca caggagactg gacaagatcg aggatgagcg caatctgcac     180
gaggacttcg tgtttatgaa gaccatccag cggtgcaaca caggcgagag gagcctgtct     240
ctgctgaatt gtgaggagat caagtcccag ttcgagggct ttgtgaagga tatcatgctg     300
aacaaggagg agacaaagaa ggacgaggat ccacagatcg cagcacacgt ggtgtccgag     360
gcaaactcta tgccgccag cgtgctgcag tgggccaaga agggctacta taccatgaag      420
tctaacctgg tgacactgga gaatggcaag cagctgaccg tgaagaggca gggcctgtac     480
tatatctatg cccaggtgac attctgctct aacagagagg caagctccca ggcacccttc     540
atcgtgggac tgtggctgaa gccctctagc ggcagcgaga ggatcctgct gaaggccgcc     600
aatacccact cctctagcca gctgtgcgag cagcagtcca tccacctggg aggcgtgttc     660
gagctgcagc ctggagccag cgtgttcgtg aacgtgacag acccatctca ggtgagccac     720
ggcaccggct tcacaagctt tggcctgctg aagctgtga                            759
```

<210> SEQ ID NO 11
<211> LENGTH: 252
<212> TYPE: PRT
<213> ORGANISM: Artificial Sequence
<220> FEATURE:
<223> OTHER INFORMATION: Homo sapiens

<400> SEQUENCE: 11

```
Met Ile Glu Thr Tyr Asn Gln Thr Ser Pro Arg Ser Ala Ala Thr Gly
1                   5                   10                  15
Leu Pro Ile Ser Met Lys Ile Phe Met Tyr Leu Leu Thr Val Phe Leu
                20                  25                  30
Ile Thr Gln Met Ile Gly Ser Ala Leu Phe Ala Val Tyr Leu His Arg
            35                  40                  45
Arg Leu Asp Lys Ile Glu Asp Glu Arg Asn Leu His Glu Asp Phe Val
```

-continued

```
          50                    55                    60

Phe Met Lys Thr Ile Gln Arg Cys Asn Thr Gly Glu Arg Ser Leu Ser
65                   70                    75                   80

Leu Leu Asn Cys Glu Glu Ile Lys Ser Gln Phe Glu Gly Phe Val Lys
                85                    90                    95

Asp Ile Met Leu Asn Lys Glu Glu Thr Lys Lys Asp Glu Asp Pro Gln
               100                   105                   110

Ile Ala Ala His Val Val Ser Glu Ala Asn Ser Asn Ala Ala Ser Val
           115                   120                   125

Leu Gln Trp Ala Lys Lys Gly Tyr Tyr Thr Met Lys Ser Asn Leu Val
           130                   135                   140

Thr Leu Glu Asn Gly Lys Gln Leu Thr Val Lys Arg Gln Gly Leu Tyr
145                   150                   155                   160

Tyr Ile Tyr Ala Gln Val Thr Phe Cys Ser Asn Arg Glu Ala Ser Ser
               165                   170                   175

Gln Ala Pro Phe Ile Val Gly Leu Trp Leu Lys Pro Ser Ser Gly Ser
               180                   185                   190

Glu Arg Ile Leu Leu Lys Ala Ala Asn Thr His Ser Ser Ser Gln Leu
           195                   200                   205

Cys Glu Gln Gln Ser Ile His Leu Gly Gly Val Phe Glu Leu Gln Pro
   210                   215                   220

Gly Ala Ser Val Phe Val Asn Val Thr Asp Pro Ser Gln Val Ser His
225                   230                   235                   240

Gly Thr Gly Phe Thr Ser Phe Gly Leu Leu Lys Leu
               245                   250
```

```
<210> SEQ ID NO 12
<211> LENGTH: 1416
<212> TYPE: DNA
<213> ORGANISM: Homo sapiens

<400> SEQUENCE: 12
atgctgccct ttctgagcat gctggtgctg ctggtgcagc ctctgggaaa cctgggagcc        60
gagatgaaga gcctgtccca gagatctgtg cctaacacct gcacactggt catgtgcagc       120
cccaccgaga atggactgcc tggaagggac ggaagggatg aagggagggg ccctcggggc       180
gagaagggcg acccaggact gcctggacca atgggactga gcggactgca gggaccaaca       240
ggacctgtgg gaccaaaggg agagaacgga tccgccggag agccaggccc taagggcgag       300
aggggcctgt ctggcccccc tggcctgcca ggcatcccag gccccgccgg caaggagggc       360
ccatccggca agcagggcaa tatcggcccc cagggcaagc ctggcccaaa gggcgaggca       420
ggaccaaagg gagaagtggg agcacctggc atgcagggat ccaccggagc aaagggatct       480
acaggaccaa agggcgagcg cggcgcccca ggcgtgcagg cgcccccgg caatgcagga       540 gcagcaggac cagcaggacc tgcaggccca cagggcgccc ctggctctag gggcccaccc       600
ggcctgaagg gcgacagggg agtgcctggc gatagggca tcaagggaga gagcggactg       660
ccagattccg ccgccctgag gcagcagatg gaggccctga agggcaagct gcagaggctg       720
gaggtggcct ctcccacta ccagaaggcc gccctgtttc agacggcca caggagactg       780 gacaagatcg aggatgagcg caacctgcac gaggatttcg tgtttatgaa gaccatccag       840
agatgcaaca caggcgagcg gtctctgagc ctgctgaatt gtgaggagat caagtctcag       900
ttcgagggct ttgtgaagga catcatgctg aacaaggagg agaccaagaa ggagaatagc       960
ttcgagatgc agaagggcga tcagaatccc cagatcgcag cacacgtgat cagcgaggca      1020
```

```
agctccaaga ccacatccgt gctgcagtgg gccgagaagg gctactatac catgtccaac    1080
aatctggtga cactggagaa cggcaagcag ctgaccgtga agagacaggg cctgtactat    1140
atctatgccc aggtgacatt ctgctctaat cgggaggcct ctagccaggc cccttttatc    1200
gcctctctgt gcctgaagag cccaggcaga ttcgagcgga tcctgctgag ggccgccaac    1260
acccactcct ctgccaagcc atgcggacag cagagcatcc acctgggagg cgtgttcgag    1320
ctgcagccag gagcctccgt gtttgtgaat gtgacagacc catcccaggt gtctcacgga    1380
accggcttca catcctttgg cctgctgaag ctgtga                              1416
```

```
<210> SEQ ID NO 13
<211> LENGTH: 471
<212> TYPE: PRT
<213> ORGANISM: Homo sapiens

<400> SEQUENCE: 13

Met Leu Pro Phe Leu Ser Met Leu Val Leu Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
            100                 105                 110

Pro Gly Pro Ala Gly Lys Glu Gly Pro Ser Gly Lys Gln Gly Asn Ile
            115                 120                 125

Gly Pro Gln Gly Lys Pro Gly Pro Lys Gly Glu Ala Gly Pro Lys Gly
        130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
            195                 200                 205

Pro Gly Asp Arg Gly Ile Lys Gly Glu Ser Gly Leu Pro Asp Ser Ala
    210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Ile Glu Asp Glu Arg Asn Leu His Glu Asp
            260                 265                 270

Phe Val Phe Met Lys Thr Ile Gln Arg Cys Asn Thr Gly Glu Arg Ser
        275                 280                 285

Leu Ser Leu Leu Asn Cys Glu Glu Ile Lys Ser Gln Phe Glu Gly Phe
    290                 295                 300
```

-continued

```
Val Lys Asp Ile Met Leu Asn Lys Glu Glu Thr Lys Lys Glu Asn Ser
305             310             315             320

Phe Glu Met Gln Lys Gly Asp Gln Asn Pro Gln Ile Ala Ala His Val
            325             330             335

Ile Ser Glu Ala Ser Ser Lys Thr Thr Ser Val Leu Gln Trp Ala Glu
            340             345             350

Lys Gly Tyr Tyr Thr Met Ser Asn Asn Leu Val Thr Leu Glu Asn Gly
        355             360             365

Lys Gln Leu Thr Val Lys Arg Gln Gly Leu Tyr Tyr Ile Tyr Ala Gln
    370             375             380

Val Thr Phe Cys Ser Asn Arg Glu Ala Ser Ser Gln Ala Pro Phe Ile
385             390             395             400

Ala Ser Leu Cys Leu Lys Ser Pro Gly Arg Phe Glu Arg Ile Leu Leu
            405             410             415

Arg Ala Ala Asn Thr His Ser Ser Ala Lys Pro Cys Gly Gln Gln Ser
            420             425             430

Ile His Leu Gly Gly Val Phe Glu Leu Gln Pro Gly Ala Ser Val Phe
        435             440             445

Val Asn Val Thr Asp Pro Ser Gln Val Ser His Gly Thr Gly Phe Thr
    450             455             460

Ser Phe Gly Leu Leu Lys Leu
465             470
```

```
<210> SEQ ID NO 14
<211> LENGTH: 1412
<212> TYPE: DNA
<213> ORGANISM: Mus musculus

<400> SEQUENCE: 14
atgctgccct tcctgagcat gctggtgctg ctggtgcagc ctctgggcaa tctgggcgcc      60
gagatgaagt ccctgtctca gaggagcgtg ccaaacacct gcacactggt catgtgctct     120
ccaaccgaga atggactgcc aggaagggac ggaagagatg gaagggaggg accaagggga     180
gagaagggcg accctggact gcctggacca atgggactgt ccggactgca gggaccaaca     240
ggccctgtgg gaccaaaggg agagaatgga agcgccggag agccaggacc taagggagag     300
aggggcctgt ccggcccccc tggcctgcct ggcatcccag gccccgccgg caaggagggc     360
ccttctggca gcagggcaa catcggacca cagggcaagc ctggaccaaa gggagaggca     420
ggaccaaagg gagaagtggg agcacccggc atgcagggca gcaccggagc aaagggatcc     480
accggcccta agggagagag aggagcacct ggagtgcagg gcgcccag caatgcagga     540 gcagcaggac cagcaggacc tgcaggccca caggcgccc caggcagccg ggccccaccc     600
ggcctgaagg gcgacagggg agtgccaggc gatagggca tcaagggaga gtccggactg     660
ccagactctg ccgccctgag gcagcagatg gaggccctga gggcaagct gcagaggctg     720 gaggtggcct ctcccacta ccagaaggcc gccctgtttc agacggaca caggagactg     780 gataaggtgg aggaggaggt gaacctgcac gaggatttcg tgttcatcaa gaagctgaag     840
aggtgcaaca gggcgaggg cagcctgtcc ctgctgaatt gtgaggagat gcggcgccag     900
ttcgaggacc tggtgaagga tatcaccctg aacaaggagg agaagaagga gaattctttt     960
gagatgcaga gggcgacga ggatcctcag atcgcagcac acgtggtgtc cgaggcaaac    1020
tctaatgccg ccagcgtgct gcagtgggcc aagaagggct actataccat gaagtctaac    1080
ctggtcatgc tggagaatgg caagcagctg acagtgaaga gagagggcct gtactacgtg    1140
```

-continued

```
tacacccagg tgacattctg cagcaacaga gagcccagct cccagcggcc ttttatcgtg      1200
ggcctgtggc tgaagccctc tatcggaagc gagaggatcc tgctgaaggc agccaatacc      1260
cactctagct cccagctgtg cgagcagcag tccgtgcacc tgggaggcgt gttcgagctg      1320
caggcaggag caagcgtgtt cgtgaacgga cagaggccag ccaggtcatc cacagagtgg      1380
gcttctctag ctttggcctg ctgaagctgt ga                                    1412
```

```
<210> SEQ ID NO 15
<211> LENGTH: 470
<212> TYPE: PRT
<213> ORGANISM: Mus musculus

<400> SEQUENCE: 15

Met Leu Pro Phe Leu Ser Met Leu Val Leu Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
            100                 105                 110

Pro Gly Pro Ala Gly Lys Glu Gly Pro Ser Gly Lys Gln Gly Asn Ile
            115                 120                 125

Gly Pro Gln Gly Lys Pro Gly Pro Lys Gly Glu Ala Gly Pro Lys Gly
        130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
            195                 200                 205

Pro Gly Asp Arg Gly Ile Lys Gly Glu Ser Gly Leu Pro Asp Ser Ala
        210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Val Glu Glu Glu Val Asn Leu His Glu Asp
            260                 265                 270

Phe Val Phe Ile Lys Lys Leu Lys Arg Cys Asn Lys Gly Glu Gly Ser
        275                 280                 285

Leu Ser Leu Leu Asn Cys Glu Glu Met Arg Arg Gln Phe Glu Asp Leu
    290                 295                 300

Val Lys Asp Ile Thr Leu Asn Lys Glu Glu Lys Lys Glu Asn Ser Phe
305                 310                 315                 320
```

-continued

```
Glu Met Gln Arg Gly Asp Glu Asp Pro Gln Ile Ala Ala His Val Val
            325             330             335

Ser Glu Ala Asn Ser Asn Ala Ala Ser Val Leu Gln Trp Ala Lys Lys
            340             345             350

Gly Tyr Tyr Thr Met Lys Ser Asn Leu Val Met Leu Glu Asn Gly Lys
            355             360             365

Gln Leu Thr Val Lys Arg Glu Gly Leu Tyr Tyr Val Tyr Thr Gln Val
        370             375             380

Thr Phe Cys Ser Asn Arg Glu Pro Ser Ser Gln Arg Pro Phe Ile Val
    385             390             395             400

Gly Leu Trp Leu Lys Pro Ser Ile Gly Ser Glu Arg Ile Leu Leu Lys
                405             410             415

Ala Ala Asn Thr His Ser Ser Ser Gln Leu Cys Glu Gln Gln Ser Val
            420             425             430

His Leu Gly Gly Val Phe Glu Leu Gln Ala Gly Ala Ser Val Phe Val
            435             440             445

Asn Val Thr Glu Ala Ser Gln Val Ile His Arg Val Gly Phe Ser Ser
        450             455             460

Phe Gly Leu Leu Lys Leu
465             470
```

```
<210> SEQ ID NO 16
<211> LENGTH: 786
<212> TYPE: DNA
<213> ORGANISM: Homo sapiens

<400> SEQUENCE: 16
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggttg gacaagatag aagatgaaag gaatcttcat     180
gaagattttg tattcatgaa aacgatacag agatgcaaca caggagaaag atccttatcc     240
ttactgaact gtgaggagat taaaagccag tttgaaggct ttgtgaagga tataatgtta     300
aacaaagagg agacgaagaa agaaaacagc tttgaaatgc aaaaaggtga tcagaatcct     360
caaattgcgg cacatgtcat aagtgaggcc agcagtaaaa caacatctgt gttacagtgg     420
gctgaaaaag gatactacac catgagcaac aacttggtaa ccctggaaaa tgggaaacag     480
ctgaccgtta aaagacaagg actctattat atctatgccc aagtcacctt ctgttccaat     540
cgggaagctt cgagtcaagc tccatttata gccagcctct gcctaaagtc ccccggtaga     600
ttcgagagaa tcttactcag agctgcaaat acccacagtt ccgccaaacc ttgcgggcaa     660
caatccattc acttgggagg agtatttgaa ttgcaaccag gtgcttcggt gtttgtcaat     720
gtgactgatc caagccaagt gagccatggc actggcttca cgtcctttgg cttactcaaa     780
ctctga                                                                 786
```

```
<210> SEQ ID NO 17
<211> LENGTH: 261
<212> TYPE: PRT
<213> ORGANISM: Homo sapiens

<400> SEQUENCE: 17

Met Ile Glu Thr Tyr Asn Gln Thr Ser Pro Arg Ser Ala Ala Thr Gly
1               5               10              15

Leu Pro Ile Ser Met Lys Ile Phe Met Tyr Leu Leu Thr Val Phe Leu
            20              25              30
```

```
Ile Thr Gln Met Ile Gly Ser Ala Leu Phe Ala Val Tyr Leu His Arg
         35                  40                  45

Arg Leu Asp Lys Ile Glu Asp Glu Arg Asn Leu His Glu Asp Phe Val
     50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
             115                 120                 125

Glu Ala Ser Ser Lys Thr Thr Ser Val Leu Gln Trp Ala Glu Lys Gly
     130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
             195                 200                 205

Ala Asn Thr His Ser Ser Ala Lys Pro Cys Gly Gln Gln Ser Ile His
     210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
             260

<210> SEQ ID NO 18
<211> LENGTH: 783
<212> TYPE: DNA
<213> ORGANISM: Mus musculus

<400> SEQUENCE: 18
atgatagaaa catacagcca accttccccc agatccgtgg caactggact tccagcgagc        60
atgaagattt ttatgtattt acttactgtt ttccttatca cccaaatgat tggatctgtg       120 cttttttgctg tgtatcttca tagaagattg gataaggtcg aagaggaagt aaaccttcat      180
gaagattttg tattcataaa aaagctaaag agatgcaaca aaggagaagg atctttatcc       240
ttgctgaact gtgaggagat gagaaggcaa tttgaagacc ttgtcaagga tataacgtta       300
aacaaagaag agaaaaaaga aaacagcttt gaaatgcaaa gaggtgatga ggatcctcaa       360
attgcagcac acgttgtaag cgaagccaac agtaatgcag catccgttct acagtgggcc       420
aagaaaggat attataccat gaaaagcaac ttggtaatgc ttgaaaatgg gaaacagctg       480
acggttaaaa gagaaggact ctattatgtc tacactcaag tcaccttctg ctctaatcgg       540
gagccttcga gtcaacgccc attcatcgtc ggcctctggc tgaagcccag cagtggatct       600
gagagaatct tactcaaggc ggcaaatacc cacagttcct cccagctttg cgagcagcag       660
tctgttcact gggcggagt gtttgaatta caagctggtg cttctgtgtt tgtcaacgtg        720
actgaagcaa gccaagtgat ccacagagtt ggcttctcat cttttggctt actcaaactc       780
```

-continued

```
tga                                                           783
```

```
<210> SEQ ID NO 19
<211> LENGTH: 260
<212> TYPE: PRT
<213> ORGANISM: Mus musculus

<400> SEQUENCE: 19

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
                20                  25                  30

Ile Thr Gln Met Ile Gly Ser Val Leu Phe Ala Val Tyr Leu His Arg
            35                  40                  45

Arg Leu Asp Lys Val Glu Glu Glu Val Asn Leu His Glu Asp Phe Val
        50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 20
<211> LENGTH: 930
<212> TYPE: DNA
<213> ORGANISM: Mus musculus

<400> SEQUENCE: 20
atggatcagc acacactgga cgtggaggat accgctgacg ctaggcaccc agctggcacc      60
tcctgccctt ctgatgccgc tctgctgcgc gacacaggac tgctggccga tgccgctctg     120
ctgtctgaca cagtgcggcc aaccaacgcc gctctgccaa ccgatgctgc ttaccctgct     180
gtgaacgtga gggacagaga ggctgcttgg ccacctgccc tgaacttctg cagccgccac     240
cctaagctgt acggcctggt ggccctggtg ctgctgctgc tgatcgctgc ttgcgtgcca     300
```

-continued

```
atctttaccc ggacagagcc acgccccgct ctgacaatca ccacatcccc caacctgggc          360
accagggaga acaacgccga tcaggtgaca ccagtgtctc acatcggctg ccccaacacc          420
acacagcagg gaagcccagt gttcgccaag ctgctggcta agaaccaggc cagcctgtgc          480
aacaccacac tgaactggca cagccaggac ggagctggaa gctcctacct gtcccagggc          540
ctgagatacg aggaggataa gaaggagctg gtggtggact ccctggact gtactacgtg           600 ttcctggagc tgaagctgtc tccaaccttt acaaacaccg gccacaaggt gcagggatgg          660
gtgtctctgg tgctgcaggc taagccccag gtggacgatt tcgataacct ggccctgacc          720
gtggagctgt ttccttgtag catggagaac aagctggtgg acaggtcttg gagccagctg          780
ctgctgctga aggctggcca caggctgtcc gtgggactga gagcctacct gcacggcgcc          840
caggatgctt acagagactg ggagctgagc taccctaaca ccacatcctt cggactgttt          900
ctggtgaagc ctgacaaccc atgggagtga                                           930

<210> SEQ ID NO 21
<211> LENGTH: 765
<212> TYPE: DNA
<213> ORGANISM: Homo sapiens

<400> SEQUENCE: 21
atggagtacg cctctgacgc cagcctggat ccagaggccc cttggccacc tgcaccaagg           60
gcccgcgcct gccgcgtgct gccctgggcc ctggtggccg gcctgttatt actgctgctg          120
ctggccgccg cctgcgccgt gttcctggca tgtccttggg ccgtgagcgg agccagagcc          180
tccccaggct ctgccgccag ccctcggctg agagagggac cagagctgtc cccagacgat          240
ccagcaggcc tgctggacct gaggcaggga atgtttgccc agctggtggc ccagaacgtg          300
ctgctgatcg acggccccct gtcctggtac tctgatcctg gcctggccgg cgtgtctctg          360
accggcggcc tgagctataa ggaggataca aaggagctgg tggtggccaa ggccggcgtg          420
tactacgtgt tcttccagct ggagctgagg agagtggtgg caggagaggg ctctggaagc          480
gtgtccctgg ccctgcacct gcagcccctg cggagcgccg caggagccgc cgccctggcc          540
ctgaccgtgg acctgccacc agccagctcc gaggcaagga attccgcctt cggctttcag          600
ggcagactgc tgcacctgtc tgccggacag aggctgggag tgcacctgca caccgaggcc          660
agggcccgcc acgcatggca gctgacccag ggagcaacag tgctgggcct gttccgcgtg          720
acacctgaga tcccagcagg cctgcctagc ccacggtccg agtga                          765

<210> SEQ ID NO 22
<211> LENGTH: 1389
<212> TYPE: DNA
<213> ORGANISM: Mus musculus

<400> SEQUENCE: 22
atgctgcctt tcctgtccat gctggtgctg ctggtgcagc cactgggcaa cctgggagcc           60
gagatgaagt ctctgagcca gcgcagcgtg cctaacacct gcacactggt catgtgctcc          120
cctacagaga acggcctgcc aggaaggac ggaagagatg aagggagggg accaaggga           180 gagaagggcg accccggact gcctggacca atggactga gcggcctgca gggaccaacc          240
ggccccgtgg gacctaaggg agagaacgga tccgctggag agccaggacc taagggagag          300
agaggactgt ctgaccacc tggactgcca ggaatcccag gaccagctgg caaggaggga          360
ccatccggca agcagggaaa catcggacca cagggaaagc ctggaccaaa gggagaggct          420
```

-continued

```
ggacctaagg gagaagtggg cgccccagga atgcagggct ctacaggagc taagggcagc      480
accggaccaa agggagagag gggagccccc ggagtgcagg gagcccctgg caacgctgga      540
gccgctggcc cagccggacc cgctggccct cagggagccc ccggctctag gggaccacca      600
ggcctgaagg gagacagagg cgtgcccgga gatcggggca tcaagggaga gagcggcctg      660
cctgactccg ccgctctgag acagcagatg gaggctctga agggcaagct gcagcggctg      720
gaggtggcct tctcccacta ccagaaggcc gctctgtttc ctgacggaag gacagagccc      780
aggcctgctc tgaccatcac cacatctcca aacctgggca caagagagaa caacgccgat      840 caggtgacce ccgtgtctca catcggatgc cctaacacca cacagcaggg cagccccgtg      900
tttgccaagc tgctggctaa gaaccaggcc agccgtgca acaccacact gaactggcac      960
tcccaggatg gcgccggaag ctcctacctg tctcagggcc tgcggtacga ggaggacaag     1020
aaggagctgg tggtggatag cccaggcctg tactacgtgt cctggagct gaagctgtcc      1080 cccaccttta caaacaccgg acacaaggtg cagggatggg tgagcctggt gctgcaggct     1140
aagccccagg tggacgattt cgacaacctg gccctgaccg tggagctgtt tccttgctct     1200
atggagaaca gctggtgga tagatcctgg agccagctgc tgctgctgaa ggctggacac     1260
cgcctgagcg tgggcctgag ggcttacctg cacggagctc aggacgctta cagggattgg     1320
gagctgtcct accctaacac cacatctttc ggcctgtttc tggtgaagcc agacaacccc     1380
tgggagtga                                                            1389
```

<210> SEQ ID NO 23
<211> LENGTH: 1389
<212> TYPE: DNA
<213> ORGANISM: Homo sapiens
<400> SEQUENCE: 23

```
atgctgctgt tcctgctgtc cgccctggtg ctgctgaccc agcctctggg ctacctggag       60
gccgagatga agacctattc tcaccggaca atgccaagcg cctgcacact ggtcatgtgc      120
agcagcgtgg agtctggcct gccaggaagg gacggaaggg atggaaggga gggacctaga      180
ggcgagaagg gcgaccctgg cctgccagga gcagcaggac aggcaggaat gcccggccag      240
gccggccccg tgggacctaa gggcgacaac ggaagcgtgg agagccagg accaaagggc      300 gataccggcc cttccggacc acctggacca ccaggcgtgc ctggcccagc cggcagggag      360
ggccctctgg gcaagcaggg caatatcggc ccacagggca gcccggccc taagggcgag      420 gccgccccca agggcgaagt gggcgcccct ggcatgcagg gaagcgccgg agcccgcggc      480
ctggccggac ctaagggcga gagaggcgtg cctggagaga ggggcgtgcc aggaaacaca      540
ggcgcagcag gatctgccgg agcaatggga ccccagggca gccctggcgc cagggggcct      600
ccaggcctga agggcgacaa gggcatccca ggcgataagg gagcaaaggg agagagcggc      660
ctgccagatg tggcctccct cgccagcag gtgggaggccc tgcagggcca ggtgcagcac      720
ctgcaggccg ccttctctca gtacaagaag gtggagctgt ttccaaacgg cgcctgcccc      780
tgggccgtga gcggagcccg ggcctcccca ggctctgccg ccagccctag gctgcgcgag      840
ggaccagagc tgagcccaga cgatccagca ggcctgctgg acctgagaca gggaatgttc      900
gcccagctgg tggcccagaa tgtgctgctg atcgacggcc cactgtcctg gtactctgat      960
ccaggcctga ccggcgtgtc cctgaccggc ggcctgtctt ataaggagga tacaaaggag     1020 ctggtggtg ccaaggccgg cgtgtactac gtgttcttcc agctggagct gaggagagtg     1080
gtggcaggag agggatccgg atctgtgagc ctggccctgc acctgcagcc cctgcggtcc     1140
```

```
gccgcaggag ccgccgccct ggccctgacc gtggacctgc cacctgcctc tagcgaggca    1200
cgcaattccg ccttcggctt tcagggccgg ctgctgcacc tgtctgccgg acagagactg    1260
ggagtgcacc tgcacaccga ggcccgggcc agacacgcct ggcagctgac ccagggagca    1320
acagtgctgg gcctgtttag ggtgacacct gagatcccag ccggcctgcc aagcccccgc    1380
tccgagtga                                                          1389

<210> SEQ ID NO 24
<211> LENGTH: 522
<212> TYPE: DNA
<213> ORGANISM: Mus musculus

<400> SEQUENCE: 24
atggaggaga tgcctctgag ggagagctcc ccacagaggg ccgagagatg caagaagagc      60
tggctgctgt gcatcgtggc tctgctgctg atgctgctgt gctctctggg caccctgatc     120
tacacaagcc tgaagccaac cgccatcgag tcctgtatgg tgaagttcga gctgtctagc     180
tccaagtggc acatgacatc ccccaagcct cactgcgtga acaccacatc tgacggaaag     240
ctgaagatcc tgcagagcgg cacctacctg atctacggac aggtcatccc cgtggacaag     300
aagtacatca aggataacgc ccctttcgtg gtgcagatct acaagaagaa cgacgtgctg     360
cagacactga tgaacgattt tcagatcctg cccatcggcg gagtgtacga gctgcacgct     420
ggcgacaaca tctacctgaa gttcaactcc aaggatcaca tccagaagac caacacatac     480
tggggaatca tcctgatgcc agatctgccc tttatctctt ga                        522

<210> SEQ ID NO 25
<211> LENGTH: 600
<212> TYPE: DNA
<213> ORGANISM: Homo sapiens

<400> SEQUENCE: 25
atgaccctgc acccaagccc catcacatgc gagttcctgt tttctaccgc cctgatcagc      60
ccaaagatgt gcctgagcca cctggagaat atgcccctgt cccactctcg gacacaggga     120
gcccagagaa gctcctggaa gctgtggctg ttctgctcta tcgtgatgct gctgttcctg     180
tgcagctttt cctggctgat cttcatcttt ctgcagctgg agacagccaa ggagccttgc     240
atggccaagt ttggccctct gccatccaag tggcagatgg cctctagcga gcccccttgc     300
gtgaacaagg tgagcgactg gaagctggag atcctgcaga acggcctgta cctgatctat     360
ggccaggtgg cccccaacgc caattacaac gacgtggccc ctttcgaggt gcggctgtat     420
aagaacaagg atatgatcca gaccctgaca aataagtcta agatccagaa cgtgggcggc     480
acatacgagc tgcacgtggg cgacaccatc gacctgatct tcaacagcga gcaccaggtg     540
ctgaagaaca atacatattg gggcatcatc ctgctggcca accccccagtt tatctcctga     600

<210> SEQ ID NO 26
<211> LENGTH: 1164
<212> TYPE: DNA
<213> ORGANISM: Mus musculus

<400> SEQUENCE: 26
atgctgcctt tcctgtctat gctggtgctg ctggtgcagc cactgggcaa cctgggagcc      60
gagatgaaga cctgtccca gagatccgtg cccaacacct gcacactggt catgtgctct     120
cctaccgaga acggcctgcc aggaagggac ggaagagatg gaagggaggg acctcgggga     180
```

-continued

---

```
gagaagggcg acccaggact gcctggacca atgggactga gcggcctgca gggaccaaca      240
ggccccgtgg gacctaaggg agagaacgga agcgccggag agccaggacc taagggagag      300
aggggactgt ccggaccacc tggactgcct ggaatcccag gaccagctgg caaggaggga      360
ccatccggca agcagggaaa catcggacca cagggaaagc ctggaccaaa gggagaggct      420
ggaccaaagg gagaagtggg cgctcctgga atgcagggct ccaccggagc caagggctct      480
acaggaccaa aaggagagag gggagctccc ggagtgcagg gagcccctgg caacgctgga      540
gccgctggcc cagccggacc cgctggccct cagggagccc caggcagcag gggaccaccc      600
ggcctgaagg gcgacagggg cgtgccagga gataggggca tcaagggaga gtctggcctg      660
ccagacagcg ccgctctgag acagcagatg gaggccctga agggcaagct gcagcggctg      720
gaggtggctt tctcccacta ccagaaggcc gctctgtttc agatggcag cctgaagccc       780 accgccatcg agtcctgcat ggtgaagttt gagctgagct cctctaagtg gcacatgaca      840
tctcccaagc ctcactgcgt gaacaccaca tctgacggca agctgaagat cctgcagagc      900
ggcacctacc tgatctacgg ccaggtcatc cccgtggaca agaagtacat caaggataac      960
gcccctttcg tggtgcagat ctacaagaag aacgacgtgc tgcagacact gatgaacgat     1020
tttcagatcc tgccaatcgg cggagtgtac gagctgcacg ctggcgacaa catctacctg     1080
aagttcaact ctaaggatca catccagaag accaacacat actggggcat catcctgatg     1140
ccagatctgc cctttatcag ctga                                            1164
```

```
<210> SEQ ID NO 27
<211> LENGTH: 1152
<212> TYPE: DNA
<213> ORGANISM: Homo sapiens

<400> SEQUENCE: 27
atgctgctgt tcctgctgtc tgccctggtg ctgctgaccc agccactggg ctacctggag       60
gccgagatga agacctattc ccaccgcaca atgccttctg cctgcacact ggtcatgtgc      120
agcagcgtgg agagcggcct gccaggaagg gacggaagag atggaaggga gggacccaga      180
ggcgagaagg gcgaccctgg cctgccagga gcagcaggac aggcaggaat gccaggccag      240
gccggccccg tgggccctaa gggcgacaat ggatccgtgg agagccagg accaaagggc       300 gataccggcc cttctggacc acctggacca ccaggcgtgc ctggaccagc aggaagagag      360
ggacctctgg gcaagcaggg aaacatcgga ccacagggca gccaggccc taagggcgag       420 gccgcccca agggcgaagt gggcgcccct ggcatgcagg gatccgccgg agccagggc        480 ctggccggac ctaagggcga gcgcggcgtg cctggagaga ggggcgtgcc aggaaataca      540
ggcgcagcag gatctgccgg agcaatggga ccacagggca gccccggcgc cagaggccct      600
ccaggcctga gggcgacaa gggaatccct ggcgataagg gagcaaaggg agagagcggc       660
ctgccagacg tggcctccct gaggcagcag gtggaggccc tgcagggaca ggtgcagcac      720
ctgcaggccg ccttcagcca gtacaagaag gtggagctgt ttccaaatgg cgagacagcc      780
aaggagccct gcatggccaa gttcggccca ctgcccagca gtggcagat ggcctctagc       840 gagcccctt gcgtgaacaa ggtgagcgat tggaagctgg atcctgca gaacggcctg         900 tacctgatct atggccaggt ggcccccaac gccaattaca cgacgtggc cccttttgag       960 gtgcggctgt ataagaacaa ggatatgatc cagaccctga caaataagtc taagatccag     1020
aacgtgggag gcacctacga gctgcacgtg ggcgacacaa tcgacctgat cttcaacagc     1080
gagcaccagg tgctgaagaa caatacatat tggggcatca tcctgctggc caaccccag      1140
```

-continued

```
tttatctcct ga                                                      1152

<210> SEQ ID NO 28
<211> LENGTH: 597
<212> TYPE: DNA
<213> ORGANISM: Mus musculus

<400> SEQUENCE: 28
atggagggcg agggagtgca gcccctggat gagaacctgg agaacggctc ccggcctcgc     60
ttcaagtgga agaagaccct gcggctggtg gtgtctggaa tcaagggcgc cggaatgctg    120
ctgtgcttta tctacgtgtg cctgcagctg agctcctctc ccgccaagga tcccctatc     180 cagaggctga gaggagctgt gaccaggtgc gaggacggac agctgttcat cagctcctac    240
aagaacgagt accagacaat ggaggtgcag aacaacagcg tggtcatcaa gtgtgatggc    300
ctgtacatca tctacctgaa gggatccttc tttcaggagg tgaagatcga cctgcacttt    360
cgggaggatc acaacccaat ctctatcccc atgctgaacg acggcaggag aatcgtgttc    420
acagtggtgg ccagcctggc tttttaaggac aaggtgtacc tgaccgtgaa cgccccagat    480
acactgtgcg agcacctgca gatcaacgac ggagagctga tcgtggtgca gctgaccccct    540 ggctactgtg ctccagaggg atcttaccac agcacagtga accaggtgcc cctgtga        597

<210> SEQ ID NO 29
<211> LENGTH: 552
<212> TYPE: DNA
<213> ORGANISM: Homo sapiens

<400> SEQUENCE: 29
atggagaggg tgcagcccct ggaggagaac gtgggaaatg ccgcccggcc tagattcgag     60
aggaacaagc tgctgctggt ggcctctgtg atccagggcc tgggcctgct gctgtgcttc    120
acctacatct gtctgcactt ttctgccctg caggtgagcc acagataccc ccgcatccag    180
agcatcaagg tgcagttcac cgagtataag aaggagaagg ctttatcct gacatcccag     240 aaggaggacg agatcatgaa ggtgcagaac aattctgtga tcatcaactg cgatggcttc    300
tacctgatct ccctgaaggg ctattttct caggaagtga atatcagcct gcactatcag    360
aaggacgagg agccactgtt tcagctgaag aaggtgcgga gcgtgaattc cctgatggtg    420
gccagcctga cctacaagga caaggtgtat ctgaacgtga ccacagataa tacatccctg    480
gacgatttcc acgtgaacgg cggcgagctg atcctgatcc accagaatcc cggcgagttt    540
tgcgtgctgt ga                                                        552

<210> SEQ ID NO 30
<211> LENGTH: 1215
<212> TYPE: DNA
<213> ORGANISM: Mus musculus

<400> SEQUENCE: 30
atgctgccct cctgtccat gctggtgctg ctggtgcagc ctctgggcaa cctgggagcc     60
gagatgaagt ctctgagcca gagatccgtg ccaaacacct gcacactggt catgtgctct    120
cccaccgaga acggcctgcc tggaagggac ggaagagatg gaaggagggg accccggggga    180 gagaagggcg atcctggact gccaggacct atgggactga gcggcctgca gggaccaaca    240
ggccccgtgg gacctaaggg agagaacgga agcgccggag agccaggacc aaagggagag    300
aggggactgt ccggcccacc tggactgcct ggaatccctg gaccagctgg caaggaggga    360
```

```
ccttccggca agcagggaaa catcggacca cagggaaagc caggacctaa gggagaggct    420
ggaccaaagg gagaagtggg cgctcccgga atgcagggct ctaccggagc caagggcagc    480
acaggaccta agggagagag gggagctcca ggagtgcagg gagcccccgg caacgctgga    540
gctgctggac cagctggacc agctggccct cagggagccc caggctctag gggaccacca    600
ggcctgaagg gcgacagggg cgtgccagga gatagggca tcaagggaga gagcggcctg     660
ccagattccg ccgctctgag acagcagatg gaggccctga agggcaagct gcagcggctg     720
gaggtggctt tcagccacta ccagaaggcc gctctgtttc ctgacggcag ctcctctcca     780
gccaaggatc ctccaatcca gcggctgcgc ggagctgtga ccaggtgcga ggatggccag     840
ctgttcatca gctcctacaa gaacgagtac cagacaatgg aggtgcagaa caactctgtg     900
gtcatcaagt gtgacggcct gtacatcatc tacctgaagg gcagcttctt tcaggaggtg     960
aagatcgacc tgcactttag agaggatcac aacccaatct ccatccccat gctgaacgac    1020
ggcaggagaa tcgtgttcac cgtggtggcc tctctggctt ttaaggacaa ggtgtacctg    1080
accgtgaacg cccccgatac actgtgcgag cacctgcaga tcaacgacgg cgagctgatc    1140
gtggtgcagc tgacccctgg atactgtgct ccagagggct cctaccactc tacagtgaac    1200
caggtgcctc tgtga                                                      1215

<210> SEQ ID NO 31
<211> LENGTH: 1170
<212> TYPE: DNA
<213> ORGANISM: Homo sapiens

<400> SEQUENCE: 31
atgctgctgt tcctgctgag cgccctggtg ctgctgaccc agccactggg ctacctggag     60
gccgagatga gacctattc ccacagaaca atgccttctg cctgcacact ggtcatgtgc     120
agcagcgtgg agtccggcct gccaggaagg gacggcagag atggcaggga gggcccccagg    180 ggcgagaagg gcgaccccgg cctgcctgga gcagcaggcc aggccggcat gccaggccag     240
gccggcccag tgggccccaa gggcgacaac ggcagcgtgg gcgagcccgg ccctaagggc     300
gataccggcc cctccggccc ccctggccca cccggcgtgc aggaccagc aggaagggag      360 ggaccactgg gcaagcaggg caatatcgga cctcagggca gcctggacc aaagggagag      420 gcaggaccaa agggagaagt gggcgcccct ggcatgcagg gatctgccgg agcccggggc     480
ctggccggcc ccaagggcga gagaggcgtg cccggcgaga ggggcgtgcc tggcaacaca     540
ggcgccgccg gctccgccgg cgccatggga cctcagggct ctccaggagc cagaggccct     600
ccaggcctga agggcgacaa gggaatccct ggcgataagg gagcaaaggg agagagcggc     660
ctgccagacg tggcctccct gcggcagcag gtggaggccc tgcagggcca ggtgcagcac     720
ctgcaggccg ccttcagcca gtacaagaag gtggagctgt ttcctaatgg cgtgtctcac     780
cgctacccac ggatccagag catcaaggtg cagttcaccg agtataagaa ggagaagggc     840
tttatcctga catctcagaa ggaggacgag atcatgaagg tgcagaacaa tagcgtgatc     900
atcaactgcg atggcttcta cctgatcagc ctgaagggct attttttccca ggaagtgaat     960 atctctctgc actatcagaa ggatgaggag cctctgtttc agctgaagaa ggtgagatct    1020
gtgaacagcc tgatggtggc ctccctgacc tacaaggaca aggtgtatct gaacgtgacc    1080
acagataata catctctgga cgatttccac gtgaacggcg cgagctgat cctgatccac     1140 cagaatcccg gcgagttttg cgtgctgtga                                      1170
```

-continued

```
<210> SEQ ID NO 32
<211> LENGTH: 969
<212> TYPE: DNA
<213> ORGANISM: Mus musculus

<400> SEQUENCE: 32
atgcagctga agtgtccatg cttcgtgtcc ctgggaacaa gacagcccgt ctggaagaaa      60
ctgcacgtga gctccggctt ctttagcggc ctggggctgt ttctgctgct gctgtctagt     120
ctgtgcgccg cttccgcaga gactgaagtc ggagccatgg tgggcagtaa cgtggtcctg     180
tcatgcatcg acccacaccg acggcatttc aacctgtctg gcctgtacgt gtattggcag     240
attgagaatc ccgaagtgtc agtcacctac tatctgcctt acaagagccc agggatcaac     300
gtggactcaa gctataaaaa taggggggcac ctgtccctgg attctatgaa gcagggaaac     360
ttcagcctgt acctgaaaaa tgtgacccct caggacacac aggagttcac ttgtcgcgtc     420
tttatgaaca ctgcaaccga actggtgaag attctggagg aagtggtccg gctgagagtc     480
gcagccaact ttagcactcc tgtgatctct accagtgatt cctctaatcc aggccaggag     540
cggacatata cttgcatgtc taagaacgga tacccccgaac ctaatctgta ttggatcaac     600
accacagaca atagtctgat tgataccgct ctgcagaaca atacagtcta cctgaacaag     660
ctggggctgt atgacgtgat ctctactctg cggctgccat ggaccagtag aggagatgtg     720
ctgtgctgcg tggagaacgt ggccctgcac cagaatatca cctcaattag ccaggctgag     780
tcctttaccg gcaacaatac aaagaatcct caggagacac ataacaatga actgaaagtg     840
ctggtgccag tgctggccgt cctggctgca gcagctttcg tgtctttat catctacaga     900 aggacccgcc ctcaccgctc atacactgga cctaagaccg tgcagctgga actgacagac     960
catgcttga                                                           969

<210> SEQ ID NO 33
<211> LENGTH: 909
<212> TYPE: DNA
<213> ORGANISM: Homo sapiens

<400> SEQUENCE: 33
atgcgtctgg gttcacctgg tctgctgttt ctgctgtttt caagtctgcg tgctgatact      60
caggagaagg aagtccgggc tatggtcgga agtgacgtgg agctgtcatg cgcttgtccc     120
gaagggtccc ggttcgacct gaacgatgtc tacgtgtatt ggcagacctc tgagagtaag     180
accgtggtca cataccacat ccctcagaac tccagcctgg aaaatgtgga ttcaaggtat     240
cggaacagag ccctgatgtc ccctgctggc atgctgcggg gagacttctc tctgagactg     300
tttaatgtga caccacagga tgagcagaaa ttccattgcc tggtcctgtc acagtccctg     360
ggatttcagg aggtgctgag tgtcgaagtg actctgcacg tcgccgctaa tttctccgtg     420
cctgtggtca gcgcaccaca tagcccctct caggacgagc tgacctttac atgtacttcc     480
atcaacggct accccgccc taacgtgtac tggattaaca agactgacaa tagcctgctg     540
gatcaggcac tgcagaacga caccgtgttt ctgaatatgc gaggactgta cgatgtggtc     600
agcgtcctgc gtattgccag gacccccatct gtgaacatcg ggtgctgtat tgagaacgtc     660
ctgctgcagc agaatctgac agtggggagc cagactggta atgacatcgg cgagagggat     720
aagattaccg aaaaccccgt gagtacaggc gagaagaacg cagccacatg gtcaatcctg     780
gctgtgctgt gcctgctggt ggtcgtggct gtcgcaattg ctgggtgtg ccgcgatcgg     840 tgtctgcagc actcttatgc cggtgcttgg gcagtgagtc cagagactga actgaccggc     900
```

```
catgtctaa                                                                909

<210> SEQ ID NO 34
<211> LENGTH: 1574
<212> TYPE: DNA
<213> ORGANISM: Mus musculus

<400> SEQUENCE: 34
cttaagatgg aaactgatac tctgctgctc tgggtgctgc tcctctgggt gcctggttca       60
actggggaca ttcgacgggc tgacattgtg atgacccaga ccacactgag cctgcccgtg      120
tccctgggcg accaggccag catctcctgc cggagctccc agtctatcgt gcacagcaac      180
ggaaacacat acctggagtg gtatctgcag aagcctggcc agtccccaaa gctgctgatc      240
tacaaggtgt ccaacaggtt cagcggcgtg cctgaccgct tttctggaag cggctccgga      300
acagatttca ccctgaagat cagcagggtg gaggctgagg acctgggcgt gtactactgc      360
ttccagggat cccacgtgcc ttacaccttt ggcggaggca caaagctgga gatcaagaga      420
gccgatgctg ctccaaccgt gtctggaagc ggaggcgggg gttctggagg cggtgggagc      480
ggtggcggag ggtctgaggc taagctgcag gagagcggcc ccgtgctggt gaagcctgga      540
gccagcgtga agatgtcctg taaggcttct ggatacacct tcacagacta ctacatgaac      600
tgggtgaagc agagccacgg caagtccctg gagtggatcg gagtgatcaa cccttacaac      660
ggcgacacct cttacaacca gaagtttaag ggcaaggcca ccctgacagt ggataagtct      720
agctccaccg cttacatgga gctgaacagc ctgacatccg aggattctgc cgtgtactac      780
tgtgctaggt actacggaag ctggttcgcc tactgggggcc agggaacact gatcaccgtg      840
tccacagcca agaccacacc ccctagcgtg taccccctgg ctcctaggtc tagcagaggc      900
tgcaagccat gcatctgtac cgtgcccgag gtgagcagcc tgttcatctt ccacccaag       960 cccaaggacg tgctgaccat cacactgacc cctaaggtga catgcgtggt ggtggatatc     1020
agcaaggacg atcccgaggt gcagttctcc tggtttgtgg acgatgtgga ggtgcacacc     1080
gcccagacac agccaaggga ggagcagttc aactccacct ttagatccgt gtctgagctg     1140
cccatcatgc accaggactg gctgaacgga aaggagttca gtgccgggt gaactccgcc      1200 gcttttcctg ctccaatcga gaagaccatc tctaagacaa agggccgccc aaaggctcca     1260
caggtgtaca ccatccctcc acccaaggag cagatggcta aggataaggt gagcctgacc     1320
tgtatgatca cagacttctt tcccgaggat atcacagtgg agtggcagtg gaacggacag     1380
cctgccgaga actacaagaa cacccagcca atcatggaca cagatggctc ttacttcgtg     1440
tacagcaagc tgaacgtgca gaagtctaac tgggaggctg caacacctt cacctgcagc      1500 gtgctgcacg aaggtctcca taatcaccac accgaaaaga gcctcagtca cagccctggg     1560
aaatgaggcg cgcc                                                       1574

<210> SEQ ID NO 35
<211> LENGTH: 1484
<212> TYPE: DNA
<213> ORGANISM: Homo sapiens

<400> SEQUENCE: 35
cttaagatgg aaactgacac cctgctgctg tgggtcctgc tgctgtgggt gcctggatcc       60
accggcgata tcgtgctgac ccagtctcct ggcacactga gtctgtcacc aggggagcga      120
gcaacactgt cttgtagagc cagccagtct gtgggaagct cctacctggc ttggtatcag      180
cagaagccag gccaggcacc caggctgctg atctacggag ccttcagccg ggccactggc      240
```

```
attccagaca ggttctctgg aagtggctca gggaccgact tcaccctgac catcagccga       300
ctggagcccg aagacttcgc cgtgtactat tgccagcagt acggctctag tccttggact       360
tttggacagg gcaccaaagt ggagatcaag cgcggcgggg gaggctctgg gggaggcggg       420
agtggaggcg ggggatcaca ggtccagctg gtggaaagcg cgggggagt ggtccagcca        480 ggccggagcc tgcggctgag ctgcgccgct tcaggattca cattttcaag ctataccatg       540
cactgggtcc ggcaggcacc agggaaggga ctggagtggg tgaccttcat cagctatgac       600
ggcaacaaca gtattacgc tgattccgtg aaagggaggt ttaccattag ccgcgacaac        660
tccaaaaata cactgtacct gcagatgaac agcctgcggg ccgaggatac tgctatctac       720
tattgcgcaa gaaccgggtg gctgggaccc ttcgactatt ggggccaggg gactctggtc       780
accgtgtcct ctgataagac acacacatgc cctccctgtc ctgcaccaga gctgctgggc       840
gggccatccg tgttcctgtt tccacccaag cctaaagaca ccctgatgat cagccggaca       900
cctgaagtca cttgcgtggt cgtggacgtg agtcacgagg atccagaagt caagtttaac       960
tggtacgtgg atggcgtcga ggtgcataat gccaagacca aacctcgcga ggaacagtac      1020
aatagcacat atcgagtcgt gtccgtcctg actgtgctgc atcaggattg gctgaacggc      1080
aaagagtata agtgcaaagt gagcaataag gcactgcctg ccccaatcga gaaaacaatt      1140
tccaaggcta aaggccagcc cagggaacct caggtgtaca ctctgcctcc aagtcgcgag      1200
gaaatgacca agaaccaggt gagcctgacc tgtctggtga aagggttcta tccatcagac      1260
attgcagtgg agtgggaaag caatggacag cccgaaaaca attacaagac cacaccccct      1320
gtgctggaca gcgatggctc cttctttctg tattctaagc tgactgtgga taaaagtcgc      1380
tggcagcagg ggaacgtctt tagctgttcc gtgatgcatg aggctctgca caatcattac      1440
acacagaagt ctctgagtct gtcacccggc aaatgaggcg cgcc                        1484
```

```
<210> SEQ ID NO 36
<211> LENGTH: 632
<212> TYPE: DNA
<213> ORGANISM: Artificial Sequence
<220> FEATURE:
<223> OTHER INFORMATION: CMV promoter

<400> SEQUENCE: 36
gttgacattg attattgact agttattaat agtaatcaat tacggggtca ttagttcata        60
gcccatatat ggagttccgc gttacataac ttacggtaaa tggcccgcct ggctgaccgc       120
ccaacgaccc ccgcccattg acgtcaataa tgacgtatgt tcccatagta acgccaatag       180
ggactttcca ttgacgtcaa tgggtggagt atttacggta aactgcccac ttggcagtac       240
atcaagtgta tcatatgcca agtacgcccc ctattgacgt caatgacggt aaatggcccg       300
cctggcatta tgcccagtac atgaccttat gggactttcc tacttggcag tacatctacg       360
tattagtcat cgctattacc atggtgatgc ggttttggca gtacatcaat gggcgtggat       420
agcggtttga ctcacgggga tttccaagtc tccaccccat tgacgtcaat gggagtttgt       480
tttggcacca aaatcaacgg gactttccaa aatgtcgtaa caactccgcc ccattgacgc       540
aaatgggcgg taggcgtgta cggtgggagg tctatataag cagagctctc tggctaacta       600
gagaacccac tgcttactgg cttatcgaaa tt                                      632
```

```
<210> SEQ ID NO 37
<211> LENGTH: 394
<212> TYPE: DNA
```

-continued

```
<213> ORGANISM: Artificial Sequence
<220> FEATURE:
<223> OTHER INFORMATION: RSV promoter

<400> SEQUENCE: 37
tgtacgggcc agatatacgc gtatctgagg ggactagggt gtgtttaggc gaaaagcggg      60
gcttcggttg tacgcggtta ggagtcccct caggatatag tagtttcgct tttgcatagg     120
gagggggaaa tgtagtctta tgcaatacac ttgtagtctt gcaacatggt aacgatgagt     180
tagcaacatg ccttacaagg agagaaaaag caccgtgcat gccgattggt ggaagtaagg     240
tggtacgatc gtgccttatt aggaaggcaa cagacaggtc tgacatggat tggacgaacc     300
actgaattcc gcattgcaga gataattgta tttaagtgcc tagctcgata caataaacgc     360
catttgacca ttcaccacat tggtgtgcac ctcc                                 394

<210> SEQ ID NO 38
<211> LENGTH: 188
<212> TYPE: DNA
<213> ORGANISM: Artificial Sequence
<220> FEATURE:
<223> OTHER INFORMATION: BGH polyA

<400> SEQUENCE: 38
ctgtgccttc tagttgccag ccatctgttg tttgcccctc ccccgtgcct tccttgaccc      60
tggaaggtgc cactcccact gtcctttcct aataaaatga ggaaattgca tcgcattgtc     120
tgagtaggtg tcattctatt ctggggggtg gggtggggca ggacagcaag ggggaggatt     180
gggaagac                                                              188

<210> SEQ ID NO 39
<211> LENGTH: 249
<212> TYPE: DNA
<213> ORGANISM: Artificial Sequence
<220> FEATURE:
<223> OTHER INFORMATION: SV40 late polyA

<400> SEQUENCE: 39
gacatgataa gatacattga tgagtttgga caaaccacaa ctagaatgca gtgaaaaaaa      60
tgctttattt gtgaaatttg tgatgctatt gctttatttg tgaaatttgt gatgctattg     120
ctttatttgt aaccattata agctgcaata aacaagttaa caacaacaat tgcattcatt     180
ttatgtttca ggttcagggg gaggtgtggg aggttttttta aagcaagtaa aacctctaca     240
aatgtggta                                                             249

<210> SEQ ID NO 40
<211> LENGTH: 345
<212> TYPE: DNA
<213> ORGANISM: Artificial Sequence
<220> FEATURE:
<223> OTHER INFORMATION: SV40 enhancer promoter

<400> SEQUENCE: 40
gctgtggaat gtgtgtcagt tagggtgtgg aaagtccca ggctccccag caggcagaag       60
tatgcaaagc atgcatctca attagtcagc aaccaggtgt ggaaagtccc caggctcccc     120
agcaggcaga agtatgcaaa gcatgcatct caattagtca gcaaccatag tcccgcccct     180
aactccgccc atcccgcccc taactccgcc cagttccgcc cattctccgc cccatggctg     240
actaattttt tttatttatg cagaggccga ggccgcctcg gcctctgagc tattccagaa     300
gtagtgagga ggcttttttg gaggcctagg cttttgcaaa aagct                     345
```

-continued

```
<210> SEQ ID NO 41
<211> LENGTH: 99
<212> TYPE: DNA
<213> ORGANISM: Artificial Sequence
<220> FEATURE:
<223> OTHER INFORMATION: Rabbit beta-globin polyA

<400> SEQUENCE: 41
gacctctggc taataaagga aatttatttt cattgcaata gtgtgttgga attttttgtg       60
tctctcactc ggaaggacat atgggagggc aaatcattt                             99

<210> SEQ ID NO 42
<211> LENGTH: 723
<212> TYPE: DNA
<213> ORGANISM: Artificial Sequence
<220> FEATURE:
<223> OTHER INFORMATION: GFP

<400> SEQUENCE: 42
accatggtga gcaagggcga ggagctgttc accggggtgg tgcccatcct ggtcgagctg       60
gacggcgacg taaacggcca caagttcagc gtgtccggcg agggcgaggg cgatgccacc      120
tacggcaagc tgaccctgaa gttcatctgc accaccggca agctgcccgt gccctggccc      180
accctcgtga ccaccctgac ctacggcgtg cagtgcttca gccgctaccc cgaccacatg      240
aagcagcacg acttcttcaa gtccgccatg cccgaaggct acgtccagga gcgcaccatc      300
ttcttcaagg acgacggcaa ctacaagacc cgcgccgagg tgaagttcga gggcgacacc      360
ctggtgaacc gcatcgagct gaagggcatc gacttcaagg aggacggcaa catcctgggg      420
cacaagctgg agtacaacta caacagccac aacgtctata tcatggccga caagcagaag      480
aacggcatca aggtgaactt caagatccgc cacaacatcg aggacggcag cgtgcagctc      540
gccgaccact accagcagaa cacccccatc ggcgacggcc ccgtgctgct gcccgacaac      600
cactacctga gcacccagtc cgccctgagc aaagacccca acgagaagcg cgatcacatg      660
gtcctgctgg agttcgtgac cgccgccggg atcactctcg gcatggacga gctgtacaag      720
taa                                                                  723

<210> SEQ ID NO 43
<211> LENGTH: 454
<212> TYPE: DNA
<213> ORGANISM: Artificial Sequence
<220> FEATURE:
<223> OTHER INFORMATION: MoMuLV LTR

<400> SEQUENCE: 43
ttaattaagt aacgccattt tgcaaggcat ggaaaaatac ataactgaga atagagaagt       60
tcagatcaag gtcaggaaca gatggaacag ctgaatatgg gccaaacagg atatctgtgg      120
taagcagttc ctgccccggc tcagggccaa gaacagatgg aacagctgaa tatgggccaa      180
acaggatatc tgtggtaagc agttcctgcc ccggctcagg gccaagaaca gatggtcccc      240
agatgcggtc cagccctcag cagtttctag agaaccatca gatgtttcca gggtgcccca      300
aggacctgaa atgaccctgt gccttatttg aactaaccaa tcagttcgct tctcgcttct      360
gttcgcgcgc ttctgctccc cgagctcaat aaaagagccc acaacccctc actcggggcg      420
ccagtcctcc gattgactga gtcgcccgct taag                                454

<210> SEQ ID NO 44
```

```
<211> LENGTH: 1349
<212> TYPE: DNA
<213> ORGANISM: Artificial Sequence
<220> FEATURE:
<223> OTHER INFORMATION: EF1alpha promoter

<400> SEQUENCE: 44
ttaattaaga gtaattcata caaaaggact cgccctgcc ttggggaatc ccagggaccg        60
tcgttaaact cccactaacg tagaacccag agatcgctgc gttcccgccc cctcacccgc       120
ccgctctcgt catcactgag gtggagaaga gcatgcgtga ggctccggtg cccgtcagtg       180
ggcagagcgc acatcgccca cagtccccga gaagttgggg ggaggggtcg gcaattgaac       240
cggtgcctag agaaggtggc gcggggtaaa ctgggaaagt gatgtcgtgt actggctccg       300
cctttttccc gagggtgggg gagaaccgta tataagtgca gtagtcgccg tgaacgttct       360
ttttcgcaac gggtttgccg ccagaacaca ggtaagtgcc gtgtgtggtt cccgcgggcc       420
tggcctcttt acgggttatg gcccttgcgt gccttgaatt acttccacgc ccctggctgc       480
agtacgtgat tcttgatccc gagcttcggg ttggaagtgg gtgggagagt tcgaggcctt       540
gcggttaagg agcccttcg cctcgtgctt gagttgaggc ctggcttggg cgctggggcc       600
gccgcgtgcg aatctggtgg caccttcgcg cctgtctcgc tgctttcgat aagtctctag       660
ccatttaaaa tttttgatga cctgctgcga cgctttttt ctggcaagat agtcttgtaa       720
atgcgggcca agatctgcac actggtattt cggtttttgg ggccgcgggc ggcgacgggg       780
cccgtgcgtc ccagcgcaca tgttcggcga ggcggggcct gcgagcgcgg ccaccgagaa       840
tcggacgggg gtagtctcaa gctggccggc ctgctctggt gcctggcctc gcgccgccgt       900
gtatcgcccc gccctgggcg gcaaggctgg cccggtcggc accagttgcg tgagcggaaa       960
gatggccgct tccccggccct gctgcaggga gctcaaaatg gaggacgcgg cgctcggagag      1020 agcgggcggg tgagtcaccc acacaaagga aaagggcctt tccgtcctca gccgtcgctt       1080
catgtgactc cacggagtac cgggcgccgt ccaggcacct cgattagttc tcgagctttt       1140
ggagtacgtc gtctttaggt tgggggagg ggttttatgc gatggagttt ccccacactg       1200
agtgggtgga gactgaagtt aggccagctt ggcacttgat gtaattctcc ttggaatttg       1260 cccttttttga gtttggatct tggttcattc tcaagcctca gacagtggtt caaagttttt       1320
ttcttccatt tcaggtgtcg tgacttaag                                        1349

<210> SEQ ID NO 45
<211> LENGTH: 481
<212> TYPE: DNA
<213> ORGANISM: Artificial Sequence
<220> FEATURE:
<223> OTHER INFORMATION: HGH polyA

<400> SEQUENCE: 45
gacgggtggc atcctgtga cccctcccca gtgcctctcc tggccctgga agttgccact        60
ccagtgccca ccagccttgt cctaataaaa ttaagttgca tcattttgtc tgactaggtg       120
tccttctata atattatggg gtggaggggg gtggtatgga gcaagggca agttgggaag        180 acaacctgta gggcctgcgg ggtctattgg gaaccaagct ggagtgcagt ggcacaatct       240
tggctcactg caatctccgc ctcctgggtt caagcgattc tcctgcctca gcctcccgag       300
ttgttgggat tccaggcatg catgaccagg ctcagctaat ttttgttttt ttggtagaga       360
cggggtttca ccatattggc caggctggtc tccaactcct aatctcaggt gatctaccca       420
ccttggcctc ccaaattgct gggattacag gcgtgaacca ctgctcccctt ccctgtcctt       480
``` t                                                                481

<210> SEQ ID NO 46
<211> LENGTH: 108
<212> TYPE: PRT
<213> ORGANISM: Homo sapiens

<400> SEQUENCE: 46

Ile Val Leu Thr Gln Ser Pro Gly Thr Leu Ser Leu Ser Pro Gly Glu
1               5                   10                  15

Arg Ala Thr Leu Ser Cys Arg Ala Ser Gln Ser Val Gly Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Phe Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg
            100                 105

<210> SEQ ID NO 47
<211> LENGTH: 215
<212> TYPE: PRT
<213> ORGANISM: Homo sapiens

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

-continued

```
Ser Phe Asn Arg Gly Glu Cys
    210                 215

<210> SEQ ID NO 48
<211> LENGTH: 118
<212> TYPE: PRT
<213> ORGANISM: Homo sapiens

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 49
<211> LENGTH: 103
<212> TYPE: PRT
<213> ORGANISM: Homo sapiens

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 50
<211> LENGTH: 227
<212> TYPE: PRT
<213> ORGANISM: Homo sapiens

<400> SEQUENCE: 50

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
```

-continued

```
             35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
    210                 215                 220
Pro Gly Lys
225

<210> SEQ ID NO 51
<211> LENGTH: 448
<212> TYPE: PRT
<213> ORGANISM: Homo sapiens

<400> SEQUENCE: 51

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
                20                  25                  30
Thr Met His Trp Val Arg Gln Ala Pro Gly Lys Gly Leu Glu Trp Val
            35                  40                  45
Thr Phe Ile Ser Tyr Asp Gly Asn Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Thr Gly Trp Leu Gly Pro Phe Asp Tyr Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 52
<211> LENGTH: 21
<212> TYPE: PRT
<213> ORGANISM: Mus musculus

<400> SEQUENCE: 52

Met Glu Thr Asp Thr Leu Leu Leu Trp Val Leu Leu Leu Trp Val Pro
1               5                   10                  15

Gly Ser Thr Gly Asp
            20

<210> SEQ ID NO 53
<211> LENGTH: 15
<212> TYPE: PRT
<213> ORGANISM: Artificial Sequence
<220> FEATURE:
<223> OTHER INFORMATION: (Gly4Ser)3 linker

<400> SEQUENCE: 53

Gly Gly Gly Gly Ser Gly Gly Gly Gly Ser Gly Gly Gly Gly Ser
1               5                   10                  15
```

-continued

<210> SEQ ID NO 54
<211> LENGTH: 489
<212> TYPE: PRT
<213> ORGANISM: Homo sapiens

<400> SEQUENCE: 54

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Gly Ser Ser Tyr Leu Ala Trp Tyr Gln Gln Lys Pro Gly Gln Ala
    50                  55                  60

Pro Arg Leu Leu Ile Tyr Gly Ala Phe Ser Arg Ala Thr Gly Ile Pro
65                  70                  75                  80

Asp Arg Phe Ser Gly Ser Gly Ser Gly Thr Asp Phe Thr Leu Thr Ile
            85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Lys Val Glu Ile Lys
        115                 120                 125

Arg Gly Gly Gly Gly Ser Gly Gly Gly Gly Ser Gly Gly Gly Gly Ser
    130                 135                 140

Gln Val Gln Leu Val Glu Ser Gly Gly Gly Val Val Gln Pro Gly Arg
145                 150                 155                 160

Ser Leu Arg Leu Ser Cys Ala Ala Ser Gly Phe Thr Phe Ser Ser Tyr
            165                 170                 175

Thr Met His Trp Val Arg Gln Ala Pro Gly Lys Gly Leu Glu Trp Val
            180                 185                 190

Thr Phe Ile Ser Tyr Asp Gly Asn Asn Lys Tyr Tyr Ala Asp Ser Val
            195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Ile Tyr Tyr Cys
225                 230                 235                 240

Ala Arg Thr Gly Trp Leu Gly Pro Phe Asp Tyr Trp Gly Gln Gly Thr
            245                 250                 255

Leu Val Thr Val Ser Ser Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380
```

-continued

```
Pro Arg Glu Pro Gln Val Tyr Thr Leu Pro Pro Ser Arg Glu Glu Met
385             390             395             400

Thr Lys Asn Gln Val Ser Leu Thr Cys Leu Val Lys Gly Phe Tyr Pro
            405             410             415

Ser Asp Ile Ala Val Glu Trp Glu Ser Asn Gly Gln Pro Glu Asn Asn
        420             425             430

Tyr Lys Thr Thr Pro Pro Val Leu Asp Ser Asp Gly Ser Phe Phe Leu
        435             440             445

Tyr Ser Lys Leu Thr Val Asp Lys Ser Arg Trp Gln Gln Gly Asn Val
        450             455             460

Phe Ser Cys Ser Val Met His Glu Ala Leu His Asn His Tyr Thr Gln
465             470             475             480

Lys Ser Leu Ser Leu Ser Pro Gly Lys
                485
```

```
<210> SEQ ID NO 55
<211> LENGTH: 1470
<212> TYPE: DNA
<213> ORGANISM: Homo sapiens

<400> SEQUENCE: 55
atggaaactg acaccctgct gctgtgggtc ctgctgctgt gggtgcctgg atccaccggc      60
gatatcgtgc tgacccagtc tcctggcaca ctgagtctgt caccagggga gcgagcaaca     120
ctgtcttgta gagccagcca gtctgtggga agctcctacc tggcttggta tcagcagaag     180
ccaggccagg cacccaggct gctgatctac ggagccttca gccgggccac tggcattcca     240
gacaggttct ctggaagtgg ctcagggacc gacttcaccc tgaccatcag ccgactggag     300
cccgaagact tcgccgtgta ctattgccag cagtacggct ctagtccttg gactttttgga     360 cagggcacca aagtggagat caagcgcggc gggggaggct ctgggggagg cgggagtgga     420
ggcgggggat cacaggtcca gctggtggaa agcggcgggg gagtggtcca gccaggccgg     480
agcctgcggc tgagctgcgc cgcttcagga ttcacatttt caagctatac catgcactgg     540
gtccggcagg caccagggaa gggactggag tgggtgacct tcatcagcta tgacggcaac     600
aacaagtatt acgctgattc cgtgaaaggg aggtttacca ttagccgcga caactccaaa     660
aatacactgt acctgcagat gaacagcctg cgggccgagg atactgctat ctactattgc     720
gcaagaaccg ggtggctggg acccttcgac tattggggcc aggggactct ggtcaccgtg     780
tcctctgata agacacacac atgccctccc tgtcctgcac cagagctgct gggcgggcca     840
tccgtgttcc tgtttccacc caagcctaaa gacaccctga tgatcagccg gacacctgaa     900
gtcacttgcg tggtcgtgga cgtgagtcac gaggatccag aagtcaagtt taactggtac     960
gtggatggcg tcgaggtgca taatgccaag accaaacctc gcgaggaaca gtacaatagc    1020
acatatcgag tcgtgtccgt cctgactgtg ctgcatcagg attggctgaa cggcaaagag    1080
tataagtgca aagtgagcaa taaggcactg cctgccccaa tcgagaaaac aatttccaag    1140
gctaaaggcc agcccaggga acctcaggtg tacactctgc ctccaagtcg cgaggaaatg    1200
accaagaacc aggtgagcct gacctgtctg gtgaaagggt ctatccatc agacattgca    1260 gtggagtggg aaagcaatgg acagcccgaa aacaattaca gaccacacc ccctgtgctg    1320 gacagcgatg gctccttctt tctgtattct aagctgactg tggataaaag tcgctggcag    1380
caggggaacg tctttagctg ttccgtgatg catgaggctc tgcacaatca ttacacacag    1440
aagtctctga gtctgtcacc cggcaaatga                                     1470
```

<210> SEQ ID NO 56
<211> LENGTH: 127
<212> TYPE: PRT
<213> ORGANISM: Mus musculus

<400> SEQUENCE: 56

Ile Arg Arg Ala Asp Ile Val Met Thr Gln Thr Thr Leu Ser Leu Pro
1               5                   10                  15

Val Ser Leu Gly Asp Gln Ala Ser Ile Ser Cys Arg Ser Ser Gln Ser
            20                  25                  30

Ile Val His Ser Asn Gly Asn Thr Tyr Leu Glu Trp Tyr Leu Gln Lys
        35                  40                  45

Pro Gly Gln Ser Pro Lys Leu Leu Ile Tyr Lys Val Ser Asn Arg Phe
    50                  55                  60

Ser Gly Val Pro Asp Arg Phe Ser Gly Ser Gly Ser Gly Thr Asp Phe
65                  70                  75                  80

Thr Leu Lys Ile Ser Arg Val Glu Ala Glu Asp Leu Gly Val Tyr Tyr
                85                  90                  95

Cys Phe Gln Gly Ser His Val Pro Tyr Thr Phe Gly Gly Gly Thr Lys
            100                 105                 110

Leu Glu Ile Lys Arg Ala Asp Ala Ala Pro Thr Val Ser Gly Ser
        115                 120                 125

<210> SEQ ID NO 57
<211> LENGTH: 134
<212> TYPE: PRT
<213> ORGANISM: Mus musculus

<400> SEQUENCE: 57

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Pro Pro Ser Val Tyr Pro Leu
        115                 120                 125

Ala Pro Arg Ser Ser Arg
    130

<210> SEQ ID NO 58
<211> LENGTH: 356
<212> TYPE: PRT
<213> ORGANISM: Mus musculus

<400> SEQUENCE: 58

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr

-continued

```
              20                  25                  30

Tyr Met Asn Trp Val Lys Gln Ser His Gly Lys Ser Leu Glu Trp Ile
            35                  40                  45

Gly Val Ile Asn Pro Tyr Asn Gly Asp Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Pro Pro Ser Val Tyr Pro Leu
            115                 120                 125

Ala Pro Arg Ser Ser Arg Gly Cys Lys Pro Cys Ile Cys Thr Val Pro
        130                 135                 140

Glu Val Ser Ser Val Phe Ile Phe Pro Pro Lys Pro Lys Asp Val Leu
145                 150                 155                 160

Thr Ile Thr Leu Thr Pro Lys Val Thr Cys Val Val Val Asp Ile Ser
                165                 170                 175

Lys Asp Asp Pro Glu Val Gln Phe Ser Trp Phe Val Asp Asp Val Glu
            180                 185                 190

Val His Thr Ala Gln Thr Gln Pro Arg Glu Glu Gln Phe Asn Ser Thr
            195                 200                 205

Phe Arg Ser Val Ser Glu Leu Pro Ile Met His Gln Asp Trp Leu Asn
        210                 215                 220

Gly Lys Glu Phe Lys Cys Arg Val Asn Ser Ala Ala Phe Pro Ala Pro
225                 230                 235                 240

Ile Glu Lys Thr Ile Ser Lys Thr Lys Gly Arg Pro Lys Ala Pro Gln
                245                 250                 255

Val Tyr Thr Ile Pro Pro Pro Lys Glu Gln Met Ala Lys Asp Lys Val
            260                 265                 270

Ser Leu Thr Cys Met Ile Thr Asp Phe Phe Pro Glu Asp Ile Thr Val
            275                 280                 285

Glu Trp Gln Trp Asn Gly Gln Pro Ala Glu Asn Tyr Lys Asn Thr Gln
        290                 295                 300

Pro Ile Met Asp Thr Asp Gly Ser Tyr Phe Val Tyr Ser Lys Leu Asn
305                 310                 315                 320

Val Gln Lys Ser Asn Trp Glu Ala Gly Asn Thr Phe Thr Cys Ser Val
            325                 330                 335

Leu His Glu Gly Leu His Asn His His Thr Glu Lys Ser Leu Ser His
            340                 345                 350

Ser Pro Gly Lys
        355

<210> SEQ ID NO 59
<211> LENGTH: 519
<212> TYPE: PRT
<213> ORGANISM: Mus musculus

<400> SEQUENCE: 59

Met Glu Thr Asp Thr Leu Leu Leu Trp Val Leu Leu Leu Trp Val Pro
1               5                   10                  15

Gly Ser Thr Gly Asp Ile Arg Arg Ala Asp Ile Val Met Thr Gln Thr
            20                  25                  30
```

-continued

```
Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
            115                 120                 125

Gly Gly Gly Thr Lys Leu Glu Ile Lys Arg Ala Asp Ala Ala Pro Thr
    130                 135                 140

Val Ser Gly Ser Gly Gly Gly Ser Gly Gly Gly Gly Ser Gly Gly
145                 150                 155                 160

Gly Gly Ser Glu Ala Lys Leu Gln Glu Ser Gly Pro Val Leu Val Lys
                165                 170                 175

Pro Gly Ala Ser Val Lys Met Ser Cys Lys Ala Ser Gly Tyr Thr Phe
            180                 185                 190

Thr Asp Tyr Tyr Met Asn Trp Val Lys Gln Ser His Gly Lys Ser Leu
            195                 200                 205

Glu Trp Ile Gly Val Ile Asn Pro Tyr Asn Gly Asp Thr Ser Tyr Asn
    210                 215                 220

Gln Lys Phe Lys Gly Lys Ala Thr Leu Thr Val Asp Lys Ser Ser Ser
225                 230                 235                 240

Thr Ala Tyr Met Glu Leu Asn Ser Leu Thr Ser Glu Asp Ser Ala Val
            245                 250                 255

Tyr Tyr Cys Ala Arg Tyr Tyr Gly Ser Trp Phe Ala Tyr Trp Gly Gln
            260                 265                 270

Gly Thr Leu Ile Thr Val Ser Thr Ala Lys Thr Thr Pro Pro Ser Val
            275                 280                 285

Tyr Pro Leu Ala Pro Arg Ser Ser Arg Gly Cys Lys Pro Cys Ile Cys
    290                 295                 300

Thr Val Pro Glu Val Ser Ser Val Phe Ile Phe Pro Pro Lys Pro Lys
305                 310                 315                 320

Asp Val Leu Thr Ile Thr Leu Thr Pro Lys Val Thr Cys Val Val Val
            325                 330                 335

Asp Ile Ser Lys Asp Asp Pro Glu Val Gln Phe Ser Trp Phe Val Asp
            340                 345                 350

Asp Val Glu Val His Thr Ala Gln Thr Gln Pro Arg Glu Glu Gln Phe
            355                 360                 365

Asn Ser Thr Phe Arg Ser Val Ser Glu Leu Pro Ile Met His Gln Asp
    370                 375                 380

Trp Leu Asn Gly Lys Glu Phe Lys Cys Arg Val Asn Ser Ala Ala Phe
385                 390                 395                 400

Pro Ala Pro Ile Glu Lys Thr Ile Ser Lys Thr Lys Gly Arg Pro Lys
                405                 410                 415

Ala Pro Gln Val Tyr Thr Ile Pro Pro Pro Lys Glu Gln Met Ala Lys
            420                 425                 430

Asp Lys Val Ser Leu Thr Cys Met Ile Thr Asp Phe Phe Pro Glu Asp
            435                 440                 445

Ile Thr Val Glu Trp Gln Trp Asn Gly Gln Pro Ala Glu Asn Tyr Lys
```

-continued

```
        450              455              460
Asn Thr Gln Pro Ile Met Asp Thr Asp Gly Ser Tyr Phe Val Tyr Ser
465                 470                 475                 480

Lys Leu Asn Val Gln Lys Ser Asn Trp Glu Ala Gly Asn Thr Phe Thr
                485                 490                 495

Cys Ser Val Leu His Glu Gly Leu His Asn His His Thr Glu Lys Ser
            500                 505                 510

Leu Ser His Ser Pro Gly Lys
        515

<210> SEQ ID NO 60
<211> LENGTH: 1560
<212> TYPE: DNA
<213> ORGANISM: Mus musculus

<400> SEQUENCE: 60
atggaaactg atactctgct gctctgggtg ctgctcctct gggtgcctgg ttcaactggg      60
gacattcgac gggctgacat tgtgatgacc cagaccacac tgagcctgcc cgtgtccctg     120
ggcgaccagg ccagcatctc ctgccggagc tcccagtcta tcgtgcacag caacggaaac     180
acatacctgg agtggtatct gcagaagcct ggccagtccc caaagctgct gatctacaag     240
gtgtccaaca ggttcagcgg cgtgcctgac cgcttttctg aagcggctc cggaacagat      300 ttcaccctga gatcagcag ggtggaggct gaggacctgg gcgtgtacta ctgcttccag      360
ggatcccacg tgccttacac ctttggcgga ggcacaaagc tggagatcaa gagagccgat     420
gctgctccaa ccgtgtctgg aagcggaggc ggggggttctg gaggcggtgg gagcggtggc    480
ggagggtctg aggctaagct gcaggagagc ggccccgtgc tggtgaagcc tggagccagc    540
gtgaagatgt cctgtaaggc ttctggatac accttcacag actactacat gaactgggtg     600
aagcagagcc acggcaagtc cctggagtgg atcggagtga tcaacccctta caacggcgac    660 acctcttaca ccagaagtt taagggcaag gccaccctga cagtggataa gtctagctcc     720
accgcttaca tggagctgaa cagcctgaca tccgaggatt ctgccgtgta ctactgtgct    780
aggtactacg gaagctggtt cgcctactgg ggccagggaa cactgatcac cgtgtccaca    840
gccaagacca caccccctag cgtgtacccc ctggctccta ggtctagcag aggctgcaag    900
ccatgcatct gtaccgtgcc cgaggtgagc agcgtgttca tctttccacc caagcccaag    960
gacgtgctga ccatcacact gaccccctaag gtgacatgcg tggtggtgga tatcagcaag   1020
gacgatccag aggtgcagtt ctcctggttt gtggacgatg tggaggtgca caccgcccag   1080
acacagccaa gggaggagca gttcaactcc acctttagat ccgtgtctga gctgcccatc   1140
atgcaccagg actggctgaa cggaaaggag ttcaagtgcc gggtgaactc cgccgctttt   1200
cctgctccaa tcgagaagac catctctaag acaaagggcc gcccaaaggc tccacaggtg   1260
tacaccatcc ctccacccaa ggagcagatg gctaaggata aggtgagcct gacctgtatg   1320
atcacagact ctttcccga ggatatcaca gtggagtggg agtggaacgg acagcctgcc    1380
gagaactaca gaacacccca gccaatcatg gacacagatg gctcttactt cgtgtacagc   1440
aagctgaacg tgcagaagtc taactgggag gctggcaaca ccttcacctg cagcgtgctg   1500
cacgaaggtc tccataatca ccacaccgaa aagagcctca gtcacagccc tgggaaatga   1560

<210> SEQ ID NO 61
<211> LENGTH: 1574
<212> TYPE: DNA
<213> ORGANISM: Mus musculus
```

-continued

<400> SEQUENCE: 61
cttaagatgg aaactgatac tctgctgctc tgggtgctgc tcctctgggt gcctggttca        60
actggggaca ttcgacgggc tgacattgtg atgacccaga ccacactgag cctgcccgtg       120
tccctgggcg accaggccag catctcctgc cggagctccc agtctatcgt gcacagcaac       180
ggaaacacat acctggagtg gtatctgcag aagcctggcc agtccccaaa gctgctgatc       240
tacaaggtgt ccaacaggtt cagcggcgtg cctgaccgct tttctggaag cggctccgga       300
acagatttca ccctgaagat cagcagggtg gaggctgagg acctgggcgt gtactactgc       360
ttccagggat cccacgtgcc ttacaccttt ggcggaggca caaagctgga gatcaagaga       420
gccgatgctg ctccaaccgt gtctggaagc ggaggcgggg gttctggagg cggtgggagc       480
ggtggcggag ggtctgaggc taagctgcag gagagcggcc ccgtgctggt gaagcctgga       540
gccagcgtga agatgtcctg taaggcttct ggatacacct tcacagacta ctacatgaac       600
tgggtgaagc agagccacgg caagtccctg agtggatcg gagtgatcaa cccttacaac       660
ggcgacacct cttacaacca gaagtttaag ggcaaggcca ccctgacagt ggataagtct       720
agctccaccg cttacatgga gctgaacagc ctgacatccg aggattctgc cgtgtactac       780
tgtgctaggt actacggaag ctggttcgcc tactggggcc agggaacact gatcaccgtg       840
tccacagcca agaccacacc ccctagcgtg taccccctgg ctcctaggtc tagcagaggc       900
tgcaagccat gcatctgtac cgtgcccgag gtgagcagcg tgttcatctt ccacccaag       960 cccaaggacg tgctgaccat cacactgacc cctaaggtga catgcgtggt ggtggatatc      1020
agcaaggacg atccagaggt gcagttctcc tggtttgtgg acgatgtgga ggtgcacacc      1080
gcccagacac agccaaggga ggagcagttc aactccacct ttagatccgt gtctgagctg      1140
cccatcatgc accaggactg gctgaacgga aaggagttca gtgccgggt gaactccgcc      1200 gctttttcctg ctccaatcga gaagaccatc tctaagacaa agggccgccc aaaggctcca      1260
caggtgtaca ccatccctcc acccaaggag cagatggcta aggataaggt gagcctgacc      1320
tgtatgatca cagacttctt tcccgaggat atcacagtgg agtggcagtg gaacggacag      1380
cctgccgaga actacaagaa caccagcca atcatggaca cagatggctc ttacttcgtg      1440
tacagcaagc tgaacgtgca gaagtctaac tgggaggctg gcaacacctt cacctgcagc      1500
gtgctgcacg aaggtctcca taatcaccac accgaaaaga gcctcagtca cagccctggg      1560
aaatgaggcg cgcc                                                         1574

<210> SEQ ID NO 62
<211> LENGTH: 1484
<212> TYPE: DNA
<213> ORGANISM: Homo sapiens

<400> SEQUENCE: 62
cttaagatgg aaactgacac cctgctgctg tgggtcctgc tgctgtgggt gcctggatcc        60
accggcgata tcgtgctgac ccagtctcct ggcacactga gtctgtcacc aggggagcga       120
gcaacactgt cttgtagagc cagccagtct gtgggaagct cctacctggc ttggtatcag       180
cagaagccag gccaggcacc caggctgctg atctacggag ccttcagccg ggccactggc       240
attccagaca ggttctctgg aagtggctca gggaccgact tcaccctgac catcagccga       300
ctggagcccg aagacttcgc cgtgtactat tgccagcagt acggctctag tccttggact       360
tttggacagg gcaccaaagt ggagatcaag cgcggcgggg gaggctctgg gggaggcggg       420

-continued

```
agtggaggcg ggggatcaca ggtccagctg gtggaaagcg gcgggggagt ggtccagcca      480
ggccggagcc tgcggctgag ctgcgccgct tcaggattca cattttcaag ctataccatg      540
cactgggtcc ggcaggcacc agggaaggga ctggagtggg tgaccttcat cagctatgac      600
ggcaacaaca agtattacgc tgattccgtg aaagggaggt ttaccattag ccgcgacaac      660
tccaaaaata cactgtacct gcagatgaac agcctgcggg ccgaggatac tgctatctac      720
tattgcgcaa gaaccgggtg gctgggaccc ttcgactatt ggggccaggg gactctggtc      780
accgtgtcct ctgataagac acacacatgc cctccctgtc ctgcaccaga gctgctgggc      840
gggccatccg tgttcctgtt tccacccaag cctaaagaca ccctgatgat cagccggaca      900
cctgaagtca cttgcgtggt cgtggacgtg agtcacgagg atccagaagt caagtttaac      960
tggtacgtgg atggcgtcga ggtgcataat gccaagacca aacctcgcga ggaacagtac     1020
aatagcacat atcgagtcgt gtccgtcctg actgtgctgc atcaggattg gctgaacggc     1080
aaagagtata agtgcaaagt gagcaataag gcactgcctg ccccaatcga gaaaacaatt     1140
tccaaggcta aaggccagcc cagggaacct caggtgtaca ctctgcctcc aagtcgcgag     1200
gaaatgacca agaaccaggt gagcctgacc tgtctggtga aagggttcta tccatcagac     1260
attgcagtgg agtgggaaag caatggacag cccgaaaaca attacaagac cacacccct      1320 gtgctggaca gcgatggctc cttctttctg tattctaagc tgactgtgga taaaagtcgc     1380
tggcagcagg ggaacgtctt tagctgttcc gtgatgcatg aggctctgca caatcattac     1440
acacagaagt ctctgagtct gtcacccggc aaatgaggcg cgcc                       1484
```

TREATMENT USING ONCOLYTIC VIRUS

CROSS REFERENCE TO RELATED APPLICATIONS

This application is a national phase under 35 U.S.C. § 371 of International Application No. PCT/GB2019/051769, filed Jun. 21, 2019, which claims the benefit of priority to U.S. Priority Application Nos. 62/687,881, 62/687,910, 62/687,920, and 62/687,931 all filed Jun. 21, 2018. The entire contents of each of which are hereby incorporated by reference in their entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself. The immune response is also enhanced due to the recognition by the host of so called damage associated molecular patterns (DAMPs) which aid in the activation of the immune response.

Viruses also engage with various mediators of the innate immune response as part of the host response to the recognition of a viral infection through, for example, toll-like receptors, cGAS/STING signalling and/or the recognition of pathogen associated molecular patterns (PAMPs) resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micro-metastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to induce immune responses or increase the immunogenicity of antigens released following virus replication and cell death, genes intended to shape the immune response which is generated, genes to increase the general immune activation status of the tumor, or genes to increase the direct oncolytic properties (i.e. cytotoxic effects) of the virus. Importantly, viruses have the ability to deliver encoded molecules which are intended to help to initiate, enhance or shape the systemic anti-tumor immune response directly and selectively to tumors, which may have benefits of e.g. reduced toxicity or of focusing beneficial effects on tumors (including those not infected by the virus) rather than off-target effects on normal (i.e. non-cancerous) tissues as compared to the systemic administration of these same molecules or systemic administration of other molecules targeting the same pathways.

It has been demonstrated that a number of viruses including, for example, herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models. Clinical trials of ICP34.5 deleted, or ICP34.5 and ICP6 deleted, HSV have also shown safety and selective replication in tumor tissue in humans.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. GM-CSF is a pro-inflammatory cytokine which has multiple functions including the stimulation of monocytes to exit the circulation and migrate into tissue where they proliferate and mature into macrophages and dendritic cells. GM-CSF is important for the proliferation and maturation of antigen presenting cells, the activity of which is needed for the activation of an anti-tumor immune response. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy and oncolytic immunotherapy are clearly needed. These may serve to increase the direct oncolytic effects of therapy, the anti-tumor immune stimulating effects of the therapy, or both of these effects together.

Recently it has been shown that oncolytic immunotherapy can result in additive or synergistic therapeutic effects in conjunction with immune checkpoint blockade (i.e. inhibition or 'antagonism' of immune checkpoint pathways), also referred to as immune co-inhibitory pathway blockade. Checkpoint (immune co-inhibitory pathway) blockade is intended to block host immune inhibitory mechanisms which usually serve to prevent the occurrence of auto-immunity. However, in cancer patients these mechanisms can also serve to block (e.g. inhibit the induction of) the potentially beneficial effects of any immune responses induced to tumors. Alternatively, immune responses may not be fully potentiated due to a lack of activation or lack of full activation of immune potentiating pathways. Therefore, drugs which alleviate these blocks (inhibit "immune co-inhibitory pathways") or stimulate immune potentiating pathways (i.e. which activate, or are 'agonists' of "immune co-stimulatory pathways") are attractive for testing and developing cancer treatments. Targets for such approved or experimental drugs include CTLA-4, PD-1, PD-L1, LAG-3, TIM-3, VISTA, CSF1R, IDO, CEACAM1, G1TR, 4-1-BB, KIR, SLAMF7, OX40, CD40, ICOS or CD47.

Systemic blockade of these pathways by agents targeting CTLA-4, PD-1 or PD-L1 have shown efficacy in a number of tumor types, including melanoma and lung cancer. However, unsurprisingly, based on the mechanism of action, off target toxicity can occur due to the induction of auto-immunity. Even so, these agents are sufficiently tolerable to provide considerable clinical utility. Other immune co-inhibitory pathway and related targets for which agents (mainly antibodies) are in development include LAG-3, TIM-3, VISTA, CSF1R, IDO, CEACAM1, CD47. Optimal clinical activity of these agents, for example PD1, PDL1, LAG-3, TIM-3, VISTA, CSF1R, IDO, CD47, CEACAM1, may require systemic administration or presence in all tumors due to the mechanism of action, i.e. including targeting of the interface of immune effector cells with tumors or other immune inhibitory mechanisms in/of tumors. In some cases, more localised presence in e.g. just some tumors or in some lymph nodes may also be optimally effective, for example agents targeting CTLA-4.

An alternative approach to increasing the anti-tumor immune response in cancer patients is to target (activate) immune co-stimulatory pathways, i.e. in contrast to inhibiting immune co-inhibitory pathways. These pathways send activating signals into T cells and other immune cells, usually resulting from the interaction of the relevant ligands on antigen presenting cells (APCs) and the relevant receptors on the surface of T cells and other immune cells. These signals, depending on the ligand/receptor, can result in the increased activation of T cells and/or APCs and/or NK cells and/or B cells, including particular sub-types, increased differentiation and proliferation of T cells and/or APCs and/or NK cells and/or B cells, including particular sub-types, or suppression of the activity of immune inhibitory T cells such as regulatory T cells. Activation of these pathways would therefore be expected to result in enhanced anti-tumor immune responses, but it might also be expected that systemic activation of these pathways, i.e. activation of immune responses generally rather than anti-tumor immune responses specifically or selectively, would result in considerable off target toxicity in non-tumor tissue, the degree of such off target toxicity depending on the particular immune co-stimulatory pathway being targeted. Nevertheless agents (mainly agonistic antibodies, or less frequently the soluble ligand to the receptor in question) targeting immune co-stimulatory pathways, including agents targeting GITR, 4-1-BB, OX40, CD40 or ICOS, and intended for systemic use (i.e. intravenous delivery) are in or have been proposed for clinical development.

For these approaches to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed. Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the activity, e.g. optimal activity, of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely explains the promising combined anti-tumor effects of onco-lytic agents and immune co-inhibitory pathway blockade in mice and humans that have so far been observed.

The indoleamine 2,3-dioxygenase (IDO) pathway contributes to tumor-induced tolerance by creating a tolerogenic environment in the tumor and the tumor-draining lymph nodes, both by direct suppression of T cells and enhancement of local regulatory T cell (Treg)-mediated immuno-suppression. IDO catalyses the rate-limiting step of trypto-phan degradation along the kynurenine pathway, and both the reduction in local tryptophan concentration and the production of immunomodulatory tryptophan metabolites contribute to the immunosuppressive effects of IDO. IDO is chronically activated in many cancer patients with IDO activation correlating with more extensive disease. It can also function as an antagonist to other activators of antitu-mor immunity. Therefore, inhibitors of the IDO pathway are being developed as anticancer agents, particularly in combination with checkpoint blockade agents such as those which target CTLA-4, PD-1 or PDL-1. IDO inhibitors may also be synergistic with oncolytic immunotherapy, including together with drugs targeting other immune checkpoint or immune co-stimulatory pathways.

The above discussion demonstrates that there is still much scope for improving oncolytic agents and cancer therapies utilising oncolytic agents.

SUMMARY

The disclosure provides improved oncolytic viruses. The improved oncolytic viruses have improved direct oncolytic effects. The improved direct oncolytic effects provided by the viruses of the disclosure will also lead to improved systemic anti-tumor immune effects. The improved direct oncolytic effects provided by the viruses of the disclosure will also lead to improved therapeutic effects in patients. Enhanced replication in and killing of tumor cells will result in enhanced tumor antigen release and enhanced systemic immune responses to the released antigens. The expression levels of any genes inserted to augment the direct oncolytic effects and/or immune stimulation will also be increased.

Virus species naturally exist in a range of variants (strains) within the natural population which may differ by a small or larger number of nucleotides while still retaining the antigenic characteristics and sufficient sequence identity to still be recognized as the same virus species. These strains, due to their differing sequences, may exhibit a range of differing properties, including properties which have been selected for by natural selection in their natural host or hosts (for example the ability to infect or replicate in the target cell types of the virus in question, spread between these cells, or to evade the host innate or adaptive immune system, or to spread between infected individuals of the host species) and properties which have not been specifically selected for (e.g. the ability to replicate in and kill or spread between cell types which are not the natural targets of the virus in question, including tumor or other non-target cell types or tissues). The inventors have recognised that sampling a range of viral strains of a particular viral species which are present in the natural host population (in the case of viruses infecting humans, here termed 'clinical isolates') and comparing these to each other to select for the strain with the best properties for the intended purpose for which it is to be used (e.g. infection and killing of tumor cells) can be used to identify a virus (i.e. a virus strain) with optimal properties for that purpose. The optimal properties may be properties that offer the best starting point for development to produce a virus that can be used as a therapeutic. A virus identified by this approach is likely to have more optimal properties for the intended purpose than a 'prototype' or 'laboratory' virus strain or a clinical strain which has not been selected for the required property or properties from a broad group of viral strains. This is because the full biological complexity in the natural population, particularly with respect to the particular desirable property or properties, is unlikely to have been sampled through taking a narrow approach to screening for the desired property or properties, bearing in mind the degree of sequence variation present in natural virus populations. In particular, these may vary in sequence within an infected host (as is often the case with RNA or retroviral populations where so-called quasi-species are often present), between individual infected hosts, or between different geographically separated viral populations.

Viruses of the disclosure have therefore been selected by sampling a range of viral strains present in the natural population of a particular viral species and testing these against each other for the desired property or properties (e.g. the ability to infect and kill tumor cells). The virus strain or strains with the best properties for the intended purpose are used for further development.

Where the intended use is oncolytic viral therapy, taking such an approach provides an improved starting point for development of an oncolytic agent, which may require further manipulation of the advantageous virus strains. Such manipulation includes the deletion of viral genes to provide, for example, tumor selectivity, and/or the insertion of exogenous genes to improve oncolytic or immune potentiating properties further.

The viruses of the disclosure therefore include novel clinical isolates of a viral species that have better anti-tumor effects than the other clinical isolates to which they were compared and through which comparison they were identified. In particular, the clinical isolates of the disclosure kill tumor cell lines in vitro more quickly and/or at a lower dose than these reference clinical isolates of the same virus type. Typically, a clinical isolate of the disclosure will have been identified through comparison of >5 clinical isolates of a viral species for the required property or properties, preferably through comparison of >10 clinical isolates of the viral species, and more preferably through comparison of >20 clinical isolates of the viral species. A clinical isolate of the disclosure typically shows better tumor cell killing activity than 3/5, 6/10 or 11/20ths, preferably better than 4/5, 8/10 or 17/20ths, more preferably better than 9/10 or 19/20ths of the viral strains tested.

Typically, a clinical isolate of the disclosure can kill two or more tumor cell lines in vitro within 24 to 48 hours after infection at a multiplicity of infection (MOI) of 0.01 to 0.001 or less.

The clinical isolates of the disclosure may be modified to further enhance their anti-tumor effects. The genome of a clinical isolate of the disclosure may be modified to delete or alter expression of one or more viral genes, and/or the genome of the clinical isolate may be modified to express one or more heterologous genes, such as genes encoding a fusogenic protein and/or an immune stimulatory molecule or molecules.

The disclosure provides oncolytic viruses expressing a fusogenic protein and at least one immune stimulatory molecule.

Oncolytic viruses of the disclosure provide improved treatment of cancer through improved direct oncolytic effects, viral replication and spread through tumors, which (i) increases the amount of tumor antigens, including neoantigens, which are released for the induction of an anti-tumor immune response; and (ii) enhances the expression of the virus-encoded immune stimulatory molecule(s). Expression of immune stimulatory molecule(s) by the virus can further enhance and potentiate the anti-tumor immune effect. Expression of fusogenic protein(s) by the virus can further enhance viral spread through tumors. Expression of fusogenic protein(s) by the virus can further enhance tumor cell killing. Where a fusogenic gene is expressed by the virus spread through tumors can be mediated by the fusogenic protein.

In one embodiment, the present disclosure provides oncolytic viruses expressing an inhibitor of CTLA-4. The virus may further comprise other immunomodulatory agents. In particular the virus may comprise GM-CSF and/or at least one molecule targeting an immune co-stimulatory pathway. The CTLA-4 inhibitor acts to block a co-inhibitory pathway, i.e. interferes with the interaction between CTLA-4 and B7. GM-CSF aids in the induction of an inflammatory tumor micro-environment and stimulates the proliferation and maturation of antigen presenting cells, including dendritic cells, aiding the induction of an anti-tumor immune responses. These immune responses may be amplified through activation of an immune co-stimulatory pathway or pathways using an immune co-stimulatory pathway activating molecule or molecules also delivered by the oncolytic virus.

Oncolytic viruses replicate within tumors, causing lysis of tumor cells and release of tumor antigens, combined with local inflammation and activation of innate immune responses, all of which are beneficial for the activation of an anti-tumor immune response and for the activity of inhibitors of the CTLA-4/B7 interaction.

Delivery of molecules that inhibit the CTLA-4/B7 interaction directly into an immune response initiating-tumor, including where it would be expected to traffic to draining lymph nodes, focuses immune potentiation by the inhibitor on the tumor and therefore on tumor antigens present within it, reduces systemic toxicity and blocks regulatory T cell (Treg) activation that would otherwise inhibit T-cell activation at the site of immune response initiation.

The use of an oncolytic virus to deliver molecules targeting immune co-stimulatory pathways, for example molecules targeting CTLA-4, to tumors focuses the amplification of immune effects on anti-tumor immune responses, and reduces the amplification of immune responses to non-tumor antigens. Thus, immune cells in tumors and tumor draining lymph nodes are selectively engaged by the molecules activating immune co-stimulatory pathways rather than immune cells in general. This results in enhanced efficacy of immune co-stimulatory pathway activation and anti-tumor immune response amplification, and can also result in reduced off target toxicity. It is also important for focusing the effects of combined systemic immune co-inhibitory pathway blockade and immune co-stimulatory pathway activation on tumors, i.e. such that the amplified immune responses from which co-inhibitory blocks are released are antitumor immune responses rather than responses to non-tumor antigens.

The disclosure utilizes the fact that, when delivered by an oncolytic virus, the site of action of heterologous gene expression, such as co-stimulatory pathway activation and of GM-CSF expression and/or CTLA-4 blockade, is in the tumor and/or tumor draining lymph node, but the results of such activation (an amplified systemic anti-tumor-immune response) are systemic. This targets tumors generally, and not only tumors to which the oncolytic virus has delivered the molecule or molecules encoded by the heterologous genes, such as molecule or molecules targeting an immune co-stimulatory pathway or pathways and GM-CSF and/or CTLA-4 inhibitors. Oncolytic viruses of the disclosure therefore provide improved treatment of cancer through the generation of improved tumor focused immune responses. The oncolytic virus of the disclosure also offers improved anti-tumor immune stimulating effects such that the immune-mediated effects on tumors which are not destroyed by oncolysis, including micro-metastatic disease, are enhanced, resulting in more effective destruction of these tumors, and more effective long term anti-tumor vaccination to prevent future relapse and improve overall survival.

Anti-tumor efficacy of an oncolytic virus of the disclosure is achieved when the virus is used as a single agent and also when the virus is used in combination with other anti-cancer modalities, including chemotherapy, treatment with targeted agents, radiation, immune checkpoint blockade (i.e. administration of one or more antagonist of an immune co-inhibitory pathway for example antibodies against PD1 or PD-L1) and/or immune potentiating drugs (e.g. one or more agonists of an immune co-stimulatory pathway). The improved direct oncolytic effects (i.e. virus replication in, spread between, and direct killing of tumor cells) and improved systemic anti-tumor immune effects of the viruses of the disclosure improve on the combined benefits of oncolytic therapy and immune co-inhibitory pathway blockade and/or immune co-stimulatory pathway activation.

Accordingly, provided is an oncolytic virus for use in a method of treating or preventing cutaneous squamous cell carcinoma (CSCC), renal cell carcinoma (RCC), non-small cell lung cancer (NSCLC), triple negative breast cancer (TNBC), small cell lung cancer (SCLC), advanced recurrent head and neck cancer, squamous cell carcinoma of the head and neck (SCCHN), nasopharyngeal carcinoma (NPC), hepatocellular carcinoma (HCC), anal cancer, colorectal cancer (CRC), basal cell carcinoma (BCC), Merkel cell carcinoma, appendiceal carcinoma, sarcoma of the skin, recurrent melanoma after surgery, advanced or metastatic urothelial carcinoma, liver metastases, microsatellite instability high cancer (MSI-H), mixed advanced solid tumors, virally caused cancer, locoregionally advanced cancer, pediatric cancer, cancer in patients with no or minimal pre-existing anti-cancer immunity, cancer as first line therapy, cancer in previously treated patients, cancer in patients who have not received checkpoint blockade therapy, and/or cancer in patients who have received checkpoint blockade therapy, wherein:
  (a) the oncolytic virus is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel;

(b) the oncolytic virus comprises: (i) a fusogenic protein-encoding gene; and (ii) an immune stimulatory molecule-encoding gene;
  (c) the oncolytic virus comprises: (i) a GM-CSF-encoding gene; and (ii) an immune co-stimulatory pathway activating molecule or immune co-stimulatory pathway activating molecule-encoding gene; and/or
  (d) encoding a CTLA-4 inhibitor.
The clinical isolate may be modified. A modified clinical isolate may have mutations, such as deletions in the viral genome and/or may express one or more heterologous genes.
The virus may be a strain of any virus species which may be used for the oncolytic treatment of cancer, including strains of herpes virus, pox virus, adenovirus, retrovirus, rhabdovirus, paramyxovirus or reovirus. The virus is preferably a herpes simplex virus (HSV), such as HISV1. The HSV typically does not express functional ICP34.5 and/or functional ICP47 and/or expresses the US11 gene as an immediate early gene.
The virus may comprise (i) a fusogenic protein-encoding gene; and/or (ii) an immune stimulatory molecule or an immune stimulatory molecule-encoding gene. The virus may encode more than one fusogenic protein and/or more than one immune stimulatory molecule. The fusogenic protein-encoding gene is a non-viral gene, i.e. it is a heterologous gene. The immune stimulatory molecule-encoding gene is a non-viral gene, i.e. it is a heterologous gene. The fusogenic protein is preferably the glycoprotein from gibbon ape leukemia virus (GALV) and has the R transmembrane peptide mutated or removed (GALV-R–). The immune stimulatory molecule is preferably GM-CSF and/or an agonist of an immune co-stimulatory pathway such as GITRL, 4-1-BBL, OX40L, ICOSL, CD40L or flt3, or a modified version of any thereof. Examples of modified versions include agonists of a co-stimulatory pathway that are secreted rather than being membrane bound, and/or agonists modified such that multimers of the protein are formed. The immune stimulatory molecule may be a protein capable of blocking signaling through CTLA-4, for example an antibody or a fragment thereof which binds CTLA-4.
The virus may encode more than one immune co-stimulatory pathway activating molecule/gene. The immune co-stimulatory pathway activating molecule is preferably an agonist of GITR, 4-1-BBL, OX40, ISCOL, CD40 or flt3, such as GITRL, 4-1-BBL, OX40L, ICOSL, CD40L or flt3 ligand or a modified version of any thereof or a protein capable of blocking signaling through CTLA-4, for example an antibody which binds CTLA-4. Examples of modified versions include agonists of a co-stimulatory pathway that are secreted rather than being membrane bound, and/or agonists modified such that multimers of the protein are formed.
The CTLA-4 inhibitor is preferably an anti-CTLA-4 antibody or antibody like molecule, or an antigen binding fragment thereof.
Also provided are:
  a virus of the disclosure for use in a method of treating cancer, wherein the method comprises administering a further anti-cancer agent, wherein the further anti-cancer agent is a tyrosine kinase inhibitor;
  a pharmaceutical composition comprising a virus of the disclosure and a pharmaceutically acceptable carrier or diluent for use in a method of treating or preventing cutaneous squamous cell carcinoma (CSCC), renal cell carcinoma (RCC), non-small cell lung cancer (NSCLC), triple negative breast cancer (TNBC), small cell lung cancer (SCLC), advanced recurrent head and neck cancer, squamous cell carcinoma of the head and neck (SCCHN), nasopharyngeal carcinoma (NPC), hepatocellular carcinoma (HCC), anal cancer, colorectal cancer (CRC), basal cell carcinoma (BCC), Merkel cell carcinoma, appendiceal carcinoma, sarcoma of the skin, recurrent melanoma after surgery, advanced or metastatic urothelial carcinoma, liver metastases, microsatellite instability high cancer (MSI-H), mixed advanced solid tumors, virally caused cancer, locoregionally advanced cancer, pediatric cancer, cancer in patients with no or minimal pre-existing anti-cancer immunity, cancer as first line therapy, cancer in previously treated patients, cancer in patients who have not received checkpoint blockade therapy, and/or cancer in patients who have received checkpoint blockade therapy;

a virus of the disclosure for use in a method of treating or preventing cutaneous squamous cell carcinoma (CSCC), renal cell carcinoma (RCC), non-small cell lung cancer (NSCLC), triple negative breast cancer (TNBC), small cell lung cancer (SCLC), advanced recurrent head and neck cancer, squamous cell carcinoma of the head and neck (SCCHN), nasopharyngeal carcinoma (NPC), hepatocellular carcinoma (HCC), anal cancer, colorectal cancer (CRC), basal cell carcinoma (BCC), Merkel cell carcinoma, appendiceal carcinoma, sarcoma of the skin, recurrent melanoma after surgery, advanced or metastatic urothelial carcinoma, liver metastases, microsatellite instability high cancer (MSI-H), mixed advanced solid tumors, virally caused cancer, locoregionally advanced cancer, pediatric cancer, cancer in patients with no or minimal pre-existing anti-cancer immunity, cancer as first line therapy, cancer in previously treated patients, cancer in patients who have not received checkpoint blockade therapy, and/or cancer in patients who have received checkpoint blockade therapy, optionally wherein the method comprises administering the virus in combination with a further anti-cancer agent, optionally wherein the further anti-cancer agent is a tyrosine kinase inhibitor;

a method of treating cancer, which comprises administering a therapeutically effective amount of a virus or a pharmaceutical composition of the disclosure to a patient in need thereof, wherein the cancer is selected from the group consisting of cutaneous squamous cell carcinoma (CSCC), renal cell carcinoma (RCC), non-small cell lung cancer (NSCLC), triple negative breast cancer (TNBC), small cell lung cancer (SCLC), advanced recurrent head and neck cancer, squamous cell carcinoma of the head and neck (SCCHN), nasopharyngeal carcinoma (NPC), hepatocellular carcinoma (HCC), anal cancer, colorectal cancer (CRC), basal cell carcinoma (BCC), Merkel cell carcinoma, appendiceal carcinoma, sarcoma of the skin, recurrent melanoma after surgery, advanced or metastatic urothelial carcinoma, liver metastases, microsatellite instability high cancer (MSI-H), mixed advanced solid tumors, virally caused cancer, locoregionally advanced cancer, pediatric cancer, and/or cancer in patients with no or minimal pre-existing anti-cancer immunity, cancer as first line therapy, cancer in previously treated patients, cancer in patients who have not received checkpoint blockade therapy or cancer in patients who have received checkpoint blockade therapy, and wherein the method optionally comprises administering a further anti-cancer agent which is optionally an antagonist of an immune co-inhibitory pathway, or an agonist of an immune co-stimulatory pathway and/or a tyrosine kinase inhibitor; and a method of treating cancer, which comprises administering a therapeutically effective amount of the virus or pharmaceutical composition of the disclosure to a patient in need thereof in combination with a tyrosine kinase inhibitor.

BRIEF DESCRIPTION OF THE FIGURES

FIG. 1 depicts the structure of an exemplary virus that comprises a gene encoding GALV-R− and a gene encoding GM-CSF inserted into the ICP34.5 gene locus, and in which the ICP47 gene is deleted such that the US11 gene is under the control of the ICP47 immediate early promoter (top panel). FIG. 1 also shows similar exemplary viruses expressing only a GALV-R-encoding gene (second panel), or only a GM-CSF-encoding gene (third panel). Also shown is an exemplary virus in which the ICP34.5 gene and the ICP47 gene are deleted, but without any inserted genes.

FIG. 2 depicts the structure of an exemplary virus that comprises a gene encoding GALV-R−, a gene encoding GM-CSF and a gene encoding CD40L.

FIG. 3 shows the differential abilities of the eight top ranking HSV1 clinical isolate strains as assessed by crystal violet staining 24 hours or 48 hours after infection with a MOI of 0.1, 0.01 or 0.001 as indicated in the Figure to kill Fadu, SK-mel-28, A549, HT1080, MIA-PA-CA-2, HT29 and MDA-MIB-231 human tumor cell lines. The virus strains ranked first and second on each cell line are indicated. The virus RH018A was ranked first on each of the Fadu, HT1080, MIA-PA-CA-2 and HT29 cell lines and second on each of the SK-mel-28, A549 and MDA-MB-231 cell lines. RH004A was ranked joint first with RH018A and RH015A on the HT29 cell line, first on the SK-mel-28 and A549 cell lines and second on the Fadu cell line. RH023A was ranked first on the MDA-M3-231 cell line and second on the HT1080 cell line. RH031A was ranked second on each of the MIA-PA-CA-2 and HT29 cell lines. RH040A was ranked joint second on the HT29 cell line.

FIG. 11 shows the antitumor effects of Virus 16 in Balb/c mice harboring mouse CT26 tumors in the left and right flanks. Groups of 10 mice were then treated with: Vehicle (3 injections into right flank tumors every other day); 5×10exp6 pfu of Virus 16 (mRP1) injected in the right flank tumor every other day; anti-mouse PD1 alone (10 mg/kg i.p. every three days, BioXCell clone RMP1-14); anti-mouse CTLA-4 (3 mg/kg i.p every three days, BioXCell clone 9D9); anti-mouse PD1 together with Virus 16; anti-mouse CTLA4 together with Virus 16; 1-methyl trypotophan (I-MT; IDO inhibitor (5 mg/ml in drinking water)); anti-mouse PD1 together with 1-methyl trypotophan; or anti-mouse PD1 together with 1-methyl trypotophan and Virus 16. Effects on tumor size were observed for a further 30 days. Greater tumor reduction was seen in animals treated with combinations of virus and checkpoint bockade than with the single treatment groups.

Figure 4:
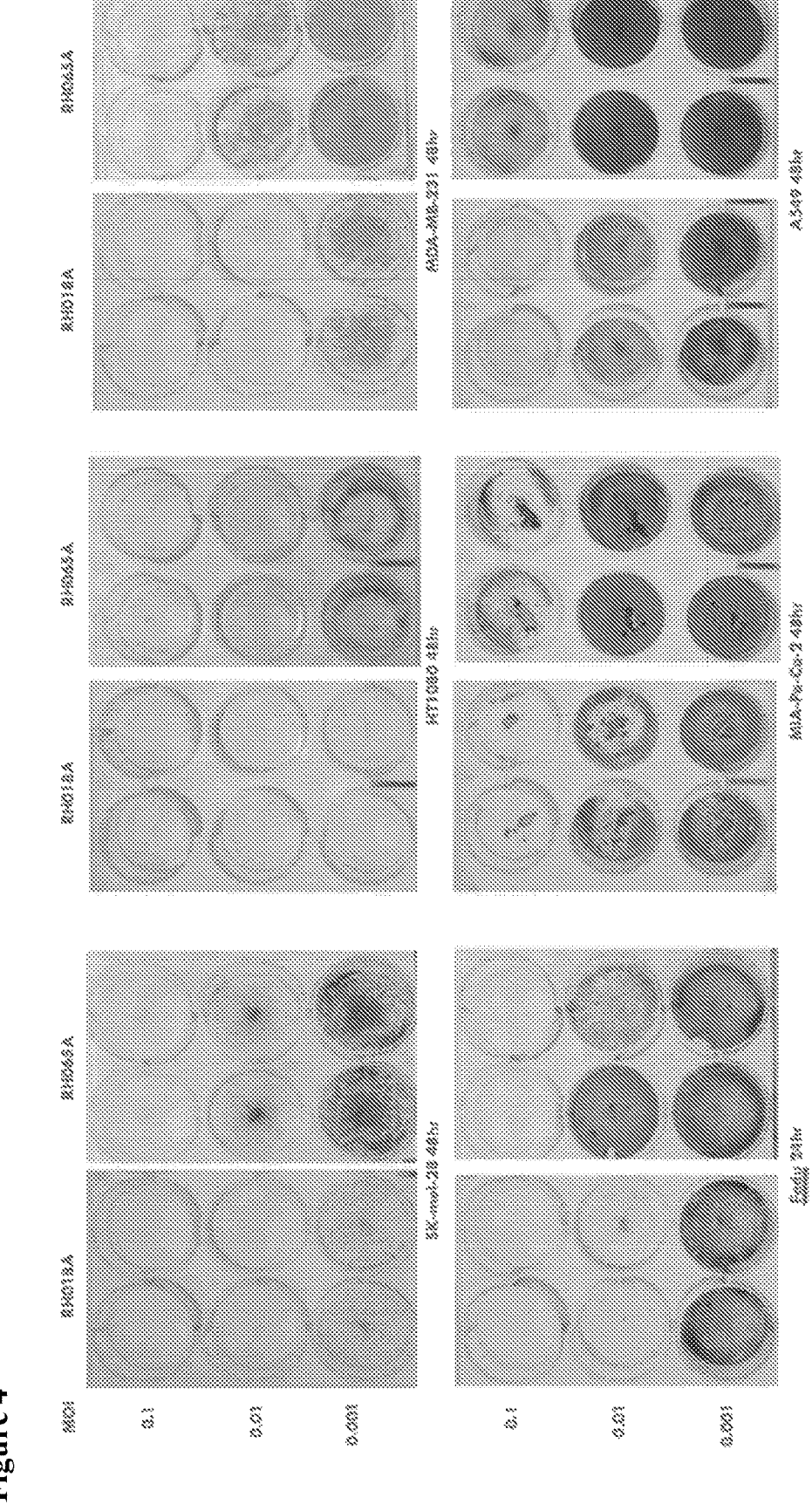
FIG. 4 shows a comparison between strain RH018A, the strain ranked first of all the strains tested, with an 'average' strain from the screen (i.e. strain RH065A). Approximately 10 fold less of strain RH018A was needed to kill an equal proportion of cells than was needed of strain RH065A as shown by crystal violet staining 24 or 48 hours post infection with MOIs of 0.1, 0.01 and 0.001 in SK-mel-28, HT1080, MDA-MB-231, Fadu, MIA-PA-CA-2 and A549 cell lines.
Figure 5A:
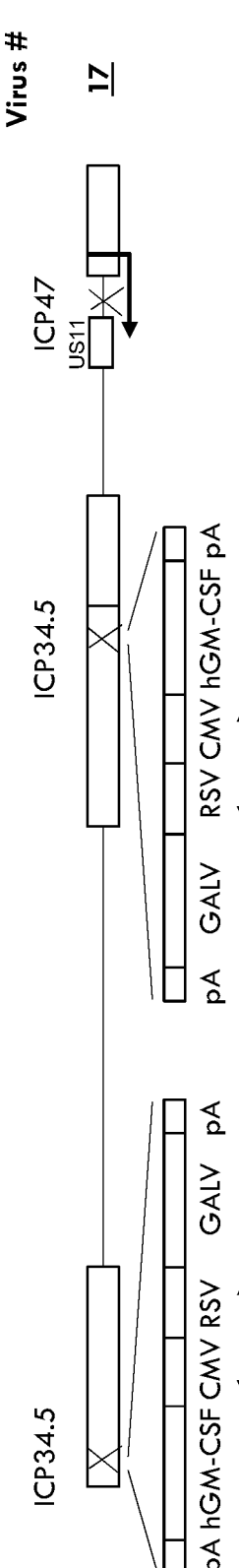
FIG. 5 depicts structures of HSV1 viruses modified by the deletion of ICP34.5 and ICP47 such that the US11 gene is under control of the ICP457 immediate early promoter and containing heterologous genes in the ICP34.5 locus. The viruses were constructed using the RH018A strain unless otherwise stated in the Figure.
Figure 5B:
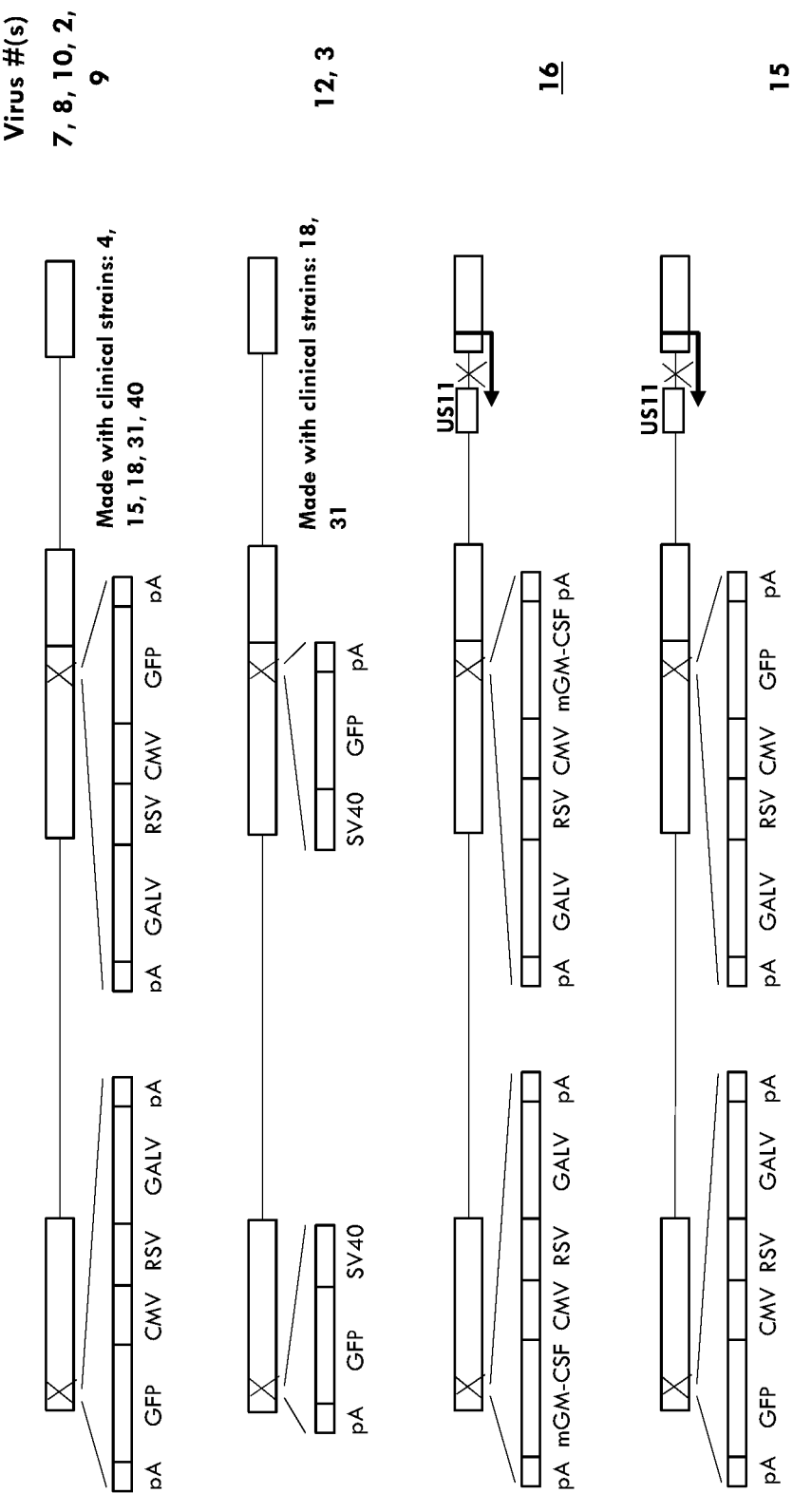
Figure 5C:
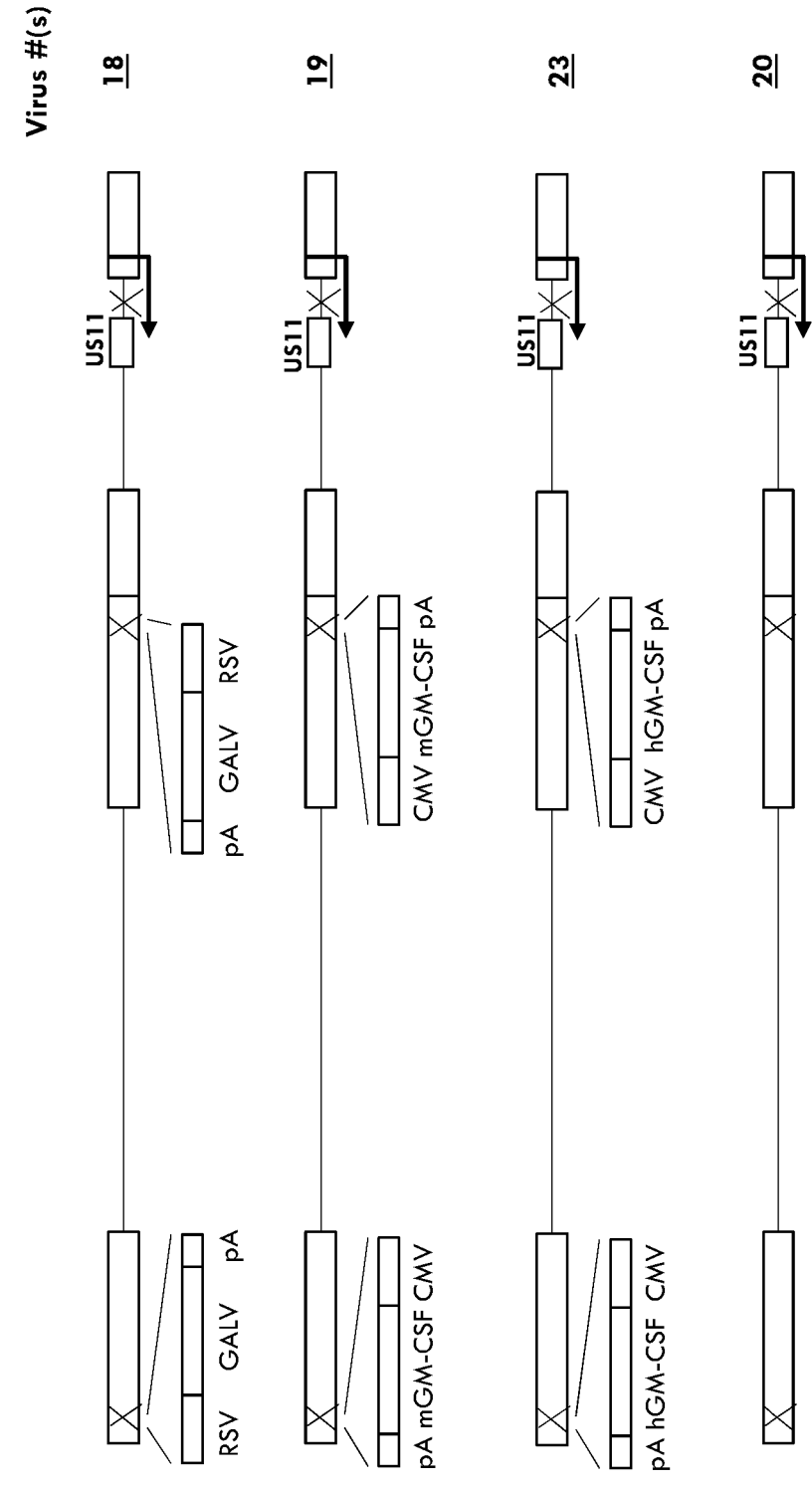
Figure 5D:
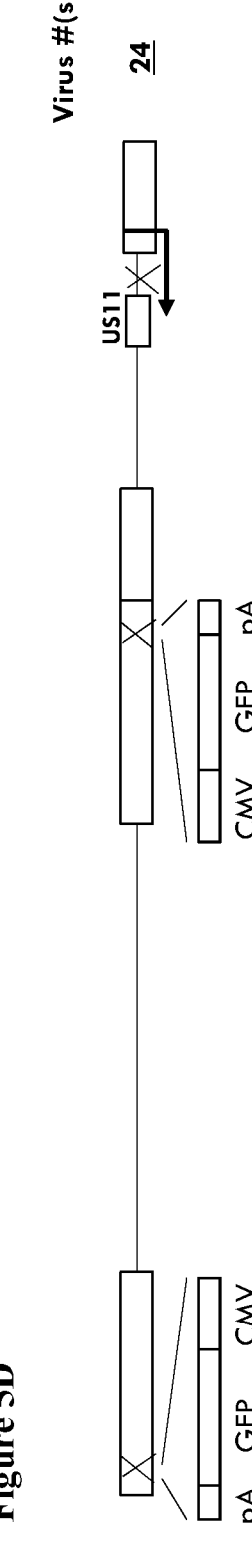
Figure 5E:
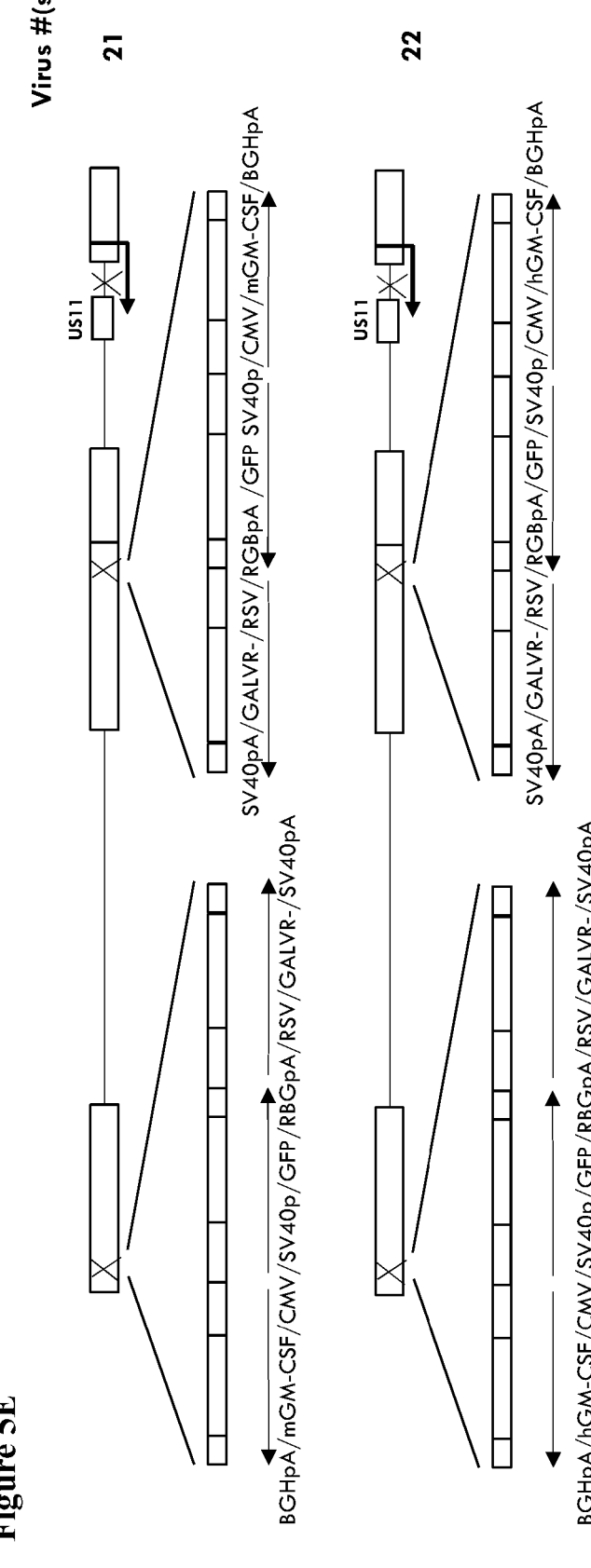
Figure 5I:
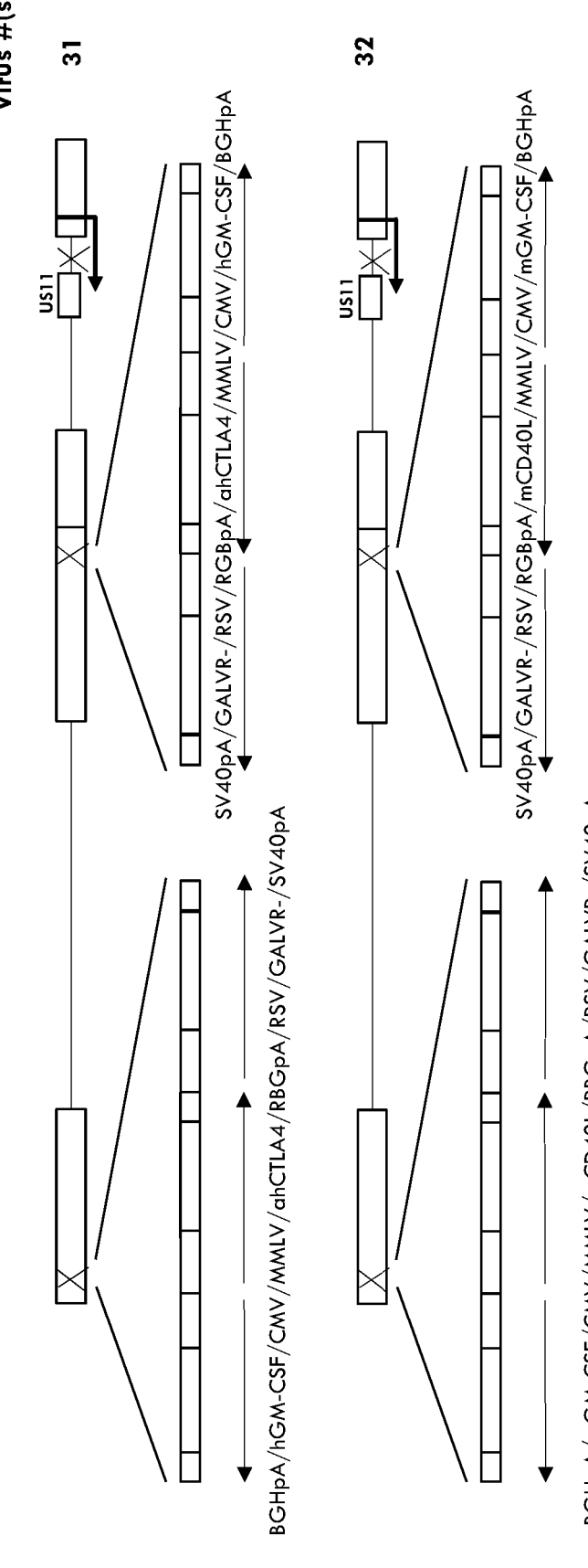
Figure 5K:
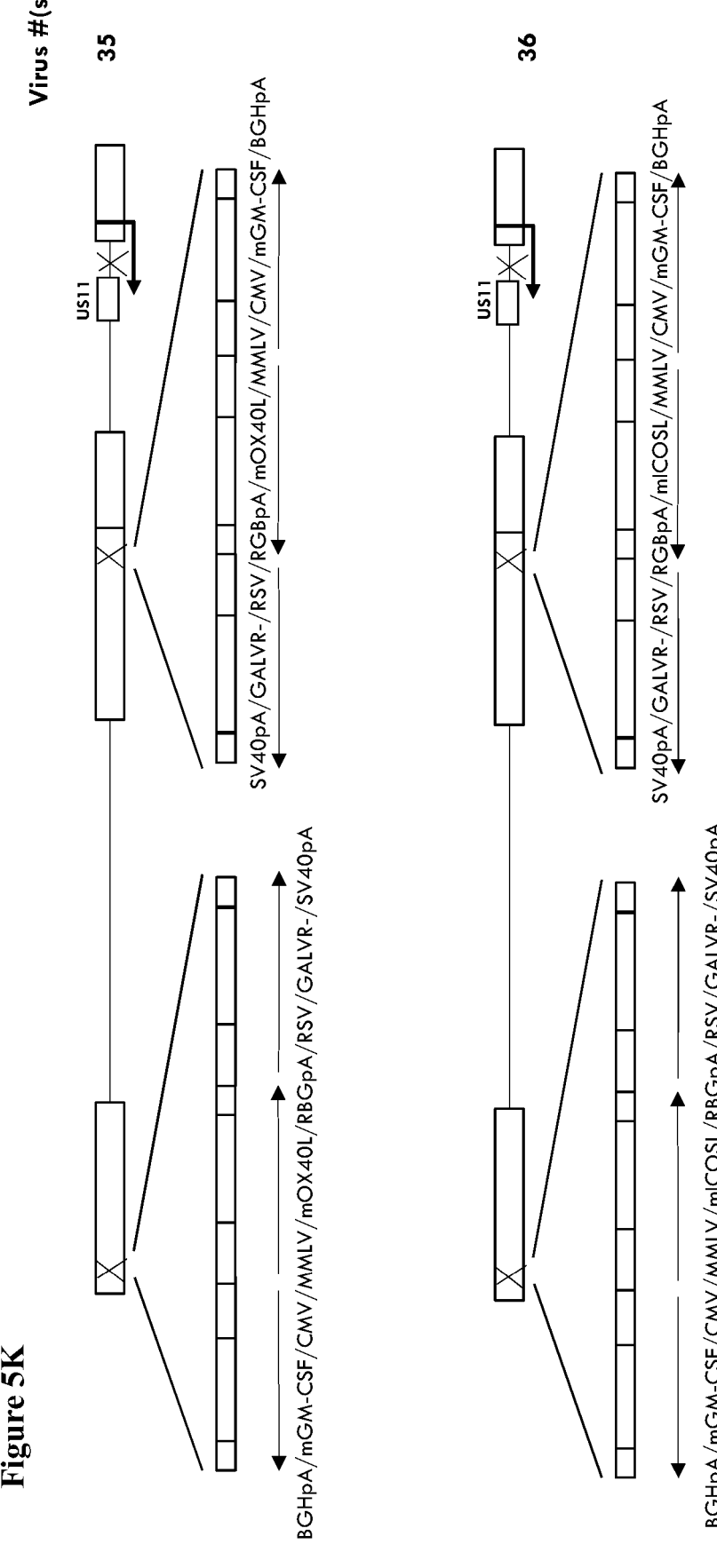

BRIEF DESCRIPTION OF THE SEQUENCE
LISTING

SEQ ID NO: 1 is the nucleotide sequence of mouse GM-CSF.

SEQ ID NO: 2 is the nucleotide sequence of a codon optimized version of mouse GM-CSF.

SEQ ID NO: 3 is the nucleotide sequence of human GM-CSF.

SEQ ID NO: 4 is the nucleotide sequence of a codon optimized version of human GM-CSF.

SEQ ID NO: 5 is the amino acid sequence of mouse GM-CSF.

SEQ ID NO: 6 is the amino acid sequence of human GM-CSF.

SEQ ID NO: 7 is the nucleotide sequence of GALV-R–.

SEQ ID NO: 8 is the nucleotide sequence of a codon optimized version of GALV-R– (the first three nucleotides are optional)

SEQ ID NO: 9 is the amino acid sequence of GALV-R–.

SEQ ID NO: 10 is the nucleotide sequence of a codon optimized version of a human membrane bound version of CD40L.

SEQ ID NO: 11 is the amino acid sequence of a human membrane bound version of CD40L.

SEQ ID NO: 12 is the nucleotide sequence of a codon optimized version of a multimeric secreted version of human CD40L.

SEQ ID NO: 13 is the amino acid sequence of a multimeric secreted version of human CD40L.

SEQ ID NO: 14 is the nucleotide sequence of a codon optimized version of a multimeric secreted version of mouse CD40L.

SEQ ID NO: 15 is the amino acid sequence of a multimeric secreted version of mouse CD40L.

SEQ ID NO: 16 is a codon optimized version of the nucleotide sequence of wild-type human CD40L.

SEQ ID NO: 17 is the amino acid sequence of wild-type human CD40L.

SEQ ID NO: 18 is a codon optimized version of the nucleotide sequence of wild-type mouse CD40L.

SEQ ID NO: 19 is the amino acid sequence of wild-type mouse CD40L.

SEQ ID NO: 20 is the nucleotide sequence of a codon optimized version of murine 4-1BBL.

SEQ ID NO: 21 is the nucleotide sequence of a codon optimized version of human 4-1BBL.

SEQ ID NO: 22 is the nucleotide sequence of a codon optimized version of secreted mouse 4-1BBL.

SEQ ID NO: 23 is the nucleotide sequence of a codon optimized version of human secreted 4-1BBL.

SEQ ID NO: 24 is the nucleotide sequence of a codon optimized version of murine GITRL.

SEQ ID NO: 25 is the nucleotide sequence of a codon optimized version of human GITRL.

SEQ ID NO: 26 is the nucleotide sequence of a codon optimized version of secreted murine GITRL.

SEQ ID NO: 27 is the nucleotide sequence of a codon optimized version of secreted human GITRL.

SEQ ID NO: 28 is the nucleotide sequence of a codon optimized version of murine OX40L.

SEQ ID NO: 29 is the nucleotide sequence of a codon optimized version of human OX40L.

SEQ ID NO: 30 is the nucleotide sequence of a codon optimized version of secreted murine OX40L.

SEQ ID NO: 31 is the nucleotide sequence of a codon optimized version of secreted human OX40L.

SEQ ID NO: 32 is the nucleotide sequence of a codon optimized version of murine ICOSL.

SEQ ID NO: 33 is the nucleotide sequence of a codon optimized version of human ICOSL.

SEQ ID NO: 34 is the nucleotide sequence of a murine scFv CTLA-4 antibody. The first six and last eight nucleotides are restriction sites added for cloning purposes.

SEQ ID NO: 35 is the nucleotide sequence of a murine scFv CTLA-4 antibody. The first six and last eight nucleotides are restriction sites added for cloning purposes.

SEQ ID NO: 36 is the nucleotide sequence of the CMV promoter.

SEQ ID NO: 37 is the nucleotide sequence of the RSV promoter.

SEQ ID NO: 38 is the nucleotide sequence of BGH polyA.

SEQ ID NO: 39 is the nucleotide sequence of SV40 late polyA.

SEQ ID NO: 40 is the nucleotide sequence of the SV40 enhancer promoter.

SEQ ID NO: 41 is the nucleotide sequence of rabbit beta-globulin (RBG) polyA.

SEQ ID NO: 42 is the nucleotide sequence of GFP.

SEQ ID NO: 43 is the nucleotide sequence of the MoMuLV LTR promoter.

SEQ ID NO: 44 is the nucleotide sequence of the EF1a promoter.

SEQ ID NO: 45 is the nucleotide sequence of HGH polyA.

SEQ ID NO: 46 is the light chain variable region amino acid sequence of the human CTLA-4 antibody used in the Examples.

SEQ ID NOs: 47 is the complete light chain amino acid sequence comprising the light chain variable region amino acid sequence of the human CTLA-4 antibody used in the Examples.

SEQ ID NO: 48 is the heavy chain variable region amino acid sequence of the human CTLA-4 antibody used in the Examples.

SEQ ID NO: 49 is the heavy chain CH1 amino acid sequence of the human CTLA-4 antibody used in the Examples.

SEQ ID NO: 50 is the heavy chain CH2/3 amino acid sequence of the human CTLA-4 antibody used in the Examples.

SEQ ID NO: 51 is the complete heavy chain amino acid sequence of the human CTLA-4 antibody used in the Examples.

SEQ ID NO: 52 is the amino acid sequence of the signal peptide present in the CTLA-4 antibodies of the Examples.

SEQ ID NO: 53 is the amino acid sequence of the linker present between the light chain variable region and the heavy chain variable region in the CTLA-4 antibodies of the Examples.

SEQ ID NO: 54 is the amino acid sequence of the human scFv CTLA-4 antibody of the Examples.

SEQ ID NO: 55 is the nucleotide sequence of the human scFv CTLA-4 antibody of the Examples.

SEQ ID NO: 56 is the light chain variable region amino acid sequence of the murine CTLA-4 antibody used in the Examples.

SEQ ID NO: 57 is the heavy chain variable region amino acid sequence of the murine CTLA-4 antibody used in the Examples.

SEQ ID NO: 58 is the complete heavy chain amino acid sequence of the murine CTLA-4 antibody used in the Examples.

SEQ ID NO: 59 is the amino acid sequence of the murine scFv CTLA-4 antibody of the Examples.

SEQ ID NO: 60 is the nucleotide sequence of the murine scFv CTLA-4 antibody of the Examples.

SEQ ID NO: 61 is the nucleotide sequence of the murine scFv CTLA-4 antibody of the Examples with inserted restriction sites for cloning purposes located at the N and C terminals, that is present in the exemplary virus. The restriction sites are the first six and last eight nucleotides of the sequence.

SEQ ID NO: 62 is the nucleotide sequence of the human scFv CTLA-4 antibody of the Examples with inserted restriction sites for cloning purposes located at the N and C terminals, that is present in the exemplary virus. The restriction sites are the first six and last eight nucleotides of the sequence.

DETAILED DESCRIPTION

Oncolytic Virus

The virus of the disclosure is oncolytic. An oncolytic virus is a virus that infects and replicates in tumor cells, such that the tumor cells are killed. Therefore, the virus of the disclosure is replication competent. Preferably, the virus is selectively replication competent in tumor tissue. A virus is selectively replication competent in tumor tissue if it replicates more effectively in tumor tissue than in non-tumor tissue. The ability of a virus to replicate in different tissue types can be determined using standard techniques in the art.

Oncolytic effects rely on the virus replicating in and killing initially infected cells, and progeny virions going on to infect and kill other tumor cells, spreading within the tumor as a result. Thus, the ability of the virus of the disclosure to effectively kill tumor cells and spread within tumors results in optimal direct anti-tumor effects. Efficient spread and virus replication associated lysis of tumor cells also maximises the amount of tumor antigen released and therefore also maximises the potency of the anti-tumor immune response induced.

The virus of the disclosure may be any virus which has these properties, including a herpes virus, pox virus, adenovirus, retrovirus, rhabdovirus, paramyxovirus or reovirus, or any species or strain within these larger groups. Viruses of the disclosure may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. In particularly preferred embodiments the virus of the disclosure is based on a clinical isolate of the virus species to be used. The clinical isolate may have been selected on the basis of it having particular advantageous properties for the treatment of cancer.

The clinical isolate/virus of the disclosure has surprisingly good anti-tumor effects compared to other strains of the same virus isolated from other patients, wherein a patient is an individual harbouring the virus species to be tested. The virus strains used for comparison to identify viruses of the disclosure may be isolated from a patient or an otherwise healthy (i.e. other than harboring the virus species to be tested) volunteer, preferably an otherwise healthy volunteer. HSV1 strains used to identify a virus of the disclosure are typically isolated from cold sores of individuals harboring HSV1, typically by taking a swab using e.g. Virocult (Sigma) brand swab/container containing transport media followed by transport to the facility to be used for further testing.

After isolation of viruses to be compared from individuals, stocks of the viruses are typically prepared, for example by growing the isolated viruses on BHK or vero cells. Preferably, this is done following no more than 3 cycles of freeze thaw between taking the sample and it being grown on, for example, BHK or vero cells to prepare the virus stock for further use. More preferably the virus sample has undergone 2 or less than 2 cycles of freeze thaw prior to preparation of the stock for further use, more preferably one cycle of freeze thaw, most preferably no cycles of freeze thaw. Lysates from the cell lines infected with the viruses prepared in this way after isolation are compared, typically by testing for the ability of the virus to kill tumor cell lines in vitro. Alternatively, the viral stocks may be stored under suitable conditions, for example by freezing, prior to testing. Viruses of the disclosure may have surprisingly good antitumor effects compared to other strains of the same virus isolated from other individuals, preferably when compared to those isolated from >5 individuals, more preferably >10 other individuals, most preferably >20 other individuals.

The stocks of the clinical isolates identified as viruses of the disclosure, or for modification to produce viruses of the disclosure (i.e. having surprisingly good properties for the killing of tumor cells as compared to other viral strains to which they were compared) may be stored under suitable conditions, before or after modification, and used to generate further stocks as appropriate.

A clinical isolate is a strain of a virus species which has been isolated from its natural host. The clinical isolate has preferably been isolated for the purposes of testing and comparing the clinical isolate with other clinical isolates of that virus species for a desired property, in the case of viruses of the disclosure that being the ability to kill human tumor cells. Clinical isolates which may be used for comparison also include those from clinical samples present in clinical repositories, i.e. previously collected for clinical diagnostic or other purposes. In either case the clinical isolates used for comparison and identification of viruses of the disclosure will preferably have undergone minimal culture in vitro prior to being tested for the desired property, preferably having only undergone sufficient culture to enable generation of sufficient stocks for comparative testing purposes. As such, the viruses used for comparison to identify viruses of the disclosure may also include deposited strains, wherein the deposited strain has been isolated from a patient, preferably an HSV1 strain isolated from the cold sore of a patient.

The virus of the disclosure may be an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel. Thus, the virus may be a clinical isolate that kills two or more tumor cell lines more rapidly and/or at a lower dose in vitro than one or more reference clinical isolates of the same species of virus, or may be a modified version of such a clinical isolate. The modified clinical isolate typically retains substantially the same tumor cell killing activity of the clinically isolated strain, but expresses one or more heterologous genes as disclosed herein to improve its anti-tumor properties and/or has one or more viral genes deleted to improve its selectivity for tumor cells.

Typically, the clinical isolate of the disclosure will kill two or more tumor cell lines within 72 hours, preferably within 48 hours, more preferably within 24 hours, of infection at multiplicities of infection (MOI) of less than or equal to 0.1, preferably less than or equal to an MOI of 0.01, more preferably less than or equal to an MOI of 0.001. Preferably the clinical isolate will kill a broad range of tumor cell lines, such as 2, 3, 4, 6, 7, 8, 9, 10 or, for example, all of the following human tumor cell lines: U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1(pancreas), HT1080 (fibrosarcoma).

Thus, the virus of the disclosure may be capable of killing cells from two or more, such as 3, 4, 5, 6, 7 or more, different types of tumor such as two or more, such as 3, 4, 5, 6, 7 or more, solid tumors, including but not limited to colorectal tumor cells, prostate tumor cells, breast tumor cells, ovarian tumor cells, melanoma cells, squamous cell carcinoma cells, lung tumor cells, pancreatic tumor cells, sarcoma cells and/or fibrosarcoma cells.

Tumor cell line killing can be determined by any suitable method. Typically, a sample is first isolated from a patient, preferably, in the case of HSV1, from a cold sore, is used to infect BHK cells, or another suitable cell line such as vero cells. Positive samples are typically identified by the presence of a cytopathic effect (CPE) 24-72 hours post infection, such as 48 hours post infection, and confirmed to be the target viral species by, for example, immunohistochemistry or PCR. Viral stocks are then generated from the positive samples. A sample from the viral stock is typically tested and compared to other samples generated in the same way using swabs from different patients. Testing may be carried out by determining the level of CPE achieved at a range of multiplicity of infection (MOI) and at various times post infection.

For example, cell lines at 80% confluency may be infected with the viral sample at MOI of 1, 0.1, 0.01 and 0.001 and duplicate plates incubated for 24 and 48 hours at 37° C., 5% $CO_2$ prior to determination of the extent of viral cell killing. This may be determined by, for example, fixing the cells with glutaraldehyde and staining with crystal violet using standard methods. The level of cell lysis may then be assessed by standard methods such as gross observation, microscopy (cell counts) and photography. The method may be repeated with the cells being incubated for shorter time periods, such as 8, 12 or 16 hours, or longer time periods, such as 72 hours, before cell killing is determined, or at additional MOIs such as 0.0001 or less.

Growth curve experiments may also be conducted to assess the abilities of different clinical isolates to replicate in tumor cell lines in vitro. For example, cell lines at 80% confluency may be infected with the viral sample at MOI of 1, 0.1, 0.01 and 0.001 are incubated at 37° C., 5% $CO_2$ and the cells lysed, typically by freeze/thawing, at 0, 8, 16, 24 and 48 hours post infection prior to determination of the extent of viral cell killing. This may be determined by, for example, assessing viral titres by a standard plaque assay.

A clinical isolate of the disclosure can kill infected tumor cell lines more rapidly and/or at a lower MOI than the other clinical isolates to which it is compared, preferably 2, 3, 4, 5 or 10 or more, other clinical isolates of the same virus species. The clinical isolates of the disclosure typically kill a 10%, 25% or 50% greater proportion of the tumor cells present at a particular MOI and time point than at least one, preferably 2, 3, 4, 5 or 10 or more, other clinical isolates of the same virus type at the same MOI and time point to which it was compared. The clinical isolate of the disclosure typically kills the same or a greater proportion of tumor cells at a MOI that is half or less than half that of the MOI at which one or more, preferably 2, 3, 4, 5, 10 or 15 or more, other clinical isolates of the same virus species used for the comparison at the same time point, typically at 12, 24 and/or 48 hours, kills the same proportion of tumor cells. Preferably, a clinical isolate of the disclosure typically kills the same or a greater proportion of tumor cells at a MOI that is 5 or 10 times lower than the MOI at which one or more, preferably 2, 3, 4, 5, 10 or 15 or more, other clinical isolates of the same virus used for the comparison at the same time point, typically at 12, 24 and/or 48 hours kills the same proportion of tumor cells. The improved tumor cell killing abilities of a virus of the disclosure are typically achieved compared to at least 50%, 75% or 90% of the other clinical isolates of the same viral species used for the comparison.

The virus is preferably compared to at least 4 other virus strains, such as, for example, 7, 9, 19, 39 or 49 other virus strains of the same species.

The isolated strains may be tested in batches, for example of 4-8 viral strains at a time, on, for example, 4-8 of the tumor cell lines at a time. For each batch of experiments, the degree of killing achieved is ranked on each cell line for the best (i.e. least surviving cells at each time point/MOI) to the worst (i.e. most surviving cells for each time point/MOI) for the viruses being compared in that experiment. The virus strains from each experiment which perform the best across the range of tumor cell line tested (i.e. that consistently ranked as one of the best at killing the cell lines) may then be compared head to head in further experiments using other clinical isolates and/ore other tumor cell lines to identify the best virus strains in the total of, for example, >20 virus strains sampled. Those ranked as the best overall are the viruses of the disclosure.

In a preferred embodiment, the virus of the disclosure is a strain selected from:

strain RH018A having the accession number ECACC 16121904;

strain RH004A having the accession number ECACC 16121902;

strain RH031A having the accession number ECACC 16121907;

strain RH040B having the accession number ECACC 16121908;

strain RH015A having the accession number ECACC 16121903;

strain RH021A having the accession number ECACC 16121905;

strain RH023A having the accession number ECACC 16121906; and strain RH047A having the accession number ECACC 16121909.

More preferably, the virus of the disclosure is a strain selected from:

strain RH018A having the accession number ECACC 16121904;

strain RH004A having the accession number ECACC 16121902;

strain RH031A having the accession number ECACC 16121907;

strain RH040B having the accession number ECACC 16121908; and strain RH015A having the accession number ECACC 16121903;

Most preferably, the virus of the disclosure is strain RH018A having the accession number ECACC 16121904. Any one of the deposited strains may be modified as defined herein.

An HSV of the disclosure is capable of replicating selectively in tumors, such as human tumors. Typically, the HSV replicates efficiently in target tumors but does not replicate efficiently in non-tumor tissue. This HSV may comprise one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5-encoding genes are mutated to confer selective oncolytic activity on the HSV. Mutations of the ICP34.5-encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, such as genes encoding fusogenic protein(s), immune modulatory molecules, for example GM-CSF or immune co-stimulatory pathway activating molecule(s), and/or genes encoding a CTLA-4 inhibitor) gene expression and increases the amount of tumor antigen released as tumor cells die, both of which may also improve the immunogenic properties of the therapy for the treatment of cancer. For example, in a preferred embodiment of the disclosure, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the disclosure. Such mutations allow expression of US11 before HSV replication occurs and enhance viral replication in tumors. In particular, such mutations enhance replication of an HSV lacking functional ICP34.5-encoding genes.

Accordingly, in one embodiment the HSV of the disclosure comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of β-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV IE promoter may be the promoter driving expression of ICP0, ICP4, ICP22, ICP27 or ICP47.

The genes referred to above, the functional inactivation of which may provide the property of tumor selectivity to the virus, may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the disclosure. Alternatively bacterial artificial chromosome (BAC)-based approaches may be used.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the disclosure it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5-encoding gene loci.

A virus of the disclosure may be used to express a fusogenic protein and/or an immune stimulatory protein in tumors. A virus of the disclosure is used to express GM-CSF and an immune co-stimulatory pathway activating molecule in tumors. A virus of the disclosure may be used to express a CTLA-4 inhibitor, and optionally GM-CSF, a fusogenic protein and/or an immune stimulatory protein in tumors. This is typically achieved by inserting a heterologous gene encoding the fusogenic protein and/or a heterologous gene encoding the immune stimulatory protein in the genome of a selectively replication competent virus. This is typically achieved by inserting a heterologous gene encoding GM-CSF and a heterologous gene encoding the immune co-stimulatory pathway activating molecule in the genome of a selectively replication competent virus. This is typically achieved by inserting a heterologous gene encoding a CTLA-4 inhibitor, and optionally a heterologous gene encoding GM-CSF and/or a heterologous gene encoding the immune co-stimulatory pathway activating molecule, in the genome of a selectively replication competent virus. Each gene is under the control of a promoter sequence. As replication of such a virus will occur selectively in tumor tissue, expression of the proteins encoded by the heterologous genes by the virus is also enhanced in tumor tissue as compared to non-tumor tissue in the body. Enhanced expression occurs where expression is greater in tumors as compared to other tissues of the body. Proteins expressed by the oncolytic virus would also be expected to be present in oncolytic virus-infected tumor draining lymph nodes, including due to trafficking of expressed protein and of virus in and on antigen presenting cells from the tumor. Accordingly, the disclosure provides benefits of expression of both a fusogenic protein and/or an immune stimulatory protein selectively in tumors combined with the anti-tumor effect provided by oncolytic virus replication. Accordingly, the disclosure provides benefits of expression of both GM-CSF and an immune co-stimulatory pathway activating molecule selectively in tumors and tumor draining lymph nodes combined with the anti-tumor effect provided by oncolytic virus replication. Accordingly, the disclosure provides benefits of expression of GM-CSF and an immune co-stimulatory pathway activating molecule selectively in tumors and tumor draining lymph nodes combined with the anti-tumor effect provided by oncolytic virus replication.

The virus of the disclosure may comprise one or more further heterologous genes in addition to the fusogenic protein and an immune stimulatory protein, including further fusogenic or immune stimulatory proteins.

The virus of the disclosure comprises GM-CSF. The sequences of the genes encoding heterologous proteins, for example, the gene encoding GM-CSF, may be codon optimized so as to increase expression levels of the respective proteins in target cells as compared to if the unaltered sequence is used.

Fusogenic Protein

The virus of the disclosure may comprise a gene encoding a fusogenic protein. The fusogenic protein may be any heterologous protein capable of promoting fusion of a cell infected with the virus of the disclosure to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R–versions). In a preferred embodiment the fusogenic protein is from GALV and has the R– peptide removed (GALV-R–).

The virus of the disclosure may comprise multiple copies of the fusogenic protein-encoding gene, preferably 1 or 2 copies. The virus may comprise two or more different fusogenic proteins, including any of the fusogenic proteins listed above.

The fusogenic protein or proteins expressed by a virus of the disclosure may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

Immune Stimulatory Molecule

The virus of the disclosure may comprise one or more immune stimulatory molecules and/or one or more genes encoding an immune stimulatory molecule, such as an immune co-stimulatory pathway activating molecule. Immune stimulatory molecules include proteins which may aid in the induction of an immune response, proteins which may relieve inhibitory signals to the induction or effectiveness of an immune response and RNA molecules (e.g. shRNA, antisense RNA, RNAi or micro RNA) which inhibit the expression of immune inhibitory molecules. Immune co-stimulatory pathway activating molecules include proteins and nucleic acid molecules (e.g. aptamer sequences).

Examples of immune stimulatory molecules include IL-2, IL12, IL-15, IL-18, IL-21, IL-24, CD40 ligand, GITR ligand, 4-1-BB ligand, OX40 ligand, ICOS ligand, flt3 ligand, TL1A, CD30 ligand, CD70, type I interferons, including interferon alpha and interferon beta, interferon gamma, type III interferon (IL-28, IL-29), other cytokines such as TNF alpha or GM-CSF, TGF beta or immune checkpoint antagonists. Immune checkpoint antagonists include antibodies, single chain antibodies targeting the respective receptors for these molecules (CD40, GITR, 4-1-BB, OX40, ICOS, ft3, DR3, CD30, CD27) and RNA1/ siRNA/microRNA/antisense RNA knockdown approaches. The CD40L, GITRL, 4-1-BBL, OX40L, ICOSL, ft3L, TL1A, CD30L or CD70L may be a modified version of any thereof, such as a soluble version.

Agonists of immune potentiating/co-stimulatory pathways include mutant or wild type, soluble, secreted and/or membrane bound ligands, and agonistic antibodies including single chain antibodies. With regard to the targeting of immune co-inhibitory or immune co-stimulatory pathways, proteins or other molecules (agonistic or antagonistic depending on the case) targeting CTLA-4 (antagonist), PD-1 (antagonist), PD-L1 (antagonist), LAG-3 (antagonist), TIM-3 (antagonist), VISTA (antagonist), CSF1R (antagonist), IDO (antagonist), CEACAM1 (antagonist), GITR (agonist), 4-1-BB (agonist), KIR (antagonist), SLAMF7 (antagonist), OX40 (agonist), CD40 (agonist), ICOS (agonist) or CD47 (antagonist) are particularly preferred. Viruses of the disclosure therefore preferably encode one or more of these molecules. More preferably viruses of the disclosure encode GM-CSF and/or a wild type or modified version of CD40L, ICOSL, 4-1-BBL, GITRL or OX40L, most preferably GM-CSF.

The inhibitor of a co-inhibitory pathway may be a CTLA-4 inhibitor. The CTLA-4 inhibitor is typically a molecule such as a peptide or protein that binds to CTLA-4 and reduces or blocks signaling through CTLA-4, such as by reducing activation by B7. By reducing CTLA-4 signalling, the inhibitor reduces or removes the block of immune stimulatory pathways by CTLA-4.

The CTLA-4 inhibitor is preferably an antibody or an antigen binding fragment thereof.

The term "antibody" as referred to herein includes whole antibodies and any antigen binding fragment (i.e., "antigen-binding portion") or single chains thereof. An antibody refers to a glycoprotein comprising at least two heavy (H) chains and two light (kappa)(L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')₂ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference. The scFv may be encoded by the nucleotide sequence shown in SEQ ID NO: 34 the nucleotide sequence shown in SEQ ID NO: 35.

The antibody encoding sequences typically encode an antibody or antibody fragment having a N-terminal signal sequence. The signal sequence may have the amino acid sequence shown in SEQ ID NO: 52. For example, this signal sequence is included in a scFv having the amino acid sequence shown in SEQ ID NO: 54 and encoded by the nucleotide sequence shown in SEQ ID NO: 55, and in a scFv having the amino acid sequence shown in SEQ ID NO: 59 and encoded by the nucleotide sequence shown in SEQ ID NO: 60.

In the antibody or antibody fragment, the light chain and heavy chain sequences may be joined by an amino acid linker. The linker typically comprises from about 15 to about 25 amino acids, such as about 18 or 20 amino acids. Any suitable linker may be used, such as linkers comprising glycine and serine residues, for example the amino acid sequence shown in SEQ ID NO: 53. For example, this linker is included in a scFv having the amino acid sequence shown in SEQ ID NO: 54 and encoded by the nucleotide sequence shown in SEQ ID NO: 55, and in a scFv having the amino acid sequence shown in SEQ ID NO: 59 and encoded by the nucleotide sequence shown in SEQ ID NO: 60. Both are preferred antibody fragments.

Other antibody fragments having similar structures are also preferred. Accordingly the virus an antibody or fragment comprising, or consisting essentially of, a light chain variable region, a linker a heavy chain variable region, a heavy chain CH1 domain, a heavy chain CH2 domain and a heavy chain CH3 domain. The virus may further encode a signal sequence at the N-terminus of the antibody.

The antibodies or antibody fragments may virus comprise an Fc region which is an IgG1, IgG2, IgG3 or IgG4 region an IgG1 region. Preferably, the antibody is an scFv antibody in which the scFv is linked to IgG heavy chain CH2 and CH3 domains.

A preferred CTLA-4 antibody or fragment comprises the heavy chain variable region shown in SEQ ID NO: 48 and/or the light chain variable region shown in SEQ ID NO: 46 or the heavy chain variable region shown in SEQ ID NO: 56 and/or the light chain variable region shown in SEQ ID NO: 57. The antibody may comprise the heavy chain CH1 domain having the amino acid sequence shown in SEQ ID NO: 4 and/or the CH2/CH3 domains shown in SEQ ID NO: 50. The antibody may comprise the light chain amino acid sequence shown in SEQ ID NO: 47. The antibody may alternatively comprise a variant of one of these heavy or light chain variable regions or CDR sequences. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above, whilst maintaining the activity of the antibodies described herein. "Deletion" variants may comprise the deletion of, for example, 1, 2, 3, 4 or 5 individual amino acids or of one or more small groups of amino acids such as 2, 3, 4 or 5 amino acids. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

The virus of the disclosure comprises one or more polynucleotide sequence encoding the CTLA-4 inhibitor. The polynucleotide sequence is under the control of a suitable promoter. The virus may comprise a first polynucleotide sequence encoding an antibody heavy chain variable region and a second polynucleotide encoding an antibody light chain variable region. The first polynucleotide may encode a full length heavy chain and/or the second polynucleotide may encode a full length light chain. The first and second polynucleotide may be under the control of a single promoter, optionally with an IRES, or may be under the control of two separate promoters. The separate promoters may be the same or different.

The first polynucleotide may comprise, consist essentially of, or consist of, the heavy chain variable region encoding sequence shown in SEQ ID NO: 54 and/or the second polynucleotide may comprise, consist essentially of, or consist of, the heavy chain variable region encoding sequence shown in SEQ ID NO: 55. The first polynucleotide may comprise, consist essentially of, or consist of, the heavy chain variable region encoding sequence shown in SEQ ID NO: 2 and/or the second polynucleotide may comprise, consist essentially of, or consist of, the heavy chain variable region encoding sequence shown in SEQ ID NO: 3.

A first and/or second polynucleotide sequences may be a variant of SEQ ID NO: 54, 55, 2 or 3. For example, a variant may be a substitution, deletion or addition variant of either of these nucleic acid sequences. A variant polynucleotide may comprise 1, 2, 3, 4, 5, up to 10, up to 20, up to 30, up to 40, up to 50, up to 75 or more nucleic acid substitutions and/or deletions from SEQ ID NO: 54, 55, 2 or 3.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids. The codons may be optimized so as to increase expression levels of the encoded proteins in target cells as compared to if the unaltered sequence is used.

The virus of the disclosure preferably comprises GM-CSF. The sequence of the gene encoding GM-CSF may be codon optimized so as to increase expression levels of the respective proteins in target cells as compared to if the unaltered sequence is used.

The virus of the disclosure preferably comprises one or more immune co-stimulatory pathway activating molecules and/or one or more genes encoding an immune co-stimulatory pathway activating molecule. Immune co-stimulatory pathway activating molecules include proteins and nucleic acid molecules (e.g. aptamer sequences). Examples of immune co-stimulatory pathway activating molecules include CD40 ligand, GITR ligand, 4-1-BB ligand, OX40 ligand, ICOS ligand, flt3 ligand, TL1A, CD30 ligand, CD70 and single chain antibodies targeting the respective receptors for these molecules (CD40, GITR, 4-1-BB, OX40, ICOS, flt3, DR3, CD30, CD27).

Activators of immune co-stimulatory pathway include mutant or wild type, soluble, secreted and/or membrane bound ligands, and agonistic antibodies including single chain antibodies. Viruses of the disclosure preferably encode one or more of CD40L, ICOSL, 4-1-BBL, GITRL or OX40L.

Viruses of the disclosure may encode one or more immune stimulatory molecules, preferably 1, 2, 3 or 4 immune stimulatory molecules, more preferably 1 or 2 immune stimulatory molecules.

Viruses of the disclosure may encode one or more immune co-stimulatory pathway activating molecules, preferably 1, 2, 3 or 4 immune co-stimulatory pathway activating molecules, more preferably 1 or 2 immune co-stimulatory pathway activating molecules.

For example, the virus may comprise genes encoding:
CD40L and one or more of ICOSL, 4-1-BBL, GITRL, OX40L and a CTLA-4 inhibitor;
ICOSL and one or more of CD40L, 4-1-BBL, GITRL, OX40L and a CTLA-4 inhibitor;
4-1-BBL and one or more of CD40L, ICOSL, GITRL, OX40L and a CTLA-4 inhibitor;
GITRL and one or more of CD40L, ICOSL, 4-1-BBL, OX40L and a CTLA-4 inhibitor;
OX40L and one or more of CD40L, ICOSL, 4-1-BBL, GITRL and a CTLA-4 inhibitor;
a CTLA-4 inhibitor and one or more of CD40L, ICOSL, 4-1-BBL, GITRL and OX40L.

The sequence of the gene encoding the immune stimulatory molecule, such as the immune co-stimulatory activating molecule, may be codon optimized so as to increase expression levels of the respective protein(s) in target cells as compared to if the unaltered sequence is used.

The virus of the disclosure may in some embodiments comprise one or more further heterologous genes in addition to GM-CSF and/or an immune co-stimulatory pathway activating molecule and/or a CTLA-4 inhibitor. In a preferred embodiment, the virus may further comprise a fusogenic protein such as GALVR–.

The fusogenic protein may be any heterologous protein capable of promoting fusion of a cell infected with the virus of the disclosure to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R– versions). In a preferred embodiment the fusogenic protein is from GALV and has the R– peptide removed (GALV-R–).

The virus of the disclosure may optionally comprise multiple copies of the fusogenic protein-encoding gene, preferably 1 or 2 copies. The virus may comprise two or more different fusogenic proteins, including any of the fusogenic proteins listed above.

The fusogenic protein or proteins optionally expressed by a virus of the disclosure may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic may, for example, be modified to increase the fusogenic properties of the encoded protein, or to provide codon optimisation and therefore increase the efficiency of expression of the encoded protein.

Modification of Virus Strains

Modified viruses of the disclosure are modified versions of viruses, such as modified versions of clinical isolates identified as having advantageous properties for killing tumor cells as compared to other virus strains used for the comparison. Modified viruses of the disclosure are constructed using methods well known in the art. For example plasmids (for smaller viruses and single and multiple genome component RNA viruses) or BACS (for larger DNA viruses including herpes viruses) encoding the viral genome to be packaged, including any genes encoding desired hererologous genes, such as genes encoding fusogenic and/ or immune stimulating molecules, under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental virus, such as the parental clinical isolate, occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding at least one heterologous protein, such as, for example, a fusogenic protein and an immune stimulatory molecule, or GM-CSF and an immune co-stimulatory pathway activating molecule, and/or a CTLA-4 inhibitor. In this case, the parental virus, such as the parental clinical isolate, may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

Heterologous genes, such as fusogenic protein encoding sequences, immune stimulatory molecule encoding sequences, for example CTLA-4 inhibitor encoding sequences, GM-CSF encoding sequences and/or immune co-stimulatory pathway activating molecule encoding sequences may be inserted into the viral genome under appropriate regulatory control. This may be under the regulatory control of natural promoters of the virus species of the disclosure used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR, other retroviral LTR promoters, or promoters derived from SV40. Preferably each exogenous gene (e.g. encoding the fusogenic protein, immune modulatory molecule, GM-CSF, immune co-stimulatory pathway activating molecule and/or CLT-4 inhibitor) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine or human growth hormone (BGH) poly A sequence, synthetic polyadenylation sequences, the rabbit betaglobin polyadenylation sequence, or viral sequences such as the SV40 early or late polyadenylation sequence).

The disclosure also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV (SEQ ID NO:43), also known as MoMuLV. The heterologous genes may be terminated by poly adenylation sequences. The poly adenylation sequences may be the same or different. Preferably each heterologous gene is terminated by a different poly adenylation sequence, which is preferably selected from the BGH, SV40, HGH and RBG poly adenylation sequences.

The disclosure also provides a virus, such as a pox virus or a HSV, preferably HSV1, which expresses at least three heterologous genes, wherein each of the three heterologous genes is terminated by a different poly adenylation sequence selected from the BGH, SV40, HGH and RBG poly adenylation sequences. The virus may, for example, express four heterologous genes terminated by each of the BGH, SV40, HGH and RBG poly adenylation sequences, respectively.

Each of the heterologous genes in the virus is typically under the control of a promoter. The promoters controlling expression of the heterologous genes may be the same or different. For example, the anti-CTLA-4, and one or more of the GM-CSF, fusogenic gene and immune co-stimulatory pathway activating molecule-encoding gene may each be under the control of the CMV promoter, the RSV promoter, the EF1a promoter, the SV40 promoter or a retroviral LTR promoter. Alternatively, for example, the anti-CTLA-4 may be under the control of a retroviral LTR promoter such as the MMLV promoter, the GM-CSF gene may be under the control of the CMV promoter and/or the fusogenic gene, such as GALVR– may be under the control of the RSV promoter.

The at least three heterologous genes may, for example, be selected from a CTLA-4 inhibitor, a gene encoding GM-CSF, a gene encoding an immune co-stimulatory pathway activating molecule and a fusogenic gene. Examples of the three heterologous genes are a CTLA-4 inhibitor, a gene encoding GM-CSF and a gene encoding an immune co-stimulatory pathway activating molecule; a CTLA-4 inhibitor, a gene encoding GM-CSF and a fusogenic gene; and a CTLA-4 inhibitor, a gene encoding an immune co-stimulatory pathway activating molecule and a fusogenic gene. The four heterologous genes may, for example, be a CTLA-4 inhibitor, a gene encoding GM-CSF, a gene encoding an immune co-stimulatory pathway activating molecule and a fusogenic gene. The three or four heterologous genes may comprise, for example, two ore more genes encoding immune co-stimulatory pathway activating molecules and/or two ore more fusogenic genes.

In one embodiment, the promoters controlling expression of the three heterologous genes are the CMV, RSV and MMLV promoters. For example, a preferred virus may comprise a GM-CSF gene under the control of a CMV promoter, a GALV gene under the control of a RSV promoter and a CTLA-4 inhibitor under the control of a MMLV promoter.

In one embodiment, the polyadenylation sequence terminating the at least three heterologous genes are SV40, BGH and RBG polyadenylation sequences. controlling expression of the three heterologous genes are the CMV, RSV and MMLV promoters. For example, a preferred virus may comprise a GM-CSF gene terminated by a BGH polyadenylation sequence, a GALV gene terminated by a SV40 polyadenylation sequence and a CTLA-4 inhibitor terminated by a RGB polyadenylation sequence.

Any combination of the various promoters and polyadenylation sequences may be used with any of the heterologous genes. For example, a preferred virus may comprise a GM-CSF gene under the control of a CMV promoter and terminated by a BGH polyadenylation sequence, a GALV gene under the control of a RSV promoter and terminated by a SV40 polyadenylation sequence, and a CTLA-4 inhibitor under the control of a MMLV promoter terminated by a RGB polyadenylation sequence.

Pharmaceutical Compositions The disclosure provides a pharmaceutical composition comprising a virus of the disclosure and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this disclosure, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present disclosure also provides a product of manufacture comprising a virus of the disclosure in a sterile vial, ampoule or syringe.

Medical Uses/Methods of Treatment

The disclosure provides the virus of the disclosure for use in the treatment of the human or animal body by therapy, particularly for use in a method of treating cancer. The cancer is typically in a mammal, preferably in a human. The virus kills infected tumour cells by virus mediated toxicity, including by lysis, necrosis or apoptosis, preferably by lysis or necrosis, and where the virus encodes a fusogenic protein by causing infected tumor cells to fuse with one another. The virus of the disclosure also elicits a systemic anti-tumor immune response, augmented through the expression of the immune stimulatory molecule, for example through expression of GM-CSF and an immune co-stimulatory pathway activating molecule, which also kills cancer cells.

The disclosure also provides a method of treating cancer, the method comprising administering a therapeutically effective amount of the virus of the disclosure to an individual in need thereof.

The disclosure additionally provides the use of the virus of the disclosure in the manufacture of a medicament for treating cancer.

The virus of the disclosure is particularly useful in treating any solid tumor including any adenocarcinoma, carcinoma, melanoma or sarcoma. For example, the virus of the disclosure is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The cancer is preferably selected from cutaneous squamous cell carcinoma (CSCC), renal cell carcinoma (RCC), non-small cell lung cancer (NSCLC), triple negative breast cancer (TNBC), small cell lung cancer (SCLC), advanced recurrent head and neck cancer, squamous cell carcinoma of the head and neck (SCCHN), nasopharyngeal carcinoma (NPC), hepatocellular carcinoma (HCC), anal cancer, colorectal cancer (CRC), basal cell carcinoma (BCC), Merkel cell carcinoma, appendiceal carcinoma, sarcoma of the skin, recurrent melanoma after surgery, advanced or metastatic urothelial carcinoma, liver metastases, microsatellite instability high cancer (MSI-H), mixed advanced solid tumors, virally caused cancer, locoregionally advanced cancer, and pediatric cancer. The basal cell cancer may, for example, be basal cell cancer of the skin. The NMSC may, for example, be a rare skin malignancy such as any one of dermatofibroma protuberans, angiosarcoma of the skin, non-HIV-related Kaposi's sarcoma, sebaceous cell carcinoma or eccrine carcinoma. The MSI-H tumor may, for example, occur in any one of the following cancer types: endometrial, ovarian, gastric, colorectal, pancreas, ovary, prostate, central nervous system and NSCLC. The virally caused cancer may, for example, be caused by HBV or HPV. The liver metastases may be of any tumor type. The cancer may be in patients with no or minimal pre-existing anti-cancer immunity, in previously treated patients, in patients who have not received checkpoint blockade therapy or in patients who have received checkpoint blockade therapy. For example, previously treated patients include those with bladder cancer who have failed platinum-containing chemotherapy. The treatment may be a first line therapy.

The virus of the disclosure may be used to treat malignant tumors, including tumors that have metastasized from the site of the original tumor. In this embodiment, the virus may be administered to the primary tumor or to one or more secondary tumors.

The virus of the disclosure may be administered in combination with other therapeutic agents, including chemotherapy, targeted therapy, immunotherapy (including immune co-inhibitory pathway blockade (immune checkpoint bloackade) or immune co-stimulatory pathway activation, such as using one or more antagonist of an immune co-inhibitory pathway and/or one or more agonist of an immune co-stimulatory pathway) and/or in combination with radiotherapy and/or in combination with any combination of these. The therapeutic agent is preferably an anti-cancer agent.

The therapeutic agent may be a tyrosine kinase inhibitor, such as a MEK inhibitor, such as for example trametinib, a BRAF inhibitor, such as for example verurafenib and/or dabrafenib and/or a PI3 kinase inhibitor.

The virus of the disclosure may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs) or myeloid derived suppressor cells (MDSCs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbaxine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Examples of suitable anti-PD-1 antibodies include nivolumab, pembrolizumab and cemiplimab. Examples of suitable anti-PD-L1 antibodies include avelumab, durvalumab and atezolizumab.

Immunotherapeutic agents may also include bi-specific antibodies, cell based-therapies based on dendritic cells, NK cells or engineered T cells such CAR-T cells or T cells expressing engineered T cell receptors. Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the disclosure may be used: in combination with dacarbazine, a BRAF inhibitor and/or CTLA-4, PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyl-tryptophan, indoximod (1-methyl-D-tryptophan), GDC-0919 or F001287.

The mechanism of action of IDO in suppressing anti-tumor immune responses may also suppress immune responses generated following oncolytic virus therapy. IDO expression is induced by toll like receptor (TLR) activation and interferon-γ both of which may result from oncolytic virus infection. One embodiment of the use of oncolytic virus therapy for cancer treatment includes combination of an oncolytic virus, including a virus expressing an immune stimulating protein or proteins and/or a fusogenic protein, or a virus expressing GM-CSF and an immune co-stimulatory pathway activating molecule or molecules and/or one or more additional protein encoding sequences, such as a sequence encoding a fusogenic protein such as GALVR–, and/or a virus expressing CTLA-4 inhibitor, with an inhibitor of the IDO pathway and optionally one or more further antagonist of an immune co-inhibitory pathway and/or one or more agonist of an immune co-stimulatory pathway, including those targeting CTLA-4, PD-1 and/or PD-L1.

The disclosure also provides a method of treating cancer, which comprises administering a therapeutically effective amount of an oncolytic virus, an inhibitor of the indoleamine 2,3-dioxygenase (IDO) pathway and a further antagonist of an immune co-inhibitory pathway, and/or an agonist of an immune co-stimulatory pathway to a patient in need thereof.

The oncolytic virus is preferably a modified clinical isolate. The oncolytic virus is preferably a pox virus, more preferably a HSV, such as a HSV1 and/or a HSV rendered functionally inactive for ICP34.5 and/or ICP47. The oncolytic virus may express an immune stimulating molecule, such as GM-CSF and/or co-stimulatory pathway encoding molecule such as CD40L, GITRL, OX4OL, 4-I-BBL, ICOSL or ft3, and/or a an inhibitor of CTLA-4, and/or a fusogenic protein, such as the GALV fusogenic glycoprotein with the R sequence mutated or deleted. The further antagonist of an immune co-inhibitory pathway is preferably an antagonist of CTLA-4, an antagonist of PD1 or an antagonist of PD-L1. For example, the further antagonist of an immune co-inhibitory pathway may be an inhibitor of the interaction between PD1 and PD-L1.

Where a therapeutic agent and/or radiotherapy is used in conjunction with a virus of the disclosure, administration of the virus and the therapeutic agent and/or radiotherapy may be contemporaneous or separated by time. The composition of the disclosure may be administered before, together with or after the therapeutic agent or radiotherapy. The method of treating cancer may comprise multiple administrations of the virus of the disclosure and/or of the therapeutic agent and/or radiotherapy. A skilled practitioner will readily be able to determine suitable courses of administration of the virus and the therapeutic agent.

In preferred embodiments, in the case of combination with one or more antagonist of an immune co-inhibitory pathway (checkpoint blockade), one or more agonist of an immune co-stimulatory pathway and/or other immune potentiating agents, the virus of the disclosure is administered once or multiple times prior to the concurrent administration of the antagonist of an immune co-inhibitory pathway (immune checkpoint blockade), agonist of an immune co-stimulatory pathway and/or other immune potentiating agent or agents thereafter, or concurrent with the administration of the antagonist of an immune co-inhibitory pathway (immune checkpoint blockade), agonist of an immune co-stimulatory pathway and/or other immune potentiating agent or agents without prior administration of the virus of the disclosure.

The virus of the disclosure may be administered to a subject by any suitable route. Typically, a virus of the disclosure is administered by direct intra-tumoral injection, including through the use of imaging guidance to target the tumor or tumors. Intra-tumoral injection includes direct injection into superficial skin, subcutaneous or nodal tumors, and imaging guided (including CT, MRI or ultra-sound) injection into deeper or harder to localize deposits including in visceral organs and elsewhere. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the disclosure can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In different embodiments, the compositions are administered by intravenous infusion, orally, or directly into a tumor. It is preferred that the virus is administered directly into a tumor.

The virus and/or therapeutic agent may be administered to a subject in an amount that is compatible with the dosage composition that will be therapeutically effective. The administration of the virus of the disclosure is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer, an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention (e.g. as neoadjuvant therapy, e.g. following recurrence or incomplete removal of tumors following surgery), preferably before surgical intervention (either for resection of primary or recurrent/metastatic disease), or following recurrence following surgery or following incomplete surgical removal of disease, i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu, such as $10^4$, $10^5$ or $10^6$ pfu. In the case of HSV, an initial lower dose (e.g. $10^4$ to $10^7$ pfu, such as $10^6$ pfu) may be given to patients to seroconvert patients who are seronegative for HSV and boost immunity in those who are seropositive, followed by a higher dose then being given thereafter (e.g. $10^6$ to $10^9$ pfu, such as $10^8$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor. The virus may also be administered by injection into a blood vessel or into a body cavity. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention.

Example 1. Clinical Isolates with Improved Antitumor Effects

The virus species used to exemplify the invention is HSV, specifically HSV1. Cold sore swabs were taken from more than 20 otherwise healthy volunteers. A sample of each swab was used to infect BHK cells. Samples containing HSV1 were identified by the presence of a cytopathic effect (CPE) 24-72 hours post infection and by immunohistochemistry and viral stocks of the primary clinical isolates were generated from the positive samples.

The abilities of the primary clinical isolates of HSV1 to kill a panel of human tumor-derived cell lines is tested and the virus strain with the greatest ability to kill a broad range of these rapidly, and at low dose is chosen. Tumor cell lines used for this comparison are HT29 (colorectal), MDA-MB-231 (breast), SK-MEL-28 (melanoma), Fadu (squamous cell carcinoma), MCF7 (breast), A549 (lung), MIAPACA-2 (pancreas), CAPAN-1(pancreas), HT1080 (fibrosarcoma). The cell lines are used to test for the level of CPE achieved at a range of MOI and times post infection for each of the primary clinical isolates.

More specifically, the tumor cell lines are used to seed multi-well tissue culture plates so that they are about 80% confluent on the day of infection. Representative wells from each tumor cell line are trypsinised and the number of cells in the well determined. These cell counts are used to determine the volume of each clinical isolate required to give an MOI of 1, 0.1, 0.01 and 0.001. Separate wells of a tumor cell line are infected with the clinical isolate at these MOI and overlaid with growth media and carboxymethyl-cellulose. All infections are carried out in quadruplicate. Duplicate wells are incubated for 24 hours and duplicate wells are incubated for 48 hours, both at 37° C., 5% $CO_2$, prior to fixation of the cells with glutaraldehyde and staining with crystal violet. The level of cell lysis is then assessed by gross observation, microscopy (cell counts) and photography or using a metabolic assay such as an MTT assay.

Growth curve experiments are also conducted to assess the abilities of different clinical isolates to replicate in tumor cell lines in vitro. The tumor cell lines are used to seed multi-well tissue culture plates so that they are about 80% confluent on the day of infection. Cell counts are determined as above and used to determine the volume of virus to give MOIs of 1, 0.1, 0.01 and 0.001. The tumor cells are infected in duplicate for MOI and time point. The infected cells are incubated at 37° C., 5% $CO_2$ and the cells lysed by freeze/thawing at 0, 8, 16, 24 and 48 hours post infection. Viral titres are assessed by a standard plaque assay.

Example 2. Modification of Clinical Isolates

In this example the clinical isolate selected in Example 1 is modified by deletion of ICP47 from the viral genome using homologous recombination with a plasmid containing regions flanking HSV1 nucleotides 145300 to 145582 (HSV1 nucleotides 145300 to 145582 being the sequences to be deleted; HSV1 strain 17 sequence Genbank file NC 001806.2) between which are encoded GFP. GFP expressing virus plaques are selected, and GFP then removed by homologous recombination with the empty flanking regions and plaques which do not express GFP are selected. This results in an ICP47 deleted virus in which US11 is expressed as an IE protein as it is now under the control of the ICP47 promoter. ICP34.5 is then deleted using homologous recombination with a plasmid containing regions flanking HSV1 nucleotides 124953 to 125727 (HSV1 nucleotides 124953 to 125727 being the sequences to be deleted; HSV1 strain 17 sequence Genbank file NC 001806.2) between which GFP is encoded. GFP expressing virus plaques are again selected, and GFP then removed by homologous recombination with the same flanking regions but between which are now an expression cassette comprising a codon optimized version of the mouse GM-CSF sequence and a codon optimized version of the GALV R− sequence driven by the CMV IE promoter and RSV promoter respectively, in a back to back orientation and again selecting virus plaques which do not express GFP. This virus construction is performed using methods which are standard in the art.

GFP expressing virus plaques are again selected, and GFP then removed by homologous recombination with the same flanking regions but between which are now an expression cassette comprising a codon optimized version of the mouse GM-CSF sequence and a codon optimized version of the GALV R− sequence driven by the CMV IE promoter and RSV promoter respectively, in a back to back orientation and again selecting virus plaques which do not express GFP. This virus construction is performed using methods which are standard in the art.

Figure 1:
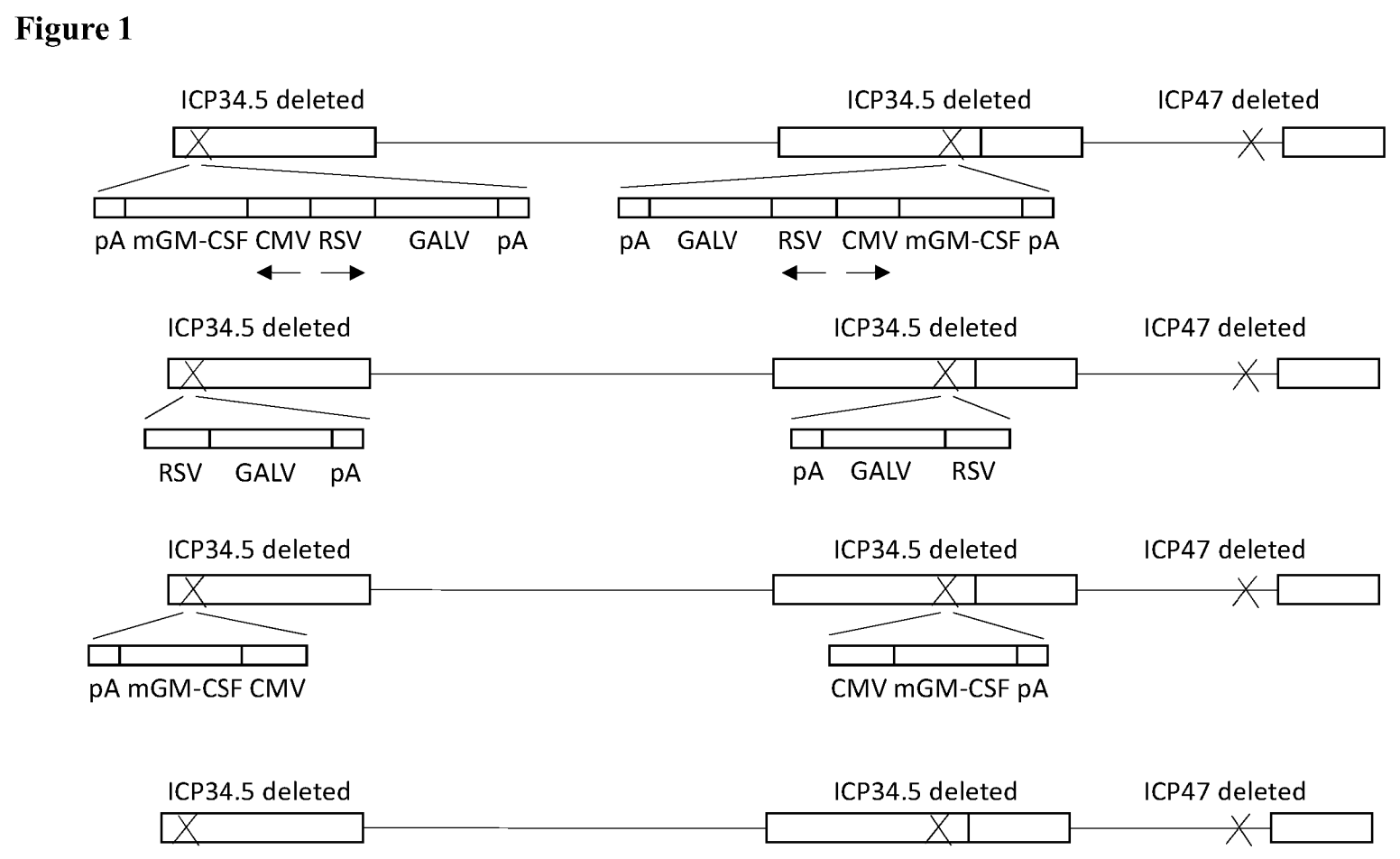

The structure of the resulting virus is shown in FIG. 1 (top panel). The mGM-CSF and GALV-R− sequences are shown in SEQ ID NOs 2 and 8 respectively. The structure of the resulting virus is confirmed by restriction digestion and Southern blot, GM-CSF expression is confirmed by ELISA, and GALV-R− expression is confirmed by infection of human HT1080 tumor cells and the observation of syncitial plaques.

Viruses are also constructed using similar procedures which have no insertion into ICP34.5, or which only have inserted the gene for mouse GM-CSF or GALV-R–. The structures of these viruses are also shown in FIG. 1.

For human use, hGM-CSF is used, the sequence for a codon optimised version of which is shown in SEQ ID NO 4.

Example 3. Expression of Two Immune Stimulatory Molecule from a Virus Expressing a Fusogenic Protein A virus similar to the GALV-R– and mGM-CSF express-ing virus described above is constructed, but additionally expressing versions of CD40L. Here, instead of using a plasmid containing ICP34.5 flanking regions and an expres-sion cassette comprising GM-CSF and GALV-R– driven by a CMV and an RSV promoter, a plasmid containing ICP34.5 flanking regions and an expression cassette comprising GM-CSF, GALV and CD40L driven by a CMV, an RSV and an SV40 promoter is used for recombination with the virus containing GFP inserted into ICP34.5 and non-GFP express-ing plaques again selected.

In more detail, deletion of ICP47 from the viral genome using homologous recombination with a plasmid containing regions flanking HSV1 nucleotides 145300 to 145582 (HSV1 nucleotides 145300 to 145582 being the sequences to be deleted; HSV1 strain 17 sequence Genbank file NC 001806.2) between which are encoded GFP. GFP expressing virus plaques are selected, and GFP then removed by homologous recombination with the empty flanking regions and plaques which do not express GFP are selected. This results in an ICP47 deleted virus in which US11 is expressed as an IE protein as it is now under the control of the ICP47 promoter. ICP34.5 is then deleted using homologous recom-bination with a plasmid containing regions flanking HSV1 nucleotides 124953 to 125727 (HSV1 nucleotides 124953 to 125727 being the sequences to be deleted; HSV1 strain 17 sequence Genbank file NC 001806.2) between which GFP is encoded. GFP expressing virus plaques are again selected, and GFP then removed by homologous recombination with the same flanking regions but between which are now an expression cassette comprising a codon optimized version of the mouse GM-CSF sequence, a codon optimized version of the GALV R– sequence and codon optimized version of mouse soluble multimeric CD40L driven by a CMV, an RSV and an SV40 promoter. Non-GFP expressing plaques are selected.

Figure 2:
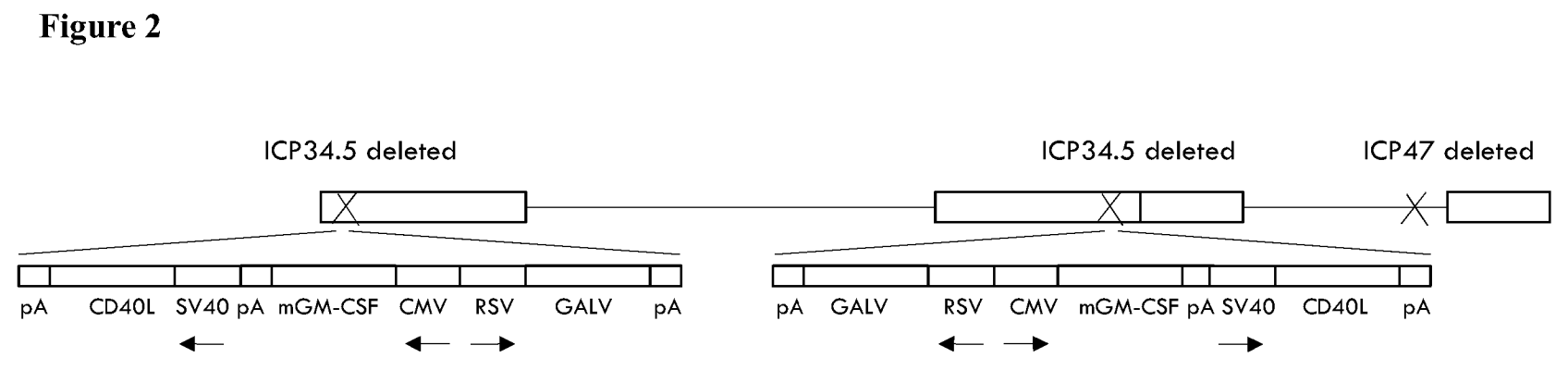

The structure of the resulting virus is shown in FIG. 2. The murine GM-CSF, murine CD40L and GALV-R– sequences are shown in SEQ ID NOs 2, 14 and 8 respec-tively. The structure of the resulting virus is confirmed by restriction digestion and Southern blot, GM-CSF and CD40L expression is confirmed by ELISA, and GALV-R– expression is confirmed by infection of human HT1080 tumor cells and the observation of syncitial plaques.

For human use, hGM-CSF and hCD40L are used, the sequence for codon optimised versions of which are shown in SEQ ID NO 4 and 13.

Example 4. The Effect of the Combined Expression of a Fusogenic Protein and an Immune Stimulatory Molecule from an Oncolytic Virus in Mouse Tumor Models The GALV R– protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells. PiT-1 expression is confirmed by western blotting in untransfected cells and in cells transfected with the PiT-1 expressing lentivirus and by transfection of a plasmid expressing GALV-R– and confirmation that cell fusion occurs.

The utility of the invention is demonstrated by adminis-tering CT26/PiT-1 cells into both flanks of Balb/c mice and allowing the CT26/PiT-1 tumors to grow to approximately 0.5 cm in diameter.

The following treatments are then administered to groups of mice (five per group), into one flank of each mouse only 3 times per week for two weeks:
  50 μl of saline (1 group);
  50 μl of $10^5$ pfu/ml, $10^6$ pfu, or $10^7$ pfu/ml of the HSV with no inserted gene (3 groups);
  50 μl of $10^5$ pfu/ml, $10^6$ pfu/ml, or $10^7$ pfu/ml of the HSV with only mouse GM-CSF inserted (3 groups);
  50 μl of $10^5$ pfu/ml, $10^6$ pfu/ml, or $10^7$ pfu/ml of the virus with only GALV-R– inserted (3 groups); or
  50 μl of $10^5$ pfu/ml, $10^6$ pfu/ml, or $10^7$ pfu/ml of the virus with both mouse GM-CSF and GALV-R– inserted (3 groups).

Effects on tumor growth are then observed for up to one month. Superior tumor control and shrinkage in both injected and uninjected tumors with the virus expressing GM-CSF and GALV-R– as compared to the other groups is observed, including through an improved dose response curve.

Example 5. The Effect of the Combined Expression of GM-CSF and an Immune Co-Stimulatory Pathway Activating Molecule from an Oncolytic Virus in Mouse Tumor Models The GALV R– protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells. PiT-1 expression is confirmed by western blotting in untransfected cells and in cells transfected with the PiT-1 expressing lentivirus and by transfection of a plasmid expressing GALV-R– and confirmation that cell fusion occurs.

The utility of the invention is demonstrated by adminis-tering CT26/PiT-1 cells into both flanks of Balb/c mice and allowing the CT26/PiT-1 tumors to grow to approximately 0.5 cm in diameter.

The following treatments are then administered to groups of mice (five per group), into one flank of each mouse only 3 times per week for two weeks:
  50 μl of saline (1 group);
  50 μl of $10^5$ pfu/ml, $10^6$ pfu/ml, or $10^7$ pfu/ml of the HSV with only GALV-R– inserted (3 groups);
  50 μl of $10^5$ pfu/m, $10^6$ pfu/ml, or $10^7$ pfu/ml of the HSV with only GALVR– and mouse GM-CSF inserted (3 groups);

50 μl of $10^5$ pfu/ml, $10^6$ pfu/m1, or $10^7$ pfu/ml of the virus with GALVR– and both mouse GM-CSF and CD40L inserted (3 groups).

Effects on tumor growth are then observed for up to one month. Superior tumor control and shrinkage in both injected and uninjected tumors with the virus expressing GM-CSF and CD40L as compared to the other groups is observed, including through an improved dose response curve.

Example 6. The Effect of Combined Expression of a Fusogenic Protein and an Immune Stimulatory Molecule from an Oncolytic Virus on the Therapeutic Effect of Immune Checkpoint Blockade in Mouse Tumor Models The experiment in Example 4 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline, (2) HSV with no inserted gene, (3) HSV with both GM-CSF and GALV-R-inserted as in Example 3, (4) PD-1 antibody, (5) CTLA-4 antibody, (6) HSV with no inserted gene plus PD-1 antibody, (7) HSV with no inserted gene plus CTLA-4 antibody, (8) HSV with GM-CSF and GALV-R– and PD-1 antibody or (9) HSV with GM-CSF and GALV-R– and CTLA-4 antibody. Superior tumor control and shrinkage in both injected and uninjected tumors with the virus expressing GM-CSF and GALV-R– together with the anti-PD-1 antibody or the anti-CTLA-4 antibody as compared to the other groups is observed, including through an improved dose response curve.

Example 7. The Effect of Combined Expression of GM-CSF and an Immune Co-Stimulatory Pathway Activating Molecule from an Oncolytic Virus on the Therapeutic Effect of Immune Checkpoint Blockade in Mouse Tumor Models The experiment in Example 5 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline, (2) HSV with GALVR– inserted as in Example 5, (3) HSV with GM-CSF and GALV-R– inserted as in Example 2, (4) HSV with GM-CSF, CD40L and GALV-R– inserted as in Example 2, (5) PD-1 antibody, (6) CTLA-4 antibody, (7) HSV with GALV-R– inserted plus PD-1 antibody, (8) HSV with GALV-R– inserted gene plus CTLA-4 antibody, (9) HSV with GM-CSF and GALV-R– and PD-1 antibody or (10) HSV with GM-CSF and GALV-R– and CTLA-4 antibody (11) HSV with GM-CSF, CD40L and GALV-R– and PD-1 antibody or (12) HSV with GM-CSF, CD40L and GALV-R– and CTLA-4 antibody. Superior tumor control and shrinkage in both injected and uninjected tumors with the virus expressing GM-CSF and CD40L together with the anti-PD-1 antibody or the anti-CTLA-4 antibody as compared to the other groups is observed, including through an improved dose response curve.

Example 8. Collection of Clinical Isolates

The virus species used to exemplify the disclosure is HSV, specifically HSV1. 181 volunteers were recruited who suffered from recurrent cold sores. These volunteers were given sample collection kits (including Sigma Virovult collection tubes), and used these to swab cold sores when they appeared following which these samples were shipped to Replimune, Oxford UK. From June 2015-February 2016, swabs were received from 72 volunteers. A sample of each swab was used to infect BHK cells. Of these 36 live virus samples were recovered following plating out and growth on BHK cells. These samples are detailed in Table 1.

TABLE 1

| Details of Tested Swab Samples & Result | |
| --- | --- |
| Sample Number | Virus retrieved |
| RH001A | No |
| RH001B | |
| RH002A | Yes |
| RH003A | No |
| RH004A | Yes |
| RH004B | |
| RH005A | No |
| RH005B | |
| RH006A | No |
| RH006B | |
| RH007A | Yes |
| RH007B | |
| RH007C | |
| RH008A | No |
| RH008B | |
| RH008C | |
| RH009A | No |
| RH009B | |
| RH010A | No |
| RH011A | No |
| RH011B | |
| RH011C | |
| RH012A | No |
| RH013A | No |
| RH014A | Yes |
| RH014B | |
| RH015A | Yes |
| RH016A | No |
| RH016B | |
| RH017A | Yes |
| RH018A | Yes |
| RH018B | |
| RH018C | |
| RH019A | No |
| RH019B | |
| RH019C | |
| RH020A | Yes-RH020A only |
| RH020B | |
| RH020C | |
| RH021A | Yes |
| RH021B | |
| RH022A | Yes |
| RH022B | |
| RH023A | Yes |
| RH024A | No |
| RH025A | Yes-RH025B only |
| RH025B | |
| RH026A | Yes |
| RH027A | No |
| RH027B | |
| RH027C | |
| RH028A | No |
| RH028B | |
| RH028C | |
| RH029A | No |
| RH030A | No |
| RH031A | Yes-RH031A to |
| RH031B | RH031D |

TABLE 1-continued

Details of Tested Swab Samples & Result

| Sample Number | Virus retrieved |
|---|---|
| RH031C | |
| RH031D | |
| RH031E | |
| RH031F | |
| RH032A | No |
| RH033A | No |
| RH033B | |
| RH033C | |
| RH034A | No |
| RH034B | |
| RH034C | |
| RH035A | No |
| RH036A | Yes |
| RH037A | Yes |
| RH038A | Yes |
| RH039A | No |
| RH039B | |
| RH039C | |
| RH040A | Yes |
| RH040B | |
| RH040C | |
| RH041A | Yes |
| RH042A | Yes |
| RH043A | No |
| RH043B | |
| RH043C | |
| RH044A | No |
| RH045A | No |
| RH046A | Yes |
| RH047A | Yes-RH047A and |
| RH047B | RH047C |
| RH047C | |
| RH048A | No |
| RH049A | No |
| RH049B | |
| RH049C | |
| RH050A | No |
| RH051A | Yes |
| RH051B | |
| RH052A | Yes-RH052A only |
| RH052B | |
| RH053A | No |
| RH054A | No |
| RH055A | No |
| RH055B | |
| RH056A | Yes |
| RH057A | No |
| RH058A | Yes |
| RH058B | |
| RH059A | No |
| RH060A | No |
| RH061A | Yes |
| RH062A | No |
| RH063A | No |
| RH064A | Yes |
| RH065A | Yes |
| RH065B | |
| RH066A | No |
| RH067A | No |
| RH067B | |
| RH068A | No-contaminated |
| RH069A | No |
| RH069A | |
| RH070A | Yes |
| RH071A | Yes |
| RH072A | No |
| RH073A | Yes |
| RH073B | |
| RH074A | No |
| RH074B | |
| RH075A | No |
| RH076A | No |
| RH078A | No |
| RH078B | |
| RH079B | Yes |
| RH079B | |

TABLE 1-continued

Details of Tested Swab Samples & Result

| Sample Number | Virus retrieved |
|---|---|
| RH080A | No |
| RH081A | Yes |
| RH082A | No |
| RH082B | |
| RH083A | Yes |
| RH083B | |
| RH084A | Yes |
| RH084B | |
| RH084C | |
| RH085A | No |
| RH086A | No |
| RH087A | Yes-RH078B only |
| RH087B | |

Designations A, B, C etc. indicate multiple swabs from the same volunteer.

Example 9. Identification of Clinical Isolates with Improved Anti-Tumor Effects

The abilities of the primary clinical isolates of HSV1 to kill a panel of human tumor-derived cell lines was tested. The tumor cell lines used for this comparison were HT29 (colorectal), MDA-MB-231 (breast), SK-MEL-28 (melanoma), Fadu (squamous cell carcinoma), MCF7 (breast), A549 (lung), MIAPACA-2 (pancreas) and HT1080 (fibrosarcoma). The cell lines were used to test for the level of CPE achieved at a range of MOI and times post infection for each of the primary clinical isolates.

Experiments were conducted in parallel using 5 to 8 of the new viruses strains at the same time. The virus strains were plated out in duplicate at a range of MOIs (0.001-1), and the extent of CPE following crystal violet staining was assessed at 24 and 48 hours following infection. The viral strains which were most effective at killing the tumor cell lines were scored, and the most effective two or three strains from each screen of 5-8 strains were identified and compared in parallel in a further experiment to identify the top strains for further development.

The initial screens demonstrated substantial variability in the ability of the different strains to kill the different tumor cell lines. Of an initial 29 strains tested, 8 strains of interest were identified in the initial screens for further comparison. These were strains RH004A, RH015A, RH018A, RH021A, RH023A, RH31A, RH040A, and RH1047A.

Figure 3:
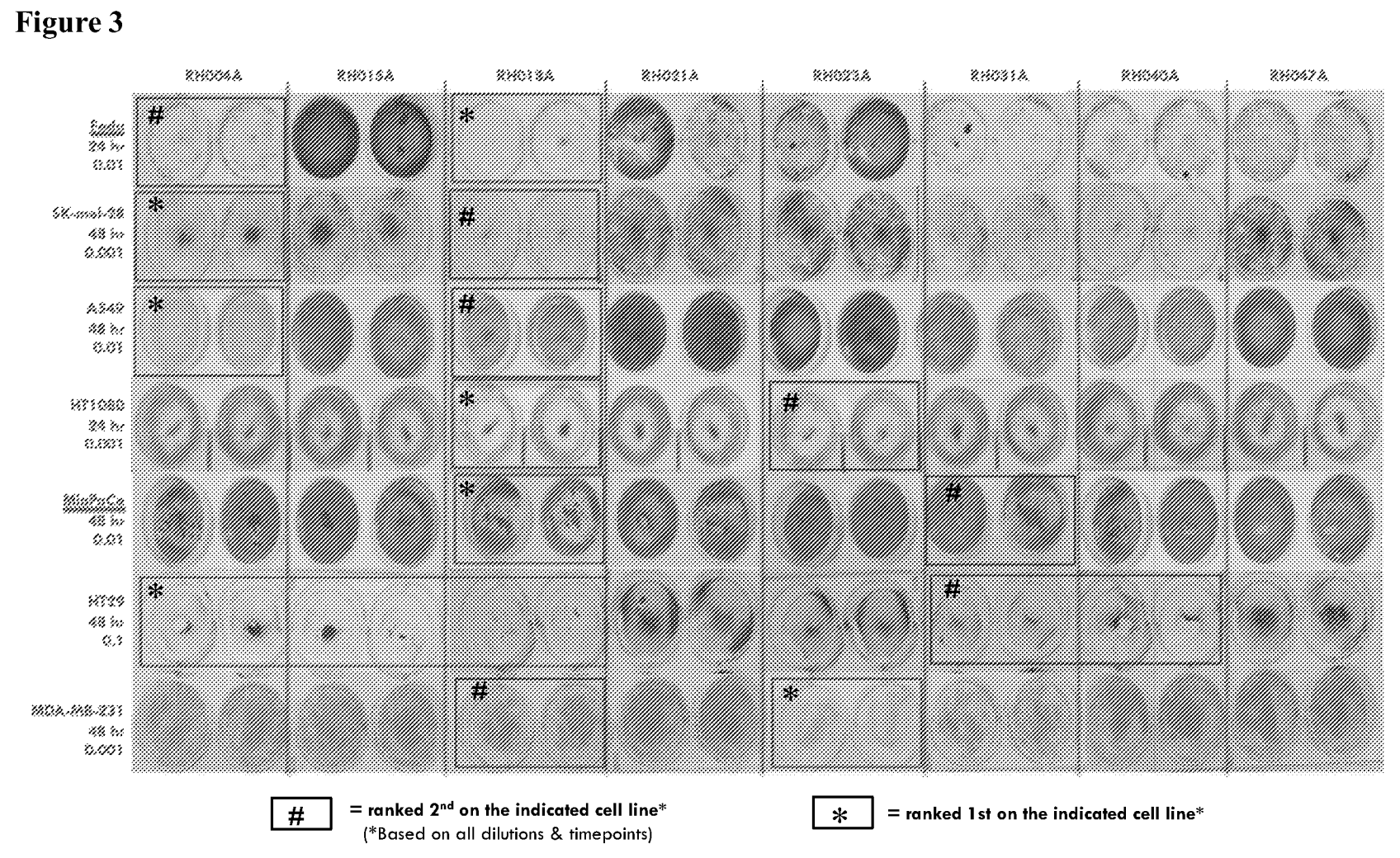

The 8 strains for further comparison were tested in parallel on the panel of tumor cell lines, and their relative ability to kill these tumor cell lines was assessed following crystal violet staining and observation for CPE. FIG. 3 shows a representative time point and MOI for these viruses on each of the viruses on each of the cell lines demonstrating the differential ability of the viruses to kill the target tumor cell lines observed.

There was substantial variation amongst the strains, and it was found that while a particular strain may be particularly effective at killing one cell line, it is not necessarily particularly effective at killing other cell lines too, further demonstrating the degree of variability in the ability of clinical strains of HSV to kill tumor cells of different types.

FIG. 3 also indicates which of the virus strains was both best and second best at killing each of the cell lines, enabling the virus strains to be rank ordered as to their overall relative ability to kill the panel of cell lines as a whole. This analysis demonstrated that strains RH004A, RH015A, RH018A, RH031A and RH040A were relatively more effective than the other strains, and these five strains were chosen for potential further development as oncolytic agents. Of these top five strains, the relative rank order based on their abilities to kill across the panel of cell lines was RH018A>RH1004A>RH031A>RH040A>RH015A.

More specifically, in these experiments, the tumor cell lines were used to seed multi-well tissue culture plates so that they were about 80% confluent on the day of infection. Representative wells from each tumor cell line were trypsinised and the number of cells in the well determined. These cell counts are used to determine the volume of each clinical isolate required to give an MOI of 1, 0.1, 0.01 and 0.001. Separate wells of a tumor cell line were infected with the clinical isolate at these MOI. All infections are carried out in quadruplicate. Duplicate wells were incubated for 24 hours and duplicate wells were incubated for 48 hours, both at 37° C., 5% $CO_2$, prior to fixation of the cells with glutaraldehyde and staining with crystal violet. The level of cell lysis was then assessed by gross observation, microscopy (cell counts) and photography.

Strain RH018A, the strain ranked first of all the strains tested was compared to an 'average' strain from the screen (i.e. a strain which was not in the top 8, but was also not in the group of strains which were least effective and killing the panel of tumor cell lines). This comparison showed that Strain RH018A was approximately 10 fold more effective than this average strain (Strain RH065A) at killing the tumor cell lines (i.e. approximately 10 fold less of Strain RH018A was needed to kill an equal proportion of cells than was needed of Strain RH1065A). This is shown in FIG. 4.

Example 10. Modification of Clinical Isolates

In this Example the clinical isolates selected in Example 9 were modified by deletion of ICP34.5 from the viral genome using homologous recombination with a plasmid containing regions flanking the ICP34.5 encoding gene (nucleotides 143680-145300 and 145,582-147,083; HSV1 strain 17 sequence Genbank file NC 001806.2) between which are encoded GFP and the GALV-R-fusogenic glycoprotein. The structure of this virus, (Virus 10) is shown in FIG. 5.

Additional viruses based on Strain RH01A were also constructed in which both ICP34.5 and CP47 (using flanking regions containing nucleotides 123464-124953 and 125727-126781; HSV1 strain 17 sequence Genbank file NC 001806.2) were deleted (resulting in placement of US11 under the control of the ICP47 promoter). To construct these viruses, GFP expressing virus plaques, with GFP expressed in place of ICP47 were first selected. GFP was then removed by homologous recombination with the empty flanking regions, and plaques not expressing GFP were selected. This resulted in an ICP47 deleted virus in which US11 is expressed as an IE protein as it is now under the control of the ICP47 promoter. ICP34.5 was then deleted using homologous recombination with a plasmid containing regions flanking HSV1 nucleotides 143680-145300 and 145,582-147,083; HSV1 strain 17 sequence Genbank file NC 001806.2) between which GFP is encoded. GFP expressing virus plaques were again selected, and GFP then removed by homologous recombination with the same flanking regions but between which are now an expression cassette comprising the genes to be inserted. The viruses that were constructed are shown in FIGS. 1 and 5. These included a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction was performed using methods which are standard in the art.

The mGM-CSF and GALV-R- sequences are shown in SEQ ID NOs 2 and 8 respectively. The structure of the resulting virus was confirmed by PCR, GM-CSF expression was confirmed by ELISA, and GALV-R- expression was confirmed by infection of human HT1080 tumor cells and the observation of syncitial plaques.

Figure 6:
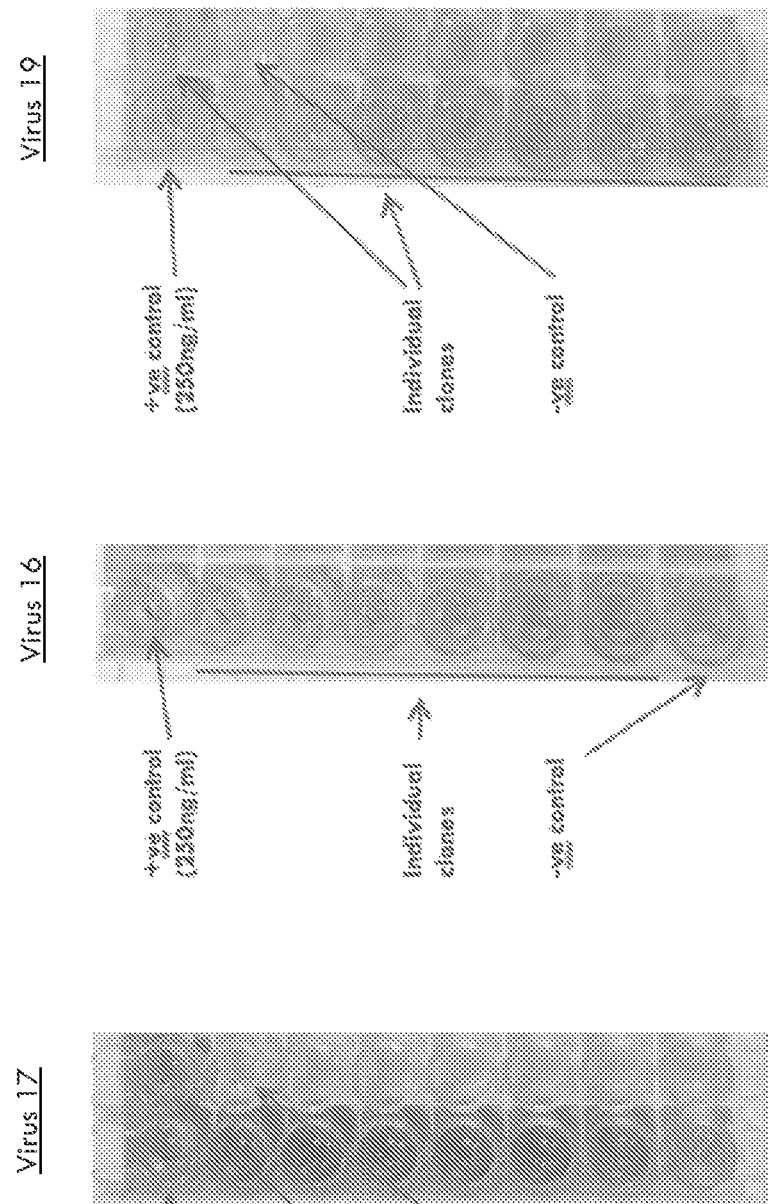
FIG. 6 shows the results of an ELISA to detect expression of human or mouse GM-CSF in supernatants from BHK cells infected with virus 16 (mGM-CSF and GALVR−), virus 17 (hGM-CSF and GALVR−) and virus 19 (mGM-CSF).

For human use, hGiM-CSF is used, the sequence for a codon optimised version of which is shown in SEQ ID NO 4. The structure of this virus is shown in FIG. 5. Expression of mouse or human GM-CSF from viruses 16, 17 and 19 is shown in FIG. 6.

Figure 7A:
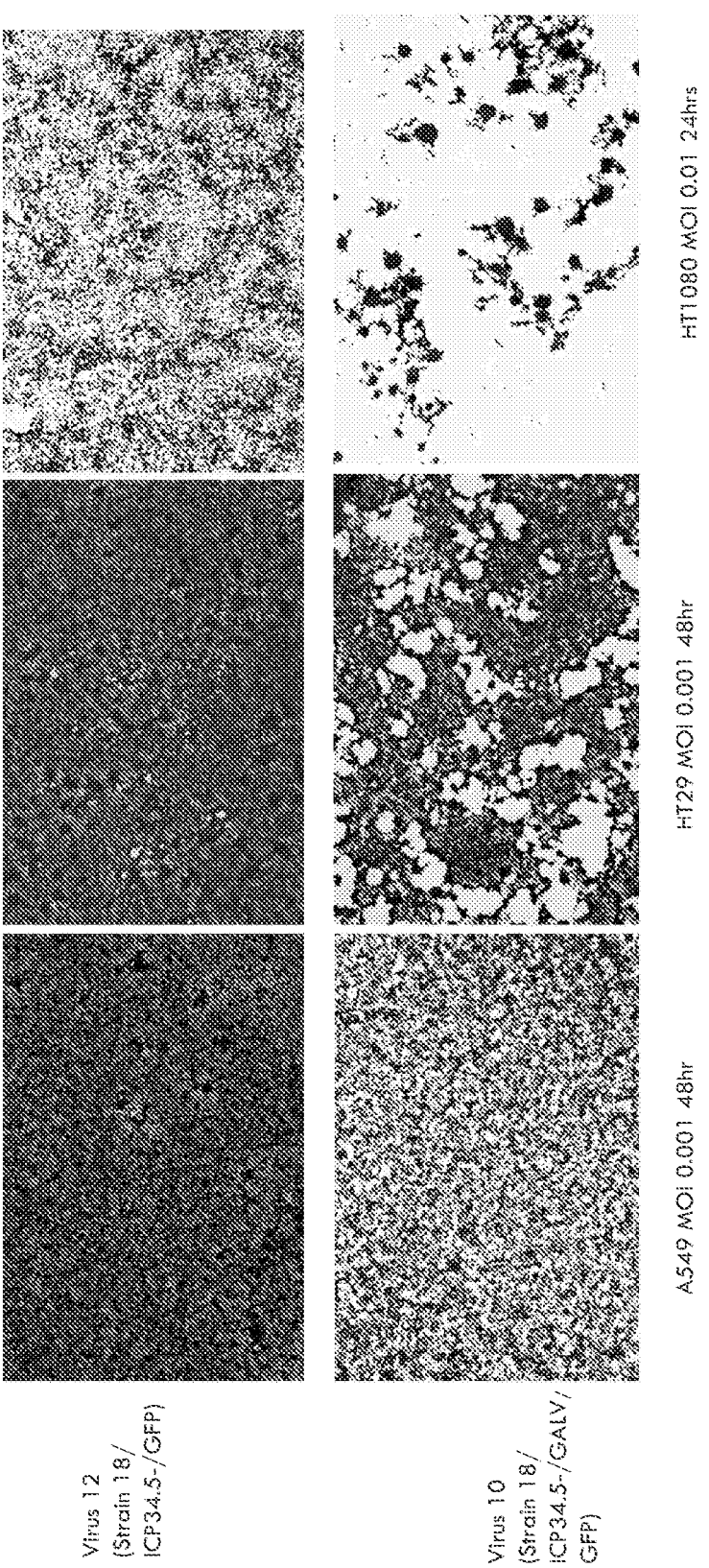
FIG. 7 is a comparison between the cell-killing abilities of strain RH018A in which ICP34.5 is deleted and which expresses GALVR− and GFP (virus 10) with a virus that expresses only GFP (virus 12) as determined by crystal violet staining in three cell lines at low magnification.
Figure 7B:
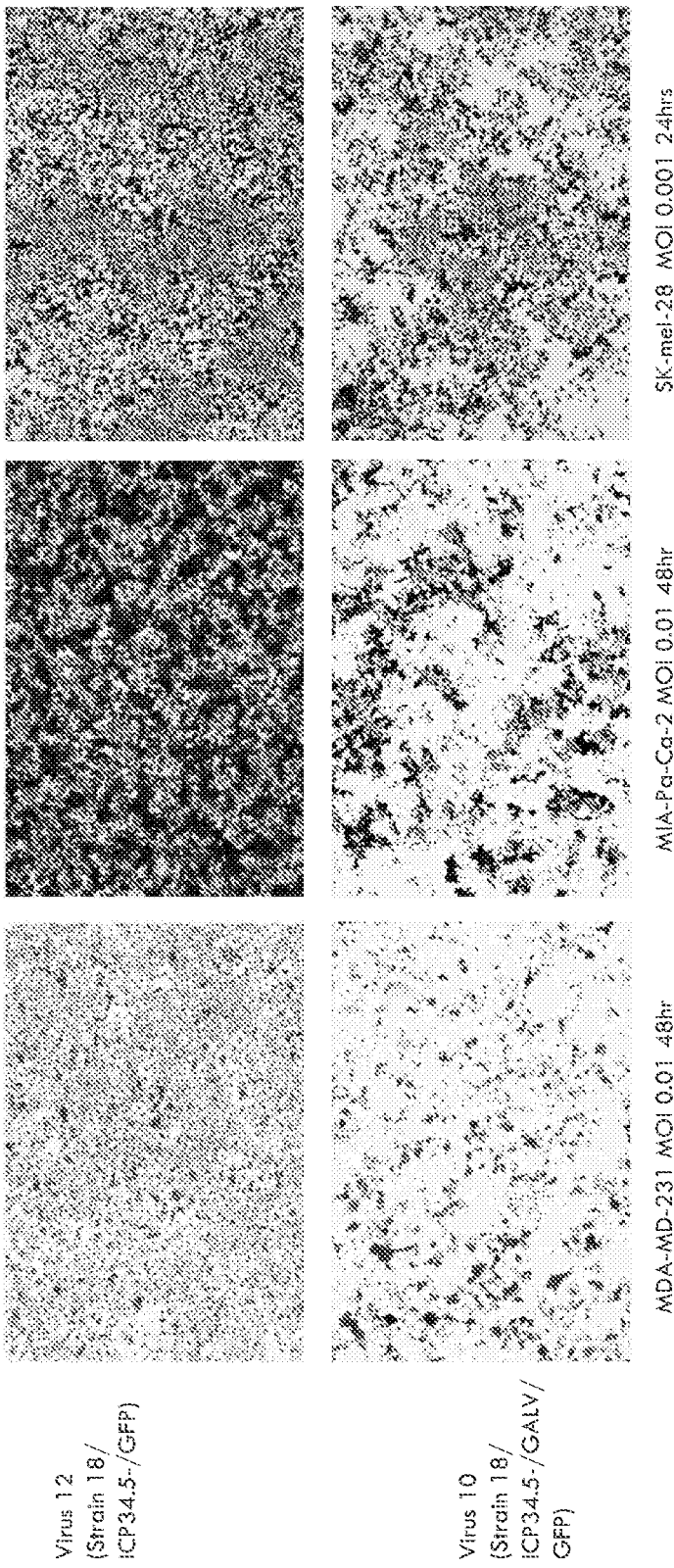

Example 11. A Virus Modified for Oncolytic Use and Expressing a Fusogenic Glycoprotein Shows Enhanced Tumor Cell Killing In Vitro as Compared to a Virus which does not Express a Fusogenic Glycoprotein Virus 10 (see FIG. 5), based on clinical Strain RH018A in which ICP34.5 is deleted and which expresses GALVR- and GFP, was compared in vitro to a virus which expresses only GFP (Virus 12). Virus 10 showed enhanced killing on a panel of human tumor cell lines as compared to Virus 12, as shown in FIG. 7.

Figure 8A:
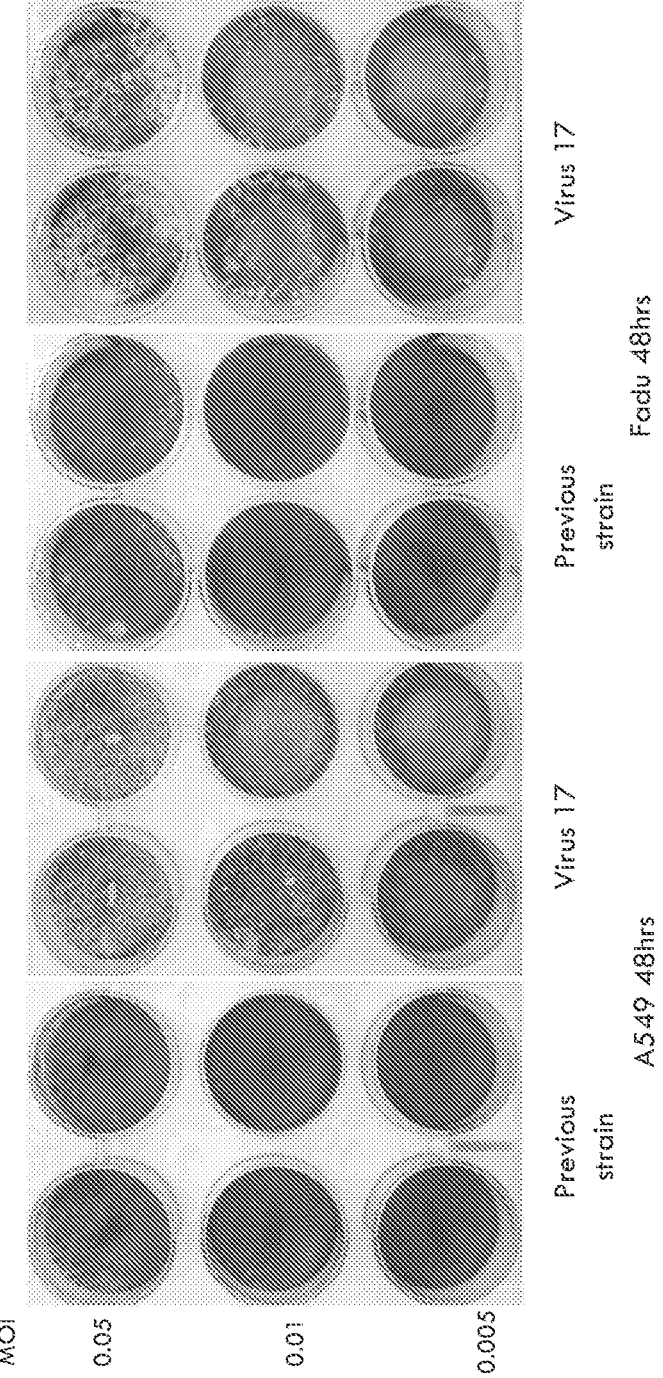
FIG. 8 is a comparison between the cell-killing abilities of strain RH018A in which ICP34.5 and ICP47 are deleted and which expresses GALVR– and GM-CSF (virus 17) with a prior art strain with the same modifications as determined by crystal violet staining in four cell lines.

Example 12. A Virus Modified for Oncolytic Use Shows Enhanced Tumor Cell Killing as Compared to a Similarly Modified Known Virus Virus 17 (see FIG. 5), based on clinical Strain RH018A in which ICP34.5 and ICP47 are deleted and which expresses GALVR- and GM-CSF, was compared in vitro to a known virus which was also deleted for ICP34.5 and ICP47 but which was derived from a known strain and which expresses only GM-CSF. Virus 17 showed enhanced killing on a panel of human tumor cell lines as compared to the previous virus, as shown in FIG. 8.

Figure 9:
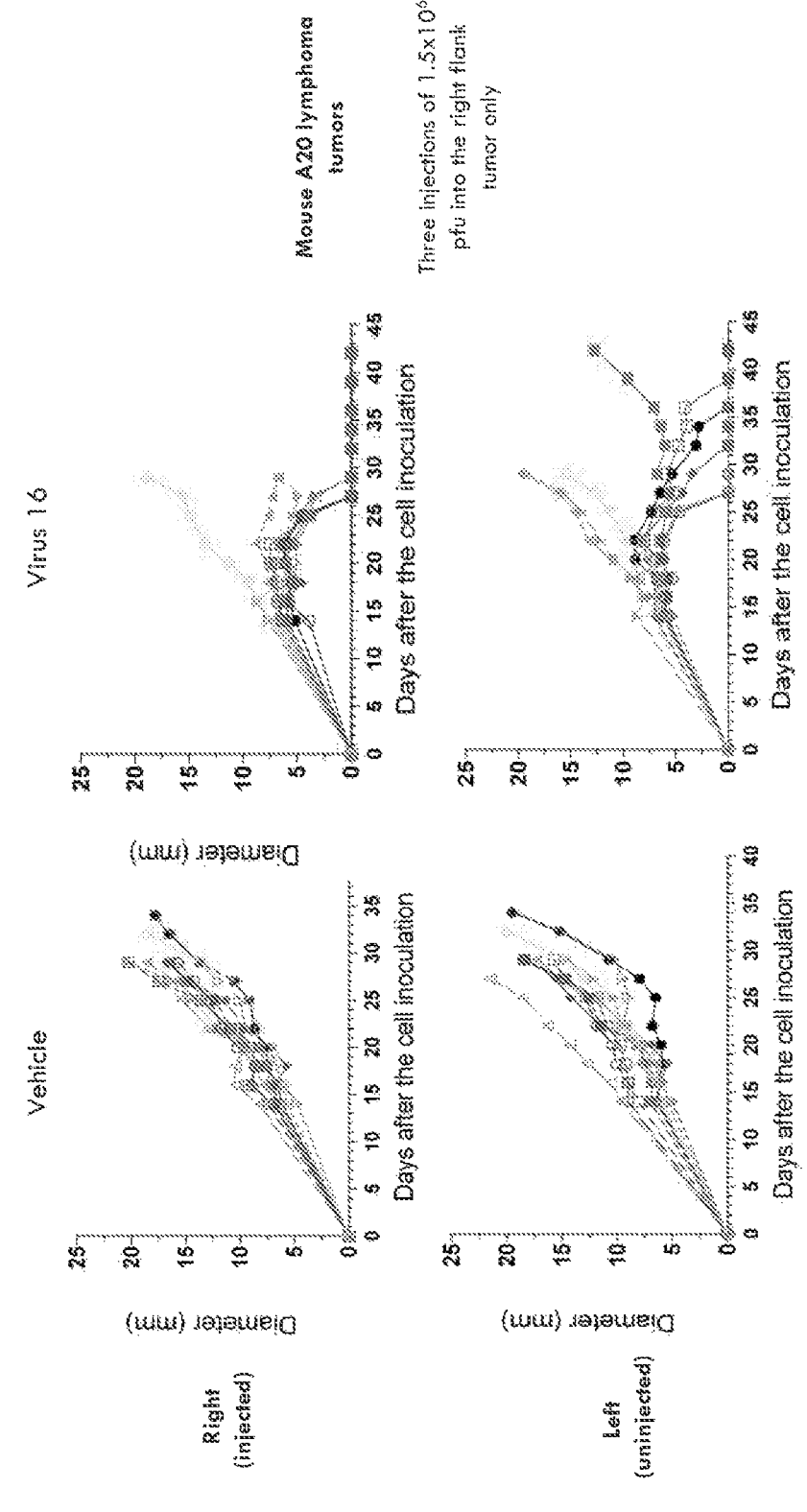
FIG. 9 shows the effectiveness of Virus 16 (ICP34.5 and ICP47 deleted expressing GALVR– and mGM-CSF) in treating mice harbouring A20 lymphoma tumors in both flanks. Tumors on the right flanks were injected with the virus or vehicle and the effects on tumor size was observed for 30 days. The virus was effective against both injected tumors and non-injected tumors.

Example 13. A Virus Modified for Oncolytic Use Effectively Treats Mouse Tumors In Vivo Virus 16 was tested in mice harboring A20 lymphoma tumors in the left and right flanks. One million tumor cells were first implanted in both flanks of Balb/c mice and tumors allowed to grow to 0.5-0.7 cm in diameter. Tumors on the right flank were then injected 3 times (every other day) with either vehicle (10 mice) or 5×10exp6 pfu of Virus 16 (10 mice), and effects on tumor size observed for a further 30 days. This demonstrated that both injected and uninjected tumors were effectively treated with Virus 16 (see FIG. 9).

Example 14. The Effect of the Combined Expression of a Fusogenic Protein and an Immune Stimulatory Molecule from an Oncolytic Virus in a Rat Tumor Model The GALV R- protein causes cell to cell fusion in human cells but not in mouse cells. However, GALV R- does cause fusion in rat cells.

The utility of the invention was further demonstrated by administering 9L cells into the flanks of Fischer 344 rats and allowing the 9L tumors to grow to approximately 0.5 cm in diameter.

The following treatments were then administered to groups of rats (ten per group), into one flank only of each rat three times per week for three weeks:

50 µl of vehicle;

50 µl of $10^7$ pfu/ml of Virus 19 (expresses mGM-CSF but not GALV R–);

50 µl of $10^7$ pfu/ml of Virus 16 (expresses both mouse GM-CSF and GALV-R–).

Figure 10:
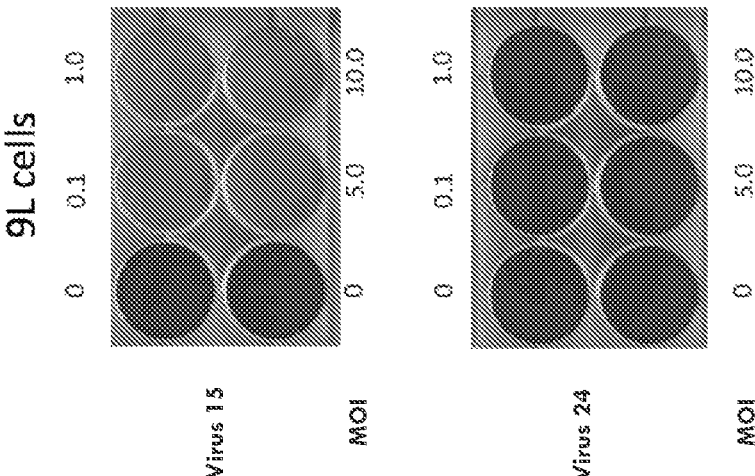
FIG. 10 demonstrates the effects of Virus 15 (ICP34.5 and ICP47 deleted expressing GALVR– and GFP) and Virus 24 (ICP34.5 and ICP47 deleted expressing GFP) on rat 9L cells in vitro as assessed by crystal violet staining. The virus expressing GALV (Virus 15) showed enhanced killing of rat 9L cells in vitro as compared to a virus which does not express GALV (Virus 24).
Figure 15:
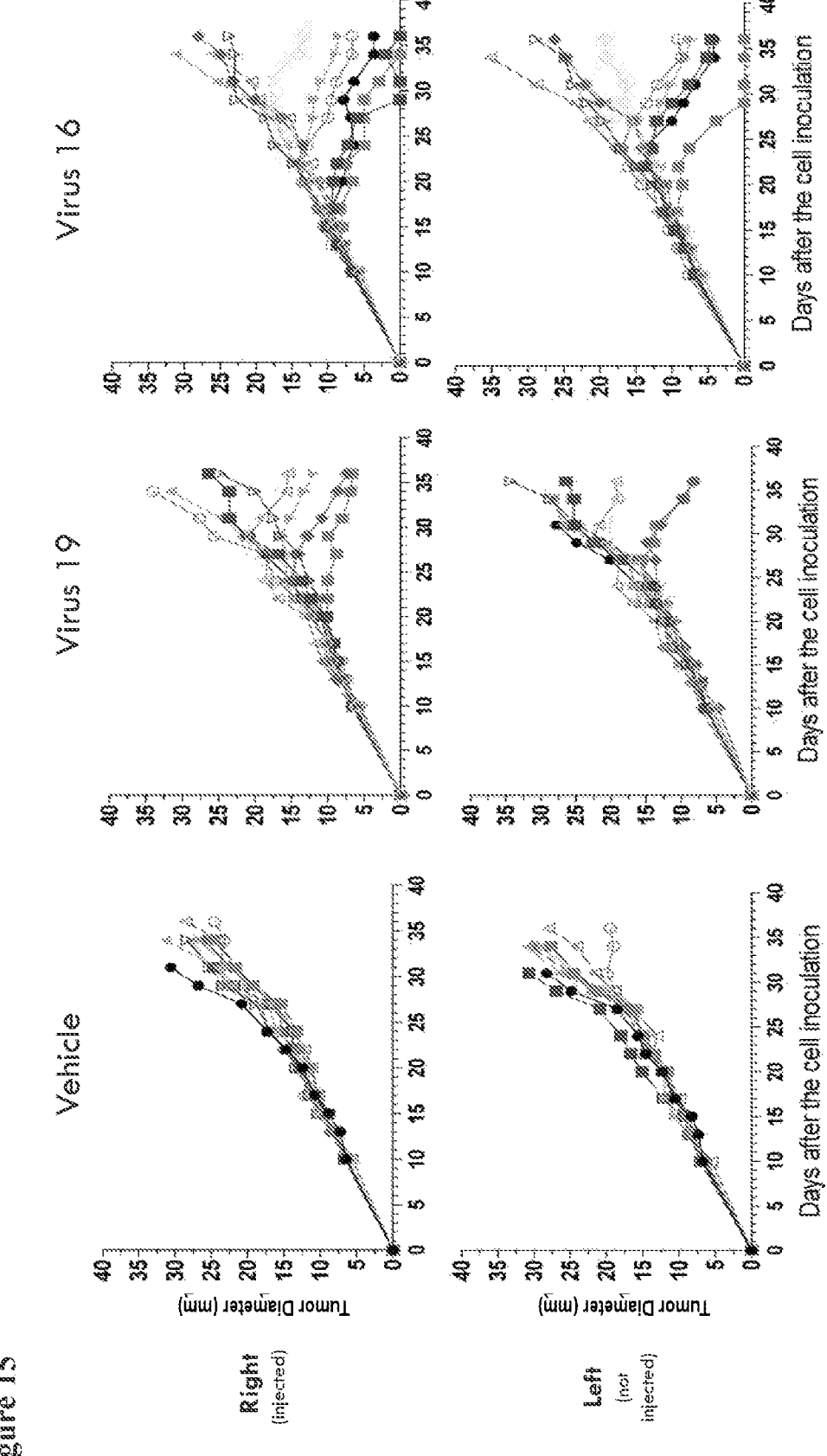
FIG. 15 demonstrates the effects of viruses expressing GALVR– on 9L cells in the flanks of Fischer 344 rats. The following treatments were administered to groups of rats (ten per group), into one flank of each rat only three times per week for three weeks: 50 µl of vehicle; 50 µl of $10^7$ pfu/ml of Virus 19 (expresses mGM-CSF but not GALV R–); or 50 µl of $10^7$ pfu/ml of Virus 16 (expresses both mouse GM-CSF and GALV-R–). Effects on tumor growth were then observed for a further 30 days. Superior tumor control and shrinkage was observed with the virus expressing GM-CSF and GALV-R– as compared to the virus expressing GM-CSF alone.

Effects on tumor growth were then observed for a further ≈30 days. This demonstrated superior tumor control and shrinkage with the virus expressing GALV-R– in both injected and uninjected tumors, demonstrating improved systemic effects. This is shown in FIG. 15. FIG. 10 shows that a virus expressing GAIN (Virus 15) also shows enhanced killing of rat 91 cells in vitro as compared to a virus which does not express GA LV (Virus 24).

Example 15. A Virus Modified for Oncolytic Use is Synergistic with Immune Checkpoint Blockade in Mouse Tumor Models Virus 16 was tested in mice harboring CT26 tumors in the left and right flanks. One million tumor cells were first implanted in both flanks of Balb/c mice and tumors allowed to grow to 0.5-0.6 cm in diameter.

Figure 11A:
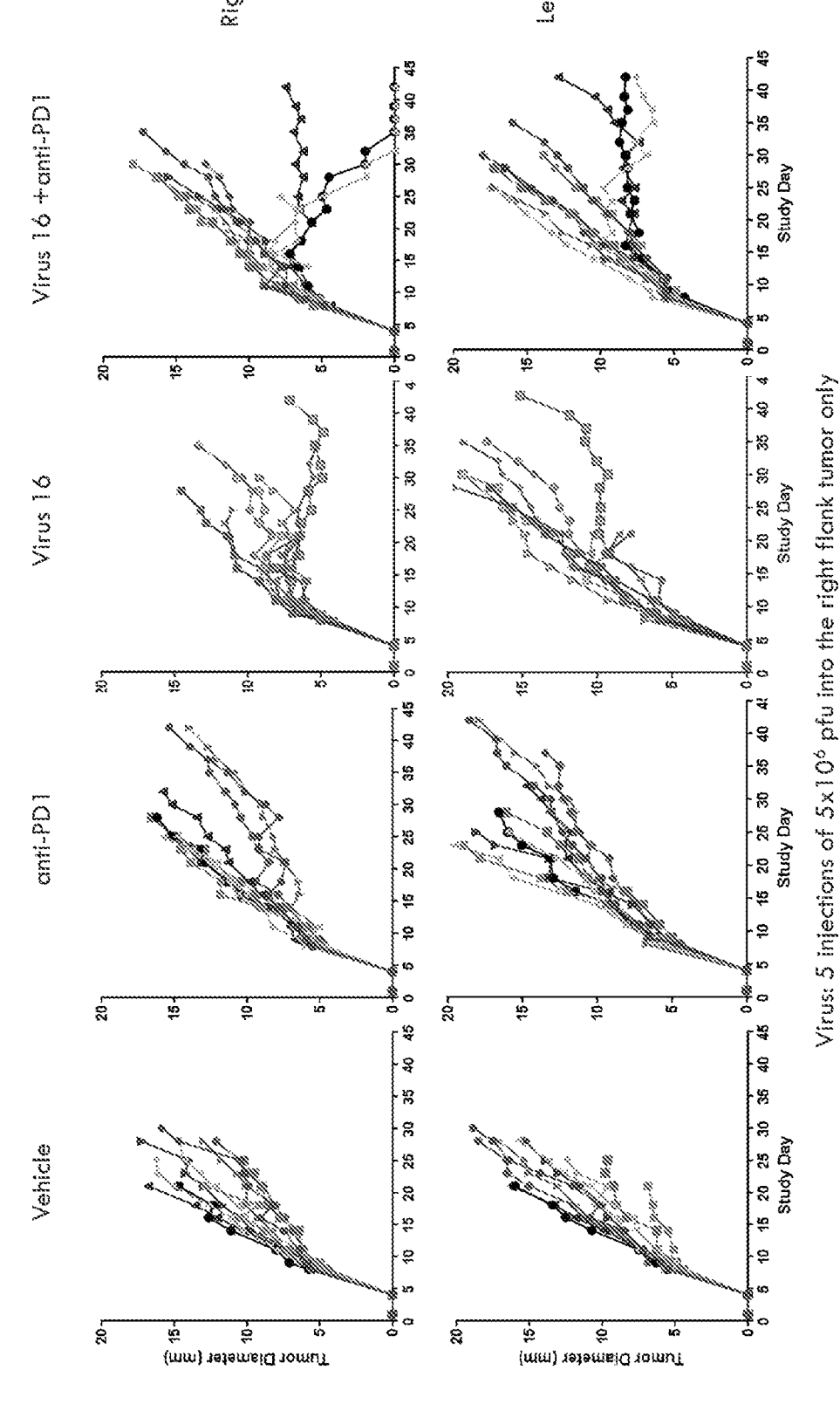
FIG. 11A shows that using Virus 16 and anti-PD1 in combination has a better anti-tumor effect than using either anti-PD1 or the virus alone.
Figure 11B:
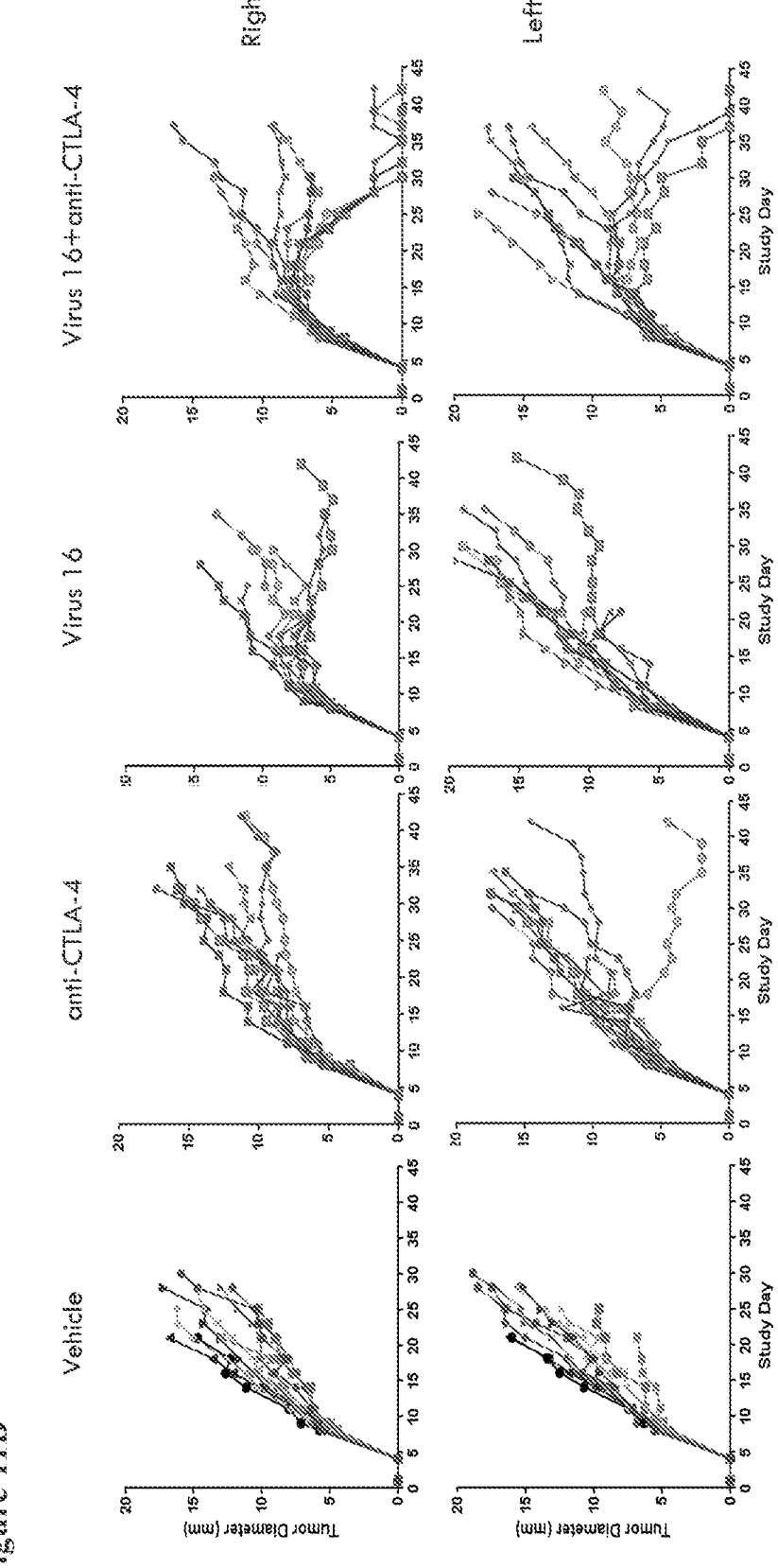
FIG. 11B shows that the anti-tumor effect of Virus 16 in combination with anti-CTLA-4 was better than the anti-tumor effect of either Virus 16 or anti-CTLA-4 alone.
Figure 11C:
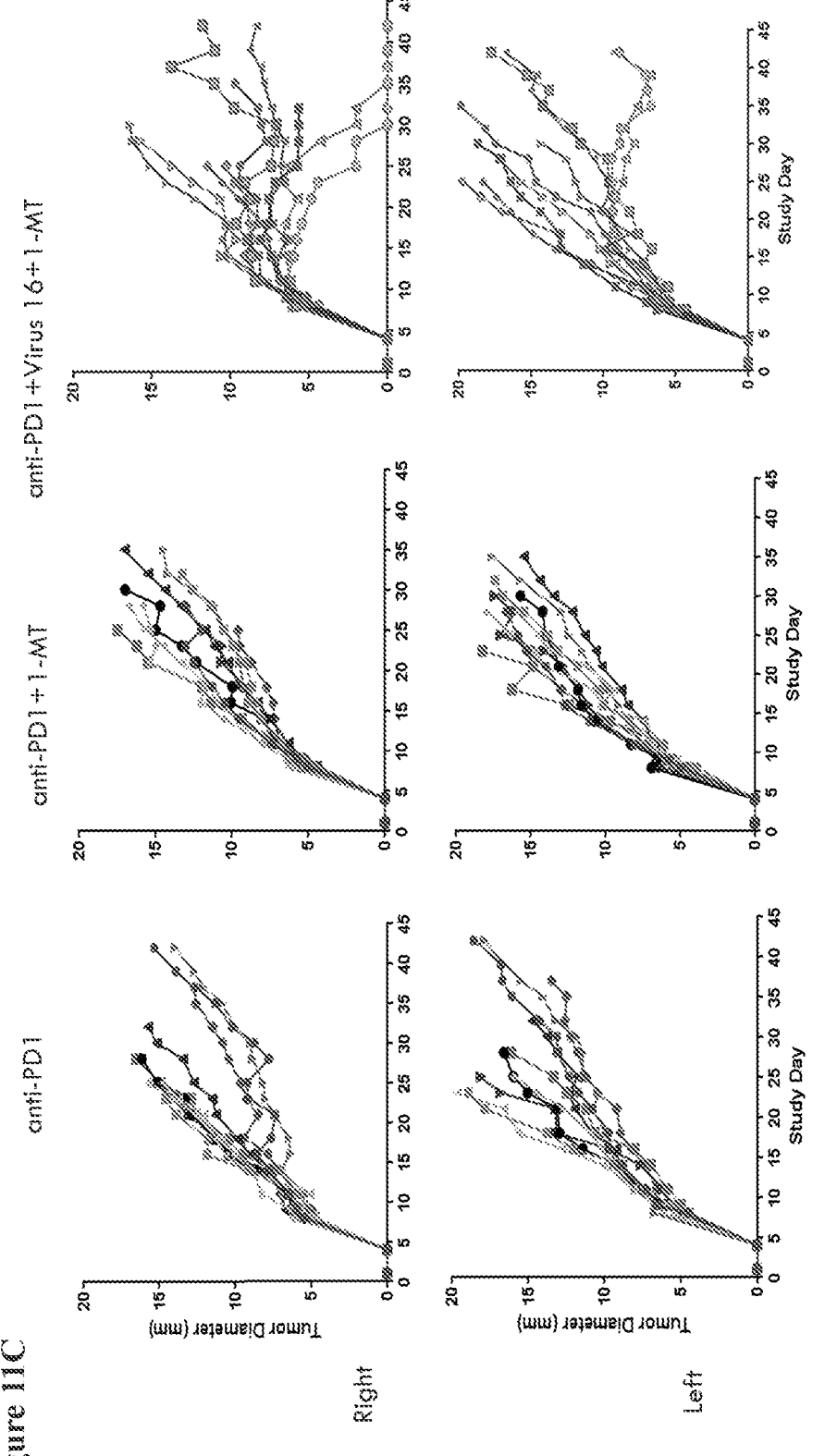
FIG. 11C shows that enhanced tumor reduction was observed using Virus 16 together with both anti-PD1 and IDO inhibition as compared to anti-PD1 and 1-MT inhibition in the absence of the virus.
Figure 12A:
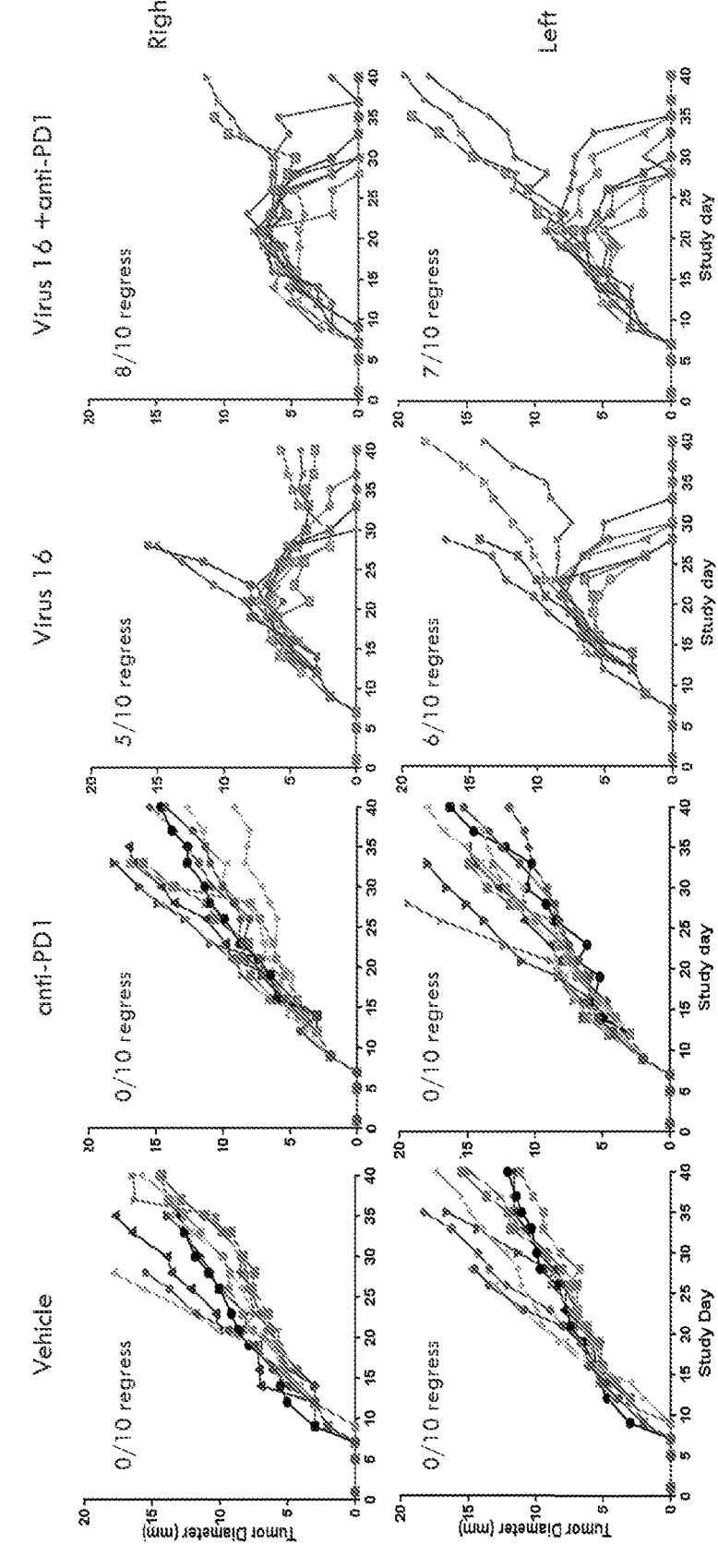
FIG. 12 shows the enhanced anti-tumor activity of Virus 16 in combination with immune checkpoint blockade in mouse A20 tumors in both flanks of Balb/c mice as compared to either virus alone or checkpoint blockade alone (anti-PD1).
Figure 12B:
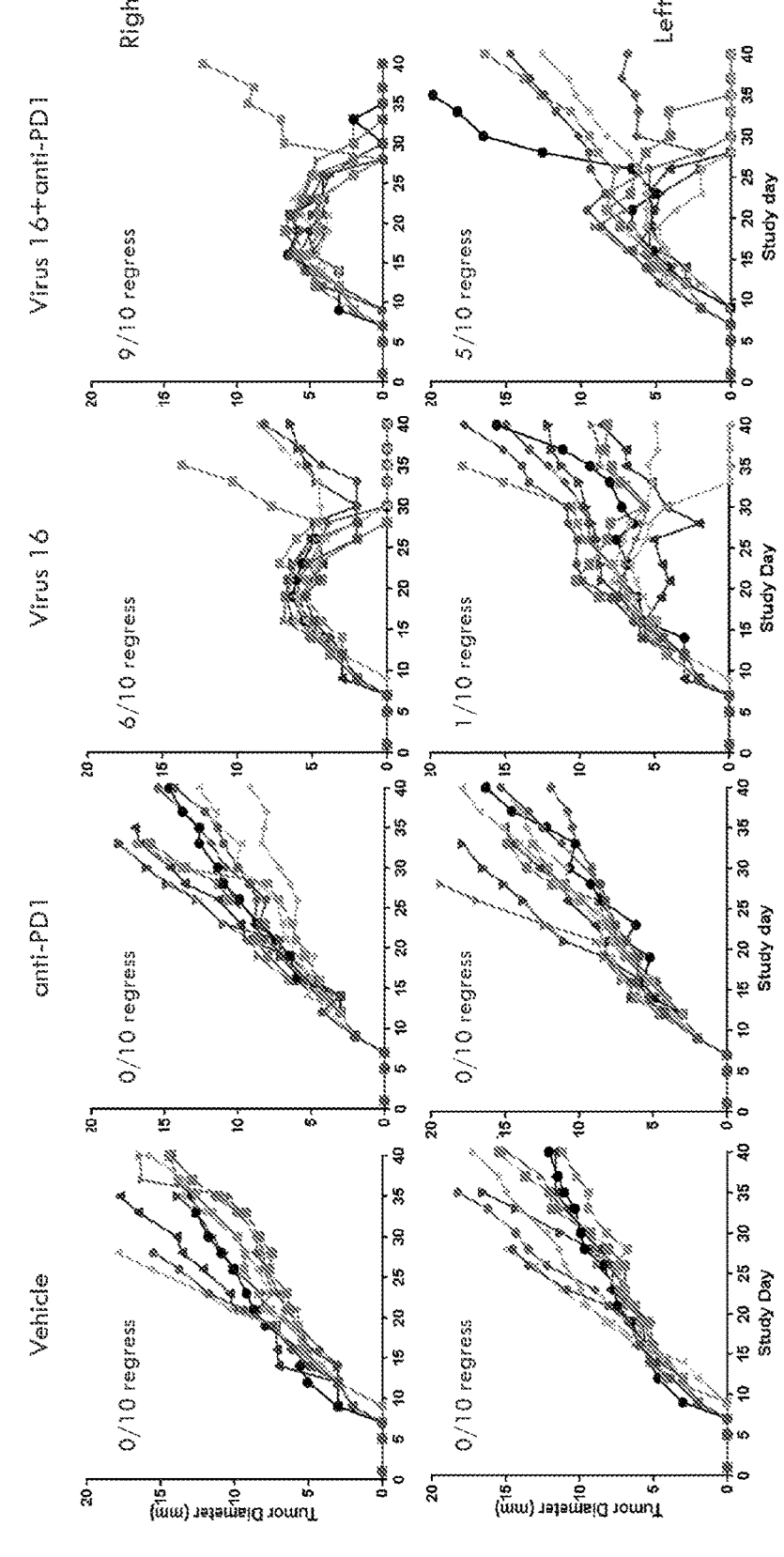
Figure 12C:
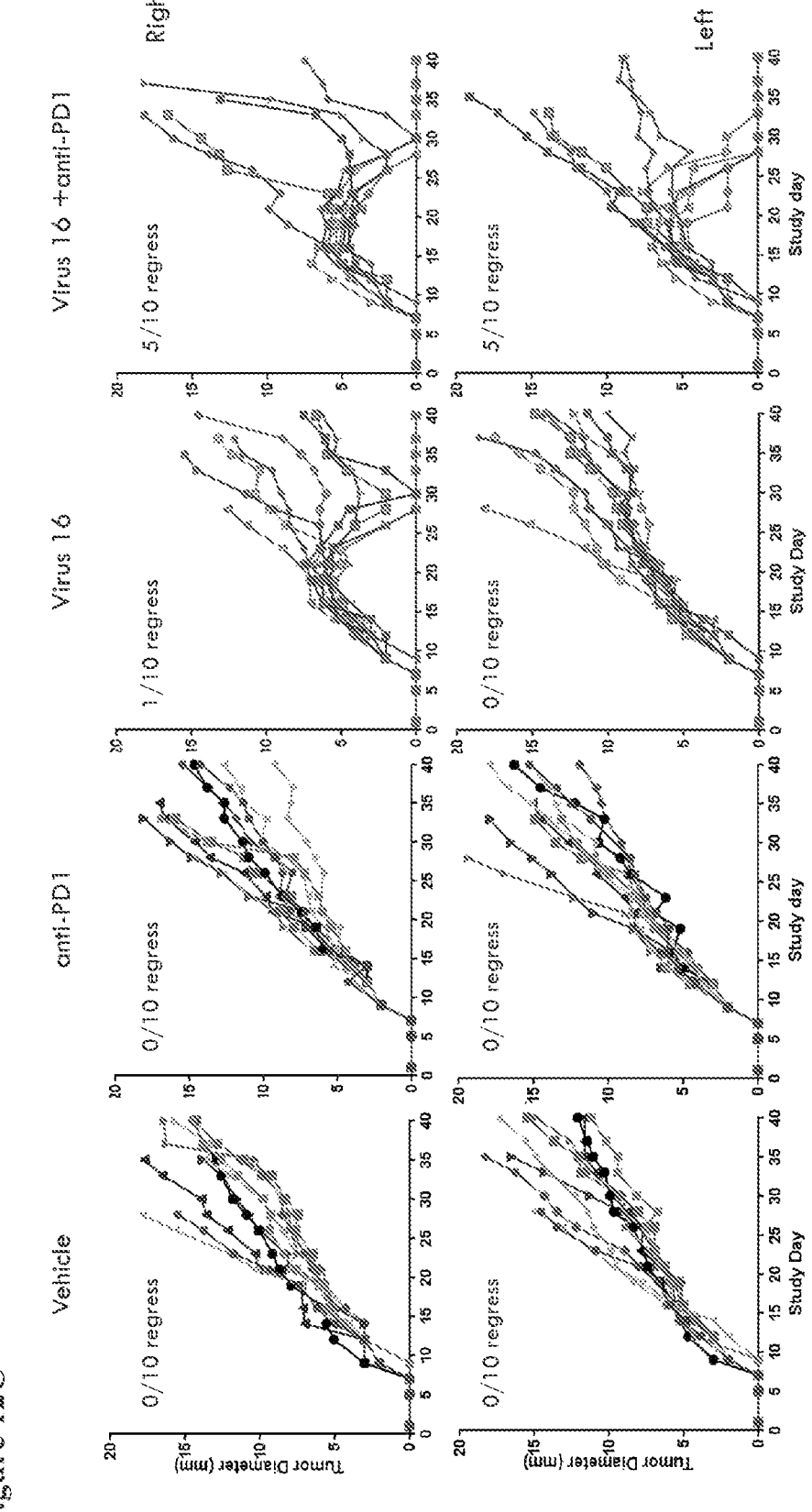
Figure 12D:
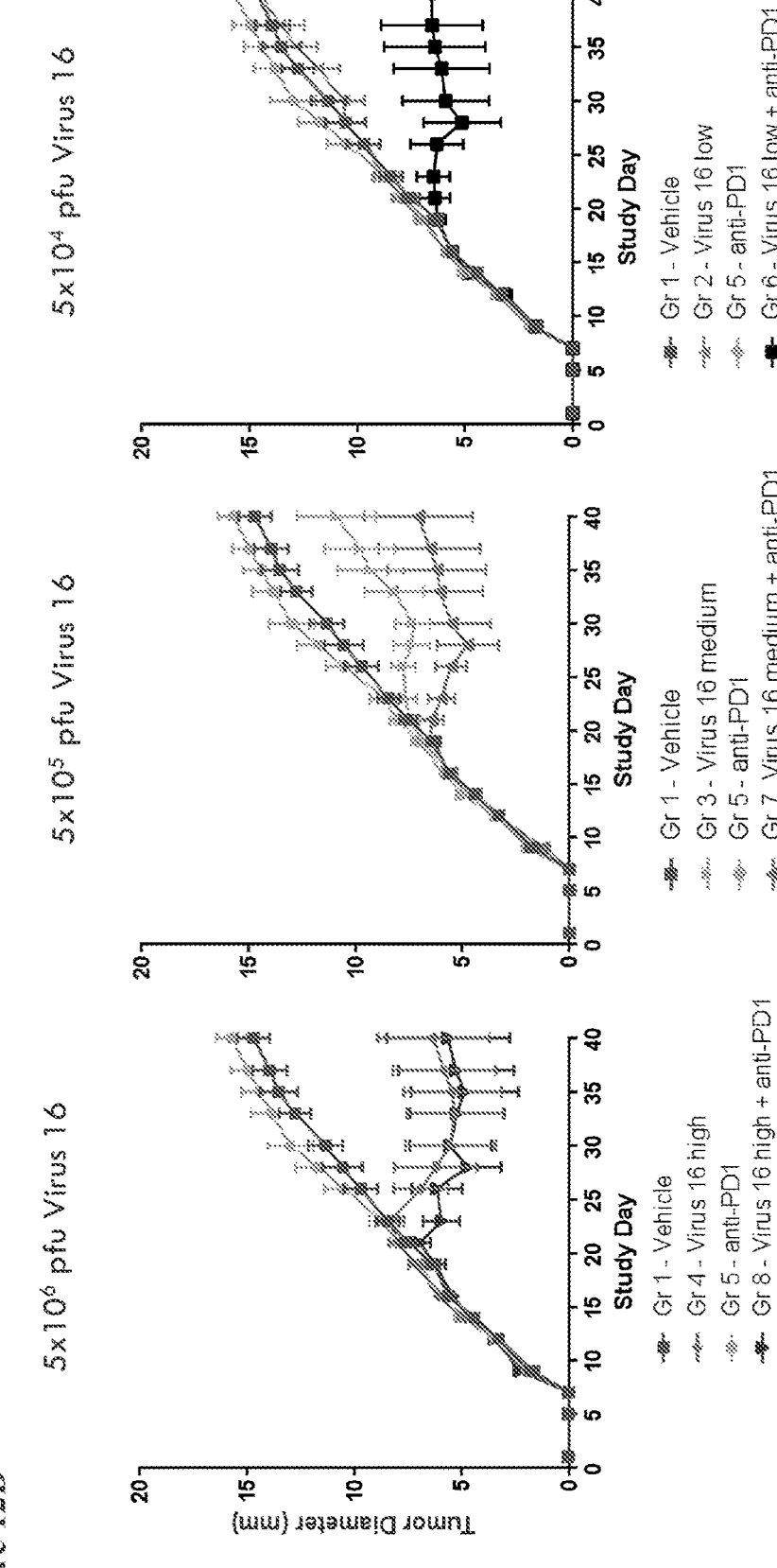

Groups of 10 mice were then treated with:

Vehicle (3 injections into right flank tumors every other day);

5×10exp6 pfu of Virus 16 injected in the right flank tumor every other day;

anti-mouse PD1 alone (10 mg/kg i.p. every three days, BioXCell clone RrMP1-14);

anti-mouse CTLA-4 (3 mg/Kg i.p every three days, BioXCell clone 9D9);

anti-mouse PD together with Virus 16;

anti-mouse CTLA4 together with Virus 16;

1-methyl trypotophan (IDO inhibitor (5 mg/ml in drinking water));

anti-mouse PD1 together with 1-methyl trypotophan;

anti-mouse PD1 together with 1-methyl trypotophan and Virus 16; Effects on tumor size were observed for a further 30 days. A greater tumor reduction in animals treated with combinations of virus and checkpoint blockade was demonstrated than in animals treated with the single treatment groups (see FIG. 11). Enhanced tumor reduction with Virus 16 together with both anti-PD1 and IDO inhibition was also demonstrated as compared to Virus 16 together with only anti-PD1 (see FIG. 11).

Enhanced activity of Virus 16 in combination with immune checkpoint blockade was also seen in A20 tumors (FIG. 12).

Example 16. The Effect of the Expression of a Fusogenic Protein from an Oncolytic Virus in Human Xenograft Models in Immune Deficient Mice The GALV R– protein causes cell to cell fusion in human cells but not in mouse cells. However, human xenograft tumors grown in immune deficient mice can be used to assess the effects of GALV expression on anti-tumor efficacy.

The utility of the invention was therefore further demonstrated by administering A549 human lung cancer cells into the flanks of nude mice and allowing the tumors to grow to approximately 0.5 cm in diameter.

The following treatments were then administered to groups of mice (ten per group), into tumor containing flank of each mouse three times over one week:

50 µl of vehicle;

50 µl of $10^7$ pfu/ml of Virus 16 (expresses both mouse GM-CSF and GALV-R–);

50 µl of $10^6$ pfu/ml of Virus 16;

50 µl of $10^5$ pfu/ml of Virus 16;

50 µl of $10^7$ pfu/ml of Virus 19 (expresses only mouse GM-CSF);

50 µl of $10^6$ pfu/ml of Virus 19;

50 µl of $10^5$ pfu/ml of Virus 19.

Figure 14:
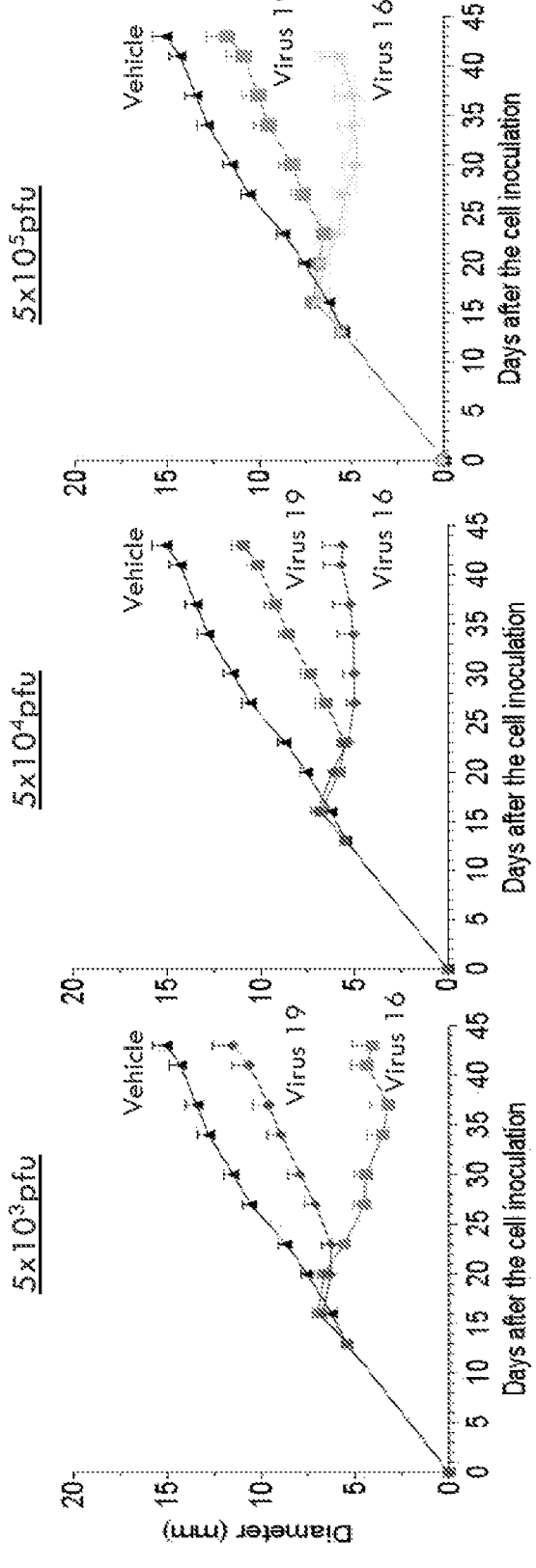
FIG. 14 shows anti-tumor effects of Virus 16 and Virus 19 in a human xenograft model (A549). There were three injections of Virus 16, Virus 19 or of vehicle over one week at three different dose levels (N=10/group). The doses of the viruses used is indicated. The anti-tumor effects of Virus 16 which expresses GALV were better than those of Virus 19 which does not express GALV.

Effects on tumor growth were then observed for a further ≈30 days. This experiment demonstrated superior tumor control and shrinkage with the virus expressing GALV-R– in both tumor models (see FIG. 14).

Figure 13:
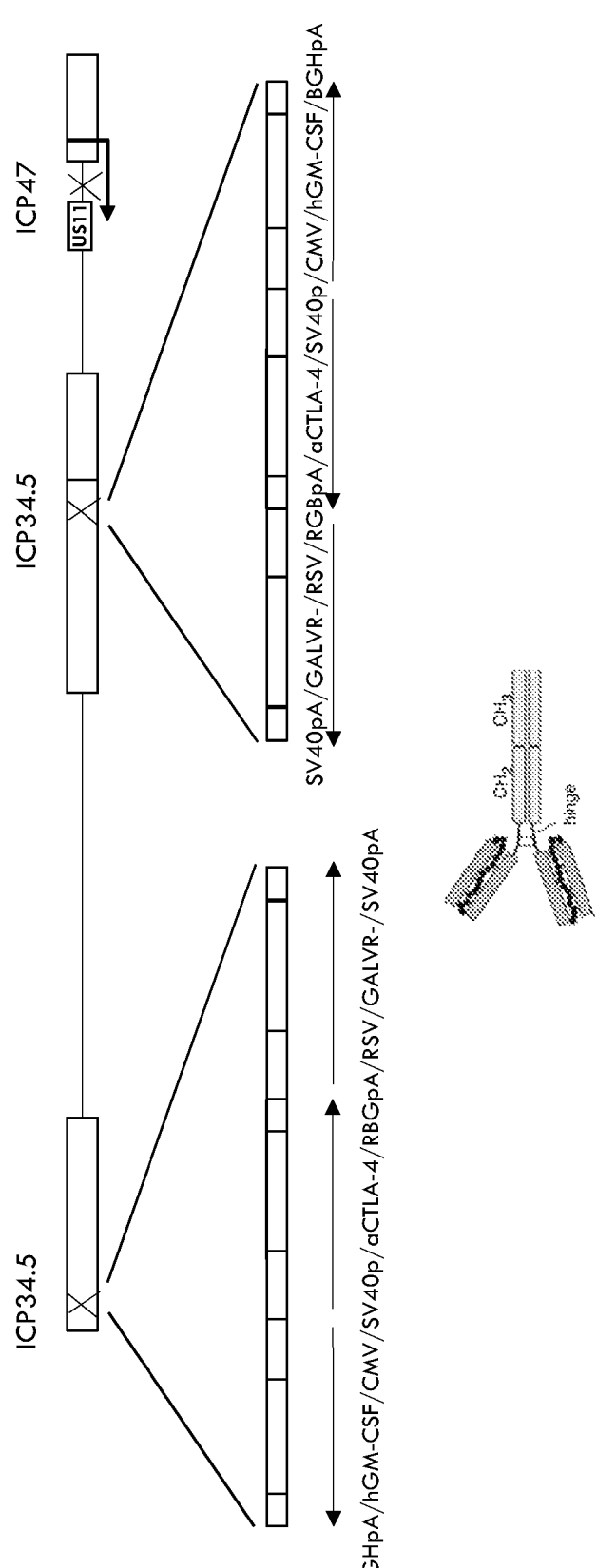
FIG. 13 shows the structure of ICP34.5 and ICP47 deleted viruses expressing GALVR–, GM-CSF and codon optimized anti-mouse or anti-human CTLA-4 antibody constructs (secreted scFv molecules linked to human or mouse IgG1 Fc regions). The scFvs contain the linked ($[G_4S]_3$) light and heavy variable chains from antibody 9D9 (US2011044953: mouse version) and from ipilimumab (US20150283234; human version). The resulting structure of the CTLA-4 inhibitor is also shown.
Figure 16:
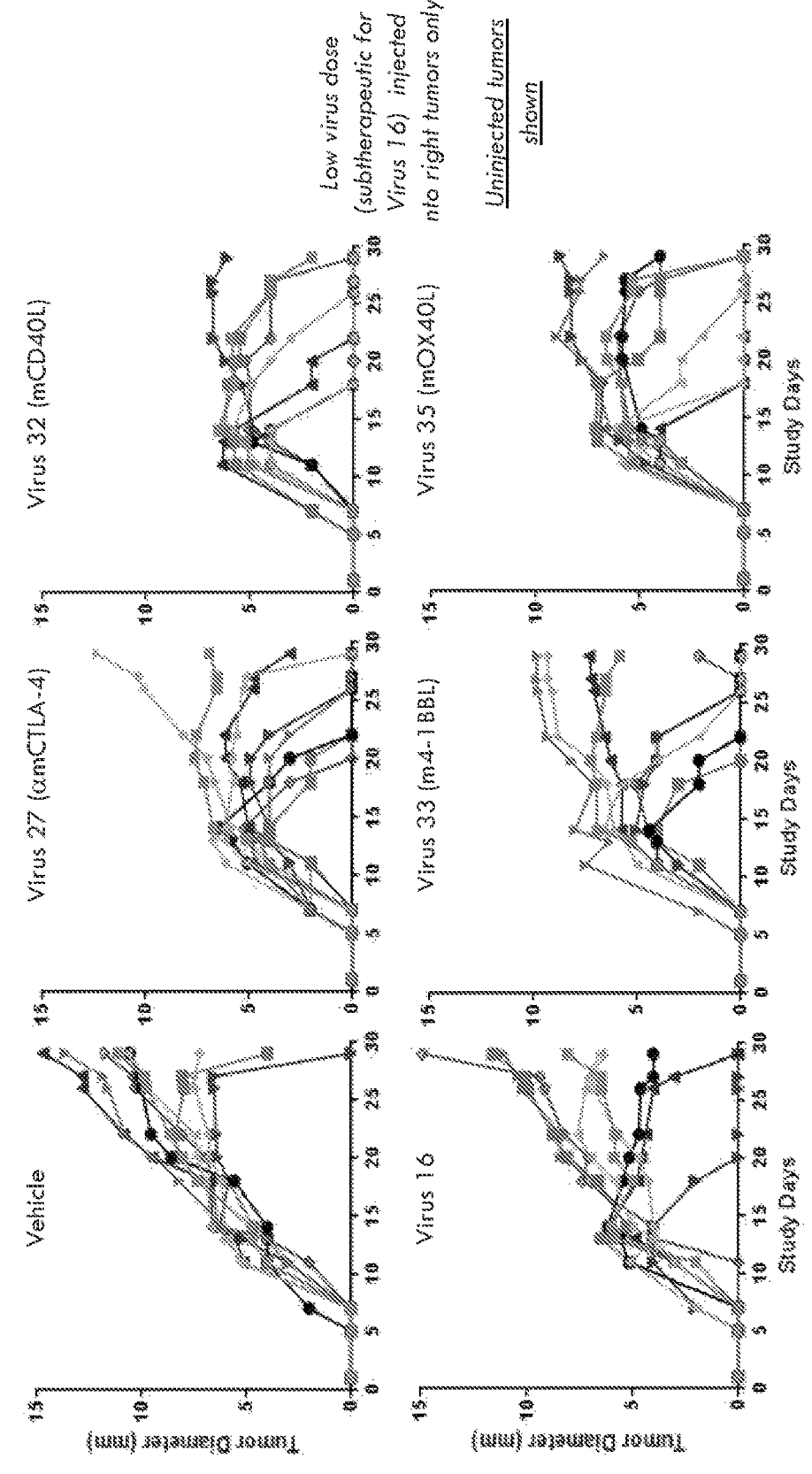
FIG. 16 shows the anti-tumor effects of viruses expressing anti-mCTLA-4 (virus 27), mCD40L (virus 32), mOX4OL (virus 35), m4-2BBL (virus 33), each also with mGM-CSF and GALV-R– compared to virus 16 (expresses GALV and mGM-CSF).

Example 17. Expression of Two Immune Stimulatory Molecules from a Virus Expressing a Fusogenic Protein Viruses similar to the GALV-R– and mGM-CSF expressing virus described above (Virus 16) were constructed, but additionally expressing mouse versions of CD40L (virus 32), ICOSL (virus 36), OX40L (virus 35), 4-1BBL (virus 33) and GITRL (virus 34). Here, instead of using a plasmid containing ICP34.5 flanking regions and an expression cassette comprising GM-CSF and GALV-R– driven by a CMV and an RSV promoter, a plasmid containing ICP34.5 flanking regions and an expression cassette comprising GM-CSF, GALV and the additional proteins driven by a CMV, an RSV and an MMLV promoter respectively were used for recombination with a virus containing GM-CSF, GALV and GFP inserted into ICP34.5. Non-GFP expressing plaques were again selected. Correct insertion was confirmed by PCR, and expression by western blotting and/or ELISA for the additional inserted gene. These viruses are shown in FIG. 5. Similarly, viruses expressing anti-mouse and anti-human CTLA-4 in addition to GALV and mGM-CSF were also constructed (Viruses 27 and 31 in FIG. 5 and see also FIG. 13). Effects of viruses expressing anti-mouse CTLA-4 (virus 27), mCD40L (virus 32), m4-1BBL (virus 33) or mOX40L (virus 35) in addition to mGM-CSF and GALVR– in vivo is shown in FIG. 16 which showed enhanced activity in A20 tumors as compared to virus 16 (expresses mGM-CSF and GALVR–). In these experiments tumors were induced in both flanks of mice, and virus or vehicle injected only into the right flank tumor. The dose of virus used was 5×$10^4$ pfu (50 ul of 1×$10^6$ pfu/ml in each case), given three times over one week. This dose level of virus is subtherapeutic for uninjected tumors for virus 16, which allows the benefits of the delivery of the additional molecules encoded by viruses 27, 32, 33 and 35 to clearly be seen.

Example 18. Construction of an Exemplary Virus

Figure 17A:
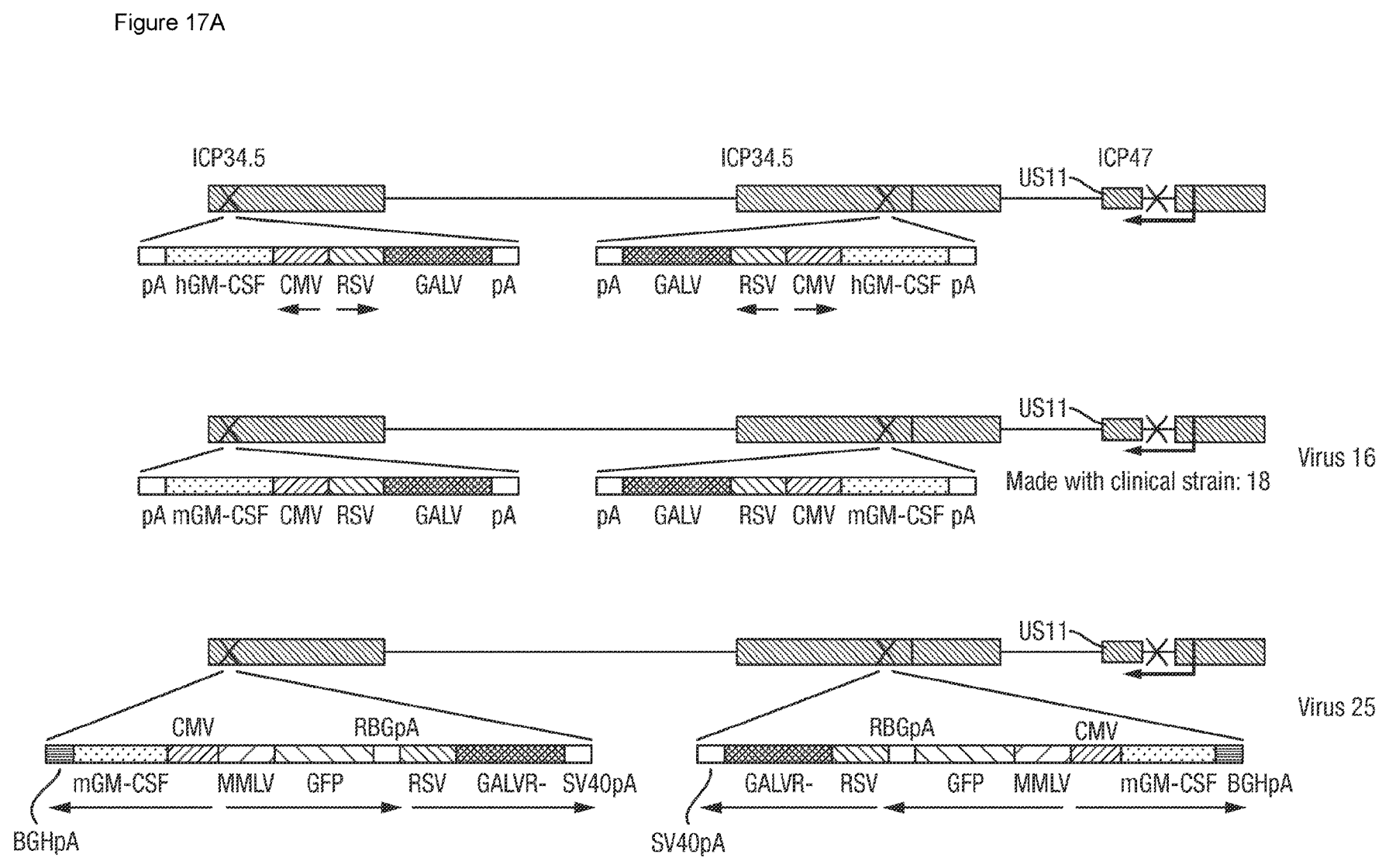
Figure 17B:
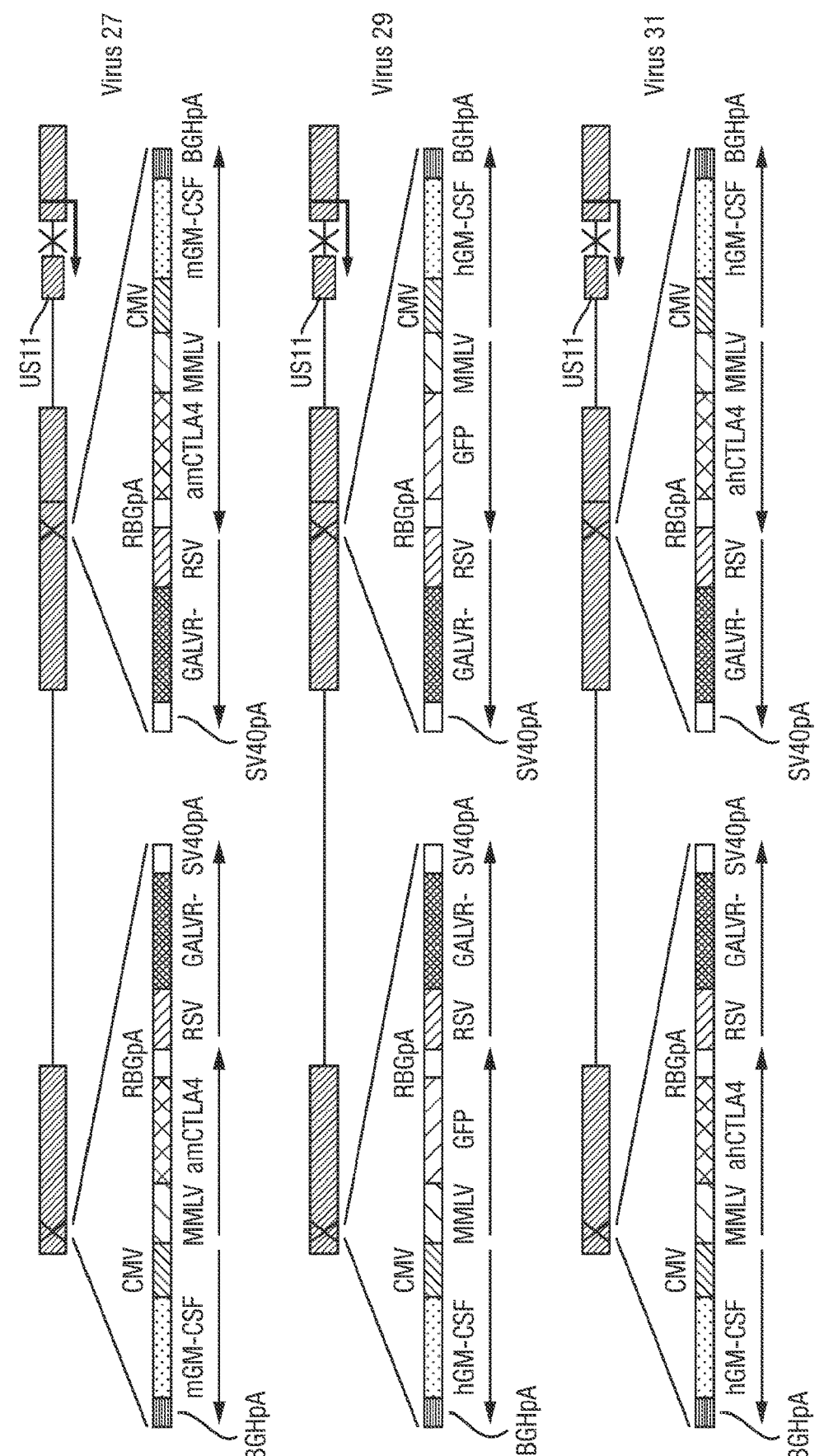
FIG. 17 depicts the structures of the viruses used to construct exemplary viruses of the invention that comprise anti-mouse or anti-human CTLA-4 constructs that are codon optimized secreted scFv molecules linked to human or mouse IgG1 Fc regions. The scFvs contain light and heavy variable chains from 9D9 (the initial mouse antibody initially used to validate CTLA-4; WO2007/123737: mouse version) or from ipilimumab. (WO2014/066532; human version) linked by the 15-mer [G4S]3 (GGGGSGGGGSGGGGS). The viruses are modified versions of strain HSV1 RH018A (clinical strain 18). The ICP34.5 and ICP47 genes are inactivated in the viruses. The US11 gene is placed under the control of the ICP47 immediate early gene promoter by deletion of the ICP47 promoter. An expression cassette is inserted into the ICP34.5 gene loci. In virus 17, the expression cassette includes the human GM-CSF gene under the control of a CMV promoter and the GALV gene under the control of a RSV promoter. Virus 16 is the same as virus 17, except that human GM-CSF is included instead of mouse GM-CSF. Viruses 25 and 29 are the same as viruses 16 and 17, respectively, except that they each additionally comprise a GFP gene under the control of a MMLV promoter in the expression cassette. Viruses 27 and 31 are the same as viruses 25 and 29, respectively, except that the GFP gene is replaced with mouse anti-CTLA4 and human anti-CTLA4, respectively.
Figure 18A:
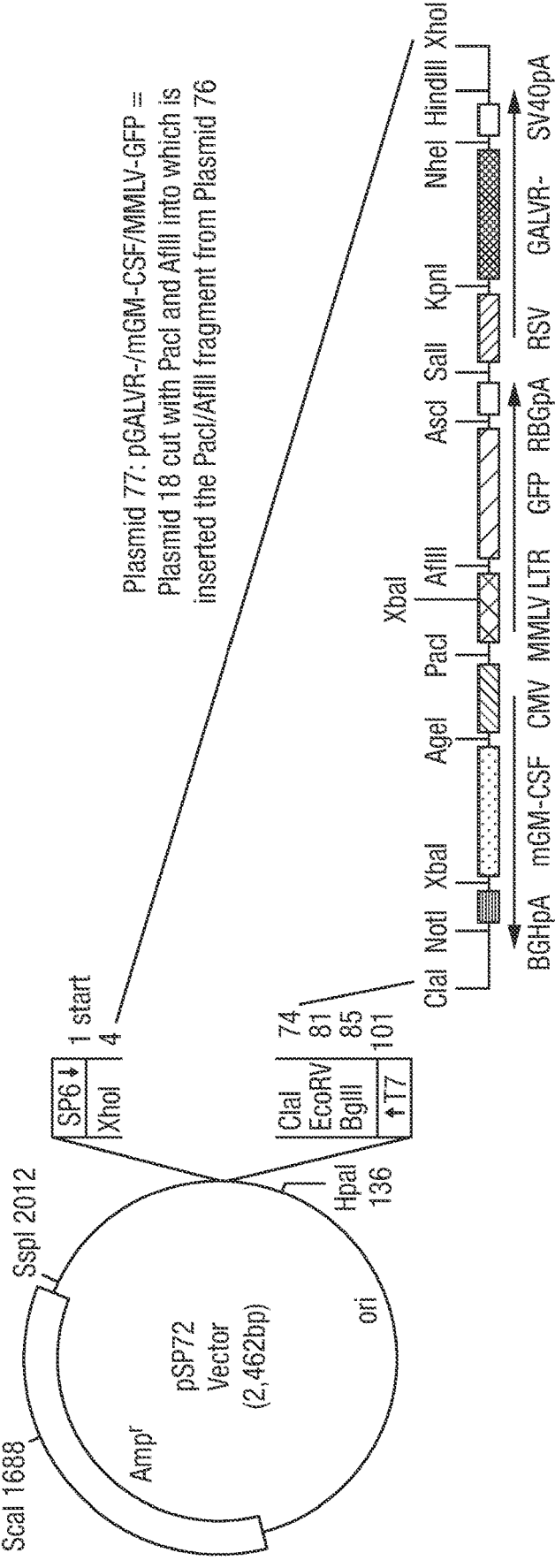
FIG. 18 depicts the structures of the plasmids used to construct the exemplary viruses of the invention.
Figure 18B:
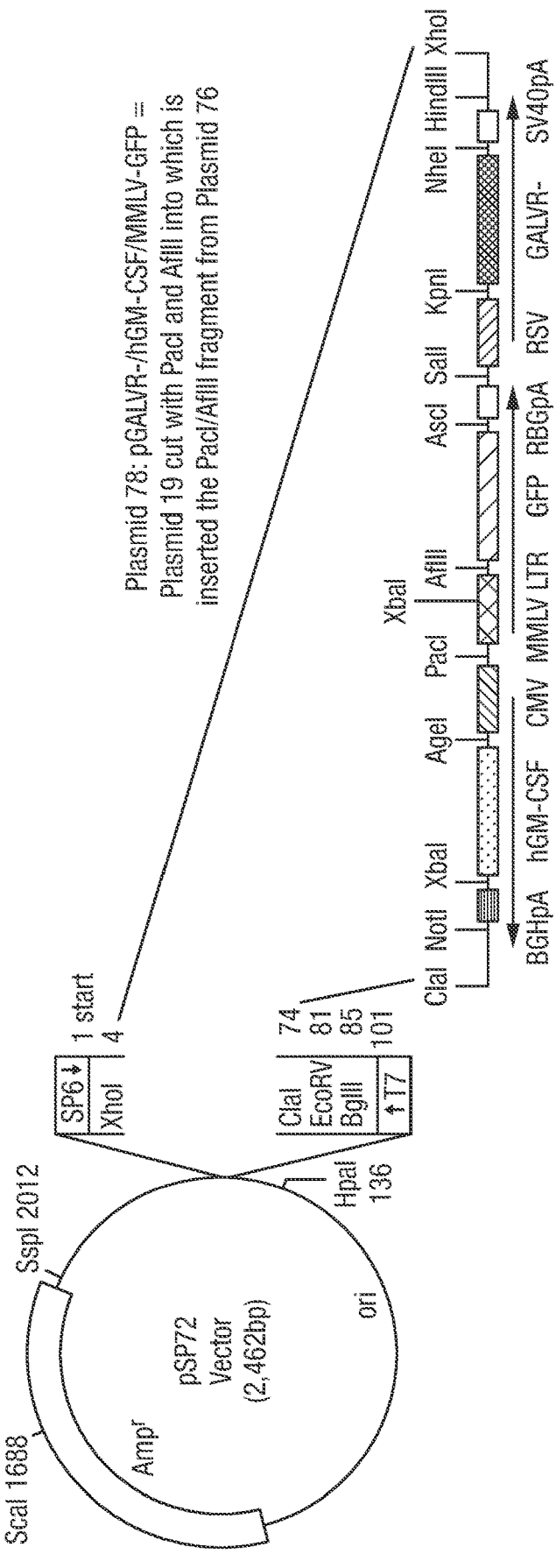
Figure 18C:
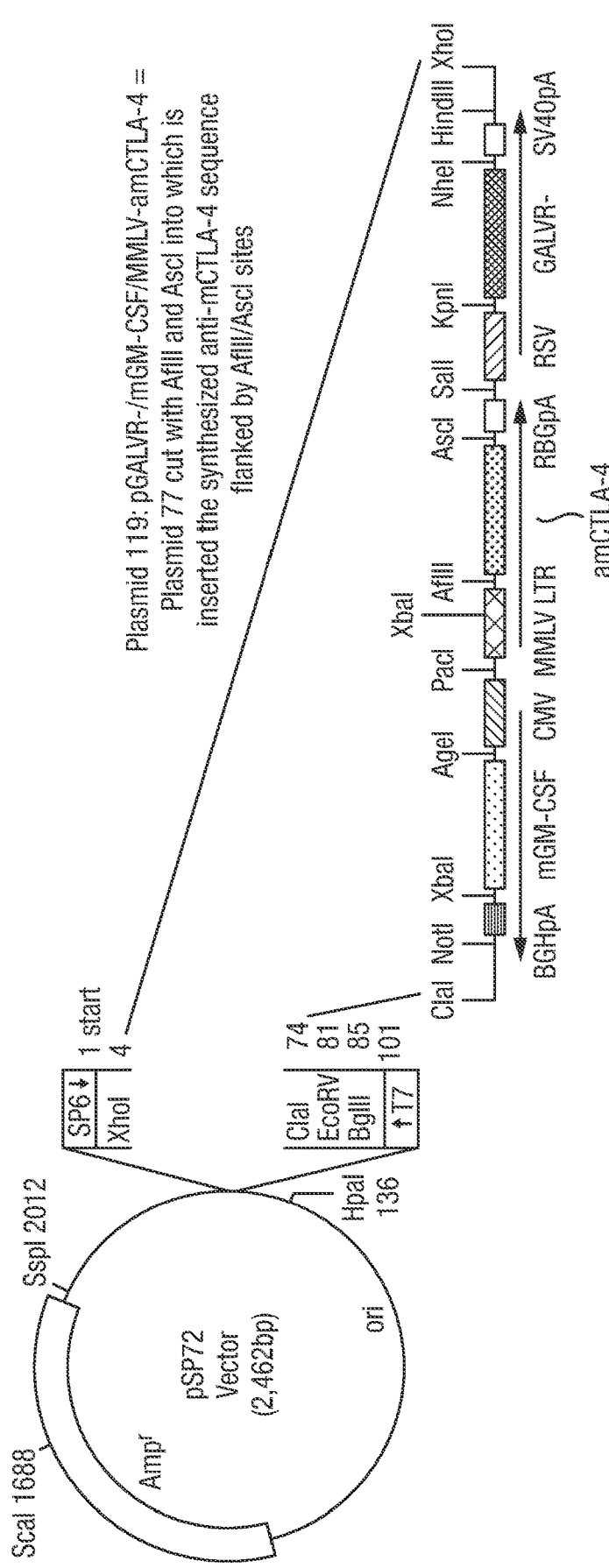
Figure 18D:
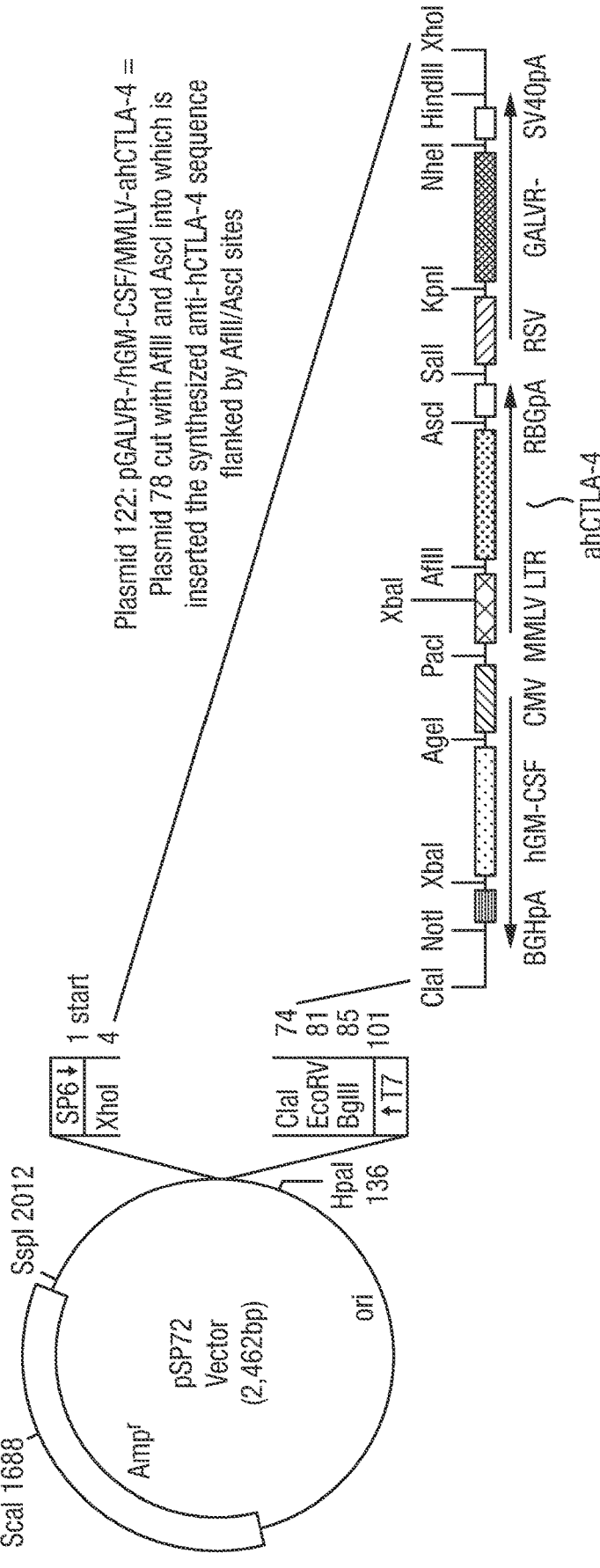
Figure 19:
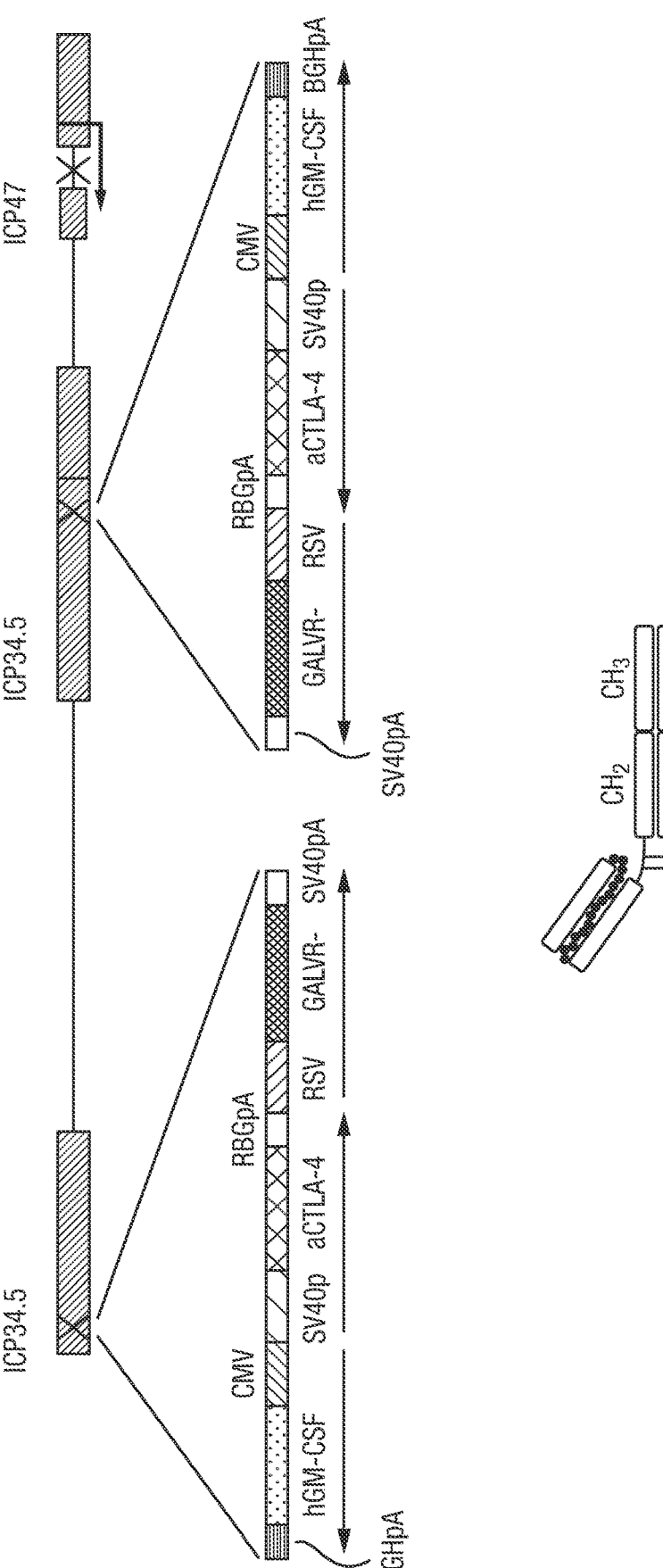
FIG. 19 shows the structure of anti-mouse or human CTLA-4 constructs that are codon optimized secreted scFv molecules linked to human or mouse IgG1 Fc regions.

The exemplified virus species is HSV, specifically HSV1. Diagrams of the plasmids used are shown in FIG. 18. Diagrams of the viruses are shown in FIG. 17. All viruses were constructed using HSV1 Strain RH018A. The plasmids used for virus construction were generated by a combination of gene synthesis and subcloning, conducted by Genscript Inc.

Viruses expressing anti-mouse CTLA4 together with mouse GM-CSF and GALV were constructed by co-transfection of Plasmid 77 with Virus 16 DNA, so as to insert GFP into Virus 16 by selection of plaques expressing GFP to give Virus 25. GFP was then knocked out of Virus 25 by co-transfection of Virus 25 DNA with Plasmid 119. This gave Virus 27.

Viruses expressing anti-human CTLA4 together with human GM-CSF and GALV were constructed by co-transfection of Plasmid 78 with Virus 17 DNA, so as to insert GFP into Virus 17 by selection of plaques expressing GFP to give Virus 29. GFP was then knocked out of Virus 29 by co-transfection of Virus 29 DNA with Plasmid 122. This gave Virus 31.

Viruses expressing anti-mouse CTLA-4 and co-stimulatory ligands together with mouse GM-CSF and GALV were constructed by co-transfection of a plasmid encoding GFP driven by an SV40 promoter between the mouse GM-CSF and anti-mouse CTLA-4 encoding sequences with Virus 27. GFP was then knocked out of the resulting virus with a plasmid encoding each of the individual mouse co-stimulatory ligands in place of GFP.

Viruses expressing anti-human CTLA-4 and co-stimulatory ligands together with human GM-CSF and GALV were constructed by co-transfection of a plasmid encoding GFP driven by an SV40 promoter between the human GM-CSF and anti-human CTLA-4 encoding sequences with Virus 31. GFP was then knocked out of the resulting virus with a plasmid encoding each of the individual human co-stimulatory ligands in place of GFP.

Figure 20:
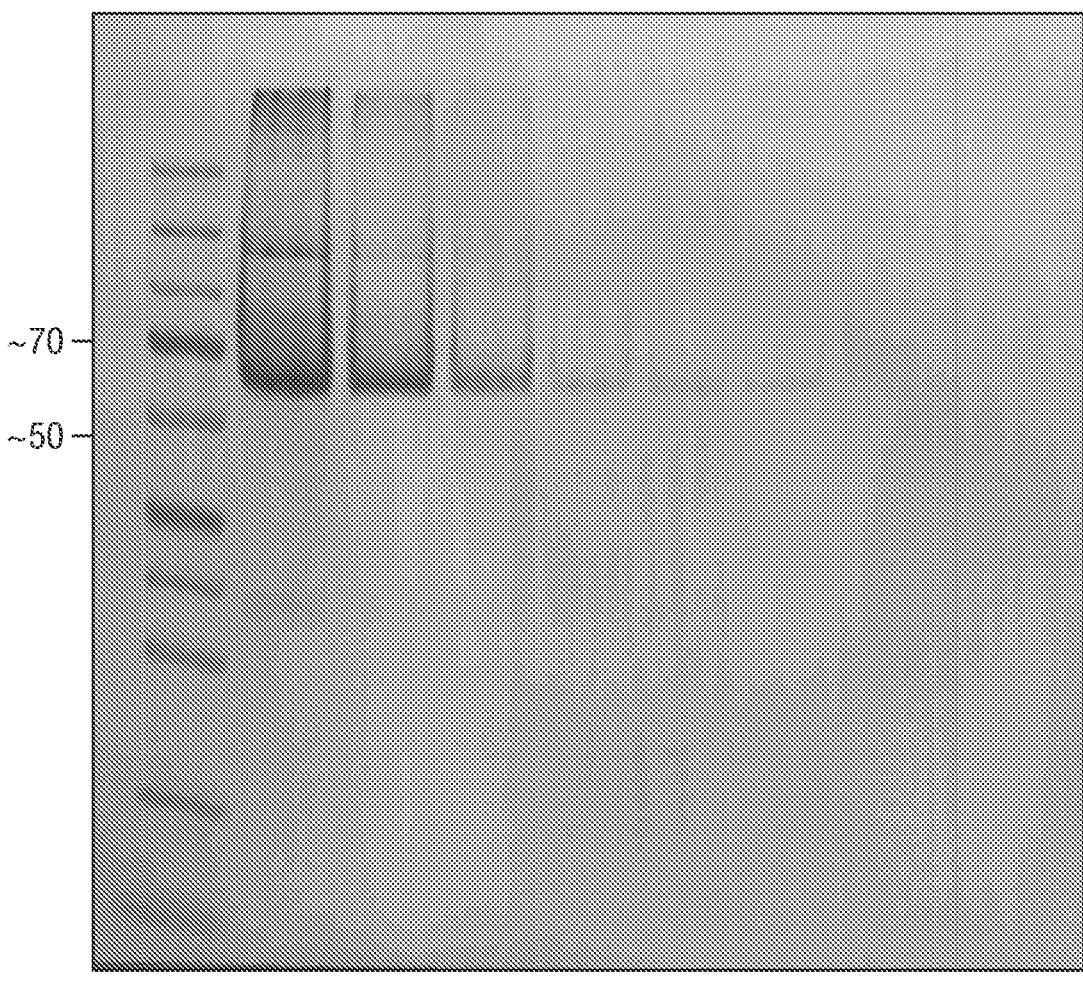
FIG. 20 is a western blot demonstrating that anti-mouse CTLA-4 is expressed from virus 27. The gel used was a reduced denatured PVDF membrane tris-glycine gel. Anti-CTLA-4 was detected using an alkaline phosphatase-tagged anti-mouse IgG1 antibody. Lane 1: spectra broad range ladder; lane 2 virus 27 neat supernatant; lane 3 virus 27 supernatant diluted 1 in 2; lane 4 virus 27 supernatant diluted 1 in 4; lane 5 virus 27 supernatant diluted 1 in 8; lane 6 virus 27 supernatant diluted 1 in 16; lane 7 virus 27 supernatant diluted 1 in 32; lane 8 negative control virus (neat supernatant). The expected size of anti-CTLA-4 (reduced) is 57 kDa.

FIG. 20 shows a western blot demonstrating expression of anti-mouse CTLA-4 from Virus 27.

Example 19. The Effect of Combined Expression of GALV, GM-CSF and Anti-CTLA4 from an Oncolytic Virus The utility of the invention is demonstrated in the following way. A20 cells were administered into both flanks of Balb/c mice and the A20 tumors were allowed to grow to approximately 0.5 cm in diameter.

Figure 21:
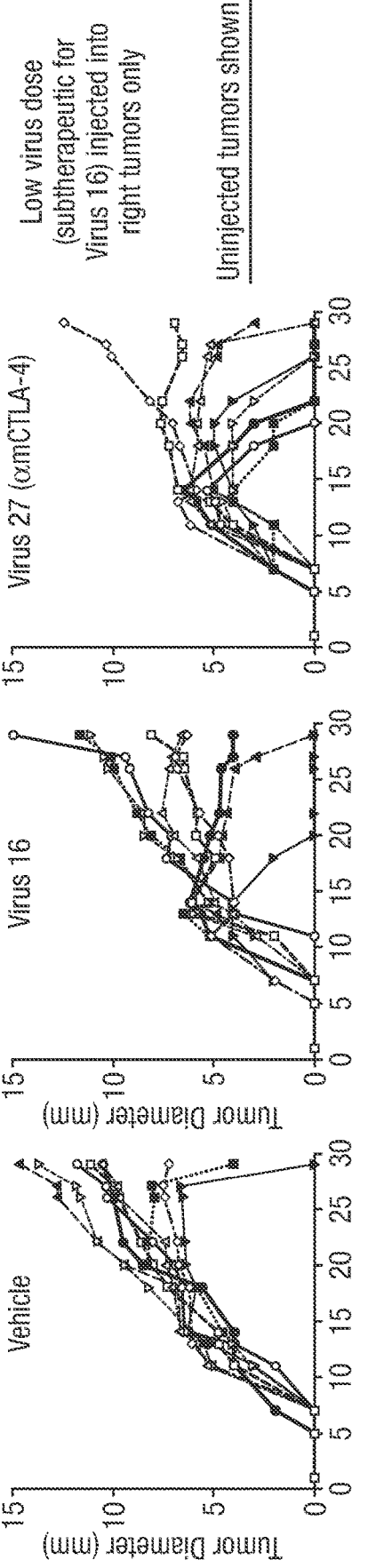
FIG. 21 shows the superior tumor control and shrinkage in uninjected tumors of a virus expressing anti-mCTLA-4 (virus 27) compared to an otherwise identical virus that does not express CTLA-4 (virus 16). The dose of virus used was $5×10^4$ pfu (50 ul of $1×10^6$ pfu/ml in each case), given three times over one week. This dose level of virus is subtherapeutic for uninjected tumors for virus 16, which allows the benefits of the delivery of the additional molecule encoded by virus 27 to clearly be seen.
Figure 22:
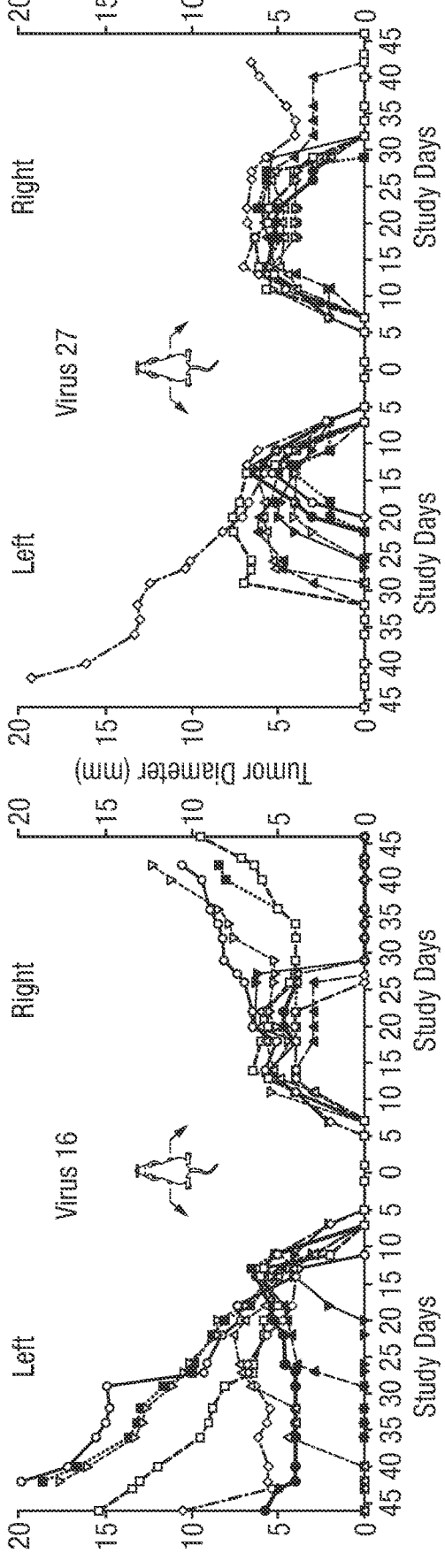
FIG. 22 shows the superior tumor control and shrinkage in both injected and uninjected tumors of a virus expressing anti-mCTLA-4 (virus 27) compared to an otherwise identical virus that does not express CTLA-4 (virus 16). The dose of the virus used was $5 \times 10^4$ pfu over one week into the right tumor of a virus expressing anti-mCTLA-4 (virus 27) compared to an otherwise identical virus that does not express CTLA-4 (virus 16). Each line represents a different mouse.

The following treatments were then administered to groups of mice, into one flank of each mouse only (right tumor) 3 times per week for one week:
    50 μl of vehicle (1 group);
    50 μl of $10^6$ pfu/ml of the HSV with only mouse GM-CSF and GALVR– inserted (Virus 16);
    50 μl of $10^6$ pfu/ml of the HSV with GALVR–, mouse GM-CSF and the anti-mouse CTLA-4 antibody inserted (Virus 27);

Effects on tumor growth were then observed for up to one month. The dose of virus used was $5 \times 10^4$ pfu (50 μl of $1 \times 10^6$ pfu/ml in each case), given three times over one week. This dose level of virus is subtherapeutic for uninjected tumors for virus 16, which allows the benefits of the delivery of the additional molecules encoded by virus 27 to clearly be seen. FIGS. 21 and 22 show the superior tumor control and shrinkage in uninjected tumors with the virus expressing anti-CTLA-4 compared to with virus 16, which does not express CTLA-4.

Example 20. The Effect of Combined Expression of GALV, GM-CSF and Anti-CTLA4 from an Oncolytic Virus with Anti-PD-1

A20 cells were administered into both flanks of Balb/c mice and the A20 tumors were allowed to grow to approximately 0.5 cm in diameter.

The following treatments were then administered to groups of mice (10 per group), into one flank of each mouse only 3 times per week for one week:
    50 μl of vehicle;
    Intraperitoneal anti-mouse PD1 (Bioxcell RMP-1-14 10 mg/kg every three days);
    50 μl of $10^7$ pfu/ml of the HSV with GALVR–, mouse GM-CSF and the anti-mouse CTLA-4 antibody inserted (Virus 27)
    50 μl of $10^7$ pfu/ml, of the HSV with GALVR–, mouse GM-CSF and the anti-mouse CTLA-4 antibody inserted (Virus 27) together with intraperitoneal anti-mouse PD1 (10 mg/kg every three days) (3 groups).

Figure 23:
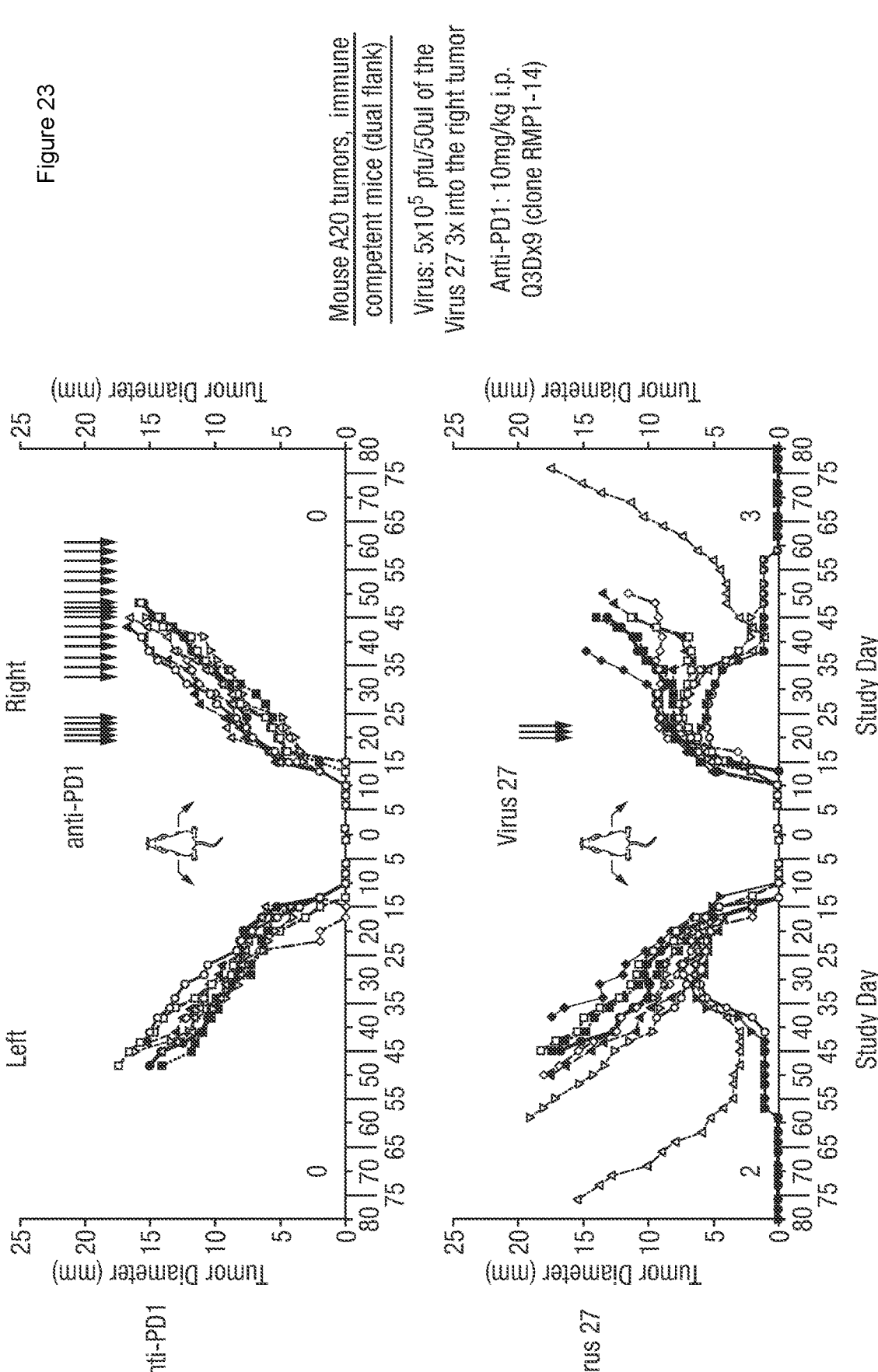
FIG. 23 shows the effect of combined treatment of bilateral mouse A20 tumors using anti-PD1 and virus 27 expressing mGM-CSF, GALVR and anti-mCTLA-4. The top panel shows the effect of anti-PD1 alone on both injected (right) and uninjected (left) tumors. The middle panel shows the effect of virus 27 alone on both injected (right) and uninjected (left) tumors. The bottom panel shows the superior tumor control and shrinkage achieved when anti-PD1 and virus 27 are both injected into the right tumor. The improved anti-tumor effect of the combined treatment is observed in both injected (right) and uninjected (left) tumors. Each line represents a different mouse.
Figure 23:
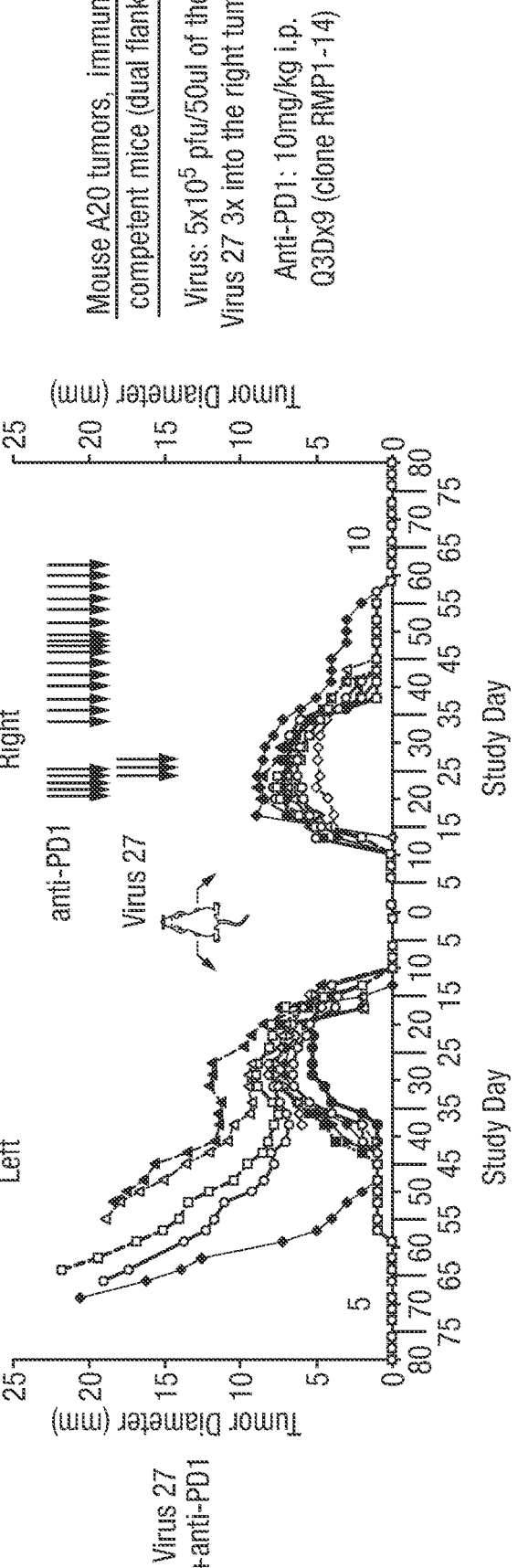

Effects on tumor growth were then observed for up to 80 days. Superior tumor control and shrinkage in both injected and un-injected tumors when treatment with the virus was combined treatment with anti-PD1. This data is shown in FIG. 23.

Example 21. The Effect of Combined Expression of GALV, GM-CSF and Anti-Human CTLA4 from an Oncolytic Virus Alone and in Combination with Anti-PD-1

MC38 cells were administered into both flanks of C57BL/6 mice engineered by gene editing to express human rather than mouse CTLA-4. This renders the mice susceptible to anti-human CTLA-4 antibodies such as ipilimumab. The MC38 tumors were allowed to grow to approximately 0.5 cm in diameter.

The following treatments are then administered to groups of mice (10 per group), into one flank of each mouse only 3 times per week for two weeks:
    50 μl of vehicle;
    50 μl of $10^8$ pfu/ml of Virus 17 (i.e. expressing hGM-CSF and GALV);
    50 μl of $10^8$ pfu/ml of Virus 31 (i.e. expressing hGM-CSF, GALV and anti-human CTLA-4);
    50 μl of $10^8$ pfu/ml of Virus 17 together with intraperitoneal anti-mouse PD1 (10 mg/kg every three days);
    50 μl of $10^8$ pfu/ml of Virus 31 together with intraperitoneal anti-mouse PD1 (10 mg/kg every three days).

Figure 24:
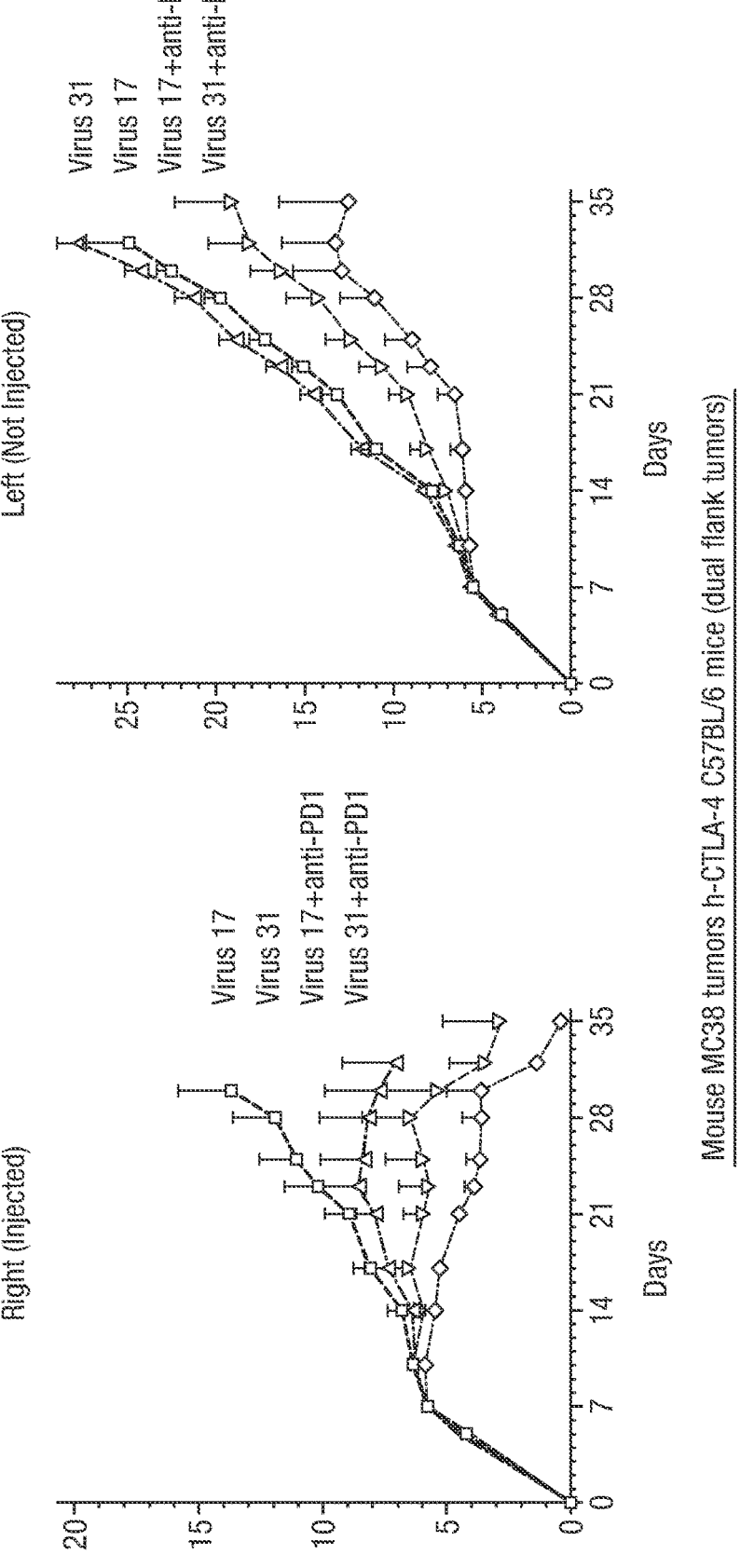
FIG. 24 shows the superior tumor control and shrinkage effects of virus 31 expressing hGM-CSF, GALVR and anti-human CTLA-4 compared to virus 17 expressing only hGM-CSF and GALVR in mouse MC38 tumors in knock-in mice expressing human CTLA-4. The anti-tumor effects of virus 31 are observed when the virus is administered alone or in combination with anti-PD1. Superior tumor control and shrinkage in injected tumors is obtained with virus 31 which expresses anti-human CTLA-4 compared with an otherwise identical virus that does not express anti-human CTLA-4 (left panel). This effect is further enhanced when treatment with the virus is combined with anti-PD1 treatment. Superior tumor control and shrinkage is also observed in uninjected tumors (right panel) when treatment with either virus is combined with anti-PD1 treatment. This improvement is more marked for the virus 31 that expresses anti CTLA-4 than for virus 17 which does not. Each line represents a different mouse.

Effects on tumor growth were then observed for up to 35 days. Superior tumor control and shrinkage in injected tumors with the virus expressing anti-human CTLA-4 was seen, which is further enhanced with combined treatment with anti-PD1. Superior tumor control and shrinkage was observed in un-injected tumors when treatment with either virus was combined with anti PD1 treatment. The improvement is more marked for the virus that expresses anti CTLA4. This data is shown in FIG. 24.

Example 22. The Induction of Memory Immune Responses Following the Treatment of Tumors with the Anti-CTLA4 Expressing Oncolytic Virus and Anti-PD1 Therapy In a further experiment using Virus 31 in combination with anti-PD-1 therapy, the durability of the anti-tumor response in mice in which tumors had been eradicated was assessed and whether these mice were protected against re-challenge with tumor cells, which would demonstrate that memory immune responses had been induced, was determined.

Figure 25:
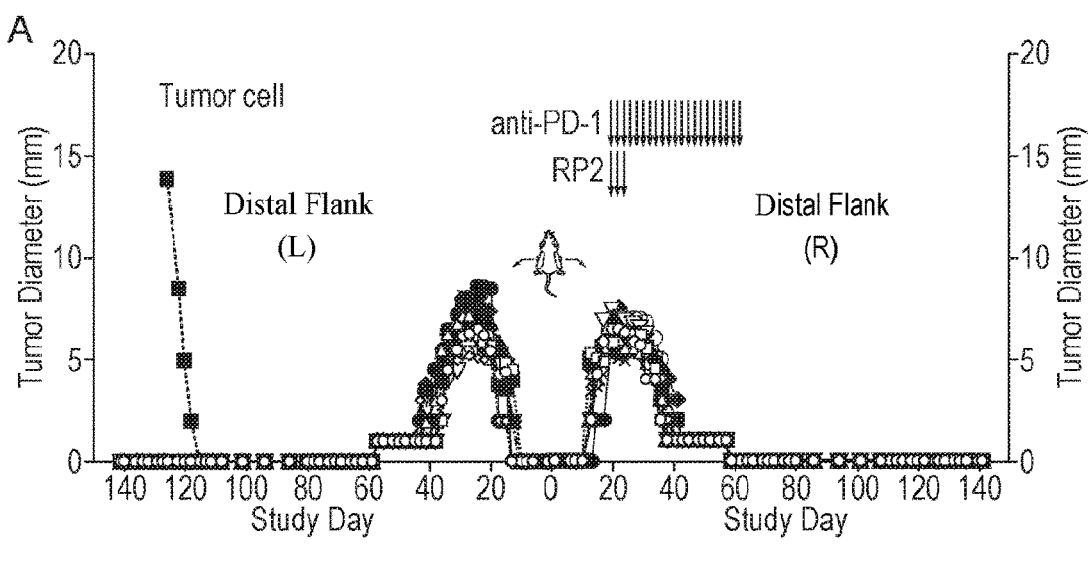
FIG. 25 shows the durability of the anti-tumor effect obtained using virus 31 expressing hGM-CSF, GALVR and anti-human CTLA-4 in combination with anti-PD1 treatment. A shows that after elimination of tumors by the combination therapy, mice were rechallenged in the left tumor, and 14 of the 15 mice were protected against tumor rechallenge. B shows that 10 tumor and virus naive mice challenged with tumor cells on the same day all grew tumors. C shows that mice treated with anti-PD-1 alone show no anti-tumor response.
Figure 25:
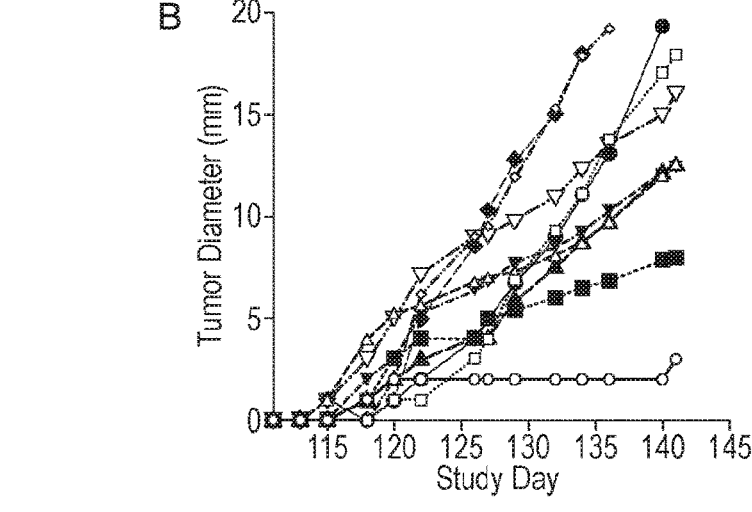
Figure 25:
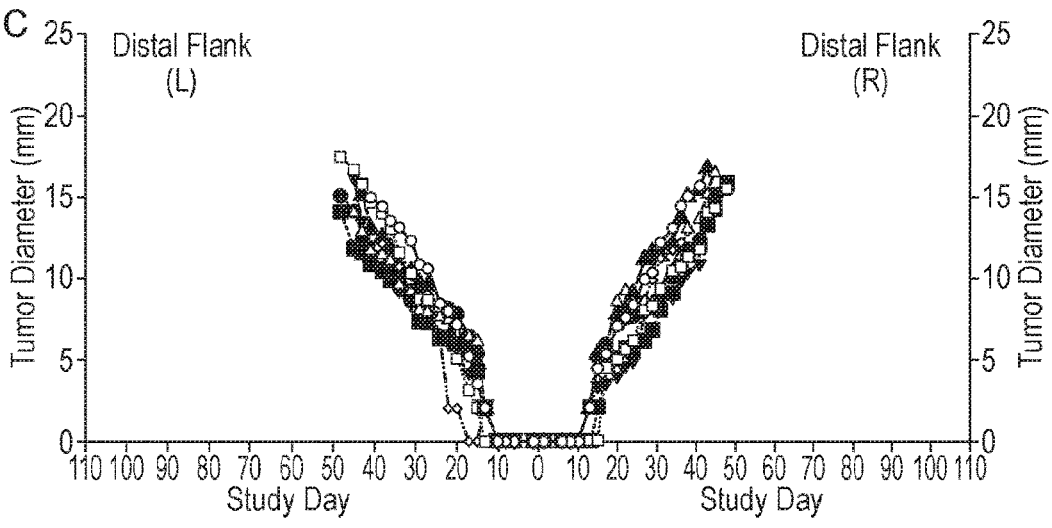

In this experiment, 15 mice cured of bilateral tumors following administration of Virus 31 combined with an anti-PD-1 antibody were observed until day 108 following initiation of the experiment and then re-challenged with tumor cells to assess whether the mice were protected against the formation of new tumors. Anti-tumor effects were maintained throughout the experiment and 14 out of the 15 mice were protected against re-challenge with tumor cells. The results are shown in FIG. 25. Treatment with anti-PD-1 alone has no anti-tumor effect in this model.

Example 23. The Effect of Combined Expression of GALV, GM-CSF, Anti-CTLA4 and an Immune Co-Stimulatory Pathway Activating Molecule from an Oncolytic Virus The experiment in Example 20 above is repeated but mice are dosed with the viruses additionally expressing the immune co-stimulatory pathway ligands as well as expressing GALV, mGM-CSF and anti-CTLA4.

More specifically, groups of mice receive:

(1) Vehicle;

(2) Intraperitoneal anti mouse PD1;

(3) HSV with mGM-CSF, GALVR– and anti-CTLA4 inserted as in Example 2;

(4) HSV with mGM-CSF, GALVR–, anti-CTLA4 and mouse CD40L inserted;

(5) HSV with mGM-CSF, GALVR–, anti-CTLA4 and mouse 4-1BBL inserted;

(6) HSV with mGM-CSF, GALVR–, anti-CTLA4 and mouse GITRL inserted;

(7) HSV with mGM-CSF, GALVR–, anti-CTLA4 and mouse OX40L inserted;

(8) HSV with mGM-CSF, GALVR–, anti-CTLA4 and mouse ICOSL inserted;

(9) HSV with mGM-CSF, GALVR– and anti-CTLA4 inserted as in Example 2, together with intraperitoneal anti-PD1;

(10) HSV with mGM-CSF, GALVR–, anti-CTLA4 and mouse CD40L inserted together with intraperitoneal anti-PD1;

(11) HSV with mGM-CSF, GALVR–, anti-CTLA4 and mouse 4-1BBL inserted together with intraperitoneal anti-PD1;

(12) HSV with mGM-CSF, GALVR–, anti-CTLA4 and mouse GITRL inserted together with intraperitoneal anti-PD1;

(13) HSV with mGM-CSF, GALVR– anti-CTLA4 and mouse OX40L inserted together with intraperitoneal anti-PD1; or

(14) HSV with mGM-CSF, GALVR–, anti-CTLA4 and mouse ICOSL inserted together with intraperitoneal anti-PD1.

Superior tumor control is seen with the viruses expressing the immune co-stimulatory ligands.

DEPOSIT INFORMATION

The following HSV1 strains were deposited at the ECACC, Culture Collections, Public Health England, Porton Down, Salisbury, SP4 0JG, United Kingdom on 19 Dec. 2016 by Replimune Limited and were allocated the indicated accession numbers:

RH004A—Accession Number 16121902

RH015A—Accession Number 16121903

RH018A—Accession Number 16121904

RH021A—Accession Number 16121905

RH1023A—Accession Number 16121906

RH031A—Accession Number 16121907

RH040B—Accession Number 16121908

RH047A—Accession Number 16121909.

The invention claimed is:

1. A method of treating melanoma in patients who have previously been treated by surgery and/or checkpoint blockade therapy,
   wherein the method comprises administering by intratumoral injection into a solid tumor a therapeutically effective amount of an oncolytic herpes simplex virus (HSV) to a patient in need thereof, wherein
   the oncolytic virus comprises (i) a fusogenic protein-encoding gene, wherein the fusogenic protein is the glycoprotein from gibbon ape leukemia virus (GALV) and has the R transmembrane peptide mutated or removed (GALV-R−); and (ii) an immune stimulatory molecule-encoding gene, wherein the immune stimulatory molecule is GM-CSF, and wherein the administration of the oncolytic virus elicits a systemic immune response to induce regression of the tumor injected by the oncolytic virus and a tumor not injected by the oncolytic virus, and to prevent tumor reoccurrence.

2. The method according to claim 1, wherein the oncolytic virus is a modified clinical isolate.

3. The method according to claim 1, wherein the virus comprises:
   (a) more than one immune stimulatory molecule encoding genes; and/or
   (b) more than one fusogenic protein-encoding genes.

4. The method according to claim 1, wherein:
   the oncolytic virus comprises a further immune stimulatory molecule selected from IL-2, IL-12, IL-15, IL-18, IL-21, IL-24, a type I interferon, interferon gamma, a type III interferon, TNF alpha, an antagonist of TGF beta, an immune checkpoint antagonist or an agonist of an immune potentiating pathway such as an agonist of CD40, ICOS, GITR, 4-1-BB, OX40 or flt3.

5. The method according to claim 4, wherein the further immune stimulatory molecule is a CTLA-4 inhibitor comprising an anti-CTLA-4 antibody, or an antigen binding fragment thereof.

6. The method according to claim 5, wherein the fragment comprises a scFv.

7. The method according to claim 5, wherein the fragment is a scFv molecule linked to one or more IgG1 constant regions.

8. The method according to claim 5, wherein the antibody or fragment comprises a light chain variable region sequence linked to an IgG heavy chain.

9. The method according to claim 5, wherein the antibody or fragment comprises (a) the light chain variable region sequence shown in SEQ ID NO: 46 and the heavy chain variable region sequence shown in SEQ ID NO: 48; or (b) the light chain variable region sequence shown in SEQ ID NO: 56 and the heavy chain variable region sequence shown in SEQ ID NO: 57.

10. The method according to claim 9, wherein the antibody or fragment comprises (a) the amino acid sequence of SEQ ID NO: 54; or (b) the amino acid sequence of SEQ ID NO: 59.

11. The method according to claim 5, wherein the antibody or fragment is encoded by (a) the nucleotide sequence of SEQ ID NO: 55; or (b) the nucleotide sequence of SEQ ID NO: 60.

12. The method according to claim 1 wherein the oncolytic virus is a HSV1.

13. The method according to claim 12, wherein the HSV1 is:
   strain RH018A having the accession number ECACC 16121904;

strain RH004A having the accession number ECACC 16121902;

strain RH031A having the accession number ECACC 16121907;

strain RH040B having the accession number ECACC 16121908;

strain RH1015A having the accession number ECACC 16121903;

strain RH021A having the accession number ECACC 16121905;

strain RH023A having the accession number ECACC 16121906; or strain RH047A having the accession number ECACC 16121909.

14. The method according to claim 13 wherein the oncolytic virus is strain RH018A having the accession number ECACC 16121904.

15. The method according to claim 1, wherein the virus:

(a) does not express functional ICP34.5;

(b) does not express functional ICP47; and/or (c) expresses the US11 gene as an immediate early gene.

16. The method according to claim 15, wherein: (a) the fusogenic protein-encoding gene and/or the immune stimulatory molecule-encoding gene are/is inserted into the ICP34.5 encoding locus, either by insertion, or partial or complete deletion, each under separate regulatory control, optionally in a back to back orientation in relation to each other; and/or (b) the sequence of the gene encoding the fusogenic protein, and/or the sequence of the gene encoding the immune stimulatory molecule is codon optimized so as to increase expression levels in target cells.

17. The method according to claim 1, wherein the oncolytic virus expresses three heterologous genes, wherein each of the three heterologous genes is driven by a different promoter selected from the CMV promoter, the RSV promoter, the SV40 promoter and a retroviral LTR promoter.

18. The method according to claim 17, wherein the oncolytic virus expresses four heterologous genes driven by each of the CMV promoter, the RSV promoter, the SV40 promoter and a retroviral LTR promoter, respectively.

19. The method according to claim 17, wherein the retroviral LTR promoter is from MMLV.

20. The method according to claim 1, wherein the oncolytic virus expresses three heterologous genes, wherein each of the three heterologous genes is terminated by a different poly adenylation sequence selected from the BGH, SV40, HGH and RBG poly adenylation sequences.

21. The method according to claim 20, wherein the oncolytic virus expresses four heterologous genes terminated by each of the BGH, SV40, HGH and RBG poly adenylation sequences, respectively.

22. The method according to claim 1, which comprises administering a therapeutically effective amount of the virus in combination with a tyrosine kinase inhibitor.

23. The method according to claim 22, wherein the tyrosine kinase inhibitor is a MEK inhibitor or a BRAF inhibitor.

24. The method according to claim 1, which further comprises administering a therapeutically effective amount of a further anti-cancer agent to a patient in need thereof.

25. The method according to claim 24, wherein the further anti-cancer agent is selected from an antagonist of an immune co-inhibitory pathway, an agonist of an immune co-stimulatory pathway, radiation and/or chemotherapy, an agent that targets a specific genetic mutation which occurs in tumors, an agent intended to induce an immune response to one or more tumor antigen(s) or neoantigen(s), a cellular product derived from T cells or NK cells, an agent intended to stimulate the STING, cGAS, TLR or other innate immune response and/or inflammatory pathway, a second virus optionally an oncolytic virus, an inhibitor of the indoleamine 2,3-dioxygenase (IDO) pathway, a tyrosine kinase inhibitor and combinations thereof.

26. The method according to claim 25, wherein the antagonist of an immune co-inhibitory pathway is a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a KIR inhibitor, a SLAM F7 inhibitor or a CD47 inhibitor, and/or the agonist of an immune co-stimulatory pathway is a GITR agonist, a 4-1-BB agonist, an OX40 agonist, a CD40 agonist or an ICOS agonist, and/or the tyrosine kinase inhibitor is a MEK inhibitor or a BRAF inhibitor.

27. The method according to claim 24, wherein the further anti-cancer agent comprises an antibody.

28. The method according to claim 24, wherein the virus and the further anti-cancer agent(s) are administered separately.

29. The method according to claim 24, wherein the virus and the further anti-cancer agent(s) are administered concurrently.

* * * * *